(12) United States Patent
Goble et al.

(10) Patent No.: US 7,700,591 B2
(45) Date of Patent: Apr. 20, 2010

(54) BENZOXAZINYL-AMIDOCYCLOPENTYL-HETEROCYCLIC MODULATORS OF CHEMOKINE RECEPTORS

(75) Inventors: Stephen D. Goble, Edison, NJ (US); Sander G. Mills, Scotch Plains, NJ (US); Lihu Yang, Edison, NJ (US); Alexander Pasternak, Princeton, NJ (US); Celine Bonnefous, San Diego, CA (US); Theodore M Kamenecka, Palm Beach Gardens, FL (US); Jean-Michel Vernier, Laguna Niguel, CA (US); John H. Hutchinson, LaJolla, CA (US); Essa Hu, Camarillo, CA (US); Steven Govek, San Diego, CA (US)

(73) Assignee: Merck & Co., Inc., Rahway, NJ (US)

( * ) Notice: Subject to any disclaimer, the term of this patent is extended or adjusted under 35 U.S.C. 154(b) by 489 days.

(21) Appl. No.: 11/129,512

(22) Filed: May 13, 2005

(65) Prior Publication Data

US 2006/0069088 A1 Mar. 30, 2006

Related U.S. Application Data

(63) Continuation-in-part of application No. PCT/US2004/011281, filed on Apr. 9, 2004.

(60) Provisional application No. 60/463,111, filed on Apr. 15, 2003.

(51) Int. Cl.
*A61K 31/535* (2006.01)
*C07D 265/12* (2006.01)
*C07D 498/00* (2006.01)

(52) U.S. Cl. ..................... 514/229.5; 544/90
(58) Field of Classification Search ............. None
See application file for complete search history.

(56) References Cited

U.S. PATENT DOCUMENTS

| | | | |
|---|---|---|---|
| 3,647,804 A | 3/1972 | Rynbrandt et al. | |
| 3,772,308 A | 11/1973 | Pioch et al. | |
| 6,812,234 B2 | 11/2004 | Jiao et al. | |
| 2002/0012664 A1 | 1/2002 | LaRosa | |
| 2007/0238723 A1* | 10/2007 | Goble et al. | 514/217.05 |
| 2008/0194548 A1* | 8/2008 | Forrest et al. | 514/230.5 |

FOREIGN PATENT DOCUMENTS

| | | |
|---|---|---|
| EP | 0 962 457 | 6/1999 |
| WO | WO 00/76512 | 12/2000 |
| WO | WO 02070523 | 9/2002 |
| WO | WO 03/093231 | 11/2003 |
| WO | WO 2004/110376 | 12/2004 |

OTHER PUBLICATIONS

Worm, M. Expert Opinion in Therapeutic Patents, 2002, 12(7), 1023-33.*
U.S. Appl. No. 10/511,614, filed Oct. 2004, Goble S.*
Vergunst et al. Arthritis & Rheumatism, 2008, 58(7), 1931-39.*
Takeda Expert Opinion on Therapeutic Patents, 2000, 10(15), 711-15.*
"Inflammation", http://www.nlm.nih.gov/cgi/mesh/2008/MB_cgi, Accessed Feb. 20, 2008.*
"Immune system diseases", http://www.nlm.nih.gov/cgi/mesh/2009/MB_cgi, Accessed Apr. 27, 2009.*
R. Horuk, Trends in Pharm. Sci., 15:159-165(1994).
O. Mitsunobu, Synthesis, 1:1-28(1981).
H.K. Deng et al., Nature, 381: 661-666(1996).
A.J. Mancuso et al., J. Org. Chem., 43:2480-2482(1978).
J.P. Depres et al., J. Org. Chem., 49: 928-931(1984).
K. Neote et al., Cell, 72:415-425(1993).
J.J. Gomez-Reino et al., Arthritis & Rheumatism, 42:989-992(1999).
S.Y. Sung et al., Arch. Pharm. Pharm. Med. Chem., 329:291-300(1996).
K.S. Warmington et al., Am. J. Path., 154:1407-1416(1999).
T. Kurihara et al., J. Exp. Med., 186:1757-1762(1997).
B. Lu et al., J. Exp. Med., 187:601-608(1998).
L. Boring et al., J. Clin. Inves., 100:2552-2561(1997).
B. J. Rollins, Blood, 90:909-928(1997).
M. Samson et al., Biochemistry, 35:3362-3367(1996).

(Continued)

*Primary Examiner*—James O Wilson
*Assistant Examiner*—Noble Jarrell
(74) *Attorney, Agent, or Firm*—Mark R. Daniels; James L. McGinnis

(57) ABSTRACT

Cyclopentyl compounds linked to a benzoxazinyl group through an amido moiety utilizing the ring nitrogen of the benzoxazine, and further substituted with a heterocyclic moiety, such compounds represented by formula I:

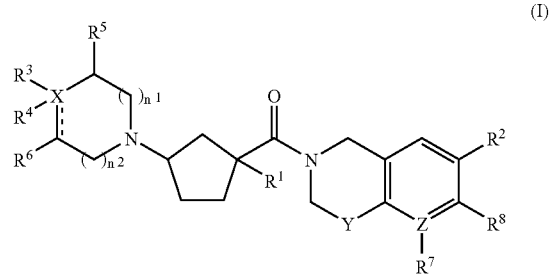

(I)

which are used to modulate the CCR-2 chemokine receptor to prevent or treat inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis; and pharmaceutical compositions comprising these compounds and the use of these compounds and compositions.

18 Claims, No Drawings

OTHER PUBLICATIONS

A.D. Luster, New Eng. J. Med., 338:436-445(1998).
R. M. Burk et al., Tetrahedron Lett., 34:975-978(1993).
S.W. Wright et al., Tetrahedron Lett., 38:7345-7348(1997).
W.A. Kuziel et al., Proc. Natl. Acad. Sci. USA, 94:12053-12058(1997).
H. Kita et al., J. Exp. Med., 183:2421-2426(1996).
B.M. Trost et al., J. Am. Chem. Soc., 105:2315-2325(1983).
A. Chaudhuri et al., J. Bio. Chem., 269:7835-7838(1994).
P.M. Murphy, Annu. Rev. Immunol., 12:593-633(1994).
T.J. Schall, Cytokine, 3:165-183(1991).
H. Stetter et al., Liebigs Ann. Chem., 944-949(1979).
L. Boring, et al., Nature, 394:894-897(1998).
Ben-Barruch, et al., J. Biol. Chem., 270, 22123-22128 (1995).
Gosling, et al., J. Clin. Invest., 103, 773-778 (1999).

* cited by examiner

BENZOXAZINYL-AMIDOCYCLOPENTYL-HETEROCYCLIC MODULATORS OF CHEMOKINE RECEPTORS

CROSS REFERENCE TO RELATED APPLICATIONS

This application is a continuation-in-part of PCT/US04/011281 filed Apr. 9, 2004 which claims the benefit of U.S. Provisional Application No. 60/463,111 filed Apr. 15, 2003.

BACKGROUND OF THE INVENTION

The present invention is directed to cyclopentyl compounds linked to a benzoxazinyl group through an amido moiety utilizing the ring nitrogen of the benzoxazine. In particular, the present invention is directed to cyclopentyl compounds linked to a benzoxazinyl group through an amido moiety utilizing the ring nitrogen of the benzoxazine, and further substituted with a heterocyclic moiety, useful as modulators of chemokine receptors.

The chemokines are a family of small (70-120 amino acids), proinflammatory cytokines, with potent chemotactic activities. Chemokines are chemotactic cytokines that are released by a wide variety of cells to attract various cells, such as monocytes, macrophages, T cells, eosinophils, basophils and neutrophils to sites of inflammation (reviewed in Schall, *Cytokine*, 3, 165-183 (1991) and Murphy, *Rev. Immun.*, 12, 593-633 (1994)). These molecules were originally defined by four conserved cysteines and divided into two subfamilies based on the arrangement of the first cysteine pair. In the CXC-chemokine family, which includes IL-8, GROα, NAP-2 and IP-10, these two cysteines are separated by a single amino acid, while in the CC-chemokine family, which includes RANTES, MCP-1, MCP-2, MCP-3, MIP-1α, MIP-1β and eotaxin, these two residues are adjacent.

The α-chemokines, such as interleukin-8 (IL-8), neutrophil-activating protein-2 (NAP-2) and melanoma growth stimulatory activity protein (MGSA) are chemotactic primarily for neutrophils, whereas β-chemokines, such as RANTES, MIP-1α, MIP-1β, monocyte chemotactic protein-1 (MCP-1), MCP-2, MCP-3 and eotaxin are chemotactic for macrophages, monocytes, T-cells, eosinophils and basophils (Deng, et al., *Nature*, 381, 661-666 (1996)).

The chemokines are secreted by a wide variety of cell types and bind to specific G-protein coupled receptors (GPCRs) (reviewed in Horuk, *Trends Pharm. Sci.*, 15, 159-165 (1994)) present on leukocytes and other cells. These chemokine receptors form a sub-family of GPCRs, which, at present, consists of fifteen characterized members and a number of orphans. Unlike receptors for promiscuous chemoattractants such as C5a, fMLP, PAF, and LTB4, chemokine receptors are more selectively expressed on subsets of leukocytes. Thus, generation of specific chemokines provides a mechanism for recruitment of particular leukocyte subsets.

On binding their cognate ligands, chemokine receptors transduce an intracellular signal though the associated trimeric G protein, resulting in a rapid increase in intracellular calcium concentration. There are at least seven human chemokine receptors that bind or respond to β-chemokines with the following characteristic pattern: CCR-1 (or "CKR-1" or "CC-CKR-1") [MIP-1α, MIP-1β, MCP-3, RANTES] (Ben-Barruch, et al., *J. Biol. Chem.*, 270, 22123-22128 (1995); Beote, et al, *Cell*, 72, 415-425 (1993)); CCR-2A and CCR-2B (or "CKR-2A"/"CKR-2A" or "CC-CKR-2A"/"CC-CKR-2A") [MCP-1, MCP-2, MCP-3, MCP-4]; CCR-3 (or "CKR-3" or "CC-CKR-3") [Eotaxin, Eotaxin 2, RANTES, MCP-2, MCP-3] (Rollins, et al., *Blood*, 90, 908-928 (1997)); CCR-4 (or "CKR-4" or "CC-CKR-4") [MIP-1α, RANTES, MCP-1] (Rollins, et al., *Blood*, 90, 908-928 (1997)); CCR-5 (or "CKR-5" or "CC-CKR-5") [MIP-1α, RANTES, MIP-1β] (Sanson, et al., *Biochemistry*, 35, 3362-3367 (1996)); and the Duffy blood-group antigen [RANTES, MCP-1] (Chaudhun, et al., *J. Biol. Chem.*, 269, 7835-7838 (1994)). The β-chemokines include eotaxin, MIP ("macrophage inflammatory protein"), MCP ("monocyte chemoattractant protein") and RANTES ("regulation-upon-activation, normal T expressed and secreted") among other chemokines.

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. Humans who are homozygous for the 32-basepair deletion in the CCR-5 gene appear to have less susceptibility to rheumatoid arthritis (Gomez, et al., *Arthritis & Rheumatism*, 42, 989-992 (1999)). A review of the role of eosinophils in allergic inflammation is provided by Kita, H., et al., *J. Exp. Med.* 183, 2421-2426 (1996). A general review of the role of chemokines in allergic inflammation is provided by Lustger, A. D., *New England J. Med.*, 338(7), 426-445 (1998).

A subset of chemokines are potent chemoattractants for monocytes and macrophages. The best characterized of these is MCP-1 (monocyte chemoattractant protein-1), whose primary receptor is CCR2. MCP-1 is produced in a variety of cell types in response to inflammatory stimuli in various species, including rodents and humans, and stimulates chemotaxis in monocytes and a subset of lymphocytes. In particular, MCP-1 production correlates with monocyte and macrophage infiltration at inflammatory sites. Deletion of either MCP-1 or CCR2 by homologous recombination in mice results in marked attenuation of monocyte recruitment in response to thioglycollate injection and *Listeria monocytogenes* infection (Lu et al., *J. Exp. Med.*, 187, 601-608 (1998); Kurihara et al. *J. Exp. Med.*, 186, 1757-1762 (1997); Boring et al. *J. Clin. Invest.*, 100, 2552-2561 (1997); Kuziel et al. *Proc. Natl. Acad. Sci.*, 94, 12053-12058 (1997)). Furthermore, these animals show reduced monocyte infiltration into granulomatous lesions induced by the injection of schistosomal or mycobacterial antigens (Boring et al. *J. Clin. Invest.*, 100, 2552-2561 (1997); Warmington et al. *Am J. Path.*, 154, 1407-1416 (1999)). These data suggest that MCP-1-induced CCR2 activation plays a major role in monocyte recruitment to inflammatory sites, and that antagonism of this activity will produce a sufficient suppression of the immune response to produce therapeutic benefits in immunoinflammatory and autoimmune diseases.

Accordingly, agents which modulate chemokine receptors such as the CCR-2 receptor would be useful in such disorders and diseases.

In addition, the recruitment of monocytes to inflammatory lesions in the vascular wall is a major component of the pathogenesis of atherogenic plaque formation. MCP-1 is produced and secreted by endothelial cells and intimal smooth muscle cells after injury to the vascular wall in hypercholesterolemic conditions. Monocytes recruited to the site of injury infiltrate the vascular wall and differentiate to foam cells in response to the released MCP-1. Several groups have now demonstrated that aortic lesion size, macrophage content and necrosis are attenuated in MCP-1–/– or CCR2–/– mice backcrossed to APO-E –/–, LDL-R –/– or Apo B transgenic mice maintained on high fat diets (Boring et al. *Nature*, 394, 894-897 (1998); Gosling et al. *J. Clin. Invest.*, 103, 773-778

(1999)). Thus, CCR2 antagonists may inhibit atherosclerotic lesion formation and pathological progression by impairing monocyte recruitment and differentiation in the arterial wall.

SUMMARY OF THE INVENTION

The present invention is directed to cyclopentyl compounds linked to a benzoxazinyl group through an amido moiety utilizing the ring nitrogen of the benzoxazine, and further substituted with a heterocyclic moiety, such compounds represented by formula I:

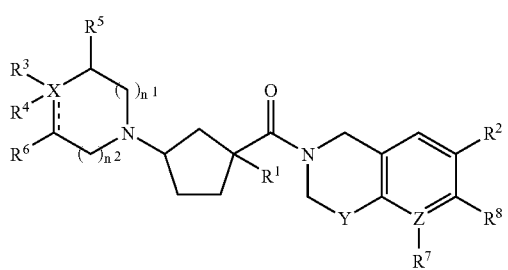

(I)

These compounds are useful as modulators of the CCR-2 chemokine receptor. The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds represented by formula I:

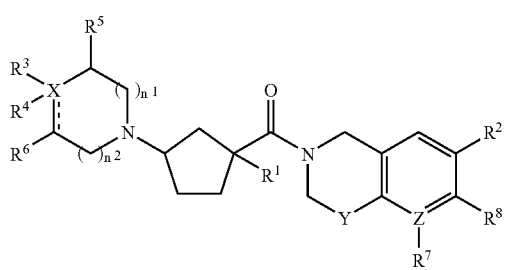

(I)

or a pharmaceutically acceptable salt thereof, or an individual diastereomer thereof, wherein:

X is C, N, O or S;

Y is O, S, SO, $SO_2$, or $NR^9$;

Z is C or N;

$R^1$ is hydrogen, —$C_{0-6}$alkyl-W—($C_{1-6}$alkyl)-, —($C_{0-6}$alkyl)-W—($C_{0-6}$alkyl)-($C_{3-7}$cycloalkyl)-($C_{0-6}$alkyl), —($C_{0-6}$alkyl)-W-phenyl, or —($C_{0-6}$alkyl)-W-heterocycle, wherein the alkyl, phenyl, heterocycle and the cycloalkyl are optionally substituted with 1-7 independent halo, hydroxy, —O—$C_{1-3}$alkyl, trifluoromethyl, $C_{1-3}$alkyl, —O—$C_{1-3}$alkyl, —$CO_2R^{10}$, —CN, —$NR^{10}R^{10}$, —$NR^{10}COR^{10}$, —$NR^{10}SO_2R^{11}$, or —$CONR^{10}R^{10}$ substituents;

W is a single bond, —O—, —S—, —SO—, —$SO_2$—, —CO—, —$CO_2$—, —$CONR^{10}$— or —$NR^9$—;

$R^2$ is -halo, —$C_{0-6}$alkyl, $C_{0-6}$alkyl-W—$C_{1-6}$-alkyl, $C_{0-6}$-alkyl-W—$C_{3-7}$cycloalkyl, $C_{0-6}$alkyl-W-phenyl, or $C_{0-6}$-alkyl-W-heterocycle, wherein the $C_{1-6}$alkyl, $C_{3-7}$cycloalkyl, phenyl and heterocycle optionally are independently substituted with 1-6 halo, trifluoromethyl, —CN, —$C_{1-6}$-alkyl, or hydroxy substituents;

$R^3$ is hydrogen, —($C_{0-6}$alkyl)-phenyl, —($C_{0-6}$alkyl)-heterocycle, —($C_{0-6}$alkyl)-$C_{3-7}$cycloalkyl, —($C_{0-6}$alkyl)-$CO_2R^{10}$, —($C_{0-6}$alkyl)-($C_{2-6}$alkenyl)-$CO_2R^{10}$, —($C_{0-6}$alkyl)-$SO_3H$, —($C_{0-6}$alkyl)-W—$C_{0-4}$alkyl, —($C_{0-6}$alkyl)-$CONR^{10}$-phenyl, —($C_{0-6}$alkyl)-$CONR^{12}$—V—$CO_2R^{10}$, and wherein $R^3$ is nothing when X is O, and wherein $C_{0-6}$alkyl is optionally substituted with 1-5 independent halo, hydroxy, —$C_{0-6}$alkyl, —O—$C_{1-3}$alkyl, trifluoromethyl, or —$C_{0-2}$alkyl-phenyl substituents, and wherein the phenyl, pyridyl, diazolyl, tetrazolyl, thiadiazolonyl, oxadiazolonyl, thiazolphenyl, N-oxide pyridyl, heterocycle, cycloalkyl, or $C_{0-4}$alkyl is optionally substituted with 1-5 independent halo, trifluoromethyl, hydroxy, $C_{1-3}$alkyl, —O—$C_{1-3}$alkyl, —$C_{0-3}$—$CO_2R^{10}$, —CN, —($C_{0-6}$alkyl)-C(O)—($C_{0-6}$alkyl), —$NR^{10}R^{10}$, —$CONR^{10}R^{10}$, or —($C_{0-3}$alkyl)-heterocycle substituents, and wherein the phenyl and heterocycle may be fused to another heterocycle, which itself optionally may be substituted with 1-2 independently hydroxy, halo, —$CO_2R^{10}$, or —$C_{1-3}$alkyl substituents, and where alkenyl is optionally substituted with 1-3 independently halo, trifluoromethyl, $C_{1-3}$alkyl, phenyl, or heterocycle substituents;

V is $C_{1-6}$alkyl or phenyl;

$R^{12}$ is hydrogen, $C_{1-4}$alkyl, or $R^{12}$ is joined via a 1-5 carbon tether to one of the carbons of V to form a ring;

$R^4$ is nothing when X is either O, or N or when a double bond joins the carbons to which $R^3$ and $R^6$ are attached, or $R^4$ is hydrogen, hydroxy, $C_{0-6}$alkyl, $C_{1-6}$alkyl-hydroxy, —O—$C_{1-3}$alkyl, —$CO_2R^{10}$, —$CONR^{10}R^{10}$, or —CN;

or $R^3$ and $R^4$ are joined together to form a 1H-indenyl, 2,3-dihydro-1H-indenyl, 2,3-dihydro-benzofuranyl, 1,3-dihydro-isobenzofuranyl, 2,3-dihydro-benzothiofuranyl, 1,3-dihydro-isobenzothiofuranyl, 6H-cyclopenta[d]isoxazol-3-olyl, cyclopentanyl, or cyclohexanyl ring, wherein the ring formed optionally is substituted with 1-5 independently halo, trifluoromethyl, hydroxy, $C_{1-3}$alkyl, —O—$C_{1-3}$alkyl, —$C_{0-3}$—$CO_2R^{10}$, —CN, —$NR^{10}R^{10}$, —$CONR^{10}R^{10}$, or —$C_{0-3}$-heterocyclyl substituents;

or $R^3$ and $R^5$ or $R^4$ and $R^6$ are joined together to form a phenyl or heterocyclyl ring, wherein the ring is optionally substituted with 1-7 independent halo, trifluoromethyl, hydroxy, $C_{1-3}$alkyl, —O—$C_{1-3}$alkyl, —$CO_2R^{10}$, —CN, —$NR^{10}R^{10}$, or —$CONR^{10}R^{10}$ substituents;

$R^5$ and $R^6$ are independently hydrogen, hydroxy, $C_{1-6}$alkyl, $C_{1-6}$alkyl-$CO_2R^{10}$, $C_{1-6}$alkyl-hydroxy, —O—$C_{1-3}$alkyl, or halo; or =O, when $R^5$ or $R^6$ is connected to the ring via a double bond;

when Z=C, $R^7$ is hydrogen, hydroxy, halo, $C_{1-6}$alkyl optionally substituted with 1-6 fluro, —O—$C_{1-6}$alkyl optionally substituted with 1-6 fluro, —$NR^{10}R^{10}$, —$NR^{10}CO_2R^{11}$, —$NR^{10}CONR^{10}R^{10}$, —$NR^{10}$—$SO_2$—$NR^{10}R^{10}$, —$NR^{10}$—$SO_2$—$R^{11}$, heterocycle, —CN, —$CONR^{10}R^{10}$, —$CO_2R^{10}$, —$NO_2$, —S—$R^{10}$, —SO—$R^{11}$, —$SO_2$—$R^{11}$, or —$SO_2$—$NR^{11}R^{11}$;

when Z=N, $R^7$ is nothing or oxide (resulting in a pyridine N-oxide);

$R^8$ is hydrogen, $C_{1-6}$alkyl, trifluoromethyl, trifluoromethoxy, chloro, fluoro, bromo, or phenyl;

$R^9$ is $SO_2R^{11}$, $COR^{10}$, $CONHR^{10}$, $CO_2R^{11}$, or $SO_2NHR^{10}$;

$R^{10}$ is hydrogen, —$C_{1-6}$ alkyl, benzyl, phenyl, or —$C_{0-6}$ alkyl-$C_{3-6}$ cycloalkyl, optionally substituted with 1-3 independent halo, $C_{1-3}$alkyl, $C_{1-3}$alkoxy or trifluoromethyl substituents;

$R^{11}$ is $C_{1-6}$alkyl, —$C_{0-6}$alkyl-$C_{3-6}$cycloalkyl, benzyl or phenyl, optionally substituted with 1-3 independent halo, $C_{1-3}$alkyl, $C_{1-3}$alkoxy or trifluoromethyl substitutents;

$n^1$ and $n^2$ are independently 0, 1 or 2, wherein the sum of $n^1$ and $n^2$ is 0, 1, 2, or 3; and the dashed line represents an optional bond.

Compounds of the present invention further include those wherein X, Y, Z, $n^1$, $n^2$, $R^1$, $R^2$, $R^3$, $R^4$, $R^5$, $R^6$, and $R^7$ are as described above with reference to formula I, wherein $R^8$ is hydrogen, $C_{1-6}$alkyl, trifluoromethyl, trifluoromethoxy, chloro, fluoro, bromo, phenyl, alkoxy or cyano.

Compounds of the present invention include those of formula Ia:

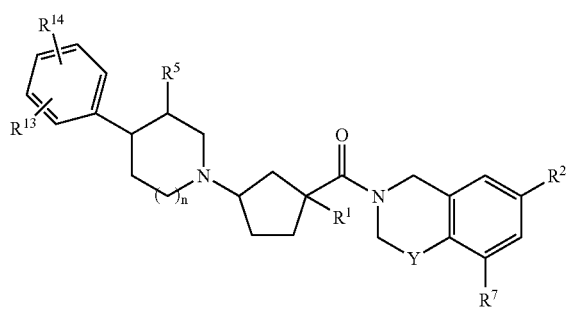

(Ia)

or pharmaceutically acceptable salts and individual diastereomers thereof, wherein $R^1$, $R^2$, $R^5$, $R^7$, and Y are defined as above for Formula I, and wherein $R^{13}$ and $R^{14}$ are independently hydrogen, halo, trifluoromethyl, hydroxy, —$C_{1-3}$alkyl, —O—$C_{1-3}$alkyl, —$C_{0-3}$—$CO_2H$, —$C_{0-3}$—$CO_2C_{1-3}$alkyl, —CN, or —$C_{0-3}$-heterocycle, or $R^{13}$ and $R^{14}$ are joined together to form a heterocycle which is fused to the phenyl ring, and which itself may be unsubstituted or substituted with 1-2 independent hydroxy, halo, —$CO_2R^{10}$, or —$C_{1-3}$alkyl substituents; and n is 0, 1, or 2.

Compounds of the present invention also include those of formula Ib:

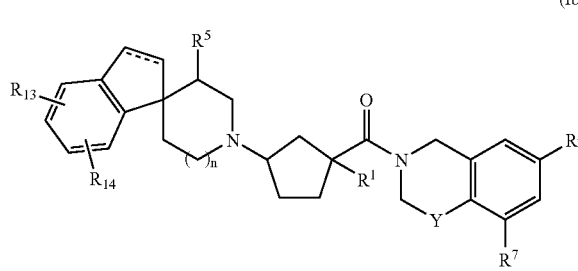

(Ib)

or pharmaceutically acceptable salts and individual diastereomers thereof, wherein the dashed line represents an optional bond, and $R^1$, $R^2$, $R^5$, $R^7$, $R^{13}$, $R^{14}$, Y, and n are defined above for Ia.

Compounds of the present invention also include those of formula Ic:

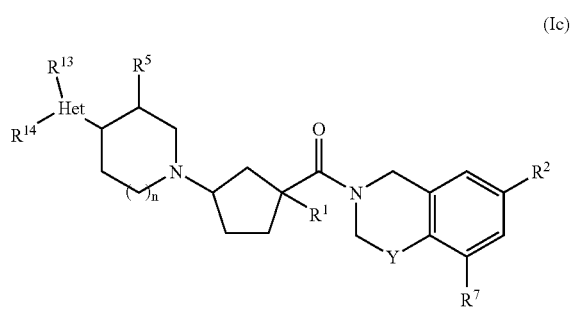

(Ic)

or pharmaceutically acceptable salts and individual diastereomers thereof, wherein $R^1$, $R^2$, $R^5$, $R^7$, $R^{13}$, $R^{14}$, Y, and n are defined above for Ia, and where Het is a heterocycle.

Compounds of the present invention also include those of formula Id:

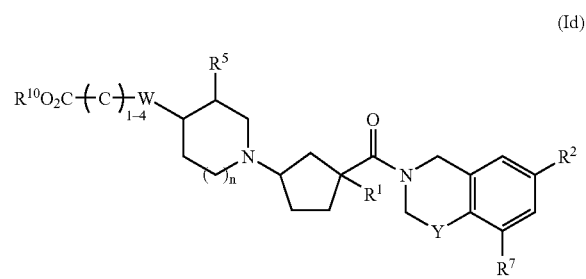

(Id)

or pharmaceutically acceptable salts and individual diastereomers thereof, wherein $R^1$, $R^2$, $R^5$, $R^7$, $R^{10}$, Y, W, and n are defined above for Ia and where the $C_{1-4}$ carbon chain is optionally substituted with 1-4 independent halo, hydroxy, —$C_{0-6}$alkyl, —O—$C_{1-3}$ alkyl, trifluoromethyl, or —$C_{0-2}$alkyl-phenyl substituents, or where the $C_{1-4}$ carbon chain is part of a $C_{3-7}$cycloalkyl ring.

Compounds of the present invention also include those of formula Ie:

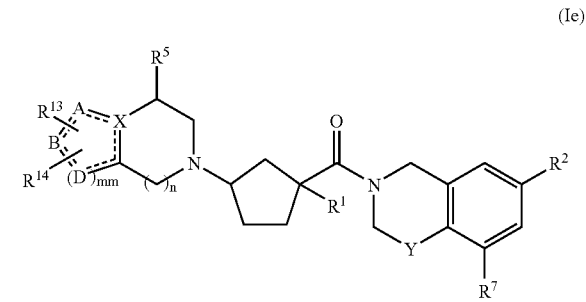

(Ie)

or pharmaceutically acceptable salts and individual diastereomers thereof, wherein $R^1$, $R^2$, $R^5$, $R^7$, $R^{13}$, $R^{14}$, X, Y, and n are as defined above for formula Ia, and wherein the dotted lines represent an optional bond, and wherein mm is 1 or 2, and wherein A, B, and D are each independently C, N, O, or S; or A, B, and D, in combination with mm=2, form a phenyl ring; or in combination form a heterocycle when at least one of X, A, B, D is N, O, or S.

Additional compounds of the present invention also include those of formula If:

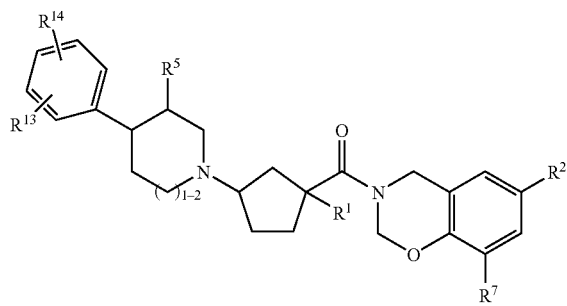

(If)

or pharmaceutically acceptable salts and individual diastereomers thereof, wherein $R^1$, $R^2$, $R^5$, $R^7$, $R^{13}$, and $R^{14}$, are as defined above for Ia, or wherein $R^{13}$ and $R^{14}$ are joined together to form a heterocycle fused to the phenyl ring, and wherein the heterocycle is itself is optionally substituted with 1-2 independent hydroxy, halo, —$CO_2R^{10}$, or —$C_{1-3}$alkyl substituents.

Compounds of the present invention also include those of formula Ig:

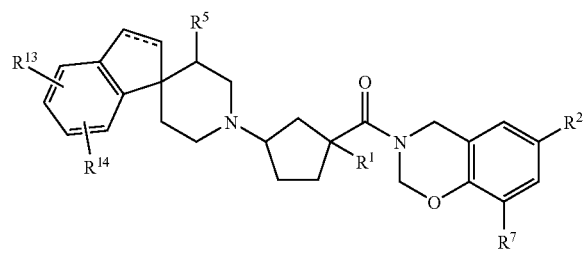

(Ig)

or pharmaceutically acceptable salts and individual diastereomers thereof, wherein the dashed line represents an optional bond and $R^1$, $R^2$, $R^5$, $R^7$, $R^{13}$, and $R^{14}$ are as defined above for Ia.

Compounds of the present invention also include those of formula Ih:

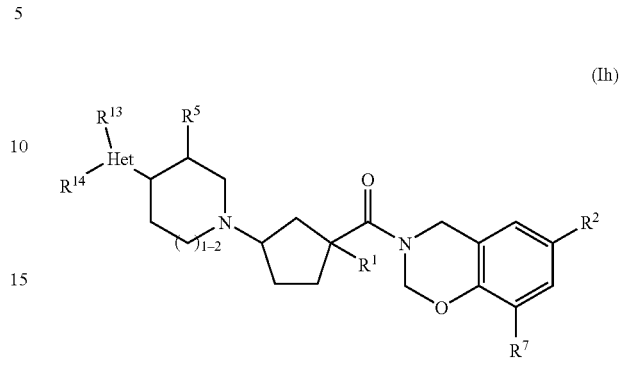

(Ih)

or pharmaceutically acceptable salts and individual diastereomers thereof, wherein $R^1$, $R^2$, $R^5$, $R^7$, $R^{13}$, and $R^{14}$ are as defined above for Ia; and wherein Het is a heterocycle.

Compounds of the present invention also include those of formula Ii:

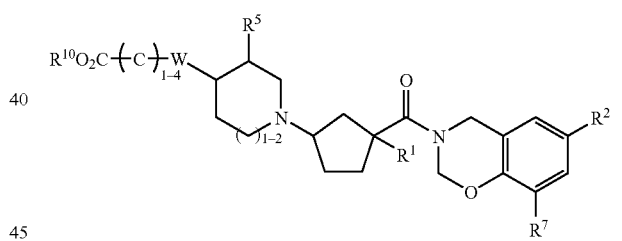

(Ii)

or pharmaceutically acceptable salts and individual diastereomers thereof, wherein $R^1$, $R^2$, $R^5$, $R^7$, $R^{10}$, and W are defined above for Ia; and wherein the $C_{1-4}$ carbon chain is optionally substituted with 1-4 independent halo, hydroxy, —$C_{0-6}$alkyl, —O—$C_{1-3}$alkyl, trifluoromethyl, or —$C_{0-2}$alkyl-phenyl substituents. In certain embodiments of the invention X is C, Y is —O— and Z is C.

Further, in certain embodiments of the invention $R^1$ is —$C_{1-6}$alkyl, —$C_{0-6}$alkyl-O—$C_{1-6}$alkyl-, or —($C_{0-6}$alkyl)-($C_{3-7}$cycloalkyl)-($C_{0-6}$alkyl), wherein the alkyl and the cycloalkyl are optionally substituted with 1-7 independent halo, hydroxy, —O—$C_{1-3}$alkyl, trifluoromethyl, —$C_{1-3}$alkyl, —O—$C_{1-3}$alkyl, —$CO_2R^{10}$, —CN, —$NR^{10}R^{10}$, or —$CONR^{10}R^{10}$ substituents.

Compounds of the invention also include those of Formula II:

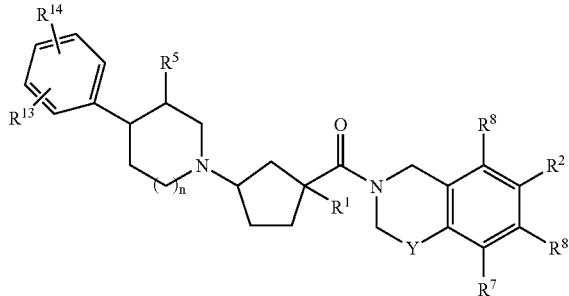

or pharmaceutically acceptable salts and individual diastereomers thereof,

Y is O, S, SO, $SO_2$, or $NR^9$;

$R^1$ is hydrogen, —$C_{0-6}$alkyl-W—($C_{1-6}$alkyl)-, —($C_{0-6}$alkyl)-W—($C_{0-6}$alkyl)-($C_{3-7}$cycloalkyl)-($C_{0-6}$alkyl), —($C_{0-6}$alkyl)-W-phenyl, or —($C_{0-6}$alkyl)-W-heterocycle, wherein the alkyl, phenyl, heterocycle and the cycloalkyl are optionally substituted with 1-7 independent halo, hydroxy, —O—$C_{1-3}$alkyl, trifluoromethyl, $C_{1-3}$alkyl, —O—$C_{1-3}$alkyl, —$CO_2R^{10}$, —CN, —$NR^{10}R^{10}$, —$NR^{10}COR^{10}$, —$NR^{10}SO_2R^{11}$, or —$CONR^{10}R^{10}$ substituents;

W is a single bond, —O—, —S—, —SO—, —$SO_2$—, —CO—, —$CO_2$—, —$CONR^{10}$— or —$NR^9$—;

$R^2$ is -halo, —$C_{0-6}$alkyl, $C_{0-6}$alkyl-W—$C_{1-6}$alkyl, $C_{0-6}$alkyl-W—$C_{3-7}$cycloalkyl, $C_{0-6}$alkyl-W-phenyl, or $C_{0-6}$alkyl-W-heterocycle, wherein the $C_{1-6}$alkyl, $C_{3-7}$cycloalkyl, phenyl and heterocycle optionally are independently substituted with 1-6 halo, trifluoromethyl, —CN, —$C_{1-6}$alkyl, or hydroxy substituents;

V is $C_{1-6}$alkyl or phenyl;

$R^{12}$ is hydrogen, $C_{1-4}$alkyl, or $R^{12}$ is joined via a 1-5 carbon tether to one of the carbons of V to form a ring;

$R^5$ is hydrogen, hydroxy, $C_{1-6}$alkyl, $C_{1-6}$alkyl-$CO_2R^{10}$, $C_{1-6}$alkyl-hydroxy, —O—$C_{1-3}$alkyl, or halo, or =O, when $R^5$ or $R^6$ is connected to the ring via a double bond;

$R^7$ is hydrogen, hydroxy, halo, $C_{1-6}$alkyl optionally substituted with 1-6 fluro, —O—$C_{1-6}$alkyl optionally substituted with 1-6 fluro, —$NR^{10}R^{10}$, —$NR^{10}CO_2R^{11}$, —$NR^{10}CONR^{10}R^{10}$, —$NR^{10}$—$SO_2$—$NR^{10}R^{10}$, —$NR^{10}$—$SO_2$—$R^{11}$, heterocycle, —CN, —$CONR^{10}R^{10}$, —$CO_2R^{10}$, —$NO_2$, —S—$R^{10}$, —SO—$R^{11}$, —$SO_2$—$R^{11}$, or —$SO_2$—$NR^{11}R^{11}$;

$R^8$ is hydrogen, $C_{1-6}$alkyl, trifluoromethyl, trifluoromethoxy, chloro, fluoro, bromo, or phenyl;

$R^9$ is $SO_2R^{11}$, $COR^{10}$, $CONHR^{10}$, $CO_2R^{11}$, or $SO_2NHR^{10}$;

$R^{10}$ is hydrogen, —$C_{1-6}$ alkyl, benzyl, phenyl, or —$C_{0-6}$alkyl-$C_{3-6}$ cycloalkyl, optionally substituted with 1-3 independent halo, $C_{1-3}$alkyl, $C_{1-3}$alkoxy or trifluoromethyl substituents;

$R^{11}$ is $C_{1-6}$alkyl, —$C_{0-6}$alkyl-$C_{3-6}$cycloalkyl, benzyl or phenyl, optionally substituted with 1-3 independent halo, $C_{1-3}$alkyl, $C_{1-3}$alkoxy or trifluoromethyl substitutents;

$R^{13}$ and $R^{14}$ are independently hydrogen, halo, trifluoromethyl, hydroxy, —$C_{1-3}$alkyl, —O—$C_{1-3}$alkyl, —$C_{0-3}$—$CO_2H$, —$C_{0-3}$—$CO_2C_{1-3}$alkyl, —CN, or —$C_{0-3}$-heterocycle, or $R^{13}$ and $R^{14}$ join to form a heterocycle fused to the phenyl ring, which heterocycle is optionally substituted with 1-2 independent hydroxy, halo, —$CO_2R^{10}$, or —$C_{1-3}$alkyl substituents;

n is 0, 1, or 2.

In another embodiment of the present invention $R^1$ is —$C_{1-6}$ alkyl optionally substituted with 1-6 independent halo, hydroxy, —O—$C_{1-3}$alkyl, trifluoromethyl, or —$CO_2R^{10}$ substituents; or that $R^1$ is —$C_{0-6}$alkyl-O—$C_{1-6}$ alkyl-optionally substituted with 1-6 independent halo, trifluoromethyl, or —$CO_2R^{10}$ substituents; or that $R^1$ is —($C_{3-5}$cycloalkyl)-($C_{0-6}$alkyl) optionally substituted with 1-7 independent halo, hydroxy, —O—$C_{1-3}$alkyl, trifluoromethyl, or —$CO_2R^{10}$ substituents.

In yet another embodiment of the present invention $R^1$ is —$C_{1-6}$alkyl, —$C_{1-6}$alkyl-hydroxy, or —$C_{1-6}$alkyl substituted with 1-6 fluoro.

In still yet another embodiment of the present invention $R^1$ is isopropyl, hydroxyethyl, or trifluoroethyl.

In the present invention $R^2$ may be —$C_{1-6}$alkyl substituted with 1-6 fluoro, —O—$C_{1-6}$alkyl substituted with 1-6 fluoro, chloro, bromo, or phenyl. Further, $R^2$ may be trifluoromethyl, trifluoromethoxy, chloro, bromo, or phenyl. In certain embodiments, $R^2$ is trifluoromethyl.

Included within the present invention are compounds where, when X is not O, $R^3$ is phenyl, heterocycle, $C_{3-7}$cycloalkyl, $C_{1-6}$alkyl, —$CO_2R^{10}$, or —CONH—V—$CO_2R^{10}$; where V is —$C_{1-6}$alkyl- or phenyl; and where the phenyl, heterocycle, $C_{3-7}$cycloalkyl, and $C_{1-6}$alkyl independently is optionally substituted with 1-5 independent halo, trifluoromethyl, hydroxy, —$C_{1-3}$ alkyl, —O—$C_{1-3}$ alkyl, —$CO_2R^{10}$, —CN, -heterocycle, or —$CONR^{10}R^{10}$ substituents.

Also included within the present invention are compounds where, when X is not O, $R^3$ is phenyl, heterocycle, $C_{1-4}$alkyl, —$CO_2R^{10}$, or —CONH—V—$CO_2R^{10}$; wherein V is —$C_{1-6}$ alkyl or phenyl; and wherein the phenyl, heterocycle, and $C_{1-4}$alkyl each independently is optionally substituted with 1-3 independent halo, hydroxy, —$C_{1-3}$alkyl, —O—$C_{1-3}$ alkyl, —$CO_2R^{10}$, or -heterocycle substituents.

The present invention further includes compounds wherein, when X is not O, $R^3$ is selected from the following table:

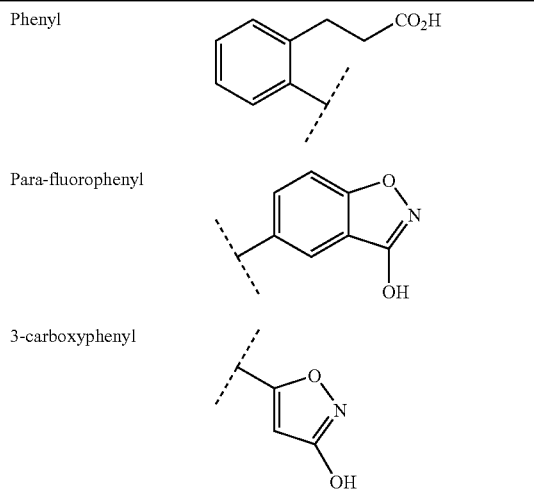

| Phenyl | |
| --- | --- |
| Para-fluorophenyl | |
| 3-carboxyphenyl | |

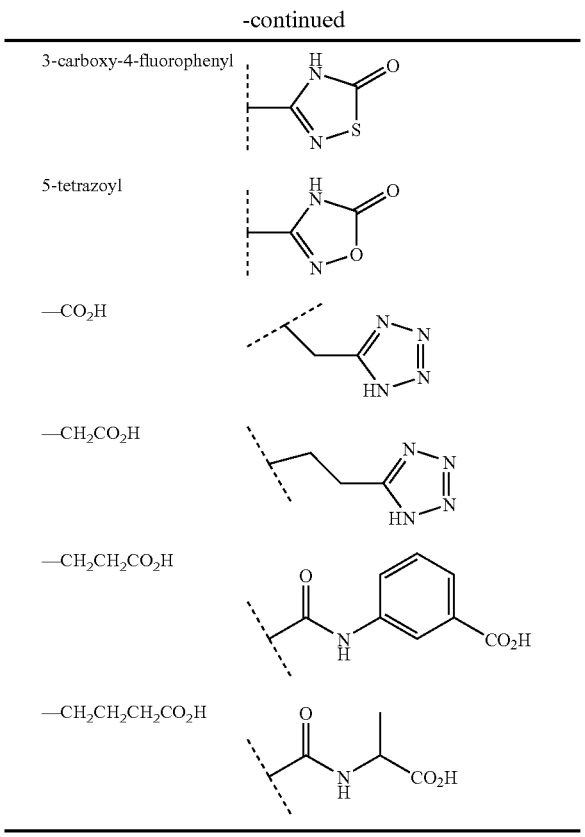

In certain embodiments of the invention, when X is C, $R^4$ is hydrogen, hydroxy, —CN, or —F.

In the present invention $R^3$ and $R^4$ may be joined together to form a 1H-indene, or 2,3-dihydro-1H-indene ring, optionally substituted with 1-3 independent halo, hydroxy, —$C_{1-3}$alkyl, —O—$C_{1-3}$alkyl, —$CO_2R^{10}$, or -heterocyclyl substituents.

Further, $R^5$ and $R^6$ may independently be hydrogen, hydroxy, —$CH_3$, —O—$CH_3$, or oxo.

In the present invention, when Z is not N, $R^7$ may be H, F, or hydroxy.

In certain embodiments of the present invention, $R^8$ is H.

In one aspect, the present invention is directed to compounds represented by formula (I), or a pharmaceutically acceptable salt thereof, or an individual diastereomer thereof, wherein:

X is C;
Y is O, S, SO, $SO_2$, or $NR^9$;
Z is C or N;
$R^1$ is hydrogen, —$C_{0-6}$alkyl-W—($C_{1-6}$alkyl)-, —($C_{0-6}$alkyl)-W—($C_{0-6}$alkyl)-($C_{3-7}$cycloalkyl)-($C_{0-6}$alkyl), —($C_{0-6}$alkyl)-W-phenyl, or —($C_{0-6}$alkyl)-W-heterocycle, wherein the alkyl, phenyl, heterocycle and the cycloalkyl are optionally substituted with 1-7 independent halo, hydroxy, —O—$C_{1-3}$alkyl, trifluoromethyl, $C_{1-3}$alkyl, —O—$C_{1-3}$alkyl, —$CO_2R^{10}$, —CN, —$NR^{10}R^{10}$, —$NR^{10}COR^{10}$, —$NR^{10}SO_2R^{11}$, or —$CONR^{10}R^{10}$ substituents;
W is a single bond, —O—, —S—, —SO—, —$SO_2$—, —CO—, —$CO_2$—, —$CONR^{10}$— or —$NR^9$—;
$R^2$ is -halo, —$C_{0-6}$alkyl, $C_{0-6}$alkyl-W—$C_{1-6}$alkyl, $C_{0-6}$alkyl-W—$C_{3-7}$cycloalkyl, $C_{0-6}$alkyl-W-phenyl, or $C_{0-6}$alkyl-W-heterocycle, wherein the $C_{1-6}$alkyl, $C_{3-7}$cycloalkyl, phenyl and heterocycle optionally are independently substituted with 1-6 halo, trifluoromethyl, —CN, —$C_{1-6}$alkyl, or hydroxy substituents;
$R^3$ is OH, —$C_{0-6}$alkyl, —($C_{0-6}$alkyl)-phenyl, —($C_{0-6}$alkyl)-heterocycle, —($C_{0-6}$alkyl)-$C_{3-7}$cycloalkyl, —($C_{0-6}$alkyl)-$CO_2R^{10}$, —($C_{0-6}$alkyl)-($C_{2-6}$alkenyl)-$CO_2R^{10}$, —($C_{0-6}$lkyl)-$SO_3H$, —($C_{0-6}$alkyl)-W—$C_{0-4}$alkyl, —($C_{0-6}$alkyl)-$CONR^{10}$-phenyl, —($C_{0-6}$alkyl)-$CONR^{12}$—V—$CO_2R^{10}$, —O—$SO_2$-phenyl-$C_{0-6}$alkyl, —C(O)—N—($C_{0-6}$alkyl)($C_{0-6}$alkyl), -oxazolyl-$C_{0-6}$alkyl, -oxazolyl-$C_{0-6}$alkyl-O—$C_{0-6}$alkyl, phenyl, pyridyl, diazolyl, tetrazolyl, thiadiazolonyl, oxadiazolonyl, thiazolphenyl, or N-oxide pyridyl, and wherein $R^3$ is nothing when X is O, and wherein $C_{0-6}$alkyl is optionally substituted with 1-5 independent halo, hydroxy, —$C_{0-6}$alkyl, —O—$C_{1-3}$alkyl, trifluoromethyl, or —$C_{0-2}$alkyl-phenyl substituents, and wherein the phenyl, pyridyl, diazolyl, tetrazolyl, thiadiazolonyl, oxadiazolonyl, thiazolphenyl, N-oxide pyridyl, heterocycle, cycloalkyl, or $C_{0-4}$alkyl is optionally substituted with 1-5 independent halo, trifluoromethyl, hydroxy, $C_{1-3}$alkyl, —O—$C_{1-3}$alkyl, —$C_{0-3}$—$CO_2R^{10}$, —CN, —($C_{0-6}$alkyl)-C(O)—($C_{0-6}$alkyl), —$NR^{10}R^{10}$, —$CONR^{10}R^{10}$, or —($C_{0-3}$alkyl)-heterocycle substituents, and wherein the phenyl and heterocycle may be fused to another heterocycle, which itself optionally may be substituted with 1-2 independently hydroxy, halo, —$CO_2R^{10}$, or —$C_{1-3}$alkyl substituents, and where alkenyl is optionally substituted with 1-3 independently halo, trifluoromethyl, $C_{1-3}$alkyl, phenyl, or heterocycle substituents;

V is $C_{1-6}$alkyl or phenyl;
$R^{12}$ is hydrogen, $C_{1-4}$alkyl, or $R^{12}$ is joined via a 1-5 carbon tether to one of the carbons of V to form a ring;
$R^4$ is nothing when X is either O, or N or when a double bond joins the carbons to which $R^3$ and $R^6$ are attached, or $R^4$ is hydroxy, $C_{0-6}$alkyl, $C_{1-6}$alkyl-hydroxy, —O—$C_{1-3}$alkyl, —$CO_2R^{10}$, —$CONR^{10}R^{10}$, or —CN;

or $R^3$ and $R^4$ are joined together to form a 1H-indenyl, 2,3-dihydro-1H-indenyl, 2,3-dihydro-benzofuranyl, 1,3-dihydro-isobenzofuranyl, 2,3-dihydro-benzothiofuranyl, 1,3-dihydro-isobenzothiofuranyl, 6H-cyclopenta[d]isoxazol-3-olyl, cyclopentanyl, or cyclohexanyl ring, wherein the ring formed optionally is substituted with 1-5 independently halo, trifluoromethyl, hydroxy, $C_{1-3}$alkyl, —O—$C_{1-3}$alkyl, —$C_{0-3}$—$CO_2R^{10}$, —CN, —$NR^{10}R^{10}$, —$CONR^{10}R^{10}$, or —$C_{0-3}$-heterocyclyl substituents;

or $R^3$ and $R^5$ or $R^4$ and $R^6$ are joined together to form a phenyl or heterocyclyl ring, wherein the ring is optionally substituted with 1-7 independent halo, trifluoromethyl, hydroxy, $C_{1-3}$alkyl, —O—$C_{1-3}$alkyl, —$CO_2R^{10}$, —CN, —$NR^{10}R^{10}$, or —$CONR^{10}R^{10}$ substituents;

$R^5$ and $R^6$ are independently hydrogen, hydroxy, $C_{1-6}$alkyl, $C_{1-6}$alkyl-$CO_2R^{10}$, $C_{1-6}$alkyl-hydroxy, —O—$C_{1-3}$alkyl, or halo; or =O, when $R^5$ or $R^6$ is connected to the ring via a double bond;

when Z=C, $R^7$ is hydrogen, hydroxy, halo, $C_{1-6}$alkyl optionally substituted with 1-6 fluro, —O—$C_{1-6}$alkyl optionally substituted with 1-6 fluro, —$NR^{10}R^{10}$, —$NR^{10}CO_2R^{11}$, —$NR^{10}CONR^{10}R^{10}$, —$NR^{10}$—$SO_2$—$NR^{10}R^{10}$, —$NR^{10}$—$SO_2$—$R^{11}$, heterocycle, —CN, —$CONR^{10}R^{10}$, —$CO_2R^{10}$, —$NO_2$, —S—$R^{10}$, —SO—$R^{11}$, —$SO_2$—$R^{11}$, or —$SO_2$—$NR^{11}R^{11}$;

when Z=N, $R^7$ is nothing or oxide (resulting in a pyridine N-oxide);

$R^8$ is hydrogen, $C_{1-6}$alkyl, trifluoromethyl, trifluoromethoxy, chloro, fluoro, bromo, or phenyl;
$R^9$ is $SO_2R^{11}$, $COR^{10}$, $CONHR^{10}$, $CO_2R^{11}$, or $SO_2NHR^{10}$;

$R^{10}$ is hydrogen, —$C_{1-6}$ alkyl, benzyl, phenyl, or —$C_{0-6}$ alkyl-$C_{3-6}$ cycloalkyl, optionally substituted with 1-3 independent halo, $C_{1-3}$alkyl, $C_{1-3}$alkoxy or trifluoromethyl substituents;

$R^{11}$ is $C_{1-6}$alkyl, —$C_{0-6}$alkyl-$C_{3-6}$cycloalkyl, benzyl or phenyl, optionally substituted with 1-3 independent halo, $C_{1-3}$alkyl, $C_{1-3}$alkoxy or trifluoromethyl substituents;

$n^1$ and $n^2$ are independently 0, 1 or 2, wherein the sum of $n^1$ and $n^2$ is 0, 1, 2, or 3; and the dashed line represents an optional bond.

In an embodiment of this one aspect, the present invention is directed to compounds represented by formula (I), or a pharmaceutically acceptable salt thereof, or an individual diastereomer thereof, wherein:

X is C;

Y is O, S, SO, $SO_2$, or $NR^9$;

Z is C or N;

$R^1$ is hydrogen, —$C_{0-6}$alkyl-W—($C_{1-6}$alkyl)-, —($C_{0-6}$alkyl)-W—($C_{0-6}$alkyl)-($C_{3-7}$cycloalkyl)-($C_{0-6}$alkyl), —($C_{0-6}$alkyl)-W-phenyl, or —($C_{0-6}$alkyl)-W-heterocycle, wherein the alkyl, phenyl, heterocycle and the cycloalkyl are optionally substituted with 1-7 independent halo, hydroxy, —O—$C_{1-3}$alkyl, trifluoromethyl, $C_{1-3}$alkyl, —O—$C_{1-3}$alkyl, —$CO_2R^{10}$, —CN, —$NR^{10}R^{10}$, —$NR^{10}COR^{10}$, —$NR^{10}SO_2R^{11}$, or —$CONR^{10}R^{10}$ substituents;

W is a single bond, —O—, —S—, —SO—, —$SO_2$—, —CO—, —$CO_2$—, —$CONR^{10}$— or —$NR^9$—;

$R^2$ is -halo, —$C_{0-6}$alkyl, $C_{0-6}$alkyl-W—$C_{1-6}$alkyl, $C_{0-6}$alkyl-W—$C_{3-7}$cycloalkyl, $C_{0-6}$alkyl-W-phenyl, or $C_{0-6}$alkyl-W-heterocycle, wherein the $C_{1-6}$alkyl, $C_{3-7}$cycloalkyl, phenyl and heterocycle optionally are independently substituted with 1-6 halo, trifluoromethyl, —CN, —$C_{1-6}$alkyl, or hydroxy substituents;

$R^3$ is OH, —$C_{0-6}$alkyl, —($C_{0-6}$alkyl)-phenyl, —($C_{0-6}$alkyl)-heterocycle, —($C_{0-6}$alkyl)-$C_{3-7}$cycloalkyl, —($C_{0-6}$alkyl)-$CO_2R^{10}$, —($C_{0-6}$alkyl)-($C_{2-6}$alkenyl)-$CO_2R^{10}$, —($C_{0-6}$ alkyl)-$SO_3H$, —($C_{0-6}$alkyl)-W—$C_{0-4}$alkyl, —($C_{0-6}$alkyl)-$CONR^{10}$-phenyl, —($C_{0-6}$alkyl)-$CONR^{12}$—V—$CO_2R^{10}$, —O—$SO_2$-phenyl-$C_{0-6}$alkyl, —C(O)—N—($C_{0-6}$alkyl)($C_{0-6}$ alkyl), -oxazolyl-$C_{0-6}$alkyl, -oxazolyl-$C_{0-6}$alkyl-O—$C_{0-6}$ alkyl, phenyl, pyridyl, diazolyl, tetrazolyl, thiadiazolonyl, oxadiazolonyl, thiazolphenyl, or N-oxide pyridyl, and wherein $R^3$ is nothing when X is O, and wherein $C_{0-6}$alkyl is optionally substituted with 1-5 independent halo, hydroxy, —$C_{0-6}$alkyl, —O—$C_{1-3}$alkyl, trifluoromethyl, or —$C_{0-2}$alkyl-phenyl substituents, and wherein the phenyl, pyridyl, diazolyl, tetrazolyl, thiadiazolonyl, oxadiazolonyl, thiazolphenyl, N-oxide pyridyl, heterocycle, cycloalkyl, or $C_{0-4}$alkyl is optionally substituted with 1-5 independent halo, trifluoromethyl, hydroxy, $C_{1-3}$alkyl, —O—$C_{1-3}$alkyl, —$C_{0-3}$ —$CO_2R^{10}$, —CN, —($C_{0-6}$alkyl)-C(O)—($C_{0-6}$alkyl), —$NR^{10}R^{10}$, —$CONR^{10}R^{10}$, or —($C_{0-3}$alkyl)-heterocycle substituents, and wherein the phenyl and heterocycle may be fused to another heterocycle, which itself optionally may be substituted with 1-2 independently hydroxy, halo, —$CO_2R^{10}$, or —$C_{1-3}$alkyl substituents, and where alkenyl is optionally substituted with 1-3 independently halo, trifluoromethyl, $C_{1-3}$alkyl, phenyl, or heterocycle substituents;

V is $C_{1-6}$alkyl or phenyl;

$R^{12}$ is hydrogen, $C_{1-4}$alkyl, or $R^{12}$ is joined via a 1-5 carbon tether to one of the carbons of V to form a ring;

$R^4$ is nothing when X is either O, or N or when a double bond joins the carbons to which $R^3$ and $R^6$ are attached, or $R^4$ is hydroxy, $C_{0-6}$alkyl, $C_{1-6}$alkyl-hydroxy, —O—$C_{1-3}$alkyl, —$CO_2R^{10}$, —$CONR^{10}R^{10}$, or —CN;

or $R^3$ and $R^4$ are joined together to form a 1H-indenyl, 2,3-dihydro-1H-indenyl, 2,3-dihydro-benzofuranyl, 1,3-di-hydro-isobenzofuranyl, 2,3-dihydro-benzothiofuranyl, 1,3-dihydro-isobenzothiofuranyl, 6H-cyclopenta[d]isoxazol-3-olyl, cyclopentanyl, or cyclohexanyl ring, wherein the ring formed optionally is substituted with 1-5 independently halo, trifluoromethyl, hydroxy, $C_{1-3}$alkyl, —O—$C_{1-3}$alkyl, —$C_{0-3}$ —$CO_2R^{10}$, —CN, —$NR^{10}R^{10}$, —$CONR^{10}R^{10}$, or —$C_{0-3}$ heterocyclyl substituents;

or $R^3$ and $R^5$ or $R^4$ and $R^6$ are joined together to form a phenyl or heterocyclyl ring, wherein the ring is optionally substituted with 1-7 independent halo, trifluoromethyl, hydroxy, $C_{1-3}$alkyl, —O—$C_{1-3}$alkyl, —$CO_2R^{10}$, —CN, —$NR^{10}R^{10}$, or —$CONR^{10}R^{10}$ substituents;

$R^5$ and $R^6$ are independently hydrogen, hydroxy, $C_{1-6}$alkyl, $C_{1-6}$alkyl-$CO_2R^{10}$, $C_{1-6}$alkyl-hydroxy, —O—$C_{1-3}$alkyl, or halo; or =O, when $R^5$ or $R^6$ is connected to the ring via a double bond;

when Z=C, $R^7$ is hydrogen, hydroxy, halo, $C_{1-6}$alkyl optionally substituted with 1-6 fluro, —O—$C_{1-6}$alkyl optionally substituted with 1-6 fluro, —$NR^{10}R^{10}$, —$NR^{10}CO_2R^{11}$, —$NR^{10}CONR^{10}R^{10}$, —$NR^{10}$—$SO_2$—$NR^{10}R^{10}$, —$NR^{10}$—$SO_2$—$R^{11}$, heterocycle, —CN, —$CONR^{10}R^{10}$, —$CO_2R^{10}$, —$NO_2$, —S—$R^{10}$, —SO—$R^{11}$, —$SO_2$—$R^{11}$, or —$SO_2$—$NR^{11}R^{11}$;

when Z=N, $R^7$ is nothing or oxide (resulting in a pyridine N-oxide);

$R^8$ is hydrogen, $C_{1-6}$alkyl, trifluoromethyl, trifluoromethoxy, chloro, fluoro, bromo, or phenyl;

$R^9$ is $SO_2R^{11}$, $COR^{10}$, $CONHR^{10}$, $CO_2R^{11}$, or $SO_2NHR^{10}$;

$R^{10}$ is hydrogen, —$C_{1-6}$ alkyl, benzyl, phenyl, or —$C_{0-6}$ alkyl-$C_{3-6}$ cycloalkyl, optionally substituted with 1-3 independent halo, $C_{1-3}$alkyl, $C_{1-3}$alkoxy or trifluoromethyl substituents;

$R^{11}$ is $C_{1-6}$alkyl, —$C_{0-6}$alkyl-$C_{3-6}$cycloalkyl, benzyl or phenyl, optionally substituted with 1-3 independent halo, $C_{1-3}$alkyl, $C_{1-3}$alkoxy or trifluoromethyl substitutents;

$n^1$ and $n^2$ are independently 0, 1 or 2, wherein the sum of $n^1$ and $n^2$ is 2; and the dashed line represents an optional bond.

In another embodiment of this one aspect, the present invention is directed to compounds represented by formula (I), or a pharmaceutically acceptable salt thereof, or an individual diastereomer thereof, wherein:

X is C;

Y is O, S, SO, $SO_2$, or $NR^9$;

Z is C or N;

$R^1$ is hydrogen, —$C_{0-6}$alkyl-W—($C_{1-6}$alkyl)-, —($C_{0-6}$alkyl)-W—($C_{0-6}$alkyl)-($C_{3-7}$cycloalkyl)-($C_{0-6}$alkyl), —($C_{0-6}$alkyl)-W-phenyl, or —($C_{0-6}$alkyl)-W-heterocycle, wherein the alkyl, phenyl, heterocycle and the cycloalkyl are optionally substituted with 1-7 independent halo, hydroxy, —O—$C_{1-3}$alkyl, trifluoromethyl, $C_{1-3}$alkyl, —O—$C_{1-3}$alkyl, —$CO_2R^{10}$, —CN, —$NR^{10}R^{10}$, —$NR^{10}COR^{10}$, —$NR^{10}SO_2R^{11}$, or —$CONR^{10}R^{10}$ substituents;

W is a single bond, —O—, —S—, —SO—, —$SO_2$—, —CO—, —$CO_2$—, —$CONR^{10}$— or —$NR^9$—;

$R^2$ is -halo, —$C_{0-6}$alkyl, $C_{0-6}$alkyl-W—$C_{1-6}$alkyl, $C_{0-6}$alkyl-W—$C_{3-7}$cycloalkyl, $C_{0-6}$alkyl-W-phenyl, or $C_{0-6}$alkyl-W-heterocycle, wherein the $C_{1-6}$alkyl, $C_{3-7}$cycloalkyl, phenyl and heterocycle optionally are independently substituted with 1-6 halo, trifluoromethyl, —CN, —$C_{1-6}$alkyl, or hydroxy substituents;

$R^3$ is OH, —$C_{0-6}$alkyl, —($C_{0-6}$alkyl)-phenyl, —($C_{0-6}$alkyl)-heterocycle, —($C_{0-6}$alkyl)-$C_{3-7}$cycloalkyl, —($C_{0-6}$alkyl)-$CO_2R^{10}$, —($C_{0-6}$alkyl)-($C_{2-6}$alkenyl)-$CO_2R^{10}$, —($C_{0-6}$ alkyl)-$SO_3H$, —($C_{0-6}$alkyl)-W—$C_{0-4}$alkyl, —($C_{0-6}$alkyl)-$CONR^{10}$-phenyl, —($C_{0-6}$alkyl)-$CONR^{12}$—V—$CO_2R^{10}$, —O—$SO_2$-phenyl-$C_{0-6}$alkyl, —C(O)—N—($C_{0-6}$ alkyl)($C_{0-6}$alkyl), -oxazolyl-$C_{0-6}$alkyl, -oxazolyl-$C_{0-6}$alkyl-O—$C_{0-6}$alkyl, phenyl, pyridyl, diazolyl, tetrazolyl, thiadiazolonyl, oxadiazolonyl, thiazolphenyl, or N-oxide pyridyl, and wherein $R^3$ is nothing when X is O, and wherein $C_{0-6}$alkyl is optionally substituted with 1-5 independent halo, hydroxy, —$C_{0-6}$alkyl, —O—$C_{1-3}$alkyl, trifluoromethyl, or —$C_{0-2}$alkyl-phenyl substituents, and wherein the phenyl, pyridyl, diazolyl, tetrazolyl, thiadiazolonyl, oxadiazolonyl, thiazolphenyl, N-oxide pyridyl, heterocycle, cycloalkyl, or $C_{0-4}$alkyl is optionally substituted with 1-5 independent halo, trifluoromethyl, hydroxy, $C_{1-3}$alkyl, —O—$C_{1-3}$alkyl, —$C_{0-3}$—$CO_2R^{10}$, —CN, —($C_{0-6}$alkyl)-C(O)—($C_{0-6}$alkyl), —$NR^{10}R^{10}$—$CONR^{10}R^{10}$, or —($C_{0-3}$alkyl)-heterocycle substituents, and wherein the phenyl and heterocycle may be fused to another heterocycle, which itself optionally may be substituted with 1-2 independently hydroxy, halo, —$CO_2R^{10}$, or —$C_{1-3}$alkyl substituents, and where alkenyl is optionally substituted with 1-3 independently halo, trifluoromethyl, $C_{1-3}$alkyl, phenyl, or heterocycle substituents;

V is $C_{1-6}$alkyl or phenyl;

$R^{12}$ is hydrogen, $C_{1-4}$alkyl, or $R^{12}$ is joined via a 1-5 carbon tether to one of the carbons of V to form a ring;

$R^4$ is nothing when X is either O, or N or when a double bond joins the carbons to which $R^3$ and $R^6$ are attached, or $R^4$ is hydroxy, $C_{0-6}$alkyl, $C_{1-6}$alkyl-hydroxy, —O—$C_{1-3}$ alkyl, —$CO_2R^{10}$, —$CONR^{10}R^{10}$, or —CN;

or $R^3$ and $R^4$ are joined together to form a 1H-indenyl, 2,3-dihydro-1H-indenyl, 2,3-dihydro-benzofuranyl, 1,3-dihydro-isobenzofuranyl, 2,3-dihydro-benzothiofuranyl, 1,3-dihydro-isobenzothiofuranyl, 6H-cyclopenta[d]isoxazol-3-olyl, cyclopentanyl, or cyclohexanyl ring, wherein the ring formed optionally is substituted with 1-5 independently halo, trifluoromethyl, hydroxy, $C_{1-3}$alkyl, —O—$C_{1-3}$alkyl, —$C_{0-3}$—$CO_2R^{10}$, —CN, —$NR^{10}R^{10}$, —$CONR^{10}R^{10}$, or —$C_{0-3}$-heterocyclyl substituents;

or $R^3$ and $R^5$ or $R^4$ and $R^6$ are joined together to form a phenyl or heterocyclyl ring, wherein the ring is optionally substituted with 1-7 independent halo, trifluoromethyl, hydroxy, $C_{1-3}$alkyl, —O—$C_{1-3}$alkyl, —$CO_2R^{10}$, —CN, —$NR^{10}R^{10}$, or —$CONR^{10}R^{10}$ substituents;

$R^5$ and $R^6$ are independently hydrogen, hydroxy, $C_{1-6}$alkyl, $C_{1-6}$alkyl-$CO_2R^{10}$, $C_{1-6}$alkyl-hydroxy, —O—$C_{1-3}$alkyl, or halo; or =O, when $R^5$ or $R^6$ is connected to the ring via a double bond;

when Z=C, $R^7$ is hydrogen, hydroxy, halo, $C_{1-6}$alkyl optionally substituted with 1-6 fluro, —O—$C_{1-6}$alkyl optionally substituted with 1-6 fluro, —$NR^{10}R^{10}$, —$NR^{10}CO_2R^{11}$, —$NR^{10}CONR^{10}R^{10}$, —$NR^{10}$—$SO_2$—$NR^{10}R^{10}$, —$NR^{10}$—$SO_2$—$R^{11}$, heterocycle, —CN, —$CONR^{10}R^{10}$, —$CO_2R^{10}$, —$NO_2$, —S—$R^{10}$, —SO—$R^{11}$, —$SO_2$—$R^{11}$, or —$SO_2$—$NR^{11}R^{11}$;

when Z=N, $R^7$ is nothing or oxide (resulting in a pyridine N-oxide);

$R^8$ is hydrogen, $C_{1-6}$alkyl, trifluoromethyl, trifluoromethoxy, chloro, fluoro, bromo, or phenyl;

$R^9$ is $SO_2R^{11}$, $COR^{10}$, $CONHR^{10}$, $CO_2R^{11}$, or $SO_2NHR^{10}$;

$R^{10}$ is hydrogen, —$C_{1-6}$ alkyl, benzyl, phenyl, or —$C_{0-6}$alkyl-$C_{3-6}$ cycloalkyl, optionally substituted with 1-3 independent halo, $C_{1-3}$alkyl, $C_{1-3}$alkoxy or trifluoromethyl substituents;

$R^{11}$ is $C_{1-6}$alkyl, —$C_{0-6}$alkyl-$C_{3-6}$cycloalkyl, benzyl or phenyl, optionally substituted with 1-3 independent halo, $C_{1-3}$alkyl, $C_{1-3}$alkoxy or trifluoromethyl substituents;

$n^1$ and $n^2$ are independently 0, 1 or 2, wherein the sum of $n^1$ and $n^2$ is 3; and the dashed line represents an optional bond.

In still another embodiment of this one aspect, the present invention is directed to compounds represented by formula (I), or a pharmaceutically acceptable salt thereof, or an individual diastereomer thereof, wherein:

X is C;

Y is O, S, SO, $SO_2$, or $NR^9$;

Z is C or N;

$R^1$ is hydrogen, —$C_{0-6}$alkyl-W—($C_{1-6}$alkyl)-, —($C_{0-6}$alkyl)-W—($C_{0-6}$alkyl)-($C_{3-7}$cycloalkyl)-($C_{0-6}$alkyl), —($C_{0-6}$alkyl)-W-phenyl, or —($C_{0-6}$alkyl)-W-heterocycle, wherein the alkyl, phenyl, heterocycle and the cycloalkyl are optionally substituted with 1-7 independent halo, hydroxy, —O—$C_{1-3}$alkyl, trifluoromethyl, $C_{1-3}$alkyl, —O—$C_{1-3}$alkyl, —$CO_2R^{10}$, —CN, —$NR^{10}R^{10}$, —$NR^{10}COR^{10}$, —$NR^{10}SO_2R^{11}$, or —$CONR^{10}R^{10}$ substituents;

W is a single bond, —O—, —S—, —SO—, —$SO_2$—, —CO—, —$CO_2$—, —$CONR^{10}$— or —$NR^9$—;

$R^2$ is -halo, —$C_{0-6}$alkyl, $C_{0-6}$alkyl-W—$C_{1-6}$alkyl, $C_{0-6}$alkyl-W—$C_{3-7}$cycloalkyl, $C_{0-6}$alkyl-W-phenyl, or $C_{0-6}$alkyl-W-heterocycle, wherein the $C_{1-6}$alkyl, $C_{3-7}$cycloalkyl, phenyl and heterocycle optionally are independently substituted with 1-6 halo, trifluoromethyl, —CN, —$C_{1-6}$alkyl, or hydroxy substituents;

$R^3$ is OH, —$C_{0-6}$alkyl, —($C_{0-6}$alkyl)-phenyl, —($C_{0-6}$alkyl)-heterocycle, —($C_{0-6}$alkyl)-$C_{3-7}$cycloalkyl, —($C_{0-6}$alkyl)-$CO_2R^{10}$, —($C_{0-6}$alkyl)-($C_{2-6}$alkenyl)-$CO_2R^{10}$, —($C_{0-6}$ alkyl)-$SO_3H$, —($C_{0-6}$alkyl)-W—$C_{0-4}$alkyl, —($C_{0-6}$alkyl)-$CONR^{10}$-phenyl, —($C_{0-6}$alkyl)-$CONR^{12}$—V—$CO_2R^{10}$, —O—$SO_2$-phenyl-$C_{0-6}$alkyl, —C(O)—N—($C_{0-6}$alkyl)($C_{0-6}$alkyl), -oxazolyl-$C_{0-6}$alkyl, -oxazolyl-$C_{0-6}$alkyl-O—$C_{0-6}$alkyl, phenyl, pyridyl, diazolyl, tetrazolyl, thiadiazolonyl, oxadiazolonyl, thiazolphenyl, or N-oxide pyridyl, and wherein $R^3$ is nothing when X is O, and wherein $C_{0-6}$alkyl is optionally substituted with 1-5 independent halo, hydroxy, —$C_{0-6}$alkyl, —O—$C_{1-3}$alkyl, trifluoromethyl, or —$C_{0-2}$alkyl-phenyl substituents, and wherein the phenyl, pyridyl, diazolyl, tetrazolyl, thiadiazolonyl, oxadiazolonyl, thiazolphenyl, N-oxide pyridyl, heterocycle, cycloalkyl, or $C_{0-4}$alkyl is optionally substituted with 1-5 independent halo, trifluoromethyl, hydroxy, $C_{1-3}$alkyl, —O—$C_{1-3}$alkyl, —$C_{0-3}$—$CO_2R^{10}$, —CN, —($C_{0-6}$alkyl)-C(O)—($C_{0-6}$alkyl), —$NR^{10}R^{10}$, —$CONR^{10}R^{10}$, or —($C_{0-3}$alkyl)-heterocycle substituents, and wherein the phenyl and heterocycle may be fused to another heterocycle, which itself optionally may be substituted with 1-2 independently hydroxy, halo, —$CO_2R^{10}$, or —$C_{1-3}$alkyl substituents, and where alkenyl is optionally substituted with 1-3 independently halo, trifluoromethyl, $C_{1-3}$alkyl, phenyl, or heterocycle substituents;

V is $C_{1-6}$alkyl or phenyl;

$R^{12}$ is hydrogen, $C_{1-4}$alkyl, or $R^{12}$ is joined via a 1-5 carbon tether to one of the carbons of V to form a ring;

$R^4$ is nothing when X is either O, or N or when a double bond joins the carbons to which $R^3$ and $R^6$ are attached, or $R^4$ is hydroxy, $C_{0-6}$alkyl, $C_{1-6}$alkyl-hydroxy, —O—$C_{1-3}$ alkyl, —$CO_2R^{10}$, —$CONR^{10}R^{10}$, or —CN;

or $R^3$ and $R^4$ are joined together to form a 1H-indenyl, 2,3-dihydro-1H-indenyl, 2,3-dihydro-benzofuranyl, 1,3-dihydro-isobenzofuranyl, 2,3-dihydro-benzothiofuranyl, 1,3-dihydro-isobenzothiofuranyl, 6H-cyclopenta[d]isoxazol-3-olyl, cyclopentanyl, or cyclohexanyl ring, wherein the ring formed optionally is substituted with 1-5 independently halo, trifluoromethyl, hydroxy, $C_{1-3}$alkyl, —O—$C_{1-3}$alkyl, —$C_{0-3}$—$CO_2R^{10}$, —CN, —$NR^{10}R^{10}$, —$CONR^{10}R^{10}$, or —$C_{0-3}$-heterocyclyl substituents;

or $R^3$ and $R^5$ or $R^4$ and $R^6$ are joined together to form a phenyl or heterocyclyl ring, wherein the ring is optionally substituted with 1-7 independent halo, trifluoromethyl, hydroxy, $C_{1-3}$alkyl, —O—$C_{1-3}$alkyl, —$CO_2R^{10}$, —CN, —$NR^{10}R^{10}$, or —$CONR^{10}R^{10}$ substituents;

$R^5$ and $R^6$ are independently hydrogen, hydroxy, $C_{1-6}$alkyl, $C_{1-6}$alkyl-$CO_2R^{10}$, $C_{1-6}$alkyl-hydroxy, —O—$C_{1-3}$alkyl, or halo; or =O, when $R^5$ or $R^6$ is connected to the ring via a double bond;

when Z=C, $R^7$ is hydrogen, hydroxy, halo, $C_{1-6}$alkyl optionally substituted with 1-6 fluro, —O—$C_{1-6}$alkyl optionally substituted with 1-6 fluro, —$NR^{10}R^{10}$, —$NR^{10}CO_2R^{11}$, —$NR^{10}CONR^{10}R^{10}$, —$NR^{10}$—$SO_2$—$NR^{10}R^{10}$, —$NR^{10}$—$SO_2$—$R^{11}$, heterocycle, —CN, —$CONR^{10}R^{10}$, —$CO_2R^{10}$, —$NO_2$, —S—$R^{10}$, —SO—$R^{11}$, —$SO_2$—$R^{11}$, or —$SO_2$—$NR^{11}R^{11}$;

when Z=N, $R^7$ is nothing or oxide (resulting in a pyridine N-oxide);

$R^8$ is hydrogen, $C_{1-6}$alkyl, trifluoromethyl, trifluoromethoxy, chloro, fluoro, bromo, or phenyl;

$R^9$ is $SO_2R^{11}$, $COR^{10}$, $CONHR^{10}$, $CO_2R^{11}$, or $SO_2NHR^{10}$;

$R^{10}$ is hydrogen, —$C_{1-6}$ alkyl, benzyl, phenyl, or —$C_{0-6}$alkyl-$C_{3-6}$ cycloalkyl, optionally substituted with 1-3 independent halo, $C_{1-3}$alkyl, $C_{1-3}$alkoxy or trifluoromethyl substituents;

$R^{11}$ is $C_{1-6}$alkyl, —$C_{0-6}$alkyl-$C_{3-6}$cycloalkyl, benzyl or phenyl, optionally substituted with 1-3 independent halo, $C_{1-3}$alkyl, $C_{1-3}$alkoxy or trifluoromethyl substitutents;

$n^1$ and $n^2$ are independently 0, 1 or 2, wherein the sum of $n^1$ and $n^2$ is 4; and the dashed line represents an optional bond.

In a second aspect, the present invention is directed to compounds represented by formula (I), or a pharmaceutically acceptable salt thereof, or an individual diastereomer thereof, wherein:

X is O;

Y is O, S, SO, $SO_2$, or $NR^9$;

Z is C or N;

$R^1$ is hydrogen, —$C_{0-6}$alkyl-W—($C_{1-6}$alkyl)-, —($C_{0-6}$alkyl)-W—($C_{0-6}$alkyl)-($C_{3-7}$cycloalkyl)-($C_{0-6}$alkyl), —($C_{0-6}$alkyl)-W-phenyl, or —($C_{0-6}$alkyl)-W-heterocycle, wherein the alkyl, phenyl, heterocycle and the cycloalkyl are optionally substituted with 1-7 independent halo, hydroxy, —O—$C_{1-3}$alkyl, trifluoromethyl, $C_{1-3}$alkyl, —O—$C_{1-3}$alkyl, —$CO_2R^{10}$, —CN, —$NR^{10}R^{10}$, —$NR^{10}COR^{10}$, —$NR^{10}SO_2R^{11}$, or —$CONR^{10}R^{10}$ substituents;

W is a single bond, —O—, —S—, —SO—, —$SO_2$—, —CO—, —$CO_2$—, —$CONR^{10}$— or —$NR^9$—;

$R^2$ is -halo, —$C_{0-6}$alkyl, $C_{0-6}$alkyl-W—$C_{1-6}$alkyl, $C_{0-6}$alkyl-W—$C_{3-7}$cycloalkyl, $C_{0-6}$alkyl-W-phenyl, or $C_{0-6}$alkyl-W-heterocycle, wherein the $C_{1-6}$alkyl, $C_{3-7}$cycloalkyl, phenyl and heterocycle optionally are independently substituted with 1-6 halo, trifluoromethyl, —CN, —$C_{1-6}$alkyl, or hydroxy substituents;

$R^3$ is OH, —$C_{0-6}$alkyl, —($C_{0-6}$alkyl)-phenyl, —($C_{0-6}$alkyl)-heterocycle, —($C_{0-6}$alkyl)-$C_{3-7}$cycloalkyl, —($C_{0-6}$alkyl)-$CO_2R^{10}$, —($C_{0-6}$alkyl)-($C_{2-6}$alkenyl)-$CO_2R^{10}$, —($C_{0-6}$ alkyl)-$SO_3H$, —($C_{0-6}$alkyl)-W—$C_{0-4}$alkyl, —($C_{0-6}$alkyl)-$CONR^{10}$-phenyl, —($C_{0-6}$alkyl)-$CONR^{12}$—V—$CO_2R^{10}$, —O—$SO_2$-phenyl-$C_{0-6}$alkyl, —C(O)—N—($C_{0-6}$alkyl)($C_{0-6}$alkyl), -oxazolyl-$C_{0-6}$alkyl, -oxazolyl-$C_{0-6}$alkyl-O—$C_{0-6}$alkyl, phenyl, pyridyl, diazolyl, tetrazolyl, thiadiazolonyl, oxadiazolonyl, thiazolphenyl, or N-oxide pyridyl, and wherein $R^3$ is nothing when X is O, and wherein $C_{0-6}$alkyl is optionally substituted with 1-5 independent halo, hydroxy, —$C_{0-6}$alkyl, —O—$C_{1-3}$alkyl, trifluoromethyl, or —$C_{0-2}$alkyl-phenyl substituents, and wherein the phenyl, pyridyl, diazolyl, tetrazolyl, thiadiazolonyl, oxadiazolonyl, thiazolphenyl, N-oxide pyridyl, heterocycle, cycloalkyl, or $C_{0-4}$alkyl is optionally substituted with 1-5 independent halo, trifluoromethyl, hydroxy, $C_{1-3}$alkyl, —O—$C_{1-3}$alkyl, —$C_{0-3}$—$CO_2R^{10}$, —CN, —($C_{0-6}$alkyl)-C(O)—($C_{0-6}$alkyl), —$NR^{10}R^{10}$, —$CONR^{10}R^{10}$, or —($C_{0-3}$alkyl)-heterocycle substituents, and wherein the phenyl and heterocycle may be fused to another heterocycle, which itself optionally may be substituted with 1-2 independently hydroxy, halo, —$CO_2R^{10}$, or —$C_{1-3}$alkyl substituents, and where alkenyl is optionally substituted with 1-3 independently halo, trifluoromethyl, $C_{1-3}$alkyl, phenyl, or heterocycle substituents;

V is $C_{1-6}$alkyl or phenyl;

$R^{12}$ is hydrogen, $C_{1-4}$alkyl, or $R^{12}$ is joined via a 1-5 carbon tether to one of the carbons of V to form a ring;

$R^4$ is nothing when X is either O, or N or when a double bond joins the carbons to which $R^3$ and $R^6$ are attached, or $R^4$ is hydroxy, $C_{0-6}$alkyl, $C_{1-6}$alkyl-hydroxy, —O—$C_{1-3}$ alkyl, —$CO_2R^{10}$, —$CONR^{10}R^{10}$, or —CN;

or $R^3$ and $R^4$ are joined together to form a 1H-indenyl, 2,3-dihydro-1H-indenyl, 2,3-dihydro-benzofuranyl, 1,3-dihydro-isobenzofuranyl, 2,3-dihydro-benzothiofuranyl, 1,3-dihydro-isobenzothiofuranyl, 6H-cyclopenta[d]isoxazol-3-olyl, cyclopentanyl, or cyclohexanyl ring, wherein the ring formed optionally is substituted with 1-5 independently halo, trifluoromethyl, hydroxy, $C_{1-3}$alkyl, —O—$C_{1-3}$alkyl, —$C_{0-3}$—$CO_2R^{10}$, —CN, —$NR^{10}R^{10}$, —$CONR^{10}R^{10}$, or —$C_{0-3}$-heterocyclyl substituents;

or $R^3$ and $R^5$ or $R^4$ and $R^6$ are joined together to form a phenyl or heterocyclyl ring, wherein the ring is optionally substituted with 1-7 independent halo, trifluoromethyl, hydroxy, $C_{1-3}$alkyl, —O—$C_{1-3}$alkyl, —$CO_2R^{10}$, —CN, —$NR^{10}R^{10}$, or —$CONR^{10}R^{10}$ substituents;

$R^5$ and $R^6$ are independently hydrogen, hydroxy, $C_{1-6}$alkyl, $C_{1-6}$alkyl-$CO_2R^{10}$, $C_{1-6}$alkyl-hydroxy, —O—$C_{1-3}$alkyl, or halo; or =O, when $R^5$ or $R^6$ is connected to the ring via a double bond;

when Z=C, $R^7$ is hydrogen, hydroxy, halo, $C_{1-6}$alkyl optionally substituted with 1-6 fluro, —O—$C_{1-6}$alkyl optionally substituted with 1-6 fluro, —$NR^{10}R^{10}$, —$NR^{10}CO_2R^{11}$, —$NR^{10}CONR^{10}R^{10}$, —$NR^{10}$—$SO_2$—$NR^{10}R^{10}$, —$NR^{10}$—$SO_2$—$R^{11}$, heterocycle, —CN, —$CONR^{10}R^{10}$, —$CO_2R^{10}$, —$NO_2$, —S—$R^{10}$, —SO—$R^{11}$, —$SO_2$—$R^{11}$, or —$SO_2$—$NR^{11}R^{11}$;

when Z=N, $R^7$ is nothing or oxide (resulting in a pyridine N-oxide);

$R^8$ is hydrogen, $C_{1-6}$alkyl, trifluoromethyl, trifluoromethoxy, chloro, fluoro, bromo, or phenyl;

$R^9$ is $SO_2R^{11}$, $COR^{10}$, $CONHR^{10}$, $CO_2R^{11}$, or $SO_2NHR^{10}$;

$R^{10}$ is hydrogen, —$C_{1-6}$ alkyl, benzyl, phenyl, or —$C_{0-6}$alkyl-$C_{3-6}$ cycloalkyl, optionally substituted with 1-3 independent halo, $C_{1-3}$alkyl, $C_{1-3}$alkoxy or trifluoromethyl substituents;

$R^{11}$ is $C_{1-6}$alkyl, —$C_{0-6}$alkyl-$C_{3-6}$cycloalkyl, benzyl or phenyl, optionally substituted with 1-3 independent halo, $C_{1-3}$alkyl, $C_{1-3}$alkoxy or trifluoromethyl substitutents;

$n^1$ and $n^2$ are independently 0, 1 or 2, wherein the sum of $n^1$ and $n^2$ is 0, 1, 2, or 3; and the dashed line represents an optional bond.

In a third aspect, the present invention is directed to compounds represented by formula (I), or a pharmaceutically acceptable salt thereof, or an individual diastereomer thereof, wherein:

X is N;

Y is O, S, SO, $SO_2$, or $NR^9$;

Z is C or N;

$R^1$ is hydrogen, —$C_{0-6}$alkyl-W—($C_{1-6}$alkyl)-, —($C_{0-6}$alkyl)-W—($C_{0-6}$alkyl)-($C_{3-7}$cycloalkyl)-($C_{0-6}$alkyl), —($C_{0-6}$alkyl)-W-phenyl, or —($C_{0-6}$alkyl)-W-heterocycle, wherein the alkyl, phenyl, heterocycle and the cycloalkyl are optionally substituted with 1-7 independent halo, hydroxy, —O—$C_{1-3}$alkyl, trifluoromethyl, $C_{1-3}$alkyl, —O—$C_{1-3}$alkyl, —$CO_2R^{10}$, —CN, —$NR^{10}R^{10}$, —$NR^{10}COR^{10}$, —$NR^{10}SO_2R^{11}$, or —$CONR^{10}R^{10}$ substituents;

W is a single bond, —O—, —S—, —SO—, —$SO_2$—, —CO—, —$CO_2$—, —$CONR^{10}$— or —$NR^9$—;

$R^2$ is -halo, —$C_{0-6}$alkyl, $C_{0-6}$alkyl-W—$C_{1-6}$alkyl, $C_{0-6}$alkyl-W—$C_{3-7}$cycloalkyl, $C_{0-6}$alkyl-W-phenyl, or $C_{0-6}$alkyl-W-heterocycle, wherein the $C_{1-6}$alkyl, $C_{3-7}$cycloalkyl, phenyl and heterocycle optionally are independently substituted with 1-6 halo, trifluoromethyl, —CN, —$C_{1-6}$alkyl, or hydroxy substituents;

$R^3$ is OH, —$C_{0-6}$alkyl, —($C_{0-6}$alkyl)-phenyl, —($C_{0-6}$alkyl)-heterocycle, —($C_{0-6}$alkyl)-$C_{3-7}$cycloalkyl, —($C_{0-6}$alkyl)-$CO_2R^{10}$, —($C_{0-6}$alkyl)-($C_{2-6}$alkenyl)-$CO_2R^{10}$, —($C_{0-6}$ alkyl)-$SO_3H$, —($C_{0-6}$alkyl)-W—$C_{0-4}$alkyl, —($C_{0-6}$ alkyl)-$CONR^{10}$-phenyl, —($C_{0-6}$alkyl)-$CONR^{12}$—V—$CO_2R^{10}$, —O—$SO_2$-phenyl-$C_{0-6}$alkyl, —C(O)—N—($C_{0-6}$alkyl)($C_{0-6}$alkyl), -oxazolyl-$C_{0-6}$alkyl, -oxazolyl-$C_{0-6}$alkyl-O—$C_{0-6}$alkyl, phenyl, pyridyl, diazolyl, tetrazolyl, thiadiazolonyl, oxadiazolonyl, thiazolphenyl, or N-oxide pyridyl, and wherein $R^3$ is nothing when X is O, and wherein $C_{0-6}$alkyl is optionally substituted with 1-5 independent halo, hydroxy, —$C_{0-6}$alkyl, —O—$C_{1-3}$alkyl, trifluoromethyl, or -$C_{0-2}$alkyl-phenyl substituents, and wherein the phenyl, pyridyl, diazolyl, tetrazolyl, thiadiazolonyl, oxadiazolonyl, thiazolphenyl, N-oxide pyridyl, heterocycle, cycloalkyl, or $C_{0-4}$alkyl is optionally substituted with 1-5 independent halo, trifluoromethyl, hydroxy, $C_{1-3}$alkyl, —O—$C_{1-3}$alkyl, —$C_{0-3}$—$CO_2R^{10}$, —CN, —($C_{0-6}$alkyl)-C(O)—($C_{0-6}$alkyl), —$NR^{10}R^{10}$, —$CONR^{10}R^{10}$, or —($C_{0-3}$alkyl)-heterocycle substituents, and wherein the phenyl and heterocycle may be fused to another heterocycle, which itself optionally may be substituted with 1-2 independently hydroxy, halo, —$CO_2R^{10}$, or —$C_{1-3}$alkyl substituents, and where alkenyl is optionally substituted with 1-3 independently halo, trifluoromethyl, $C_{1-3}$alkyl, phenyl, or heterocycle substituents;

V is $C_{1-6}$alkyl or phenyl;

$R^{12}$ is hydrogen, $C_{1-4}$alkyl, or $R^{12}$ is joined via a 1-5 carbon tether to one of the carbons of V to form a ring;

$R^4$ is nothing when X is either O, or N or when a double bond joins the carbons to which $R^3$ and $R^6$ are attached, or $R^4$ is hydroxy, $C_{0-6}$alkyl, $C_{1-6}$alkyl-hydroxy, —O—$C_{1-3}$alkyl, —$CO_2R^{10}$, —$CONR^{10}R^{10}$, or —CN;

or $R^3$ and $R^4$ are joined together to form a 1H-indenyl, 2,3-dihydro-1H-indenyl, 2,3-dihydro-benzofuranyl, 1,3-dihydro-isobenzofuranyl, 2,3-dihydro-benzothiofuranyl, 1,3-dihydro-isobenzothiofuranyl, 6H-cyclopenta[d]isoxazol-3-olyl, cyclopentanyl, or cyclohexanyl ring, wherein the ring formed optionally is substituted with 1-5 independently halo, trifluoromethyl, hydroxy, $C_{1-3}$alkyl, —O—$C_{1-3}$alkyl, —$C_{0-3}$—$CO_2R^{10}$, —CN, —$NR^{10}R^{10}$, —$CONR^{10}R^{10}$, or —$C_{0-3}$-heterocyclyl substituents;

or $R^3$ and $R^5$ or $R^4$ and $R^6$ are joined together to form a phenyl or heterocyclyl ring, wherein the ring is optionally substituted with 1-7 independent halo, trifluoromethyl, hydroxy, $C_{1-3}$alkyl, —O—$C_{1-3}$alkyl, —$CO_2R^{10}$, —CN, —$NR^{10}R^{10}$, or —$CONR^{10}R^{10}$ substituents;

$R^5$ and $R^6$ are independently hydrogen, hydroxy, $C_{1-6}$alkyl, $C_{1-6}$alkyl-$CO_2R^{10}$, $C_{1-6}$alkyl-hydroxy, —O—$C_{1-3}$alkyl, or halo; or =O, when $R^5$ or $R^6$ is connected to the ring via a double bond;

when Z=C, $R^7$ is hydrogen, hydroxy, halo, $C_{1-6}$alkyl optionally substituted with 1-6 fluro, —O—$C_{1-6}$alkyl optionally substituted with 1-6 fluro, —$NR^{10}R^{10}$, —$NR^{10}CO_2R^{11}$, —$NR^{10}CONR^{10}R^{10}$, —$NR^{10}$—$SO_2$—$NR^{10}R^{10}$, —$NR^{10}$—$SO_2$—$R^{11}$, heterocycle, —CN, —$CONR^{10}R^{10}$, —$CO_2R^{10}$, —$NO_2$, —S—$R^{10}$, —SO—$R^{11}$, —$SO_2$—$R^{11}$, or —$SO_2$—$NR^{11}R^{11}$;

when Z=N, $R^7$ is nothing or oxide (resulting in a pyridine N-oxide);

$R^8$ is hydrogen, $C_{1-6}$alkyl, trifluoromethyl, trifluoromethoxy, chloro, fluoro, bromo, or phenyl;

$R^9$ is $SO_2R^{11}$, $COR^{10}$, $CONHR^{10}$, $CO_2R^{11}$, or $SO_2NHR^{10}$;

$R^{10}$ is hydrogen, —$C_{1-6}$ alkyl, benzyl, phenyl, or —$C_{0-6}$alkyl-$C_{3-6}$ cycloalkyl, optionally substituted with 1-3 independent halo, $C_{1-3}$alkyl, $C_{1-3}$alkoxy or trifluoromethyl substituents;

$R^{11}$ is $C_{1-6}$alkyl, —$C_{0-6}$alkyl-$C_{3-6}$cycloalkyl, benzyl or phenyl, optionally substituted with 1-3 independent halo, $C_{1-3}$alkyl, $C_{1-3}$alkoxy or trifluoromethyl substitutents;

$n^1$ and $n^2$ are independently 0, 1 or 2, wherein the sum of $n^1$ and $n^2$ is 0, 1, 2, or 3; and the dashed line represents an optional bond.

In a fourth aspect, the present invention is directed to compounds represented by formula (I), or a pharmaceutically acceptable salt thereof, or an individual diastereomer thereof, wherein:

X is O;

Y is O, S, SO, $SO_2$, or $NR^9$;

Z is C or N;

$R^1$ is hydrogen, —$C_{0-6}$alkyl-W—($C_{1-6}$alkyl)-, —($C_{0-6}$alkyl)-W—($C_{0-6}$alkyl)-($C_{3-7}$cycloalkyl)-($C_{0-6}$alkyl), —($C_{0-6}$alkyl)-W-phenyl, or —($C_{0-6}$alkyl)-W-heterocycle, wherein the alkyl, phenyl, heterocycle and the cycloalkyl are optionally substituted with 1-7 independent halo, hydroxy, —O—$C_{1-3}$alkyl, trifluoromethyl, $C_{1-3}$alkyl, —O—$C_{1-3}$alkyl, —$CO_2R^{10}$, —CN, —$NR^{10}R^{10}$, —$NR^{10}COR^{10}$, —$NR^{10}SO_2R^{11}$, or —$CONR^{10}R^{10}$ substituents;

W is a single bond, —O—, —S—, —SO—, —$SO_2$—, —CO—, —$CO_2$—, —$CONR^{10}$— or —$NR^9$—;

$R^2$ is -halo, —$C_{0-6}$alkyl, $C_{0-6}$alkyl-W—$C_{1-6}$alkyl, $C_{0-6}$alkyl-W—$C_{3-7}$cycloalkyl, $C_{0-6}$alkyl-W-phenyl, or $C_{0-6}$alkyl-W-heterocycle, wherein the $C_{1-6}$alkyl, $C_{3-7}$cycloalkyl, phenyl and heterocycle optionally are independently substituted with 1-6 halo, trifluoromethyl, —CN, —$C_{1-6}$alkyl, or hydroxy substituents;

V is $C_{1-6}$alkyl or phenyl;

$R^{12}$ is hydrogen, $C_{1-4}$alkyl, or $R^{12}$ is joined via a 1-5 carbon tether to one of the carbons of V to form a ring;

$R^3$ and $R^4$ are joined together to form a 1H-indenyl, 2,3-dihydro-1H-indenyl, 2,3-dihydro-benzofuranyl, 1,3-dihydro-isobenzofuranyl, 2,3-dihydro-benzothiofuranyl, 1,3-dihydro-isobenzothiofuranyl, 6H-cyclopenta[d]isoxazol-3-olyl, cyclopentanyl, or cyclohexanyl ring, wherein the ring formed optionally is substituted with 1-5 independently halo, trifluoromethyl, hydroxy, $C_{1-3}$alkyl, —O—$C_{1-3}$alkyl, —$C_{0-3}$—$CO_2R^{10}$, —CN, —$NR^{10}R^{10}$, —$CONR^{10}R^{10}$, or —$C_{0-3}$-heterocyclyl substituents;

or $R^3$ and $R^5$ or $R^4$ and $R^6$ are joined together to form a phenyl or heterocyclyl ring, wherein the ring is optionally substituted with 1-7 independent halo, trifluoromethyl, hydroxy, $C_{1-3}$alkyl, —O—$C_{1-3}$alkyl, —$CO_2R^{10}$, —CN, —$NR^{10}R^{10}$, or —$CONR^{10}R^{10}$ substituents;

$R^5$ and $R^6$ are independently hydrogen, hydroxy, $C_{1-6}$alkyl, $C_{1-6}$alkyl-$CO_2R^{10}$, $C_{1-6}$alkyl-hydroxy, —O—$C_{1-3}$alkyl, or halo; or =O, when $R^5$ or $R^6$ is connected to the ring via a double bond;

when Z=C, $R^7$ is hydrogen, hydroxy, halo, $C_{1-6}$alkyl optionally substituted with 1-6 fluro, —O—$C_{1-6}$alkyl optionally substituted with 1-6 fluro, —$NR^{10}R^{10}$, —$NR^{10}CO_2R^{11}$, —$NR^{10}CONR^{10}R^{10}$, —$NR^{10}$—$SO_2$—$NR^{10}R^{10}$, —$NR^{10}$—

$SO_2—R^{11}$, heterocycle, —CN, —$CONR^{10}R^{10}$, —$CO_2R^{10}$, —$NO_2$, —$S—R^{10}$, —$SO—R^{11}$, —$SO_2—R^{11}$, or —$SO_2—NR^{11}R^{11}$;

when Z=N, $R^7$ is nothing or oxide (resulting in a pyridine N-oxide);

$R^8$ is hydrogen, $C_{1-6}$alkyl, trifluoromethyl, trifluoromethoxy, chloro, fluoro, bromo, or phenyl;

$R^9$ is $SO_2R^{11}$, $COR^{10}$, $CONHR^{10}$, $CO_2R^{11}$, or $SO_2NHR^{10}$;

$R^{10}$ is hydrogen, —$C_{1-6}$ alkyl, benzyl, phenyl, or —$C_{0-6}$alkyl-$C_{3-6}$ cycloalkyl, optionally substituted with 1-3 independent halo, $C_{1-3}$alkyl, $C_{1-3}$alkoxy or trifluoromethyl substituents;

$R^{11}$ is $C_{1-6}$alkyl, —$C_{0-6}$alkyl-$C_{3-6}$cycloalkyl, benzyl or phenyl, optionally substituted with 1-3 independent halo, $C_{1-3}$alkyl, $C_{1-3}$alkoxy or trifluoromethyl substitutents;

$n^1$ and $n^2$ are independently 0, 1 or 2, wherein the sum of $n^1$ and $n^2$ is 0, 1, 2, or 3; and the dashed line represents an optional bond.

Representative compounds of the present invention include those presented in the EXAMPLES and pharmaceutically acceptable salts and individual diastereomers thereof.

The compounds of the instant invention have at least two asymmetric centers at the 1- and 3-positions of the cyclopentyl ring and one asymmetric center at the 4-position of the ring bearing X. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The absolute configurations of certain compounds of this orientation, where the substituents on the cyclopentyl ring (amide and amine units) are cis, as depicted:

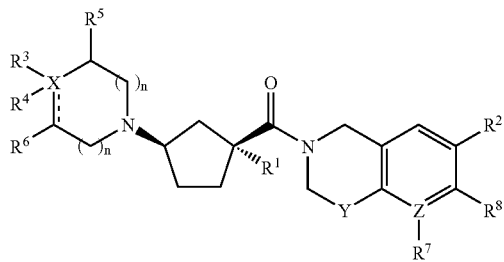

The absolute configurations of certain compounds of this invention are those of the orientation as depicted:

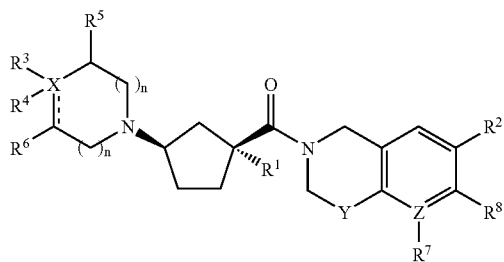

wherein the carbon bearing the amine substituent is designated as being of the (R) absolute configuration and the carbon bearing the amide subunit can be designated as being of either the (S) or (R) absolute configuration depending on the priority for $R^1$. For example if R is isopropyl then the absolute stereochemistry at the carbon bearing the amide subunit would be (S) since the amide and amine units are preferred to have the cis arrangement on the cyclopentyl ring.

The optional double bonds are depicted as a dashed line which means that the double bond may or may not be present. As appreciated by those of skill in the art, considering formula I, when X is carbon $R^4$ can reside on X only when there is no double bond between X and the carbon on which $R^6$ is present.

The independent syntheses of diastereomers and enantiomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl, cyclopropyl, cyclobutyl, cyclopentyl and cyclohexyl.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "substituted" or "substituent" in reference to substitution on alkyl, cycloalkyl, phenyl, heterocycle, or some other chemical group is intended to include mono- and poly-substitution by a named substituent to the extent such single and multiple substitution is chemically allowed in any of the named chemical groups. It is understood that the definition of a substituent at a particular location in a molecule is independent of its definition at other locations in the molecule. Thus, for example, when $R^4$ is defined as —$CONR^{10}R^{10}$ each $R^{10}$ is independently selected from the possible values thereof; i.e., each $R^{10}$ can be the same as or different from any other $R^{10}$.

The term "optionally substituted" is intended to include both substituted and unsubstituted. Thus, for example, optionally substituted alkyl, where halo was an optional substituent, could represent a propyl or fluoro-propyl.

As appreciated by those of skill in the art, halo or halogen as used herein are intended to include chloro, fluoro, bromo and iodo. Similarly, $C_{0-8}$, as in $C_{0-8}$alkyl is defined to identify the group as having 0, 1, 2, 3, 4, 5, 6, 7 or 8 carbons in a linear or branched arrangement such that $C_{0-8}$alkyl specifically includes methyl, ethyl, n-propyl, iso-propyl, n-butyl, iso-butyl, tert-butyl, pentyl, hexyl, heptyl and octyl. Similarly, $C_{0-6}$ refers to a group as having 0, 1, 2, 3, 4, 5 or 6 carbons in a linear or branched arrangement, and so on with respect to other numerical designations. $C_0$, as in $C_0$alkyl is a direct covalent bond when in a bridging position and is a hydrogen when in a terminal position. The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be prepared from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media such as ether, ethyl acetate, ethanol, isopropanol, or acetonitrile are used. Suitable salts are found, e.g. in Remington's Pharmaceutical Sciences, 17th ed., Mack Publishing Company, Easton, Pa., 1985, p. 1418.

Exemplifying the invention is the use of the compounds disclosed in the Examples and herein.

Specific compounds within the present invention include a compound which selected from the group consisting of: the title compounds of the Examples; and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, in particular CCR-2.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851-856 (1993) which may be readily adapted for measurement of CCR-2 binding.

Receptor affinity in a CCR-2 binding assay was determined by measuring inhibition of $^{125}$I-MCP-1 to the endogenous CCR-2 receptor on various cell types including monocytes, THP-1 cells, or after heterologous expression of the cloned receptor in eukaryotic cells. The cells were suspended in binding buffer (50 mM HEPES, pH 7.2, 5 mM $MgCl_2$, 1 mM $CaCl_2$, and 0.50% BSA) with and added to test compound or DMSO and $^{125}$I-MCP-1 at room temperature for 1 h to allow binding. The cells were then collected on GFB filters, washed with 25 mM HEPES buffer containing 500 mM NaCl and cell bound $^{125}$I-MCP-1 was quantified.

In a chemotaxis assay chemotaxis was performed using T cell depleted PBMC isolated from venous whole or leukophoresed blood and purified by Ficoll-Hypaque centrifugation followed by rosetting with neuraminidase-treated sheep erythrocytes. Once isolated, the cells were washed with HBSS containing 0.1 mg/ml BSA and suspended at $1 \times 10^7$ cells/ml. Cells were fluorescently labeled in the dark with 2 µM Calcien-AM (Molecular Probes), for 30 min at 37° C. Labeled cells were washed twice and suspended at $5 \times 10^6$ cells/ml in RPMI 1640 with L-glutamine (without phenol red) containing 0.1 mg/ml BSA. MCP-1 (Peprotech) at 10 ng/ml diluted in same medium or medium alone were added to the bottom wells (27 µl). Monocytes (150,000 cells) were added to the topside of the filter (30 µl) following a 15 min preincubation with DMSO or with various concentrations of test compound. An equal concentration of test compound or DMSO was added to the bottom well to prevent dilution by diffusion. Following a 60 min incubation at 37° C., 5% $CO_2$, the filter was removed and the topside was washed with HBSS containing 0.1 mg/ml BSA to remove cells that had not migrated into the filter. Spontaneous migration (chemokinesis) was determined in the absence of chemoattractant.

In particular, the compounds of the following examples had activity in binding to the CCR-2 receptor in the aforementioned assays, generally with an $IC_{50}$ of less than about 3 µM, preferably less than about 1 µM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, compounds which inhibit or promote chemokine receptor function would be useful in treating, preventing, ameliorating, controlling or reducing the risk of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the compounds of the present invention. In one embodiment, the disease or condition is one in which the actions of lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with modulators of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms), (*Trichuriasis, Enterobiasis, Ascariasis*, Hookworm, *Strongyloidiasis, Trichinosis, filariasis*), trematodes (flukes) (*Schistosomiasis, Clonorchiasis*), cestodes (tape worms) (*Echinococcosis, Taeniasis saginata, Cysticercosis*), visceral worms, visceral larva migraines (e.g., *Toxocara*), eosinophilic gastroenteritis (e.g., *Anisaki* sp., *Phocanema* sp.), and cutaneous larva migraines (*Ancylostona braziliense, Ancylostoma caninum*). In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

The compounds of the present invention are accordingly useful in treating, preventing, ameliorating, controlling or reducing the risk of a wide variety of inflammatory and immunoregulatory disorders and diseases, allergic conditions, atopic conditions, as well as autoimmune pathologies. In a specific embodiment, the present invention is directed to the use of the subject compounds for treating, preventing, ameliorating, controlling or reducing the risk of autoimmune diseases, such as rheumatoid arthritis or psoriatic arthritis.

In another aspect, the instant invention may be used to evaluate putative specific agonists or antagonists of chemokine receptors, including CCR-2. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-2. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of the present compounds in treating, preventing, ameliorating, controlling or reducing the risk of infection by a retrovirus, in particular, herpes virus or the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In an aspect of the present invention, a subject compound may be used in a method of inhibiting the binding of a chemokine to a chemokine receptor, such as CCR-2, of a target cell, which comprises contacting the target cell with an amount of the compound which is effective at inhibiting the binding of the chemokine to the chemokine receptor.

The subject treated in the methods above is a mammal, such as a human being, male or female, in whom modulation of chemokine receptor activity is desired. "Modulation" as used herein is intended to encompass antagonism, agonism, partial antagonism, inverse agonism and/or partial agonism. Modulation may refer to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

As used herein, the term "treatment" refers both to the treatment and to the prevention or prophylactic therapy of the aforementioned conditions. One in the art understands the prophylactic administration of subtherapeutic drug levels.

Combined therapy to modulate chemokine receptor activity for thereby treating, preventing, ameliorating, controlling or reducing the risk of inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in treating, preventing, ameliorating, controlling or reducing the risk of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codeine, embrel, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is created. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO 98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, desloratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CCR-1, CCR-2, CCR-3, CXCR-3 and CCR-5; (j) cholesterol lowering agents such as HMG-CoA reductase inhibitors (lovastatin, simvastatin and pravastatin, fluvastatin, atorvastatin, rosuvastatin, and other statins), sequestrants (cholestyramine and colestipol), cholesterol absorption inhibitors (ezetimibe), nicotinic acid, fenofibric acid derivatives (gemfibrozil, clofibrat, fenofibrate and benzafibrate), and probucol; (k) antidiabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents.

The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, in some instances about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In treating, preventing, ameliorating, controlling or reducing the risk of conditions which require chemokine receptor modulation an appropriate dosage level will generally be about 0.01 to 500 mg per kg patient body weight per day which can be administered in single or multiple doses. The dosage level will be about 0.1 to about 250 mg/kg per day; or in some instances about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, in certain instances 2.0 to 500, in other instances 3.0 to 200, and in yet other instances 1, 5, 10, 15, 20, 25, 30, 50, 75, 100, 125, 150, 175, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The abbreviations used herein have the following tabulated meanings. Abbreviations not tabulated below have their meanings as commonly used unless specifically stated otherwise.

| | |
|---|---|
| Ac = | acetyl |
| Bn = | benzyl |
| CAMP | cyclic adenosine-3',5'-monophosphate |
| DBU = | 1,8-diazabicyclo[5.4.0]undec-7-ene |
| dppf | 1,1'-bis(diphenylphosphino)ferrocene |
| DIBAL = | diisobutylaluminum hydride |
| DMAP = | 4-(dimethylamino)pyridine |
| DMF = | N,N-dimethylformamide |
| Et$_3$N = | triethylamine |
| GST | glutathione transferase |
| HATU | O-(7-Azabenzotriazol-1-yl)-N,N,N',N'-tetramethyl-uronium hexafluorophosphate |
| HMDS | hexamethyldisilazide |
| LDA = | lithium diisopropylamide |
| m-CPBA = | metachloroperbenzoic acid |
| MMPP = | monoperoxyphthalic acid |
| MPPM = | monoperoxyphthalic acid, magnesium salt 6H$_2$O |
| Ms = | methanesulfonyl = mesyl = SO$_2$Me |
| MsO = | methanesulfonate = mesylate |
| NSAID = | non-steroidal anti-inflammatory drug |
| o-Tol = | ortho-tolyl |
| OXONE ® = | 2KHSO$_5$•KHSO$_4$•K$_2$SO$_4$ |
| PCC = | pyridinium chlorochromate |
| PDC = | pyridinium dichromate |
| PDE | phosphodiesterase |
| Ph = | phenyl |
| Phe = | benzenediyl |
| PMB = | para-methoxybenzyl |
| Pye = | pyridinediyl |
| r.t. = | room temperature |
| Rac. = | racemic |
| SAM = | aminosulfonyl or sulfonamide or SO$_2$NH$_2$ |
| SEM = | 2-(trimethylsilyl)ethoxymethoxy |
| SPA = | scintillation proximity assay |
| TBAF = | tetra-n-butylammonium fluoride |
| Th = | 2- or 3-thienyl |
| TFA = | trifluoroacetic acid |
| TFAA = | trifluoroacetic acid anhydride |
| THF = | tetrahydrofuran |
| Thi = | thiophenediyl |
| TLC = | thin layer chromatography |
| TMS-CN = | trimethylsilyl cyanide |
| TMSI | trimethylsilyl iodide |
| Tz = | 1H (or 2H)-tetrazol-5-yl |
| CAN | ceric ammonium nitrate |
| C3H5 = | allyl |

Alkyl Group Abbreviations

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | Cyclobutyl |
| c-Pen = | cyclopentyl |
| c-Hex = | cyclohexyl |

The Examples that follow are intended as an illustration of certain embodiments of the invention and no limitation of the invention is implied.

Unless specifically stated otherwise, the experimental procedures were performed under the following conditions. All operations were carried out at room or ambient temperature—that is, at a temperature in the range of 18-25° C. Evaporation of solvent was carried out using a rotary evaporator under reduced pressure (600-4000pascals: 4.5-30 mm Hg) with a bath temperature of up to 60° C. The course of reactions was followed by thin layer chromatography (TLC) and reaction times are given for illustration only. Melting points are uncorrected and "d" indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations have also been used: v (volume), w (weight), b.p. (boiling point), m.p. (melting point), L (liter(s)),mL (milliliters), g (gram(s)), mg (milligrams(s)), mol (moles),mmol (millimoles), eq (equivalent(s)).

Several methods for preparing the compounds of this invention are illustrated in the following Schemes and Examples. Starting materials are commercially available, made by known procedures, or prepared as illustrated herein.

One of the principal routes used for preparation of compounds within the scope of the instant invention which bear a 1,1,3-trisubstituted cyclopentane framework 1-9 is depicted in Scheme 1 (a synthesis of 1-3a is described in Scheme 2). According to this route, keto acids 1-1 (preparation described in Scheme 3A, Scheme 3B, Scheme 3C, and Scheme 3D) is coupled to amines 1-2 (preparation described in Scheme 4). This can be accomplished in various ways, including by first converting the acid to its acid chloride with a reagent such as oxalyl chloride, and then combining with amine 1-2 in the presence of a base such as triethylamine. The resulting ketoamide 1-3 is then reduced with, for example, sodium borohydride to give the corresponding alcohol which is then protected (Greene, T; Wuts, P. G. M. *Protective Groups in Organic Synthesis*, John Wiley & Sons, Inc., New York, N.Y. 1991) as its acetate ester, 1-4, under standard conditions. The protecting group on Y is then removed using conditions appropriate for the Y. For example when PY is t-butoxide, the t-butyl ether group in 1-4 is cleaved under acidic conditions such as with anhydrous 4N HCl in dioxane to provide 1-5, which in this case is a phenol (YH=OH). Upon heating 1-5 with an excess of a formaldehyde equivalent such as paraformaldehyde in a solvent such as toluene and in the presence of a catalyst such as TsOH, cyclization to form the ring system in 1-6 can be achieved (when Y is oxygen the ring system is a benzoxazine). Hydrolysis of the acetate ester in 1-6 can be achieved with LiOH or some other base. The resulting alcohol is then oxidized to a ketone, 1-7. This can be accomplished using a variety of conditions, including by the Swern oxidation conditions (Mancuso, A. J., Swern, D. *Synthesis*, (1981), 165.). Reductive amination of 1-7 with an amine 1-8 using, for example, NaB(OAc)$_3$H or NaBH$_3$CN as the reducing agent gives chemokine receptor modulators 1-9. The compounds 1-9, which can be synthesized according to the chemistry described in Scheme 1 represent stereoisomeric mixtures (Eliel, E. E., Wilen, S. H., *Stereochemistry of Organic Compounds*, John Wiley & Sons, Inc., New York). In particular, compounds 1-9 are often obtained as a mixture of cis and trans isomers. When 1-1 is a single stereoisomer (1-1a) only 2 possible isomers of 1-9 can result (cis and trans); these can be separated by a variety of methods, including by preparative TLC, flash chromatography, MPLC, or by HPLC using a column with a chiral stationary phase. When 1-1 is racemic, a total of 4 possible isomers of 1-9 can be obtained. Again, these may be separated by HPLC using a column with a chiral stationary phase, or by a combination of the methods above. The synthesis of racemic 1-1 is detailed in Scheme 3A, while syntheses of the chiral 1-1a are described in Scheme 3B and Scheme 3C.

Furthermore, compounds 1-9 can themselves be modified to give new chemokine receptor modulators 1-9.1. For example, an ester functional group within compound 1-9 can be hydrolyzed to the corresponding carboxylic acid, which also can be a chemokine receptor modulator.

SCHEME 1

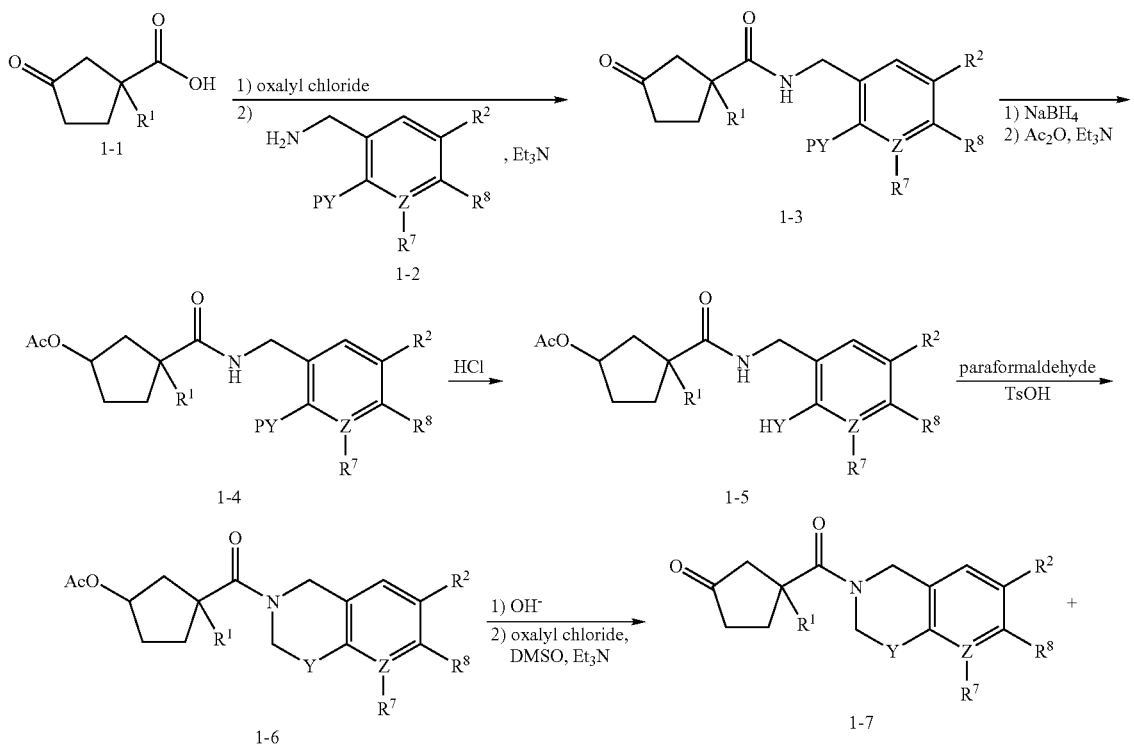

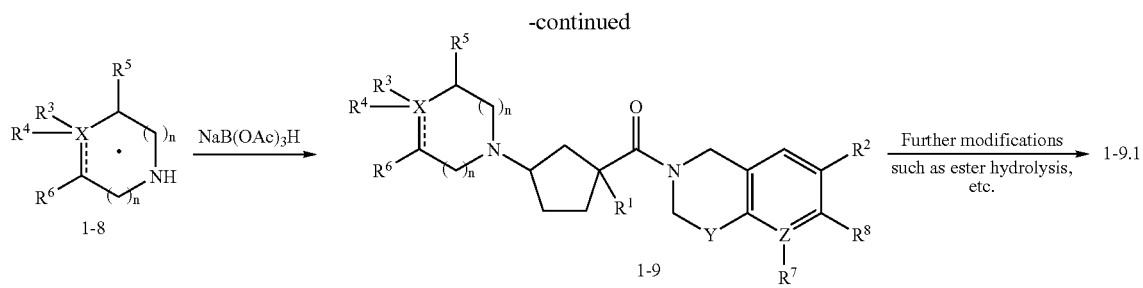

Compound 1-3 can be prepared as a single stereoisomer (1-3a) as described in Scheme 2. This synthesis involves the use of commercially available optically pure amino acid (1R, 4S)-4-aminocyclopent-2-ene-1-carboxylic acid (2-1). After the carboxylic acid was protected as a methyl ester (2-2) and the amine as a pyrrole (2-3), alkylation of 2-3 with an alkylating agent such as an alkyl chloride, bromide or iodide in the presence of an appropriate base such as lithium diisopropylamide, produces compounds 2-4. Hydrolysis of the ester can be accomplished by treatment with a base such as sodium hydroxide, lithium hydroxide, or potassium hydroxide, with or without heating. The carboxylic acid can then be coupled with amine 1-2 in the presence of a coupling reagent such as EDC or HATU. Deprotection of the amine, followed by a biomimetic oxidative deamination using reagent such as diethyl oxomalonate (see for example: Ohta, S.; Okamoto, M. Synthesis, 1982, 756 or Babler, J.; Invergo, B. J. Org. Chem. 1981, 46, 1937) led to compound 2-8. Hydrogenation of the remaining olefin yielded optically pure 1-3a.

SCHEME 2

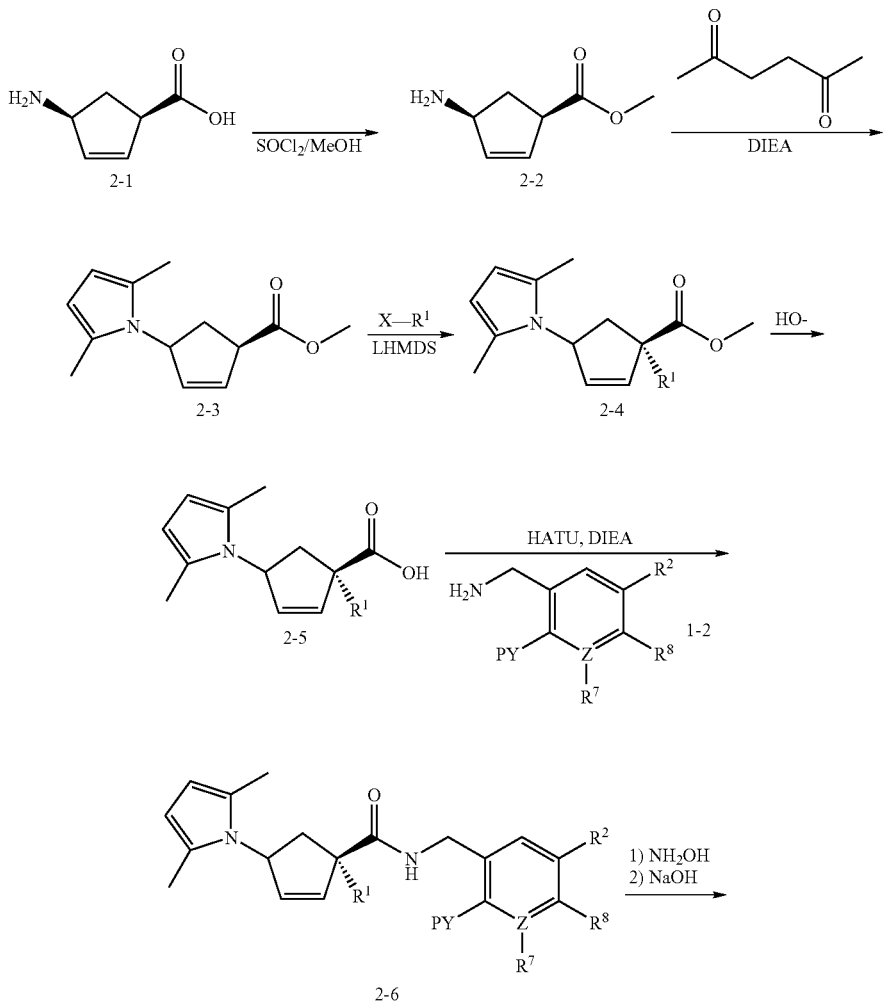

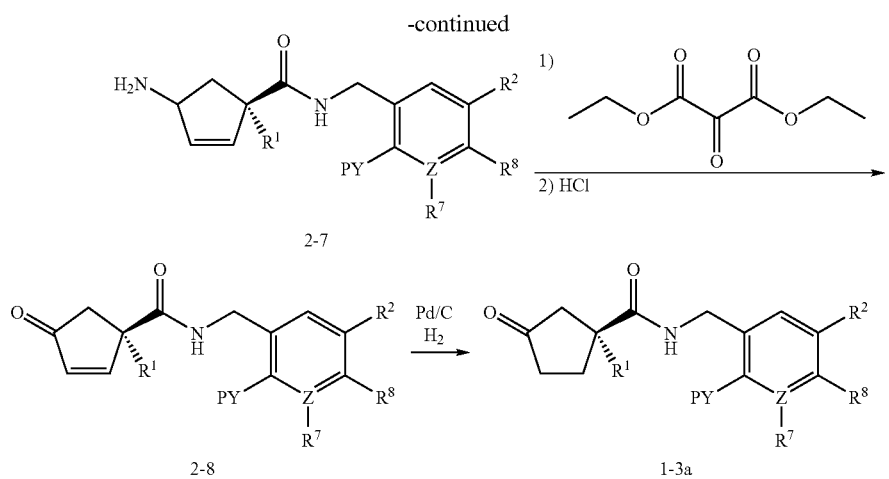

One of the principal routes used for preparation of compound 1-1 is outlined in Scheme 3A. According to this route, 3-oxocyclopentanecarboxylic acid (3-1), which can be synthesized following a known procedure (Stetter, H., Kuhlman, H., *Liebigs Ann. Chim.,* 1979, 944) is esterified under standard conditions. When $R^{15}$ represents a tert-Butyl group, the respective ester 3-2 can be prepared by reacting the appropriate alcohol, in this case tert-butanol, with acid 3-1 in the presence of sulfuric acid. Protection of the oxo-group in 3-1 can be achieved by a number of ways (Greene, T., Wuts, P. G. M., *Protective Groups in Organic Chemistry,* John Wiley & Sons, Inc., New York, N.Y. 1991). The particularly suitable dimethyl acetal protecting group can be introduced using trimethyl orthoformate as a reagent in a suitable solvent such as dichloromethane and methyl alcohol in the presence of an acidic catalyst. Alternatively, in the case of $R^{15}$ being a methyl group, the acid 3-1 can be converted to 3-3 directly by using trimethyl orthoformate and an acidic catalyst, such as para-toluenesulfonic acid. An alkylation of esters 3-3 with an alkylating agent such as an alkyl chloride, bromide or iodide in the presence of an appropriate base such as lithium diisopropylamide, produces compounds 3-4. The ester protecting group present in 3-4 can be removed in a number of ways, depending on the nature of the ester. Methyl esters ($R^{15}$=methyl) can be hydrolyzed in the presence of an acid or base at ambient or elevated temperatures, whereas tert-butyl esters ($R^{15}$=tert-butyl) can be easily cleaved under acidic conditions.

SCHEME 3A

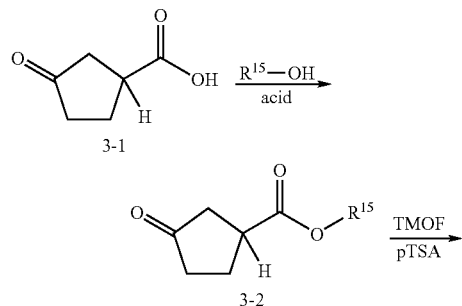

Compound 1-1 can be prepared as a single stereoisomer (1-1a) in various ways including those depicted in Scheme 3B and Scheme 3C. According to Scheme 3B, racemic 1-1 can be converted to its benzyl ester. There are many ways to effect this esterification, one of which being by a sequence involving conversion to the corresponding acid chloride with, for example oxalyl chloride, followed by treatment with benzyl alcohol in the presence of a base such as triethylamine. Then the racemic benzyl ester 3-5 can be separated by chiral preparative HPLC to give 3-5a as a single stereoisomer. Removal of the benzyl group to give the chiral ketoacid 1-1a can be accomplished in several ways. One convenient way is by hydrogenolysis in the presence of a catalyst such as Pd/C.

SCHEME 3B

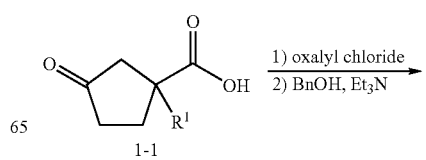

-continued

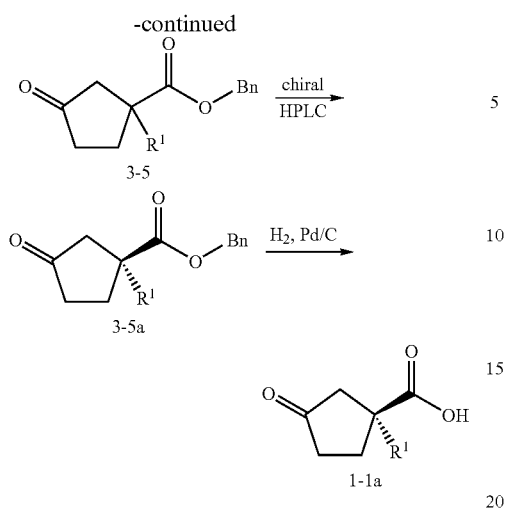

According to Scheme 3C, chiral ketoacid compound 1-1a can be prepared starting from commercially available optically pure amino acid 2-1. Protection of the carboxylic acid group can be achieved in a variety of ways. When $R^{15}$ is methyl, esterification can be accomplished by treatment with methanol in the presence of an acid catalyst such as HCl. Treatment with $Boc_2O$ results in protection of the amine group of 3-7. Stereoselective alkylation of ester 3-8 with an alkylating agent such as an alkyl chloride, bromide or iodide in the presence of an appropriate base such as lithium bis(trimethylsilyl)amide, produces compound 3-9. Hydrogenation in the presence of a catalyst such as Pd/C affords 3-10. Hydrolysis of the ester to give 3-11 can be achieved under standard conditions depending on the $R^{15}$ group. For example, when $R^{15}$ is methyl (methyl ester), hydrolysis can be accomplished by treatment with a base such as sodium hydroxide, lithium hydroxide, or potassium hydroxide, with or without heating. The Boc protecting group can be removed under standard acidic conditions, such as with HCl in a solvent such as dioxane, or with TFA. Oxidation of 3-12 to give 1-1a (as a single stereoisomer if constituent $R^1$ is achiral, or as a mixture of stereoisomers if constituent $R^1$ has a chiral center) can be achieved in several ways, including by treatment with NBS, followed by treatment with sodium methoxide.

SCHEME 3C

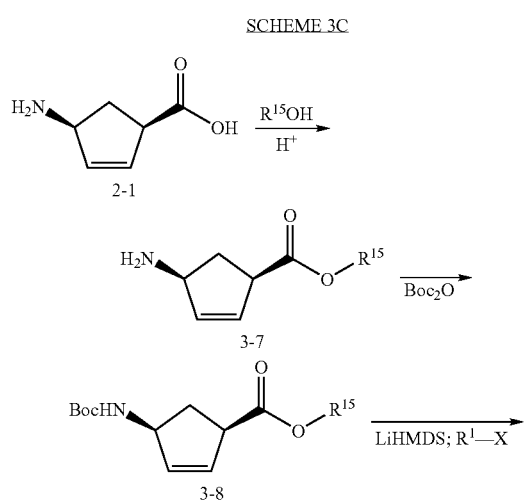

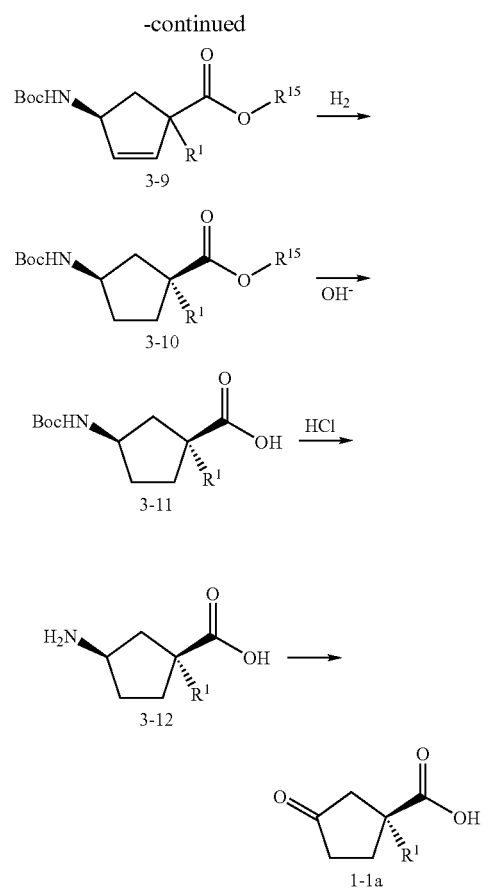

The enolate generated from ester 3-3 ($R^{15}$ being a benzyl or tert-Butyl group) in the presence of a strong base such as lithium diisopropylamide can be reacted with aldehydes ($R^{1a}CHO$) or ketones ($R^{1a}R^{2a}CO$) to produce the appropriate hydroxyalkyl substituted compounds 3-4.1 as indicated in Scheme 3D. The resulting hydroxy group can be protected in various ways, including by treatment with acetic anhydride in the presence of a base such as triethylamine to give compounds 3-4.2. Once again the ester protecting group is removed under conditions suitable for the particular protecting group. In the case of the tert-butyl esters ($R^{15}$ is t-butyl), deprotection is achieved under acidic conditions. The latter usually induces cleavage of the acetal protecting group as well, and the keto acids 1-1.1 can be prepared this way in an one-pot procedure. Their conversion to the final modulators of chemokine activity 1-9 can be achieved as described previously, with modifications to accommodate the protected hydroxy in 1-1.1.

SCHEME 3D

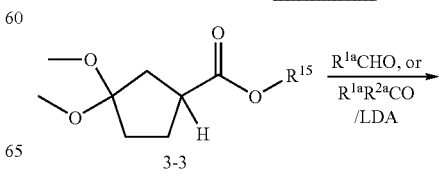

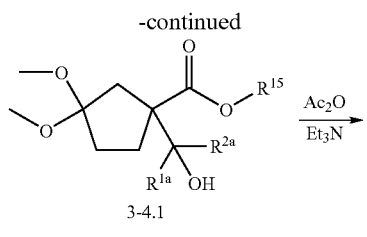

3-4.1

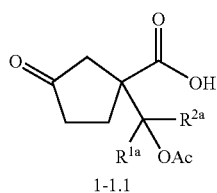

1-1.1

Amines 1-2 could be prepared in several ways. One approach is shown in Scheme 4. Fluorides 4-1 (either commercially available or prepared as detailed in the experimental section) could be treated with PYH (such as ammonia, methanesulfonamide, t-butylthiol, t-butyl alcohol) in the presence of a base such as NaH to give 4-2 arising from nucleophilic aromatic substitution. The nitrile groups could then be reduced using various conditions, such as by Raney Ni and hydrogen gas or by borane, giving amines 1-2.

SCHEME 4

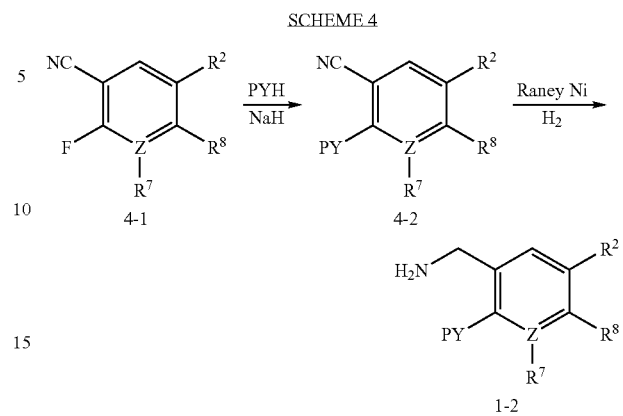

Amines 1-8 were obtained from various sources. Some were commercially available, some were known from the literature and could be prepared according to published procedures, and some were prepared as described herein. Since their structures and the methods for their preparation are diverse, only one Scheme will be outlined in this section; individual syntheses of amines 1-8 can be found below. Scheme 5 shows one method for the synthesis of 4-aryl substituted piperidines as well as 4-aryl-3-alkyl-piperidines. Enol triflate 5-1 (prepared according to Wustrow, D. J., Wise, L. D., Synthesis, (1991), 993-995.) could be coupled to boronic acids 5-2 as described by Wustrow and Wise. Hydrogenation of the olefin in 5-3 could be achieved using hydrogen in the presence of a catalyst such as Pd(OH)2/C. Oxidation of 5-4 using Ru(IV)oxide hydrate and sodium periodate leads to Boc-lactam 5-5. Alkylation with an alkyl halide in the presence of a base such as LDA gives 5-6, with the trans product being predominant. Removal of the Boc protecting group could be achieved using standard acidic conditions, such as HCl in dioxane or TFA/DCM. Reduction of the lactam 5-7 with, for example, borane provides 1-8.2. Alternatively, compound 5-4 can itself be deprotected under acidic conditions to afford piperidine 1-8.1.

SCHEME 5

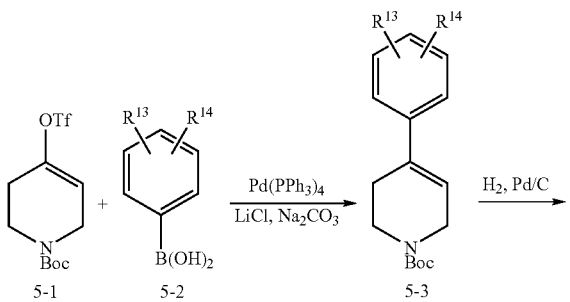

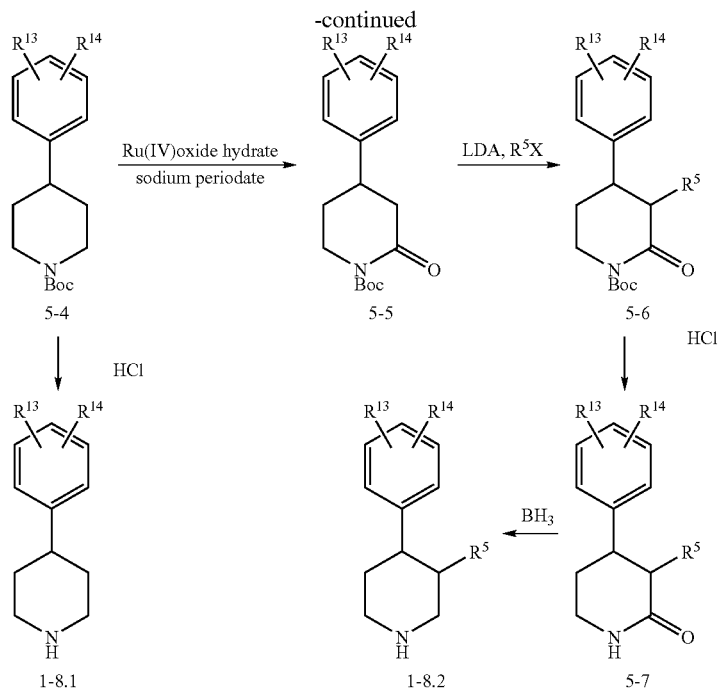

Alternatively, when $R^5$=Me, the cis analog of 1-8.2 (1-8.2a) can be obtained as a racemate following SCHEME 6. The trans compound is also isolated as a minor stereoisomer (1-8.2b). The enol triflate 6-2 was synthesized according to the Wustrow and Wise procedure (Synthesis, 1991, 993-995) followed by coupling with a boronic acid (or ester) 5-2. Hydrogenation of the olefin in 6-3 using a catalyst such as the Adam's catalyst ($PtO_2$) yielded a mixture of two racemates (6-4a:6-4b,3: 1). After separation of these two racemates, 1-8.2a and 1-8.2b were obtained by hydrogenolysis in the presence of a catalyst such as Pd/C.

SCHEME 6

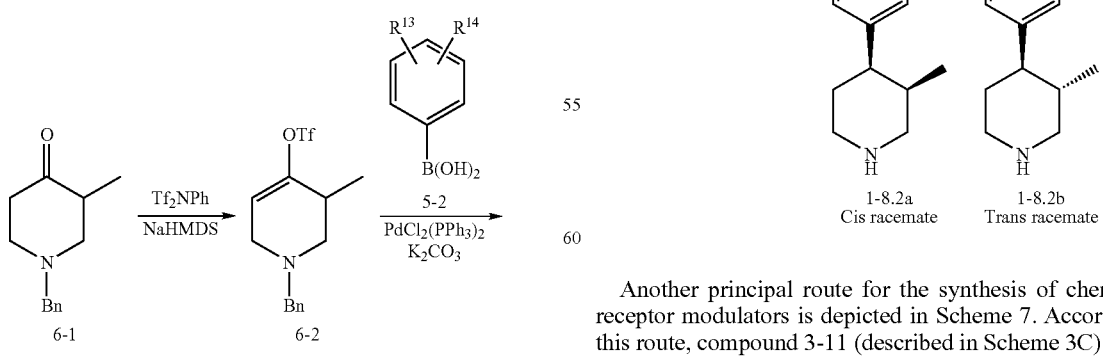

Another principal route for the synthesis of chemokine receptor modulators is depicted in Scheme 7. According to this route, compound 3-11 (described in Scheme 3C) is condensed with amine 1-2 (described in Scheme 1) using a peptide coupling reagent such as EDC to give 7-1. The Boc protecting group is removed under standard conditions such as with HCl in a solvent such as dioxane with, in the case where PY is t-butoxide, concomitant removal of the P protecting group, to provide 7-2. Protection of the amine group with an alternative protecting group such as a trifluoroacetate can be accomplished with trifluoroacetic anhydride in the presence of a base such as triethylamine to give 7-3. Cyclizaa dialdehyde 7-6 in the presence of a reducing agent such as sodium triacetoxyborohydride leads to a double reductive alkylation sequence with concomitant cyclization to give 1-9.2. In accord with Scheme 1, further modifications, such as hydrolysis of an ester group present within 1-9.2 can be effected to give new chemokine receptor modulators 1-9.3.

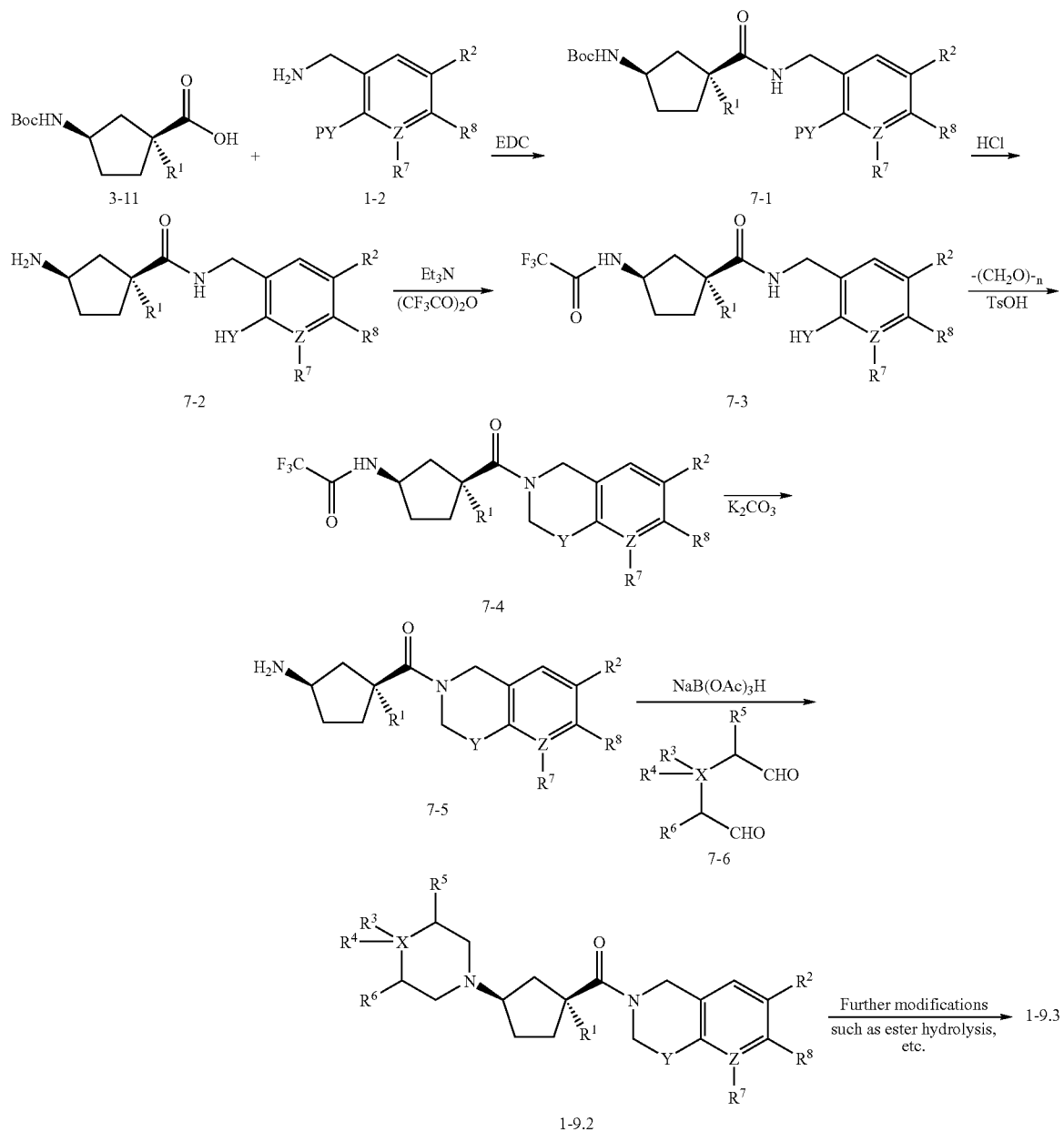

SCHEME 7 tion to form the desired fused bicyclic ring system of 7-4 is achieved using a formaldehyde equivalent such as paraformaldehyde in the presence of an acid catalyst such as TsOH. Removal of the trifluoroacetate protecting group can be accomplished in a variety of ways, including by treatment with $K_2CO_3$ in methanol, or with another suitable base such as NaOH or $NH_3$. Treatment of the resulting amine 7-5 with One way of preparing dialdehydes 7-6 is outlined in Scheme 8. According to this route, a cycloalkene 8-1 is oxidatively cleaved with, for example, ozone followed by dimethylsulfide, to give the dialdehyde. Alternatively, in place of the dialdehydes 7-6 the ozonides 8-2 can themselves be used directly in the double reductive amination reaction leading to 1-9.2.

SCHEME 8

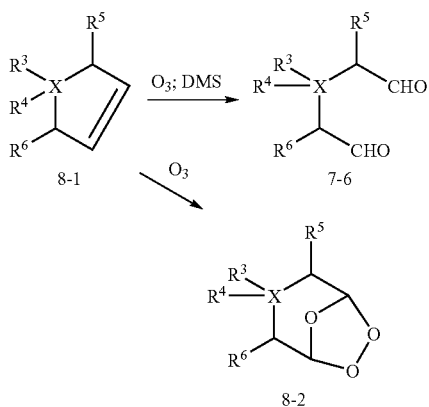

In some cases the order of carrying out the foregoing reaction schemes may be varied to facilitate the reaction or to avoid unwanted reaction products. The following examples are provided for the purpose of further illustration only and are not intended to be limitations on the disclosed invention.

Concentration of solutions was generally carried out on a rotary evaporator under reduced pressure. Flash chromatography was carried out on silica gel (230-400 mesh). MPLC refers to medium pressure liquid chromatography and was carried out on a silica gel stationary phase unless otherwise noted. NMR spectra were obtained in $CDCl_3$ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

The following are representative procedures for the preparation of the compounds used in the following Examples or which can be substituted for the compounds used in the following Examples which may not be commercially available.

Intermediate 1

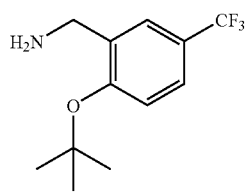

Step A:

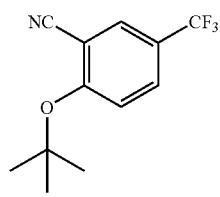

To a cooled (0° C.) solution of 2-fluoro-5-trifluoromethyl-benzonitrile (5.23 g, 27.7 mmol) in 140 mL of THF was added, dropwise at a rapid pace, a suspension of potassium t-butoxide (3.88 g, 34.6 mmol) in 35 mL of THF. The reaction mixture was permitted to slowly warm to rt and stirred overnight. The reaction mixture was concentrated under reduced pressure; then ether and 1N HCl solution were added, and the layers separated. The ethereal layer was washed with saturated $NaHCO_3$ solution, then brine, dried over anhydrous $MgSO_4$, filtered, and concentrated. Purification by MPLC (silica, 25% ethyl acetate/hexane) afforded a white crystalline solid. H NMR ($CDCl_3$, 500 MHz): δ 7.84 (d, J=2.0 Hz, 1H), 7.73 (dd, J=8.5, 2.0 Hz, 1H), 7.27 (d, J=9.0 Hz), 1.55 (s, 9H).

Step B:

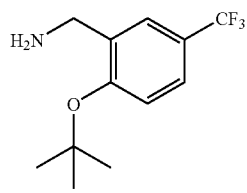

To a solution of the nitrile prepared as described in Step A (7.6 g, 31 mmol) in ethanol (100 mL) was added ammonium hydroxide solution (28-30%, 25 mL) and Raney® 2800 nickel (slurry in water, ~3.5 g). The resulting mixture was agitated under 50 psi of hydrogen gas for 24 h using a Parr apparatus. The reaction mixture was then filtered through celite washing with ethanol and then water. The filtrate was concentrated to dryness under reduced pressure, and the residue so obtained was purified by flash chromatography [silica, 5 to 10% gradient (1% increments) of (10% ammonium hydroxide solution (28-30%)/methanol) in DCM] to afford 1-[2-tert-butoxy-5-(trifluoromethyl)phenyl]methanamine as a colorless oil which crystallized upon storage in the freezer. H NMR ($CDCl_3$, 500 MHz): δ 7.56 (d, J=2.0 Hz, 1H), 7.44 (dd, J=8.5, 2.0 Hz, 1H), 7.12 (d, 8.5 Hz, 1H), 3.90 (s, 2H), 2.70 (br s, 2H), 1.51 (s, 9H).

Intermediate 2

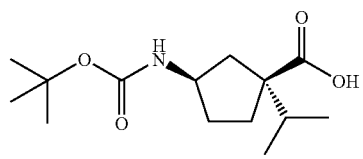

Procedure A:

Step A:

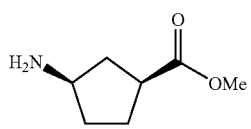

A mixture of (1S)-(+)-2-azabicyclo[2.2.1]hept-5-en-3-one (10.3 g, 94.4 mmol) in ethyl acetate (200 mL) and 10% Pd/C (0.5 g), was hydrogenated at rt. After 24 h the reaction mixture was filtered and evaporated leaving behind 10.4 g (100%) of the product that was taken in 250 mL methanol and HCl (12M, 6 mL). The resultant mixture was stirred at rt, until the reaction was complete (72 h). Evaporation of methanol followed by drying under high vacuum, yielded title compound as an off white solid. $^1$H NMR (500 MHz, D$_2$O): δ 3.70 (s, 3H), 3.01 (m, 1H), 2.38 (m, 1H), 2.16-1.73 (m, 6H).

Step B:

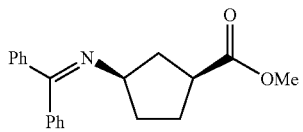

To a suspension of the intermediate from Step A (10.2 g, 56.8 mmol) in dry dichloromethane (200 mL) was added benzophenone imine (10.2 g, 56.8 mmol) at rt and the resultant mixture was stirred for 24 h. The reaction mixture was filtered and the filtrate was evaporated, to leave behind a yellow oil that was triturated with ether (100 mL), filtered and evaporated. This operation was repeated twice to ensure that the product was free of ammonium chloride impurities. The resultant oil was thoroughly dried under vacuum to yield the title compound and required no further purification. $^1$H NMR (500 MHz, CDCl$_3$): δ 7.5-7.18 (m, 10H), 3.75 (m, 1H), 3.7 (s, 3H), 2.78 (m, 1H), 2.26-1.71 (m, 6H).

Step C:

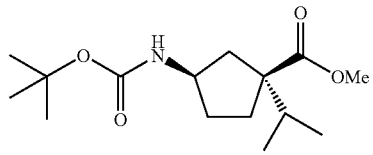

To a solution of lithium diisopropylamide (prepared from diisopropylamine (7.7 g, 76 mmol) and n-butyllithium (30.4 mL, 2.5M in hexanes, 76 mmol) in tetrahydrofuran (120 mL) at −78° C. was added the ester from Step B (18.0 g, 58.6 mmol). The resultant burgundy colored solution was stirred for 20 min after which it was quenched with 2-iodopropane (14.9 gm, 88 mmol). The reaction mixture was gradually warmed over 3 h to 0° C. and this temperature was maintained for an additional 3 h. Reaction was quenched with water and extracted with ethyl acetate. The organic layer was washed with water, brine, dried (anhydrous magnesium sulfate) and concentrated to yield an oil. To the solution of the crude Schiff base (20.0 g) in tetrahydrofuran (100 mL) was added HCl (5.0 mL, 12M). The resulting reaction mixture was allowed to stir at rt for 3 h. After the removal of all volatiles, the hydrochloride salt was taken up into dichloromethane (250 mL), saturated solution of sodium bicarbonate (250 mL) and di-tert-butyl dicarbonate (26.0 g, 1.4 Eq.) were added. The resultant mixture was vigorously stirred overnight at rt. The organic layer was separated and washed with water, brine, dried (anhydrous magnesium sulfate) and concentrated to yield an oil. Purification by flash column chromatography (eluent: hexanes/ethyl acetate 19: 1) gave the desired product. $^1$H NMR (500 MHz, CDCl$_3$): 4.79 (br, 1H), 4.01 (m, 1H), 3.71 (s, 3H), 2.18-1.60 (m, 6H), 1.44 (s, 9H), 0.87 (d, J=6.9 Hz, 3H), 0.86 (d, J=6.9 Hz, 3H).

Step D:

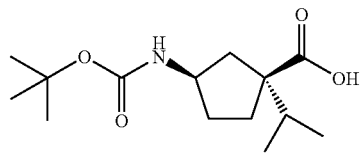

To a solution of the ester from Step C (4.91 g, 17.2 mmol) in methanol (100 mL) was added a solution of LiOH (3.6 g, 85 mmol) in water (20 mL) and tetrahydrofuran (10 mL). The resultant mixture was heated at 80° C. until the reaction was complete (18 h). The methanol was removed in vacuo and the crude product was taken up with water/ethyl acetate (200 mL, 1:4) and cooled to 0° C. The acidity of the mixture was adjusted to pH 6. The ethyl acetate layer was separated, washed with water, brine, dried (anhydrous magnesium sulfate) and concentrated to yield an oil. Purification by flash column chromatography (eluent:hexanes/ethyl acetate 1:1+ 2% AcOH) gave (1S,3R)-3-[(tert-butoxycarbonyl)amino]-1-isopropylcyclopentanecarboxylic acid. $^1$H NMR (500 MHz, CDCl$_3$): 11.36 (br, 1H), 6.49 (br, 1H), 4.83 (m, 1H), 3.71 (s, 3H), 2.30-1.55 (m, 6H), 1.46 (s, 9H), 0.94 (d, J=6.9 Hz, 3H), 0.933 (d, J=6.9 Hz, 3H).

Procedure B:

Step A:

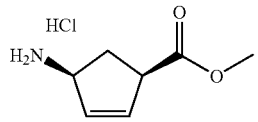

Commercially available (1R,4S)-4-aminocyclopent-2-ene-1-carboxylic acid was converted to its methyl ester hydrochloride salt via classical procedures.

Step B:

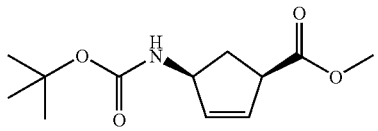

To a suspension of amine from Step A (6.31 g, 35.5 mmol) in acetone (40 mL) and water (20 mL) was added solid NaHCO$_3$ (6.6 g, 78 mmol) in portions. After 5 min, a solution of di-tert-butyl dicarbonate (8.5 g, 39 mmol) in acetone (60 mL) was added and the reaction mixture was stirred at rt. After 3 h, acetone was removed in vacuo and the residue was partitioned between ether (500 mL) and saturated aqueous NaHCO$_3$ solution (120 mL). The ether layer was further washed with aqueous NaHCO$_3$ solution (1×100 mL), brine (1×100 mL), dried over anhydrous Na$_2$SO$_4$, concentrated and purified by flash chromatography (15% ethyl acetate/hexanes) to afford the product.

Step C

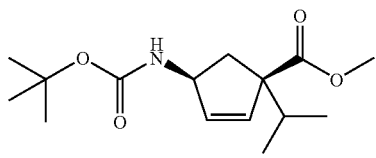

To a solution of lithium bis(trimethylsilyl)amide (10.4 g, 62.1 mmol) in tetrahydrofuran (100 mL) was added a solution of the intermediate from Step B (6.71 g, 27.8 mmol) in tetrahydrofuran (10 mL) over 10 min at −78° C. The resulted solution was stirred at −78° C. for 30 min before isopropyl iodide (3.3 mL, 33 mmol) was added in one portion. The reaction was allowed to warm up to −25° C. and this temperature was maintained overnight. The reaction was then quenched with an aqueous saturated $NH_4Cl$ solution (250 mL). The organic layer was separated and the aqueous layer was further extracted with diethyl ether (3×100 mL). The combined organic layers were then washed with brine (1×100 mL), dried over anhydrous $Na_2SO_4$, filtered, concentrated and purified by flash chromatography (5-10% ethyl acetate/hexanes) to give the product as a clear oil (cis/trans=4.3/1). $^1$H NMR (500 MHz, $CDCl_3$) cis-isomer: δ 5.79 (s, 2H), 4.75 (m, 1H), 3.72 (s, 3H), 2.28-2.20 (m, 2H), 2.0 (dd, J=15, 4 Hz, 1H), 1.45 (s, 9H), 0.85 (d, J=6.6 Hz, 3H), 0.81 (d, J=7 Hz, 3H).

Step D:

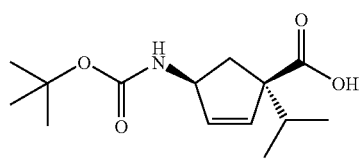

To a solution of the product from Step C (1.6 g, 5.7 mmol) in tetrahydrofuran (50 mL), methanol (50 mL) and water (10 mL) was added LiOH monohydrate (400 mg) and the reaction was heated to reflux overnight until the TLC indicated that the reaction was complete. The organic solvents were removed in vacuo and the aqueous layer was washed with ether (1×) and then acidified slowly with concentrated HCl until the pH reached 4. The resulting suspension was extracted with $CH_2Cl_2$ (3×). The combined organic layers were dried over anhydrous $MgSO_4$, filtered and concentrated to give the product as a mixture of two cis/trans isomers (1.5 g) as a foaming yellow solid. This solid was dissolved in ethyl acetate (2 mL) with heating and diluted with hexanes (50 mL) to give a clear solution. This solution was allowed to cool to rt slowly over 1 h and then maintained at −25° C. in a freezer overnight. The trans-isomer was crystalized out along with some of the desired cis-isomer. The mother solution was collected and concentrated to give the title compound (cis-isomer only). $^1$H NMR (500 MHz, $CDCl_3$) cis-isomer: δ 5.80 (m, 2H), 4.80 (m, 1H), 2.40-2.20 (m, 2H), 2.15-2.0 (m, 1H), 1.5 (m, 9H), 1.0-0.8 (m, 3H).

Step E:

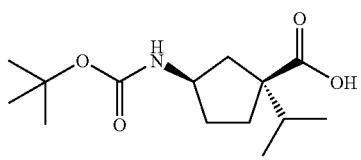

To a solution of the product from Step D (1 g) in ethanol (30 mL) was added 10% Pd/C (100 mg) and the resulting mixture was agitated on a Parr apparatus at 50 lb pressure of $H_2$ overnight. The mixture was filtered through celite and concentrated in vacuo to afford the title compound, (1S,3R)-3-[(tert-butoxycarbonyl)amino]-1-isopropylcyclopentanecarboxylic acid. $^1$H NMR (500 MHz, $CDCl_3$): 11.36 (br, 1H), 6.49 (br, 1H), 4.83 (m, 1H), 3.71 (s, 3H), 2.30-1.55 (m, 6H), 1.46 (s, 9H), 0.94 (d, J=6.9 Hz, 3H), 0.933 (d, J=6.9 Hz, 3H).

Intermediate 3

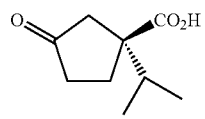

Procedure A:

Step A:

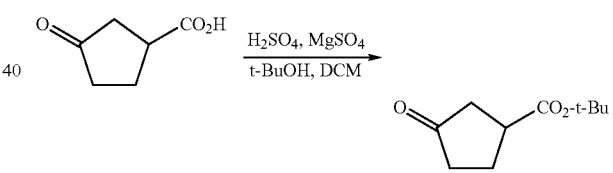

$H_2SO_4$ (conc., 15.3 g, 8.30 mL, 156 mmol) was added dropwise to a vigorously stirred suspension of $MgSO_4$ (75 g, 620 mmol) in DCM (650 mL). The mixture was stirred for 0.5 h, then known cyclopentanone-3-carboxylate (20.0 g, 156 mmol) was added, followed by t-butanol (58 g, 780 mmol). The reaction vessel was tightly sealed and the mixture was stirred overnight at rt. The next morning another 30 mL of t-butanol was added. Again the reaction vessel was tightly sealed, and the reaction mixture was stirred over the weekend. The reaction mixture was then filtered through celite. The filtrate was washed with 2 N NaOH. The aqueous layer was back-washed with DCM. The organic layers were combined, washed with water, then brine, dried over anhydrous $MgSO_4$, filtered, and concentrated to afford tert-butyl 3-oxocyclopentanecarboxylate. The reaction progress was monitored by TLC using 50% ethyl acetate/hexane and staining with anisaldehyde stain (SM and product stain purple). $^1$H NMR (500 MHz, $CDCl_3$): 3.02 (p, J=7.8 Hz, 1H), 2.05-2.50 (m, 6H), 1.45 (s, 9H). $^{13}$C NMR (125 MHz, $CDCl_3$): 217.00, 173.47, 80.99, 41.88, 41.14, 27.94, 26.57.

Step B:

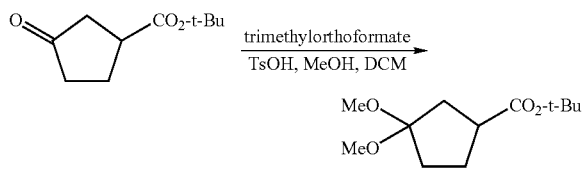

To a solution of tert-butyl 3-oxocyclopentanecarboxylate (19.8 g, 107 mmol) in 1:1 DCM/methanol (150 mL) was added trimethylorthoformate (46.8 mL, 428 mmol), followed by TsOH.H$_2$O (~0.5 g). The reaction mixture was stirred at rt for 2 h. Then more TsOH.H$_2$O (~0.25 g) was added and the reaction mixture was stirred overnight. The reaction mixture was concentrated at rt and the resulting residue was dissolved in ether and washed with saturated NaHCO$_3$ solution, then with brine. The ethereal layer was dried over anhydrous MgSO$_4$, filtered, and concentrated. Purification by flash chromatography (silica, 15% ethyl acetate/hexane) gave tert-butyl 3,3-dimethoxycyclopentanecarboxylate. $^1$H NMR (500 MHz, CDCl$_3$): 3.21 (s, 3H), 3.20 (s, 3H), 2.80 (m, 1H), 2.10 to 1.80 (bm, 6H), 1.46 (s, 9H). $^{13}$C NMR (125 MHz, CDCl$_3$): 174.9, 111.2, 80.3, 67.8, 49.2, 42.5, 37.4, 33.8, 28.3, 22.0.

Step C:

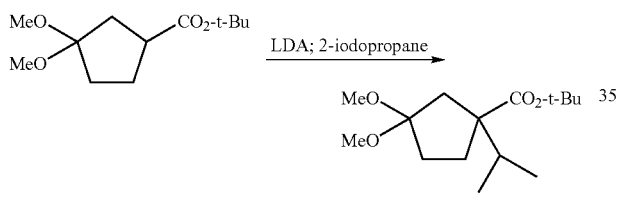

To a cooled (−78° C.) solution of LDA (1.5M in cyclohexane, 41 mL, 61 mmol) in THF (150 mL) was added dropwise over 10 min tert-butyl 3,3-dimethoxycyclopentanecarboxylate (9.37 g, 40.7 mmol) in 25 mL of THF. The resulting mixture was stirred at −78° C. for 30 min, then was treated dropwise with 2-iodopropane (16.3 mL, 163 mmol). After stirring for an additional 10 min, the reaction mixture was permitted to warm to rt. After stirring overnight, the reaction mixture was diluted with ether and washed with brine. The ethereal layer was dried over anhydrous MgSO$_4$, filtered, and concentrated. After storing the crude product under vacuum overnight, it was purified by MPLC (silica, 20% ethyl acetate/hexane) to give tert-butyl 1-isopropyl-3,3-dimethoxycyclopentanecarboxylate. $^1$H NMR (500 MHz, CDCl$_3$) δ 3.21 (s, 3H), 3.18 (s, 3H), 2.56 (app d, J=14 Hz, 1H), 2.26 (m, 1H), 1.78-1.89 (m, 3).

Step D:

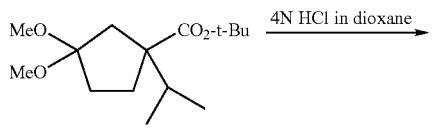

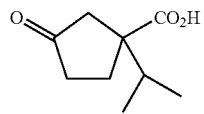

tert-Butyl 1-isopropyl-3,3-dimethoxycyclopentanecarboxylate (8.32 g, 30.5 mmol) was dissolved in 4N anhydrous HCl in dioxane (50 mL) and water (10 mL) was added. The reaction mixture was stirred at rt overnight, then was concentrated. The residue was dissolved in DCM, dried over anhydrous MgSO$_4$, filtered, and concentrated to give 1-isopropyl-3-oxocyclopentanecarboxylic acid (used without purification). $^1$H NMR (500 MHz, CDCl$_3$) δ 2.70 (d, J=18.1 Hz, 1H), 2.44-2.39 (m, 1H), 2.30-2.15 (m, 2H), 2.14 (dd, J=18.1, 1.0 Hz, 1H), 2.06 (p, J=6.9 Hz, 1H), 1.98 (m, 1H), 0.98 (dd, J=11.4, 6.9 Hz, 6H).

Step E:

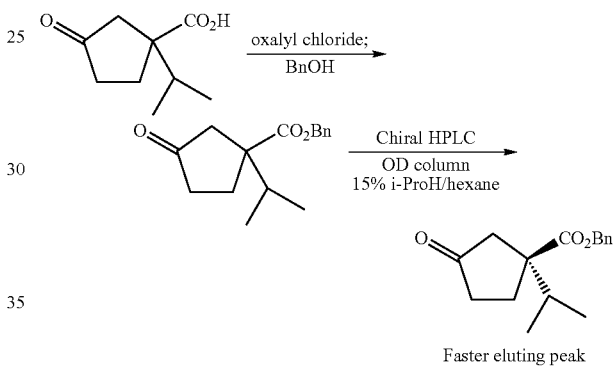

Faster eluting peak

A cooled (0° C.) solution of 1-isopropyl-3-oxocyclopentanecarboxylic acid (5.44 g, 32.0 mmol) in DCM (75 mL) was treated with oxalyl chloride (8.36 mL, 95.9 mmol), followed by 3 drops of DMF. The reaction mixture was permitted to warm to rt and stir for 1.75 h. The reaction mixture was then concentrated and stored under vacuum for 30 min. The resulting acid chloride was dissolved in DCM (75 mL), cooled to 0° C., and treated with benzyl alcohol (8.28 mL, 80.0 mmol), followed by triethyl amine (8.92 mL, 64.0 mmol, dropwise). Then approximately 100 mg of DMAP was added and the reaction mixture was warmed to rt and stirred for 2 h. The reaction mixture was diluted with DCM and washed with 1N HCl solution, saturated NaHCO$_3$ solution, and brine. The organic layer was dried over anhydrous MgSO$_4$, filtered, and concentrated. Purification by MPLC (silica, 50% ethyl acetate/hexane) gave benzyl 1-isopropyl-3-oxocyclopentanecarboxylate. $^1$HNMR (CDCl$_3$, 500 MHz): δ 7.36 (m, 5 H), 5.17 (d, J=2.5 Hz, 2H), 2.85 (d, J=18.5 Hz, 1H), 2.48 (m, 1H), 2.29 (dd, J=10.0, 3.0 Hz, 1H), 1.98-2.23 (m, 3H), 1.93 (m, 1H), 0.95 (m, 6H).

Resolution of the racemic product was accomplished by chiral HPLC using a chiralcel OD column, and eluting with 15% 2-propanol/hexane (100 mg/injection; was accomplished using a programmed Gilson HPLC system). 2.11 g of the desired faster eluting isomer, benzyl (1S)-1-isopropyl-3-oxocyclopentanecarboxylate, were obtained.

Step F:

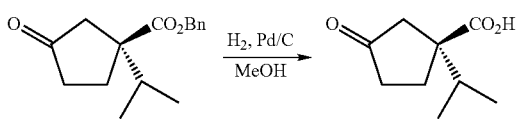

Benzyl (1S)-1-isopropyl-3-oxocyclopentanecarboxylate (1.27 g, 4.88 mmol) was combined with Pd/C (10% Degussa, 500 mg) in 20 mL of methanol and stirred under a hydrogen atmosphere (balloon) for 2 h. The reaction had only proceeded part way (~30% conversion) so the reaction mixture was filtered, another portion of Pd/C (500 mg) was added, and the mixture was stirred under a hydrogen atmosphere for 5 h. Since the reaction had now gone to completion, the reaction mixture was filtered through celite and concentrated to afford (1S)-1-isopropyl-3-oxocyclopentanecarboxylic acid that did not require further purification. Note that the large quantities of catalyst were used because the ester obtained after chiral separation must have been poisoned by an impurity. This was unique to this particular sample. Normally much smaller quantities of catalyst are used. $^1$H NMR was identical to that of the racemic acid above (Step D).

Procedure B:

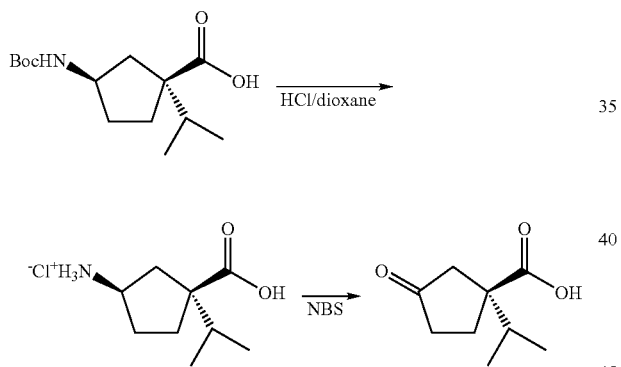

To a solution of (1S,3R)-3-[(tert-butoxycarbonyl)amino]-1-isopropylcyclopentanecarboxylic acid (7.46 g, 27.5 mmol) in dioxane (10 mL) was added 4N HCl in dioxane (30 mL). The reaction mixture was stirred at rt for 2 h, then concentrated in vacuo to give the corresponding aminoacid salt as a white solid. This solid was then dissolved in $CH_2Cl_2$ (100 mL) and solid $NaHCO_3$ (7.0 g, 82.5 mmol) was added. After cooled to 0° C., a solution of NBS (20.0 g, 110 mmol) in $CH_2Cl_2$ (200 mL) was slowly added to the reaction over 4 h. After the addition, the reaction was concentrated to dryness in vacuo and then dissolved in ethanol (100 mL). To this ethanol solution was added NaOMe (4.45 g, 82.5 mmol) and the reaction was heated to reflux. After 1 h at reflux, the reaction was cooled to 0° C. and 2N aqueous $H_2SO_4$ (50 mL) was added. The mixture was stirred at rt for 1 h before concentrating in vacuo to about 60 mL in volume. The remaining mixture was partitioned between water (150 mL) and ethyl acetate (100 mL). The aqueous layer was further extracted with ethyl acetate twice. The organic layers were combined and dried over anhydrous MgSO4, concentrated and purified by flash chromatography to give (1S)-1-isopropyl-3-oxocyclopentanecarboxylic acid.

Intermediate 4

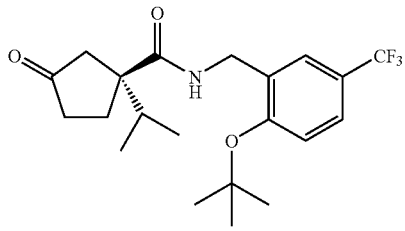

Procedure A

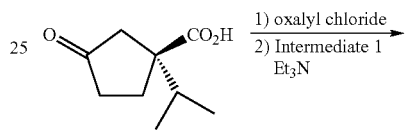

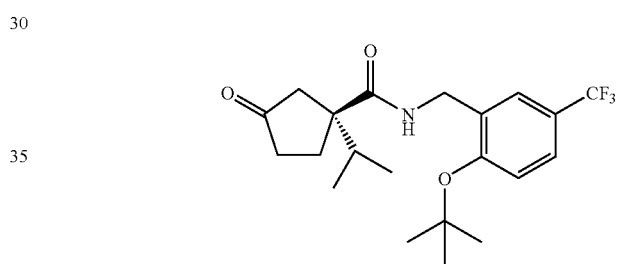

A cooled (0° C.) solution of (1S)-1-isopropyl-3-oxocyclopentanecarboxylic acid (588 mg, 3.46 mmol) under a nitrogen atmosphere was treated with oxalyl chloride (1.21 mL, 13.8 mmol), followed by 1 drop of DMF. The reaction mixture was allowed to warm to rt (bubbling indicated gas evolution) and stir for 1.5 h. The reaction mixture was then concentrated. The resulting acid chloride was redissolved in DCM (30 mL), cooled to 0° C., and treated with INTERMEDIATE 1 (1.28 g, 5.19 mmol), followed by triethylamine (0.965 mL, 6.92 mmol). The resulting reaction mixture was warmed to rt and stirred for 1.5 h, whereupon it was diluted and washed twice with 1N HCl solution, once with saturated $NaHCO_3$ solution, and once with brine. The organic layer was dried over anhydrous $MgSO_4$, filtered, and concentrated. Purification by MPLC (silica, 55% ethyl acetate/hexanes) afforded (1S)—N-[2-tert-butoxy-5-(trifluoromethyl)benzyl]-1-isopropyl-3-oxocyclopentanecarboxamide. $^1$HNMR ($CDCl_3$, 500 MHz): δ 7.53 (d, J=2.0 Hz, 1H), 7.48 (dd, J=8.0, 2.0 Hz, 1H), 7.16 (d, J=8.5 Hz, 1H), 6.16 (br s, 1H), 4.49 (m, 2H), 2.78 (dd, J=19, 2.0 Hz, 1H), 2.35 (m, 1H), 2.28 (m, 2H), 2.19 (d, J=18 Hz, 1H), 1.92-2.02 (m, 2H), 1.52 (s, 9H), 0.954 (d, J=6.5 Hz, 3H), 0.947 (d, J=7.0 Hz, 3H).

Procedure B

Step A:

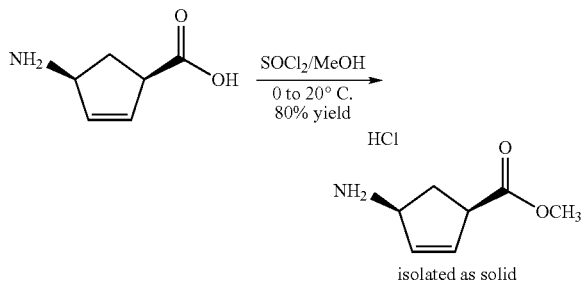

isolated as solid

To a 22 L flask was charged MeOH (3.0 L) followed by solid (1R,4S)-4-Amino-cyclopenten-2-ene carboxylic acid (1.0 Kg, 7.72 mol). The slurry was cooled to 0-5 C. Thionyl chloride (0.576 L, 7.92 mol) was added dropwise over 2 hours maintaining a temperature below 20 C. At the end of the thionyl chloride addition the cold bath was removed and the batch solution was aged at 20 C for 1-2 hours. To a 50 L flask equipped with addition funnel was charged IPAC (22.5 L). The aminocyclopentene methyl ester/MeOH solution was added to the 5-L addition funnel. The aminocyclopentene methyl ester/MeOH solution was then added dropwise to the IPAC over 1-2 hours and the product HCl salt crystallizes/precipitates directly from solution. The batch was filtered and dried in vacuo overnight to provide the aminocyclopentene methyl ester HCl salt (1,081 grams, 77% yield).

Step B:

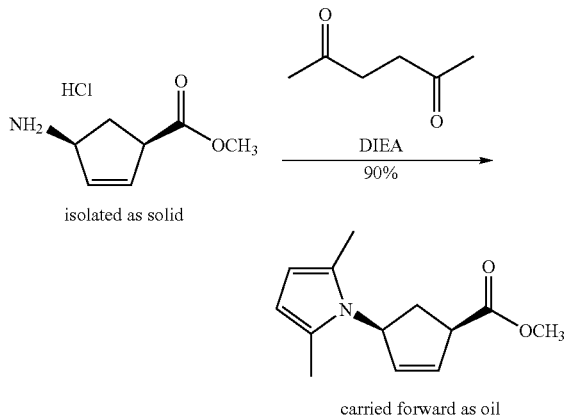

carried forward as oil

To a clean/dry 22L flask was charged the solid Aminocyclopentene methyl ester salt (1.076 kg, 6.06 mol) followed by MeOH (3 L, 2M) at 20 C under nitrogen. Diisopropylethylamine (DIEA, 0.78 kg, 6.06 mol) was added followed by acetonyl acetone (0.711 kg, 6.24 mol). The batch had an exotherm to 32-35 C. The reaction mixture was then aged at 25 C for 16 hours until complete (<1.5 A % amino-ester). The batch was diluted with IPAC (9-10 L) and washed with 10% ammonium chloride solution (2×3 L) and then 5% brine solution (2×3 L). The IPAC batch was dried over sodium sulfate and filtered through a fritted glass funnel to remove the drying agent. The IPAC batch was concentrated on a Buchi Rotovap (25" Hg, 40 C) to an oil. THF (3 L) was used as a flush on the rotovap and the batch was again concentrated to an oil. The oil (1,189 g, 92% yield) was held overnight at 5-7 C under nitrogen till next step alkylation.

Step C:

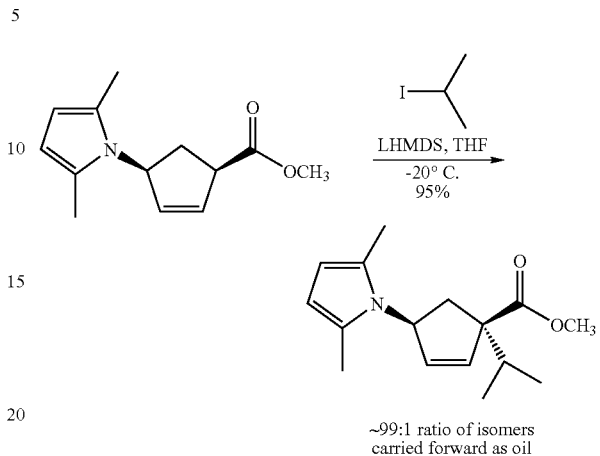

~99:1 ratio of isomers
carried forward as oil

To a clean/dry 50 L flask was charged LHMDS (1 M in THF). The solution was cooled to −20 C. The pyrrole methyl ester dissolved in THF (1.2 L) was placed in an addition funnel and added dropwise to the LHMDS over 40 minutes. The batch was then aged at −20 C for 30 minutes. 2-iodopropane was then placed in an addition funnel and charged into the batch over one hour maintaining a batch temperature of −20 C. The batch was aged at −20 C for 1 hour and then allowed to warm to 20 C over 2 hours. The batch was aged at 20 C for 1-2 hours until complete by HPLC (<0.5% starting material). The batch was transferred via pump and quenched into 6% ammonium chloride solution (10 L) in a 100-L extractor. IPAC (20 L) was charged and the layers were separated. The IPAC batch layer was washed with a 2$^{nd}$ 6% ammonium chloride wash (10 L). The layers were separated and the batch was washed with two additional 5% brine washes (2×10 L). The IPAC batch layer was then concentrated to an oil on the rotovap. The product alkylated pyrrole methyl ester oil (1,419 g, 98% yield) was held under nitrogen at 5-7 until next step saponification.

Step D:

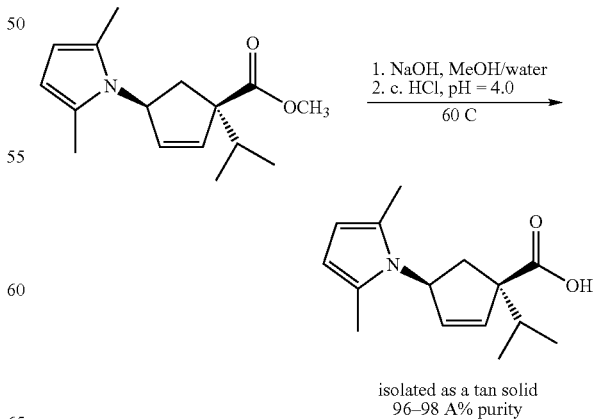

isolated as a tan solid
96–98 A% purity

To a 50 L RB flask was charged the alkylated pyrrole methyl ester oil (1.38 kg, 5.2 mol) and MeOH (7.7 L). DI water (2.5 L) was added followed by 4 equivalents 10N NaOH. The batch was then heated to 65 C for 16 hours. The batch was cooled to 10 C and c. HCl was added dropwise to pH=4.5. Batch crystallization/precipitation occurs at pH=5-6.5. The final batch pH should be pH=4.5-5.0. The batch slurry was then aged for 1 hour to allow solids to turnover and DI water (15 L) was then charged to the batch. The slurry was aged 18 hours at 20-25 C to allow the crystals to completely turnover. The batch was then filtered, washed with 10% MeOH/DI water and dried in the vacuum oven (40-50 C, 25-26" Hg) to provide the alkylated pyrrole cyclopentene acid (1,223 g, 95% yield).

Step E:

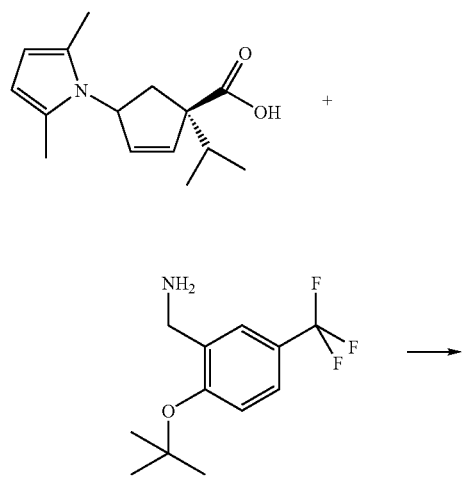

HATU (33 g, 88.4 mmol) was added to a cooled (0° C.) mixture of (1S)-4-(2,5-dimethyl-1H-pyrrol-1-yl)-1-isopropylcyclopent-2-ene-1-carboxylic acid (20 g, 80.3 mmol), [2-tert-butoxy-5-(trifluoromethyl)benzyl]amine (24 g, 96.4 mmol), and iPr$_2$EtN (42 mL, 241 mmol) in DMF (400 mL). The resulting mixture was allowed to warm to r.t. and was stirred at r.t. for 18 hr. The reaction mixture was diluted with EtOAc and washed with brine (5×). The organic phase was then dried over sodium sulfate and evaporated to dryness. The dark oily residue was purified by column chromatography on silica gel eluting with hexane:EtOAc (7:3) to yield 46 g of (1S)—N-[2-tert-butoxy-5-(trifluoromethyl)benzyl]-4-(2,5-dimethyl-1H-pyrrol-1-yl)-1-isopropylcyclopent-2-ene-1-carboxamide as a yellow oil.

Step F:

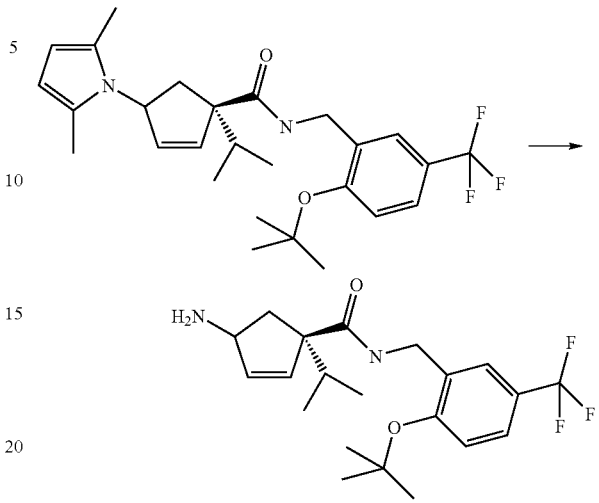

A mixture of (1S)—N-[2-tert-butoxy-5-(trifluoromethyl) benzyl]-4-(2,5-dimethyl-1H-pyrrol-1-yl)-1-isopropylcyclopent-2-ene-1-carboxamide (46 g, 97 mmol),hydroxyanime HCl (41 g, 580 mmol), and hydroxyamine (50% in H$_2$O, 50 mL) in MeOH:H$_2$O (2:1, 450 mL) was heated to 70° C. for 11 hr until no more starting material left as judged by HPLC. The reaction mixture was then cooled to r. t., the pH was adjusted to 11.0 with 1 N NaOH, and it was diluted with EtOAc. The aqueous phase was then extracted with EtOAc (5×). The organics were then combined, dried over sodium sulfate and evaporated to dryness to give 35 g of (1S)-4-amino-N-[2-tert-butoxy-5-(trifluoromethyl)benzyl]-1-isopropylcyclopent-2-ene-1-carboxamide as a yellow oil that crystallized upon standing.

Step G:

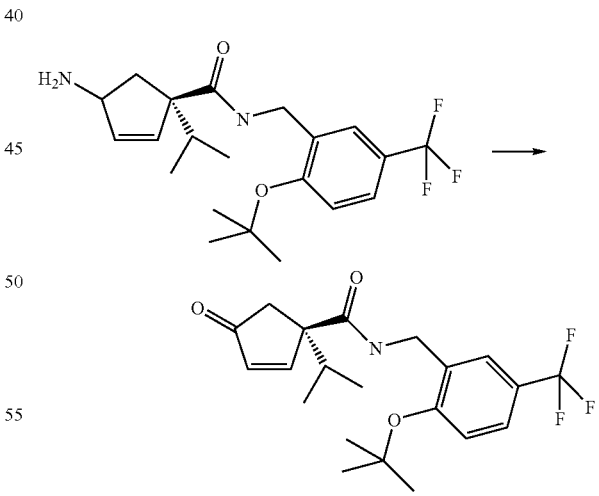

A mixture of (1S)-4-amino-N-[2-tert-butoxy-5-(trifluoromethyl)benzyl]1-isopropylcyclopent-2-ene-1-carboxamide (35 g, 88 mmol) and diethyl oxomalonate (31 g, 176 mmol) in toluene (350 mL) was refluxed until no more starting material left as judged by HPLC. The reaction mixture was cooled to 0° C. and 1,8-diazabicyclo[5.4.0]undec-7-ene (27 g, 176 mmol) was added. The reaction mixture was then warmed to r.t. and stirred at this temperature for 1 hr before being quenched with 1M HCl and vigorously stirred for 1 hr. The reaction mixture was diluted with EtOAc and the two layers were separated. The aqueous phase was then extracted with EtOAc (5×). The organics were combined, dried over sodium sulfate and evaporated to dryness. The crude was purified by column chromatography on silica gel eluting with hexane:EtOAc (11:1) to yield 32 g of (1S)—N-[2-tert-butoxy-5-(trifluoromethyl)benzyl]-1-isopropyl-4-oxocyclopent-2-ene-1-carboxamide as a pale yellow solid.

Step H:

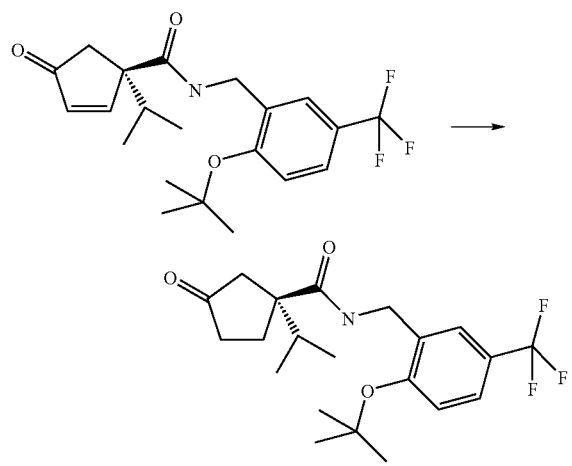

(1S)—N-[2-tert-butoxy-5-(trifluoromethyl)benzyl]-1-isopropyl-4-oxocyclopent-2-ene-1-carboxamide (32 g, 80.6 mmol) was dissolved in MeOH and was hydrogenated for 18 hr with a hydrogen balloon in the presence of a catalytic amount of 10% palladium on carbon. The palladium was filtered through a celite plug. The filtrate was evaporated to dryness to give (1S)—N-[2-tert-butoxy-5-(trifluoromethyl)benzyl]-1-isopropyl-3-oxocyclopentanecarboxamide as a yellow solid.

Intermediate 5

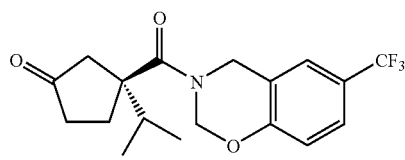

Step A:

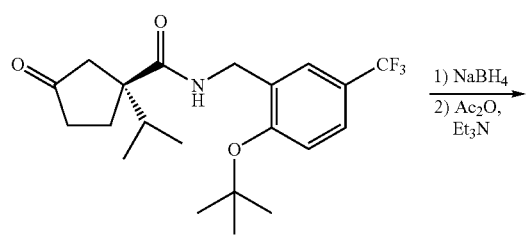

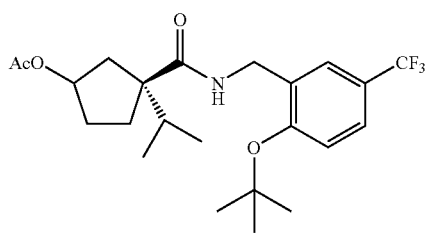

A cooled (0° C.) solution of (1S)—N-[2-tert-butoxy-5-(trifluoromethyl)benzyl]-1-isopropyl-3-oxocyclopentanecarboxamide (1.37 g, 3.43 mmol) in 10 mL of methanol was treated with sodium borohydride (130 mg, 3.43 mmol). After stirring at 0° C for 10 min, the reaction mixture was permitted to warm to rt and stir for an additional 1 h. The reaction mixture was concentrated and the residue was partitioned between DCM and water. The organic layer was washed with brine, dried over anhydrous MgSO$_4$, filtered, and concentrated to afford a mixture of cis/trans alcohols. The crude mixture of alcohols was dissolved in DCM (20 mL) and treated with acetic anhydride (0.39 mL, 4.1 mmol), triethylamine (0.57 mL, 4.1 mmol) and DMAP (25 mg). The resulting mixture was stirred at rt for 2 days (the reaction is complete after a few hours). The reaction mixture was diluted with DCM and washed with 1N HCl solution, saturated NaHCO$_3$ solution, and brine. The organic layer was dried over anhydrous MgSO$_4$, filtered, and concentrated. The crude product was purified by MPLC (silica, 50% ethyl acetate/hexanes) to give the acetate product as a mixture of two diastereomers (cis and trans isomers).

HPLC-MS Peak 1: ESI-MS calc. for C23H32F3NO4: 443; Found: 466 (M+Na$^+$).

HPLC-MS Peak 2: ESI-MS calc. for C23H32F3NO4: 443; Found: 466 (M+Na$^+$).

Step B:

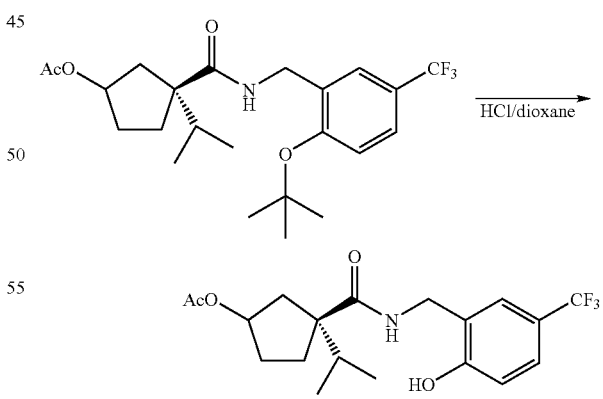

The mixture of cis/trans acetates from Step A (1.13 g, 2.55 mmol) was dissolved in 4N HCl in dioxane (Aldrich, 20 mL). The resulting mixture was stirred at rt for 1.25 h, then was concentrated and stored under vacuum overnight to give 1.08 g of crude product. ESI-MS calc. for C19H24F3NO4: 387; Found: 410 (M+Na$^+$).

Step C:

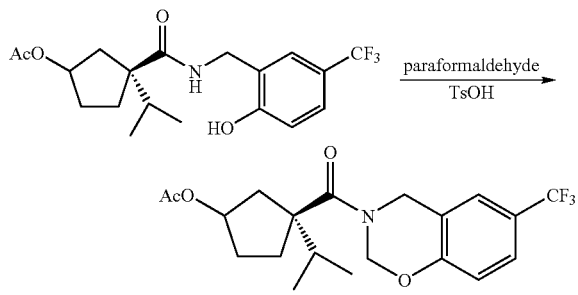

The phenol prepared as described in Step B (1.16 g crude, 2.84 mmol) was combined with paraformaldehyde (~1 g) and TsOH H$_2$O (~20 mg) in 40 mL of toluene. The flask was equipped with a Dean-Stark trap and condenser and the reaction mixture was stirred at reflux for 2.5 h. Since HPLC-MS analysis indicated that approximately 20% of the starting material remained, an additional portion of paraformaldehyde (~250 mg) was added and the mixture was stirred at reflux for 1 h. The reaction mixture was concentrated and the resulting residue was dissolved in DCM and filtered to remove any remaining paraformaldehyde. The filtrate was concentrated and purified by MPLC (silica, 50% ethyl acetate/hexanes) to give (3S)-3-isopropyl-3-{[6-(trifluoromethyl)-2H-1,3-benzoxazin-3(4H)-yl]carbonyl}cyclopentyl acetate as a mixture of two isomers (cis/trans).

HPLC-MS Peak 1: ESI-MS calc. for C20H24F3NO4: 399; Found: 422 (M+Na$^+$).

HPLC-MS Peak 2: ESI-MS calc. for C20H24F3NO4: 399; Found: 422 (M+Na$^+$).

Step D:

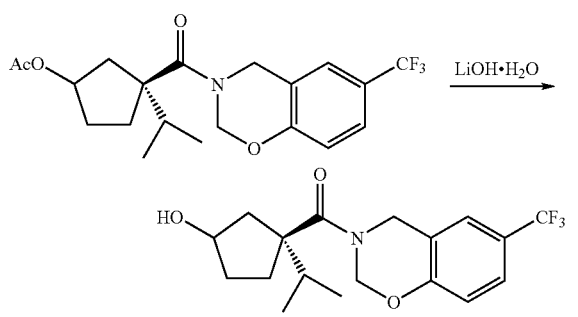

A solution of (3S)-3-isopropyl-3-{[6-(trifluoromethyl)-2H-1,3-benzoxazin-3(4H)-yl]carbonyl}cyclopentyl acetate (935 mg, 2.34 mmol) was treated with a solution of LiOH H$_2$O (491 mg, 11.7 mmol) in deionized water (5 mL). The resulting reaction mixture was stirred at rt for 40 min, then was diluted with brine and extracted with ether. The ethereal layer was dried over anhydrous MgSO$_4$, filtered, and concentrated to give (3S)-3-isopropyl-3-{[6-(trifluoromethyl)-2H-1,3-benzoxazin-3(4H)-yl]carbonyl}cyclopentanol (a mixture of two isomers), which was used as is.

HPLC-MS Peak 1: ESI-MS calc. for C18H22F3NO3: 357; Found: 380 (M+Na$^+$).

HPLC-MS Peak 2: ESI-MS calc. for C18H22F3NO3: 357; Found: 380 (M+Na$^+$).

Step E:

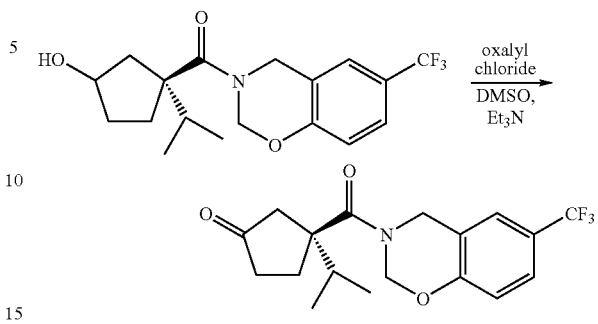

A solution of DMSO (0.656 mL, 9.24 mmol) in 7 mL of DCM was added dropwise to a cooled (−78° C.) solution of oxalyl chloride (0.403 mL, 4.62 mmol) in 30 mL of DCM. After 5 min, a solution of (3S)-3-isopropyl-3-{[6-(trifluoromethyl)-2H-1,3-benzoxazin-3(4H)-yl] carbonyl}cyclopentanol (826 mg, 2.31 mmol) in 8 mL of DCM was added dropwise. The reaction mixture was stirred at −78° C. for 25 min, then was treated dropwise with neat triethylamine (2.58 mL, 18.5 mmol). After stirring at −78° C. for an additional 10 min, the reaction mixture was allowed to warm to rt and stir for 1.5 h. The mixture was then poured into 1N HCl solution and extracted with DCM. The organic layer was washed with more 1N HCl solution, then with saturated NaHCO$_3$ solution and brine. The organic layer was then dried over anhydrous MgSO$_4$, filtered, and concentrated. The crude product was purified by MPLC (silica, 75% ethyl acetate/hexanes) to provide (3S)-3-isopropyl-3-{[6-(trifluoromethyl)-2H-1,3-benzoxazin-3(4H)-yl] carbonyl}cyclopentanone.

ESI-MS calc. for C18H20F3NO3: 355; Found: 356 (M+H).

Intermediate 6

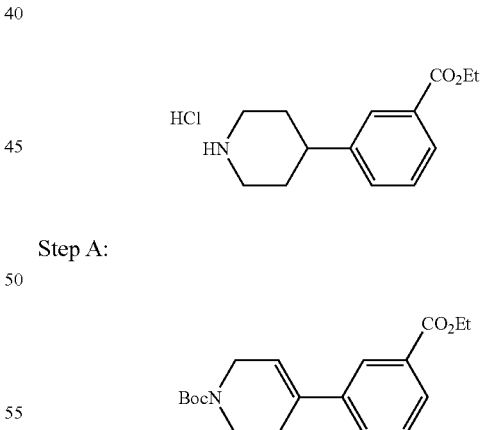

Step A:

To a mixture of tert-butyl 4-{[(trifluoromethyl)sulfonyl] oxy}-3,6-dihydropyridine-1(2H)-carboxylate (prepared according to Wustrow, D. J., Wise, L. D., *Synthesis,* (1991), 993-995.; 10.5 g, 31.6 mmol), 3-(ethoxycarbonyl)phenylboronic acid (8.59 g, 44.3 mmol), lithium chloride (3.98 g, 94.8 mmol), and 2 M Na$_2$CO$_3$ solution (44 mL) in DME (107 mL) was added Pd(PPh$_3$)$_4$ (1.82 g, 1.58 mmol), and the resulting mixture was stirred at reflux under a nitrogen atmosphere for 3.5 h. The reaction mixture was cooled to rt, stirred overnight, then partially concentrated to remove most of the DME. To the remaining aqueous mixture was added DCM, 2M Na₂CO₃ solution, and ~10 mL of 28% NH₄OH solution. The layers were separated and the organic layer was washed with brine, dried over anhydrous MgSO₄, filtered, and concentrated. Purification by flash chromatography (silica, 10% ethyl acetate/hexanes eluent) afforded tert-butyl 4-[3-(ethoxycarbonyl)phenyl]-3,6-dihydropyridine-1(2H)-carboxylate. ¹HNMR (CDCl₃, 500 MHz): δ 8.07 (s, 1H), 7.95 (d, J=7.5 Hz, 1H), 7.58 (d, J=8.0 Hz, 1H), 7.43 (t, J=8.0 Hz, 1H), 6.13 (br s, 1H), 4.41 (q, J=7.0 Hz, 2H), 4.12 (br s, 2H), 3.68 (t, J=5.5 Hz, 2H), 2.58 (br s, 2H), 1.52 (s, 9H), 1.43 (t, J=7.0 Hz, 3H).

Step B:

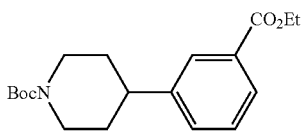

A mixture of tert-butyl 4-[3-(ethoxycarbonyl)phenyl]-3,6-dihydropyridine-1(2H)-carboxylate (6.48 g, 19.6 mmol) and Pd(OH)₂/C (20% Pd, 1g) in 50 mL of methanol was stirred under a hydrogen atmosphere (balloon) for 18 h. The reaction mixture was then filtered through a celite plug, and the filtrate was concentrated to give tert-butyl 4-[3-(ethoxycarbonyl)phenyl]piperidine-1-carboxylate which did not require further purification. ¹HNMR (CDCl₃, 500 MHz): δ 7.91 (m, 2H), 7.40 (m, 2H), 4.40 (q, J=7.0 Hz, 2H), 4.28 (br s, 2H), 2.83 (m, 2H), 2.73 (tt, J=12.5, 4.0 Hz, 1H), 1.85 (br d, J=13.0 Hz), 1.67 dq, J=4.0, 12.5 Hz, 2H), 1.51 (s, 9H), 1.42 (t, J=7.0 Hz).

Step C:

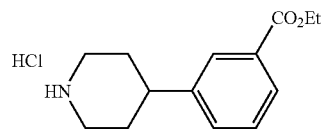

tert-Butyl 4-[3-(ethoxycarbonyl)phenyl]piperidine-1-carboxylate (3.24 g, 9.72 mmol) was dissolved in anhydrous 4N HCl in dioxane (ca. 30 mL) and stirred at rt for 1.5 h. The reaction mixture was concentrated to give ethyl 3-piperidin-4-ylbenzoate hydrochloride as a pale yellow solid that required no further purification.

ESI-MS calc. for C14H19N02: 233; Found: 234 (M+H).

EXAMPLE 1

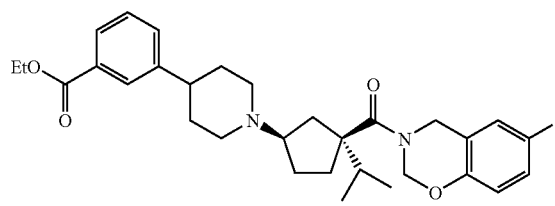

A mixture of ethyl 3-piperidin-4-ylbenzoate hydrochloride (483 mg, 1.79 mmol), (3S)-3-isopropyl-3-{[6-(trifluoromethyl)-2H-1,3-benzoxazin-3(4H)-yl]carbonyl}cyclopentanone (318 mg, 0.896 mmol), triethylamine (375 μL, 2.69 mmol), 4 Å powdered molecular sieves (~500 mg), and sodium triacetoxyborohydride (949 mg, 4.48 mmol) in 15 mL of DCM was stirred at rt for 5 days (3 days is usually sufficient). The reaction mixture was diluted with DCM and washed with saturated NaHCO₃ solution followed by brine. The organic layer was dried over anhydrous MgSO₄, filtered, and concentrated. Purification by flash chromatography {silica, 4% of [10% NH₄OH solution (28%)/methanol] in DCM} afforded the product as a mixture of cis and trans product isomers. The cis (ethyl 3-[1-((1R,3S)-3-isopropyl-3-{[6-(trifluoromethyl)-2H-1,3-benzoxazin-3(4H)-yl]carbonyl}cyclopentyl)piperidin-4-yl]benzoate) and trans (ethyl 3-[1-((1S,3S)-3-isopropyl-3-{[6-(trifluoromethyl)-2H-1,3-benzoxazin-3(4H)-yl]carbonyl}cyclopentyl)piperidin-4-yl]benzoate) isomers were separated by preparative TLC (silica, 40% TFff/hexanes eluent) to give the higher eluting (cis) isomer and the lower eluting (trans) isomer. Analysis of the separated cis and trans product isomers by chiral analytical HPLC (chiralcel OD column, 10% ethanol/hexanes) showed each to be clean single isomers.

Higher eluting (cis) isomer ESI-MS calc. for C32H39F3N2O4: 572; Found: 573 (M+H).

Lower eluting (trans) isomer ESI-MS calc. for C32H39F3N2O4: 572; Found: 573 (M+H).

In some cases where the amines used in the reductive amination reactions were themselves mixtures of more than one stereoisomer (i.e., if they had one or more stereocenters), it was generally possible to separate all possible isomers using chiral HPLC and or preparative TLC (sometimes a series of separations was required). For a representative example of how this is accomplished see EXAMPLE 3.

EXAMPLE 2

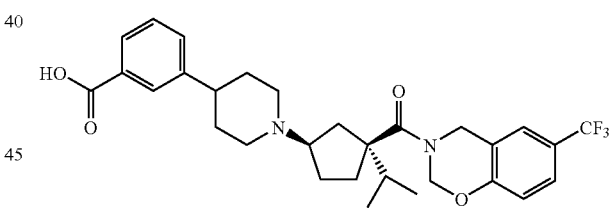

To a solution of ethyl 3-[1-((1R,3S)-3-isopropyl-3-{[6-(trifluoromethyl)-2H-1,3-benzoxazin-3(4H)-yl]carbonyl}cyclopentyl)piperidin-4-yl]benzoate (225 mg, 0.393 mmol) in ethanol (10 mL) was added a solution of LiOH H₂O (165 mg, 3.93 mmol) in 10 mL of deionized water. The resulting mixture was stirred at 50° C. for 1.5 h, then was partially concentrated to remove most of the ethanol. To the resulting aqueous mixture was added brine and chloroform. The pH of the aqueous layer was adjusted to ~7 with 1M HCl solution (~2.5-3 mL). The layers were separated and the aqueous layer was extracted two more times with chloroform. The organic layers were combined and dried over anhydrous MgSO₄, filtered, and concentrated to give crude product. Purification by reverse phase HPLC (YMC Pack Pro C 18, 100×20 mm ID) gave the product as its TFA salt. This was converted to its HCl salt by dissolving in DCM and adding excess 1N HCl/ether, then concentrating to give 3-[1-((1R, 3S)-3-isopropyl-3-{[6-(trifluoromethyl)-2H-1,3-benzoxazin-3(4H)-yl]carbonyl}cyclopentyl)piperidin-4-yl]benzoic acid hydrochloride. ESI-MS calc. for C30H35F3N2O4: 544; Found: 545 (M+H).

Intermediate 7

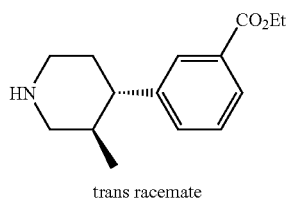

trans racemate

Procedure A

Step A:

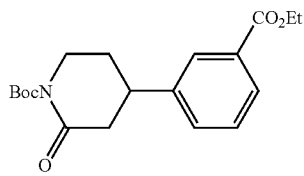

To a stirred solution of tert-butyl 4-[3-(ethoxycarbonyl)phenyl]piperidine 1-carboxylate (48 g, 220 mmol) in chloroform (900 mL) was added ruthenium (IV) oxide hydrate (6.0 g, 45 mmol) followed by a solution of sodium periodate (150 g, 700 mmol) in water (900 m L). The resulting heterogenous reaction mixture was stirred at room temperature for 11 days before being filtered through a short column of celite. The organic layer was removed and the aqueous layer was extracted twice with DCM. The combined organic layers were washed with a 10% solution of sodium thiosulfate in water twice, and once with brine. This solution was dried over MgSO4, filtered, and concentrated under reduced pressure. The product was purified by flash chromatography (silica gel, 20% EA/hexanes) to give 22.5 g (64.8 mmol) of tert-butyl 4-[3-(ethoxycarbonyl)phenyl]-2-oxopiperidine-1-carboxylate (29%).

ESI-MS calculated for C19H25NO5: 347.17; found 370.1 (M+Na)

Step B:

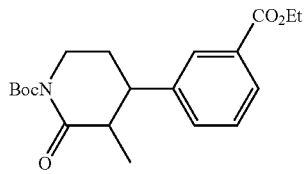

Potassium bis(trimethylsilyl)amide (14 g, 71 mmol) was mixed with 300 mL of THF in a 1000 mL flame-dried round bottomed flask and the resulting mixture was cooled to −78° C. tert-butyl 4-[3-(ethoxycarbonyl)phenyl]-2-oxopiperidine-1-carboxylate (22.5 g, 64.8 mmol) dissolved in 150 mL of THF was added slowly to the mixture, via an addition funnel, and the resulting reaction mixture was stirred at −78° C. for 30 min. Methyl iodide (12.1 mL, 195 mmol) was then added dropwise and the reaction mixture was allowed to stir at −78° C. for 4 h before being allowed to warm to room temperature overnight. The reaction was quenched with saturated ammonium chloride and extracted 3 times with ether. The combined ethereal layers were washed with brine and dried over MgSO4, filtered, and concentrated under reduced pressure. The product was purified by flash chromatography (10-20% EA/hexanes) to give 6.1 g of the trans racemate of tert-butyl 4-[3-(ethoxycarbonyl)phenyl]-3-methyl-2-oxopiperidine-1-carboxylate (26%).

ESI-MS calculated for C20H27NO5: 361.19; found 384.25 (M+Na).

Step C:

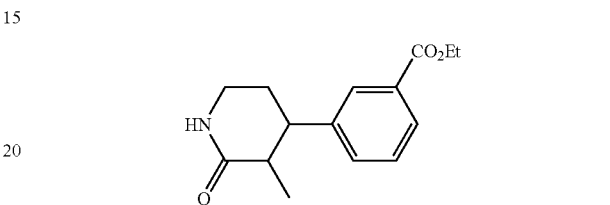

The product from Step B (6.1 g, 17 mmol) was dissolved in 4.0 M HCl in dioxane and stirred at room temperature for 2 h before being concentrated under reduced pressure to give the desired product as an orange solid which was sued directly in the next step without further purification.

ESI-MS calculated for C15H19NO3: 261.14; found 262.1 (M+H).

Step D:

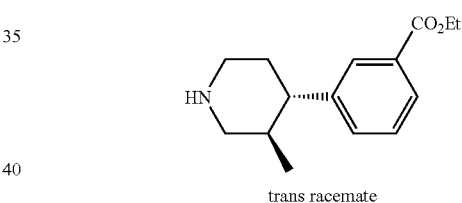

trans racemate

The product from the previous step (entire amount ~17 mmol) was dissolved in THF (100 mL) and treated dropwise with 2.0 M borane-methyl sulfide solution in THF (31 mL, 62 mmol). The resulting solution was stirred at room temperature for 4 h before being stored at 4° C. for 72 h. The solvent was removed under reduced pressure and the resulting residue was dissolved in 0.5 M HCl (aqueous ~38%) in ethanol. This solution was heated to 50° C. and stirred for 4 h. The solvent was removed and the procedure was repeated again to ensure the break up of the borane complex. The solvent was removed and the product was purified by MPLC (0-15% (10% NH4OH/MeOH)/DCM) to give the desired product which was 80% pure. This crude material was dissolved in DCM (100 mL) and treated with di-tert-butyl dicarbonate (2.95 g, 13.5 mmol), diisopropylethylamine (2.30 mL, 13.5 mmol) and DMAP (10 mg). The resulting reaction mixture was stirred overnight at room temperature before being diluted with DCM and washed with 1 N aqueous, aqueous saturated sodium bicarbonate, and brine. The organic layer was dried over MgSO4, filtered and concentrated under reduced pressure. The intermediate was purified by MPLC (0-40% EA/hexanes). The resulting colorless oil was dissolved in 4.0 M HCl in dioxane and the resulting reaction mixture was stirred at room temperature for 1.5 h. The reaction mixture was concentrated to dryness to give 2.13 g (7.52 mmol) of the desired HCl salt.

ESI-MS calculated for C15H21NO2: 247.16; found 248.15 (M+H).

Procedure B

Step A:

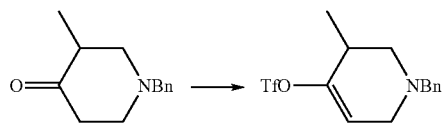

A solution of 1-benzyl-3-methylpiperidin-4-one (48 g, 0.24 mol) in THF (200 mL) was added dropwise to a cooled (−78° C.) solution of sodium bis(trimethylsilyl)amide (2M in THF, 141 mL, 0.28 mol) in THF (100 mL). The resulting dark orange mixture was stirred at −78° C. for 2 hr after which a solution of N-phenyl-bis(trifluoromethanesulfonimide) (100 g, 0.28 mol) in THF (300 mL) was added dropwise. The mixture was allowed to warm to r.t. and stirred for 3 hr. Most of the THF was removed in vacuo. The residue was partitioned between Ether and aqueous 1M NaOH. The organic layer was then washed repeatedly with aqueous 1M NaOH, dried over sodium sulfate, and evaporated to dryness. The dark orange residue was then dissolved in CH$_2$Cl$_2$ and filtered through a silica gel plug eluting with CH$_2$Cl$_2$. The desired 1-benzyl-3-methyl-1,2,3,6-tetrahydropyridin-4-yl trifluoromethanesulfonate (79 g) was obtained as a yellow oil.

Step B:

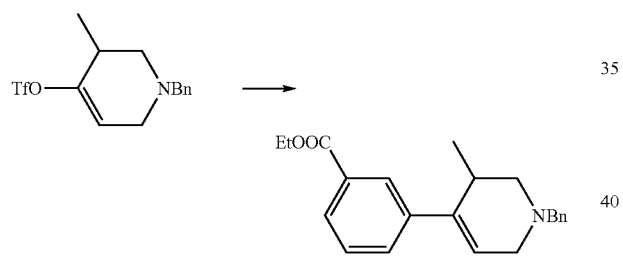

Ethyl 3-(1-benzyl-3-methyl-1,2,3,6-tetrahydropyridin-4-yl)benzoate was synthesized as described for INTERMEDIATE 6 (step A) using 1-benzyl-3-methyl-1,2,3,6-tetrahydropyridin-4-yl trifluoromethanesulfonate and [3-(ethoxycarbonyl)phenyl]boronic acid as starting materials.

Step C:

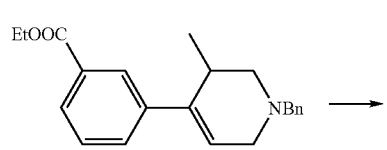

Ethyl 3-(1-benzyl-3-methyl-1,2,3,6-tetrahydropyridin-4-yl)benzoate (32.5 g, 98 mmol) was dissolved in EtOAc (400 mL) and was hydrogenated for 18 hr with a hydrogen balloon in the presence of a catalytic amount (1.1 g) of platinum oxide. Platinum oxide was filtered through a celite plug and the filtrate was evaporated to dryness. The resulting yellow oil was purified by column chromatography on silica gel eluting with a gradient of hexane:EtOAc.

Less polar compound: ethyl 3-[(3R,4R)-1-benzyl-3-methylpiperidin-4-yl]benzoate as a mixture of two diastereomers More polar compound: desired ethyl 3-[(3R,4S)-1-benzyl-3-methylpiperidin-4-yl]benzoate) as a mixture of two diastereomers (9 g, 24%).

Step D:

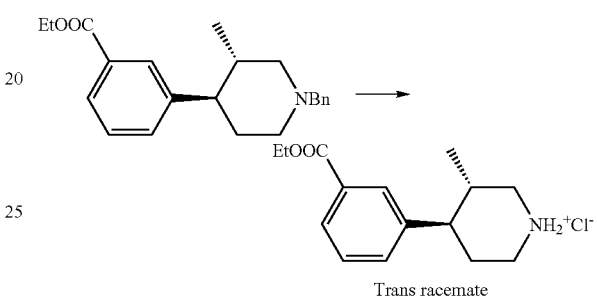

Ethyl 3-[(3S,4R)-1-benzyl-3-methylpiperidin-4-yl]benzoate (9 g, 26.7 mmol) was dissolved in EtOH:1M HCl (1:1, 160 mL) and was hydrogenated at 50 psi in the presence of a catalytic amount of palladium on carbon (1 g) for 36 hr. Palladium was filtered through a celite plug and the filtrate was evaporated to dryness to give 7.2 g of ethyl 3-[(3S,4R)-3-methylpiperidin-4-yl]benzoate as an HCl salt.

Intermediate 8

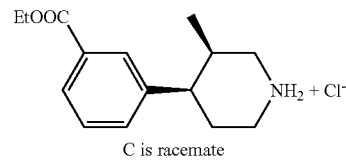

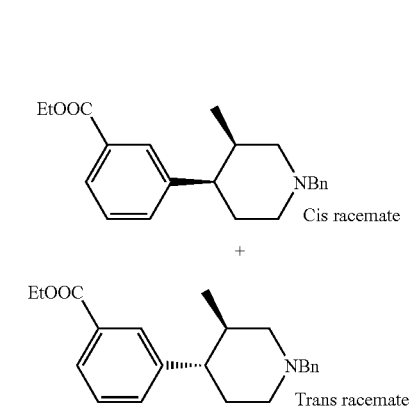

Ethyl 3-[(3R,4R)-3-methylpiperidin-4-yl]benzoate was synthesized as described for INTERMEDIATE 7 (procedure B, step D) using ethyl 3-[(3R,4R)-1-benzyl-3-methylpiperidin-4-yl]benzoate as starting material.

EXAMPLE 3

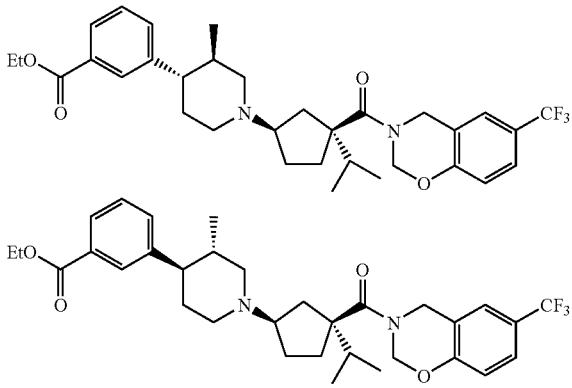

INTERMEDIATE 7 (amine) (830 mg, 2.93 mmol) was combined with INTERMEDIATE 5 (990 mg, 2.78 mmol) and diisopropylethylamine (501 μL, 2.93 mmol) in DCM (50 mL). After stirring for 10 min, this solution was treated sequentially with powdered 4 Å molecular sieves (1 g) and sodium triacetoxyborohydride (2.48 g, 11.7 mmol). The resulting reaction mixture was allowed to stir at room temperature for 4 days before being partitioned between DCM and a half saturated aqueous solution of sodium bicarbonate. The aqueous layer was back extracted 3 times with DCM. The combined organic layers were washed with brine and dried over $Na_2SO_4$, filtered, and concentrated under reduced pressure. The resulting crude product was purified by MPLC (0-10% (10% $NH_4OH$/MeOH)/DCM) to give 1.3 g of a mixture of 4 stereoisomers. The individual stereoisomers where resolved by chiral HPLC using a ChiralCel OD column, eluting with 8% ethanol/hexanes: (The two desired cis (about cyclopentane) isomers were the $3^{rd}$ and $4^{th}$ peaks)

Peak 1: 260 mg isomer—ESI-MS calculated for C33H41F3N2O3: 586.30, found 587.65 (M+H).

Peak 2: 220 mg isomer—ESI-MS calculated for C33H41F3N2O3: 586.30, found 587.65 (M+H).

Peak 3: 300 mg isomer—ESI-MS calculated for C33H41F3N2O3: 586.30, found 587.65 (M+H).

Peak 4: 280 mg isomer—ESI-MS calculated for C33H41F3N2O3: 586.30, found 587.65 (M+H).

EXAMPLE 4

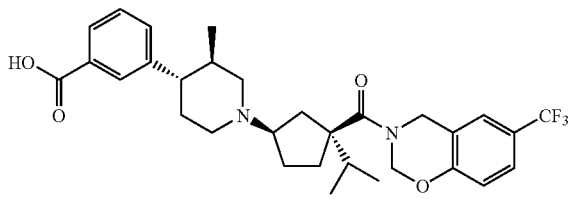

-continued

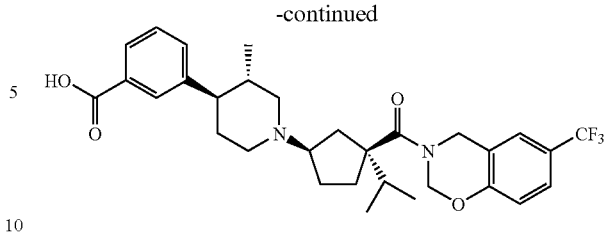

Separately, Peak 3 (8 mg, 0.01 mmol) and Peak 4 (8 mg, 0.01 mmol) from Example 3 were dissolved in ethanol (2 mL) and treated with a solution of lithium hydroxide (10 mg) in water (1 mL). The resulting solutions were stirred at room temperature for 22 h before being concentrated to dryness. The resulting crude products were purified by reverse phase HPLC (C18, 0-100% MeCN/$H_2O$) and converted to their HCl salts by dissolving the products in DCM and treating the resulting solutions with 2.0 M HCl in ether and hexanes sequentially. The cloudy solutions were concentrated to dryness to give 6.41 mg (from Peak 3) and 4.66 mg (from Peak 4) of the desired products, respectively. (from Peak 3): ESI-MS calculated for C31H37F3N2O3: 558.27, found 559.6 (M+H). (from Peak 4): ESI-MS calculated for C31H37F3N2O3: 558.27, found 559.6 (M+H).

Intermediate 9

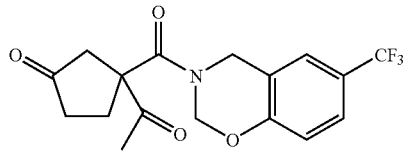

Step A:

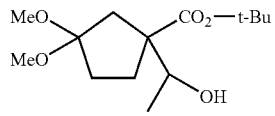

To a cooled (−78° C.) solution of LDA (2M in THF/heptane, 39 mL, 78 mmol) in THF (40 mL) was added dropwise over 15 min tert-butyl 3,3-dimethoxycyclopentanecarboxylate (15.0 g, 65.0 mmol) in 100 mL of THF. The resulting mixture was stirred at −78° C. for 40 min, then was treated dropwise with acetaldehyde (7.27 mL, 130 mmol). After stirring for an additional 45 min, the reaction mixture was poured into 500 mL of 10% citric acid solution. The mixture was extracted twice with ether and the combined ethereal layers were washed with brine. The ethereal layer was then dried over anhydrous $MgSO_4$, filtered, and concentrated. TLC analysis indicated that the reaction had not gone to completion and a considerable amount of starting material was still present. Purification/separation by flash chromatography (silica, 30% ethyl acetate/hexane) gave the tert-butyl 1-(1-hydroxyethyl)-3,3-dimethoxycyclopentanecarboxylate as an approximately 1:1 ratio of threo and erythro diastereomer pairs and recovered tert-butyl 3,3-dimethoxycyclopentanecarboxylate.

Step B:

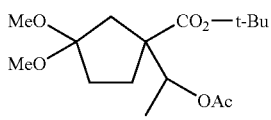

A solution of tert-butyl 1-(1-hydroxyethyl)-3,3-dimethoxycyclopentanecarboxylate (8.64 g, 31.5 mmol) in 100 mL of DCM was treated with triethylamine (8.78 mL, 63.0 mmol) followed by acetic anhydride (5.94 mL, 63.0 mmol). Then DMAP (~200 mg) was added and the resulting mixture was stirred at rt overnight. The reaction mixture was diluted with DCM, washed twice with 1N HCl solution, once with saturated NaHCO₃ solution, and once with brine. The organic layer was dried over anhydrous MgSO₄, filtered, and concentrated. Purification by flash chromatography (silica, 20% ethyl acetate/hexanes) provided tert-butyl 1-[1-(acetyloxy)ethyl]-3,3-dimethoxycyclopentanecarboxylate.

Step C:

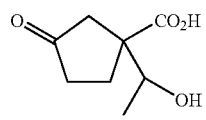

tert-Butyl 1-[1-(acetyloxy)ethyl]-3,3-dimethoxycyclopentanecarboxylate (8.04 g, 25.4 mmol) was dissolved in anhydrous 4N HCl in dioxane (ca. 50 mL) and 5 mL of water was added (this was a mistake which led to inadvertent hydrolysis of the acetate). The reaction mixture was stirred at rt for 5 h, then was concentrated. Purification by flash chromatography (silica, 8% methanol/DCM) afforded 1-(1-hydroxyethyl)-3-oxocyclopentanecarboxylic acid.

¹HNMR (CDCl₃, 500 MHz): δ 4.09 (q, J=6.5 Hz, 1H, d1 diastereomer), 3.99 (q, J=6.5 Hz, 1H, d2 diastereomer), 2.73-2.78 (m, 2H, d1+d2), 2.37-2.52 (m, ca 7H, d1+d2), 2.13-2.24 (m, ca 3H, d1+d2), 1.30 (d, J=6.5 Hz, 3H, d1 isomer?), 1.29 (d, J=6.5 Hz, 3H, d2 isomer?).

Step D:

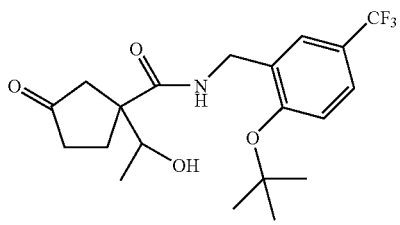

A mixture of 1-(1-hydroxyethyl)-3-oxocyclopentanecarboxylic acid (3.54 g, 20.6 mmol), 1-hydroxy-7-azabenzotriazole (4.14 g, 30.9 mmol), and EDC (5.92 g, 30.9 mmol) in 70 mL of DCM was stirred at rt for 10 min then 1-[2-tert-butoxy-5-(trifluoromethyl)phenyl]methanamine (5.08 g, 20.6 mmol) was added in 10 mL of DCM. The resulting mixture was stirred at rt for 50 min, then was diluted with DCM and washed with water followed by brine. The organic layer was dried over anhydrous MgSO₄, filtered, and concentrated. Purification by MPLC (silica, 85% ethyl acetate/hexanes) provided N-[2-tert-butoxy-5-(trifluoromethyl)benzyl]-1-(1-hydroxyethyl)-3-oxocyclopentanecarboxamide as a mixture of threo and erythro enantiomer pairs.

Step E:

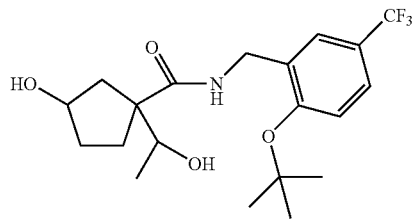

A cooled (0° C.) solution of N-[2-tert-butoxy-5-(trifluoromethyl)benzyl]-1-(1-hydroxyethyl)-3-oxocyclopentanecarboxamide (6.27 g, 15.6 mmol) in methanol was treated with sodium borohydride (591 mg, 15.6 mmol) and stirred for 20 min. The reaction mixture was concentrated and the residue was partitioned between DCM and water. The organic layer was washed with brine, dried over anhydrous MgSO₄, filtered, and concentrated to give N-[2-tert-butoxy-5-(trifluoromethyl)benzyl]-3-hydroxy-1-(1-hydroxyethyl)cyclopentanecarboxamide as a mixture of 8 isomers.

Step F:

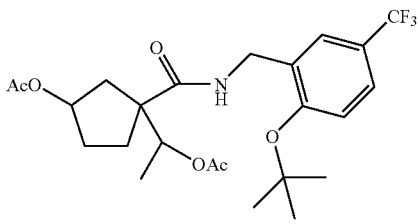

A cooled (0° C.) solution of N-[2-tert-butoxy-5-(trifluoromethyl)benzyl]-3-hydroxy-1-(1-hydroxyethyl)cyclopentanecarboxamide (6.03 g, 14.9 mmol) in 75 mL of DCM was treated with triethylamine (6.24 mL, 44.8 mmol), acetic anhydride (4.23 mL, 44.8 mmol), and DMAP (ca. 100 mg). The reaction mixture was permitted to warm to rt and after an additional 2.5 h was diluted with DCM and washed in succession with 1N HCl solution, saturated NaHCO₃ solution, and brine. The organic layer was dried over anhydrous MgSO₄, filtered, and concentrated. Purification by MPLC (silica, 60% ethyl acetate/hexanes) provided 1-[3-(acetyloxy)-1-({[2-tert-butoxy-5-(trifluoromethyl)benzyl]amino}carbonyl)cyclopentyl]ethyl acetate as a mixture of 8 diastereomers. ESI-MS calc. for C24H32F3NO6: 478; Found: 510 (M+Na⁺).

Step G:

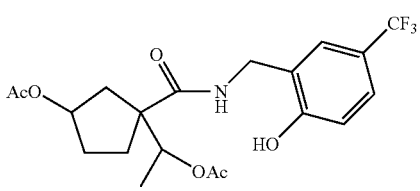

1-[3-(Acetyloxy)-1-({[2-tert-butoxy-5-(trifluoromethyl)benzyl]amino}carbonyl)cyclopentyl]ethyl acetate (7.0 g, 14.4 mmol) was dissolved in anhydrous 4N HCl in dioxane (40 mL) and stirred at rt for 65 min. The reaction mixture was then concentrated to give 3-[1-(acetyloxy)ethyl]-3-({[2-hydroxy-5-(trifluoromethyl)benzyl]amino}carbonyl)cyclopentyl acetate.

ESI-MS calc. for C20H24F3NO6: 431; Found: 432 (M+).

Step H:

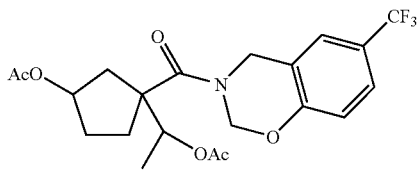

3-[1-(Acetyloxy)ethyl]-3-({[2-hydroxy-5-(trifluoromethyl)benzyl]amino}carbonyl)cyclopentyl acetate was combined with paraformaldehyde (ca. 6 g) and TsOH H$_2$O (ca. 100 mg) in 130 mL of toluene. The flask was equipped with a Dean Stark trap and condenser and the reaction mixture was stirred at reflux for 1.5 h. The reaction mixture was filtered to remove remaining paraformaldehyde and the filtrate was concentrated. Purification of the resulting residue was accomplished by MPLC (silica, 65% ethyl acetate/hexanes) to afford 3-[1-(acetyloxy)ethyl]-3-{[6-(trifluoromethyl)-2H-1,3-benzoxazin-3(4H)-yl]carbonyl}cyclopentyl acetate as a mixture of 8 diastereomers.

ESI-MS calc. for C21H24F3NO6: 443; Found: 444 (M+).

Step I:

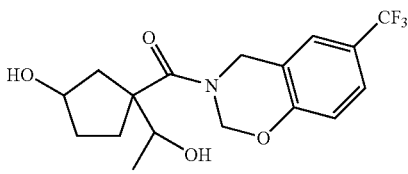

A solution of 3-[1-(acetyloxy)ethyl]-3-{[6-(trifluoromethyl)-2H-1,3-benzoxazin-3(4H)-yl]carbonyl}cyclopentyl acetate (5.50 g, 12.4 mmol) in 1:1 methanol/THF (40 mL) at 0° C. was treated dropwise with a solution of LiOH H$_2$O (520 mg, 12.4 mmol) in deionized water (20 mL). The resulting mixture was stirred at between −10 and 0° C. for 1 h, then was concentrated at rt. The residue was partitioned between ether and brine. The aqueous layer was extracted a second time with ether and the ethereal layers were combined and dried over anhydrous MgSO$_4$, filtered, and concentrated. Analysis by H NMR and ESI-MS revealed that the diol was obtained rather then the desired monoacetate, indicating that the hydrolysis was not selective. The resulting 3-(1-hydroxyethyl)-3-{[6-(trifluoromethyl)-2H-1,3-benzoxazin-3(4H)-yl]carbonyl}cyclopentanol was used without further purification in the following step.

ESI-MS calc. for C17H20F3NO4: 359; Found: 360 (M+).

Step J:

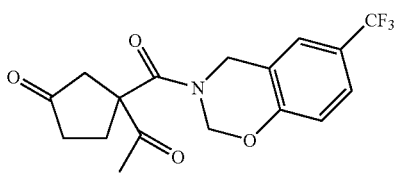

A precooled (−78° C.) solution of oxalyl chloride (2.82 mL, 32.4 mmol) in 150 mL of DCM was treated dropwise with a solution of DMSO (4.60 mL, 64.8 mmol) in 25 mL of DCM. After an additional 5 min, a solution of 3-(1-hydroxyethyl)-3-{[6-(trifluoromethyl)-2H-1,3-benzoxazin-3(4H)-yl]carbonyl}cyclopentanol (4.33 g, 10.8 mmol) in 25 mL of DCM was added dropwise. The reaction mixture was stirred for an additional 30 min, then neat triethylamine (18.1 mL, 130 mmol) was added dropwise. The mixture was stirred for an additional 10 min, then was warmed to rt and stirred for 1.5 h. The reaction mixture was poured into 1N HCl solution and the resulting mixture was extracted with DCM. The organic layer was washed again with 1N HCl solution, then with saturated NaHCO$_3$ solution, and finally with brine. The organic layer was dried over anhydrous MgSO$_4$, filtered, and concentrated. Purification by MPLC (silica, 75% ethyl acetate/hexanes) gave 3-acetyl-3-{[6-(trifluoromethyl)-2H-1,3-benzoxazin-3(4H)-yl]carbonyl}cyclopentanone as a mixture of two enantiomers. ESI-MS calc. for C17H16F3NO4: 355; Found: 356 (M+).

EXAMPLE 5

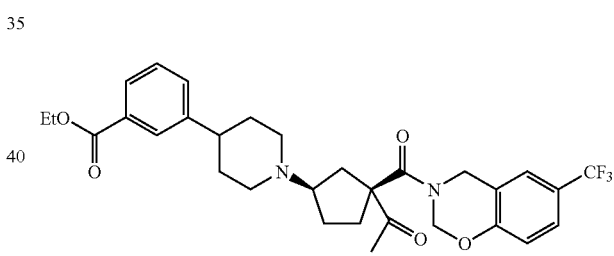

3-Acetyl-3-{[6-(trifluoromethyl)-2H-1,3-benzoxazin-3(4h)-yl]carbonyl}cyclopentanone (504 mg, 1.42 mmol) was combined with ethyl 3-piperidin-4-ylbenzoate hydrochloride (670 mg, 2.49 mmol), triethylamine (347 µL, 2.49 mmol), 4 Å powdered molecular sieves (ca. 1 g), and sodium triacetoxyborohydride (1.81 g, 8.52 mmol) in 20 mL of DCM. The resulting mixture was stirred at rt for 4 days. The reaction mixture was diluted with DCM and washed with saturated NaHCO$_3$ solution, then with brine. The organic layer was dried over anhydrous MgSO$_4$, filtered, and concentrated. Purification by flash chromatography (silica, 5% methanol/DCM) afforded the desired product as a mixture of 4 isomers. Separation of all four isomers could be achieved by sequential injections using two chiral HPLC conditions (chiralcel OD column, 2 cm×25 cm, 15% ethanol/hexanes, then chiralpak AD column, 2 cm×25 cm, 60% ethanol/hexanes; both columns are available from Chiral Technologies, Inc.). The first separation gives three peaks, where the 1$^{st}$ (132 mg) and 3$^{rd}$ (131 mg) peaks are single enantiomers and the second peak (315 mg) is a mixture of two isomers. The second separation (of peak-2) gives two single enantiomers from peaks 2-1 (98 mg) and 2-2 (116 mg). Peak 3 from the first separation conditions was found to contain the isomer having the best potency, presumed by analogy to be ethyl 3-[1-((1R,3S)-3-acetyl-3-{[6-(trifluoromethyl)-2H-1,3-benzoxazin-3(4H)-yl]carbonyl}cyclopentyl)piperidin-4-yl]benzoate.

Isomer from pk 1 ESI-MS calc. for C31H35F3N2O5: 572; Found: 573 (M+).

Isomer from pk 2-1 ESI-MS calc. for C31H35F3N2O5: 572; Found: 573 (M+).

Isomer from pk 2-2 ESI-MS calc. for C31H35F3N2O5: 572; Found: 573 (M+).

Isomer from pk 3 ESI-MS calc. for C31H35F3N2O5: 572; Found: 573 (M+).

EXAMPLE 6

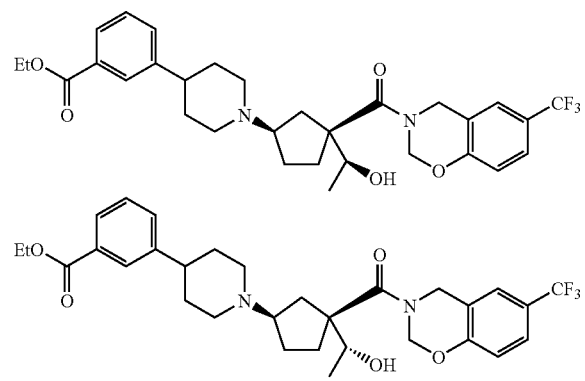

A cooled (0° C.) solution of ethyl 3-[1-((1R,3S)-3-acetyl-3-{[6-(trifluoromethyl)-2H-1,3-benzoxazin-3(4H)-yl]carbonyl}cyclopentyl)piperidin-4-yl]benzoate (129 mg, 0.224 mmol) in methanol (5 mL) was treated with sodium borohydride (17 mg, 0.45 mmol), stirred for 35 min, and concentrated. To the residue was added brine and this mixture was extracted twice with DCM. The combined organic layers were dried over anhydrous MgSO₄, filtered, and concentrated. Separation of the two diastereomeric alcohol products, ethyl 3-[1-((1R,3S)-3-(1R-hydroxyethyl)-3-{[6-(trifluoromethyl)-2H-1,3-benzoxazin-3(4H)-yl]carbonyl}cyclopentyl)piperidin-4-yl]benzoate and ethyl 3-[1-((1R,3S)-3-(1S-hydroxyethyl)-3-{[6-(trifluoromethyl)-2H-1,3-benzoxazin-3(4H)-yl]carbonyl}cyclopentyl)piperidin-4-yl]benzoate, was accomplished by chiral HPLC (chiralcel OD column, 2 cm×25 cm, 10% ethanol/hexanes) giving a faster eluting peak (peak 1) and a slower eluting peak (peak 2).

Isomer from pk 1 ESI-MS calc. for C31H37F3N2O5: 574; Found: 575 (M+).

Isomer from pk 2 ESI-MS calc. for C31H37F3N2O5: 574; Found: 575 (M+).

EXAMPLE 7

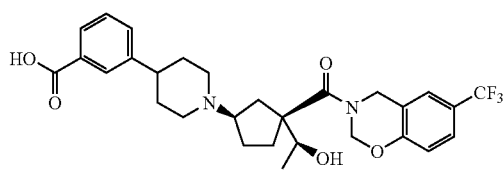

-continued

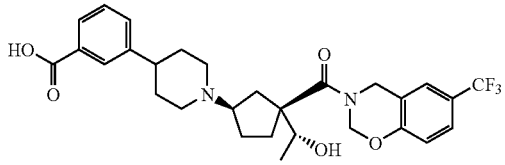

A solution of the isomer from peak 1 of the separation of ethyl 3-[1-((1R,3S)-3-(1-hydroxyethyl)-3-{[6-(trifluoromethyl)-2H-1,3-benzoxazin-3(4H)-yl]carbonyl}cyclopentyl)piperidin-4-yl]benzoate (12.5 mg, 0.0218 mmol) in 1 mL of ethanol was treated with a solution of LiOH H₂O (9 mg, 0.2 mmol) in 1 mL of deionized water. The resulting mixture was stirred at 50° C. for 1 h, then was concentrated. Purification by reverse phase HPLC (YMC Pack Pro C18, 100×20 mm ID) gave the product as its TFA salt. This was converted to its HCl salt by dissolving in DCM and adding excess 1 N HCl/ether, then concentrating to give 3-[1-((1R,3S)-3-(1-hydroxyethyl)-3-{[6-(trifluoromethyl)-2H-1,3-benzoxazin-3(4H)-yl]carbonyl}cyclopentyl)piperidin-4-yl]benzoic acid as a single isomer of unknown stereochemistry at the 1-hydroxyethyl stereocenter. ESI-MS calc. for C29H33F3N2O5: 546; Found: 547 (M+).

Similarly, the isomer from peak 2 of the separation of ethyl 3-[1-((1R,3S)-3-(1-hydroxyethyl)-3-{[6-(trifluoromethyl)-2H-1,3-benzoxazin-3(4H)-yl]carbonyl}cyclopentyl)piperidin-4-yl]benzoate (20.2 mg, 0.0352 mmol) was converted to 3-[1-((1R,3S)-3-(1-hydroxyethyl)-3-{[6-(trifluoromethyl)-2H-1,3-benzoxazin-3(4H)-yl]carbonyl}cyclopentyl)piperidin-4-yl]benzoic acid as a single isomer of unknown (but opposite to the one derived from peak I above) stereochemistry at the 1-hydroxyethyl stereocenter. ESI-MS calc. for C29H33F3N2O5: 546; Found: 547 (M+).

Intermediate 10

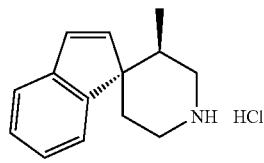

Step A:

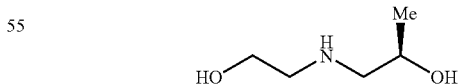

To a cooled (0° C.) solution of ethanolamine (41.8 g, 0.685 mol) in water (90 mL) was added neat (R)-propylene oxide (4.97 g, 85.6 mmol), dropwise. After 1 h at 0° C. the reaction was allowed to rise to rt and stirred overnight. The reaction mixture was concentrated at ~80° C. in vacuo to remove the water and most of the ethanolamine to give the crude product, containing some residual ethanolamine. This material was used without further purification in Step B.

Step B:

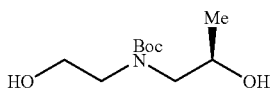

The diol prepared in Step A (11.8 g crude [~86% pure], ca. 83 mmol) was dissolved in DCM (150 mL) and treated with Boc$_2$O (23.4 g, 107 mmol) in DCM (75 mL) over 15 min. The reaction mixture was stirred over the weekend, concentrated, and purified by MPLC, eluting with 5% MeOH/EtOAc.

Step C:

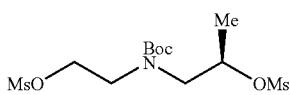

To a solution of the Boc-protected diol prepared in Step B (13.2 g, 60.3 mmol) and triethylamine (21.0 mL, 15.3 g, 151 mmol) in DCM (150 mL) at 0° C. was added dropwise methanesulfonyl chloride (9.56 mL, 14.1 g, 125 mmol). The reaction mixture was then stirred for 1.5 h, diluted with more DCM (100 mL) and washed with 3N HCl (250 mL). The aqueous layer was extracted again with DCM (200 mL), and the organic layers were combined and washed with 1N HCl (250 mL), saturated NaHCO$_3$ solution (250 mL), and brine (250 mL). The organic layer was dried over MgSO$_4$, filtered, and concentrated to give crude bis-mesylate, which was used immediately. If not used immediately the bis-mesylate underwent decomposition.

Step D:

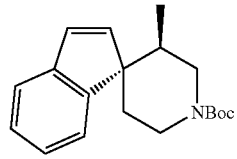

Indene (7.03 mL, 7.00 g, 60.3 mmol) was added dropwise over 4 min to a 1.0M THF solution of LHMDS (127 mL, 127 mmol) at 0° C. After stirring for an additional 30 min., this solution was transferred via cannula to a solution of bis-mesylate (22.6 g, 60.3 mmol), prepared as described in Step C above, in THF (75 mL) at 0° C. The mixture was stirred for 2 h, warmed to rt and stirred overnight. The reaction mixture was partially concentrated and then partitioned between ethyl acetate and water. The aqueous layer was extracted again with ethyl acetate and the organic layers were combined. The organic phase was then washed with brine, dried over MgSO$_4$, filtered and concentrated to give crude product. Purification by MPLC, eluting with 15% ethyl acetate/hexane, afforded piperidine as a ~3:1 mixture of trans to cis (determined by H NMR). The mixture was crystallized from hot hexane to give pure trans isomer (>20:1 by H NMR). H NMR (CDCl$_3$, 400 MHz): δ 7.29 (dt, J=6.4, 1.6 Hz, 1H), 7.20 (m, 3H), 6.83 (d, J=6.0 Hz, 1H), 6.67 (d, J=5.6 Hz, 1H), 4.20 (br s, 2H), 2.97 (br t, J=3.2 Hz, 1H), 2.69 (br t, J=2.4 Hz, 1H), 2.16 (m, 1H), 2.07 (dt, J=4.4, 13.2 Hz, 1H), 1.49 (s, 9H), 1.25 (m, 1H), 0.31 (d, J=6.8 Hz, 3H).

Step E:

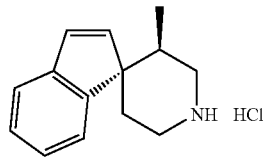

The Boc-piperidine prepared in Step D (4.35 g, 14.5 mmol) was dissolved in an anhydrous 4N HCl solution in dioxane and stirred at rt for 1 h. The reaction mixture was then concentrated to afford product. EI-MS calc. for C14H17N: 199; Found: 200 (M)$^+$.

Intermediate 11

Step A:

A cooled (0° C.) solution of Boc-isonipecotic acid (5.97 g, 26.0 mmol) and Meldrum's acid (3.75 g, 26.0 mmol) in DMF (54 mL) was treated dropwise with diethyl cyanophosphonate (4.34 mL, 28.6 mmol) and triethylamine (11.2 mL, 80.7 mmol). After stirring at 0° C. for an additional 30 min the reaction mixture was permitted to warm to rt and stir over 3 days. The reaction mixture was concentrated under reduced pressure and ether and 1N HCl solution were added. The aqueous layer was extracted again with ether and the ethereal layers were combined and washed with 1N HCl solution, twice with water, and lastly with brine. He ethereal layer was then dried over anhydrous MgSO$_4$, filtered, and concentrated to give tert-butyl 4-[(2,2-dimethyl-4,6-dioxo-1,3-dioxan-5-ylidene)(hydroxy)methyl]piperidine-1-carboxylate which contained approximately 10% of Boc-isonipecotic acid.

$^1$H NMR (500 MHz, CDCl$_3$) δ 4.24 (br m, 2H), 3.97 (tt, J=12, 3.5 Hz, 1H), 2.84 (br m, 2H), 1.83 (m, 2H), 1.76 (s, 6H), 1.69-1.75 (m, 2H), 1.48 (s, 9H).

Step B:

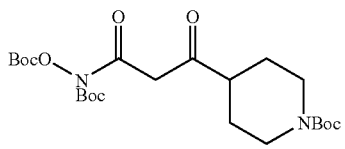

A solution of tert-butyl 4-[(2,2-dimethyl-4,6-dioxo-1,3-dioxan-5-ylidene)(hydroxy)methyl]piperidine-1-carboxylate (8.99 g, 25.3 mmol) and t-butyl N-(t-butoxycarbonyloxy)carbamate (5.90 g, 25.3 mmol) in toluene (200 mL) was stirred at 65° C. for 14 h, then at rt for 36 h. The reaction mixture was concentrated and the residue was purified by flash chromatography (silica, 25% ethyl acetate/hexanes) to afford tert-butyl 4-(3-{(tert-butoxycarbonyl)[(tert-butoxycarbonyl)oxy]amino}-3-oxopropanoyl)piperidine-1-carboxylate. H NMR analysis was consistent with product but complex due to carbamate rotamers.

Step C:

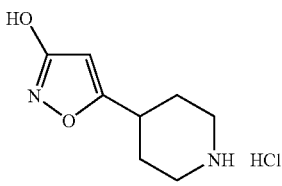

A solution of tert-butyl 4-(3-{(tert-butoxycarbonyl)[(tert-butoxycarbonyl)oxy]amino}-3-oxopropanoyl)piperidine-1-carboxylate (6.2 g, 12.7 mmol) in 100 mL of methanol was treated with 4N HCl solution (150 mL) and the resulting suspension was stirred overnight at rt. In the morning the reaction mixture had become clear. The reaction mixture was concentrated. Since the crude product could not be easily purified it was used as is in the subsequent step. ESI-MS calc. for C8H12N2O2: 168; Found: 169 (M+).

Step D:

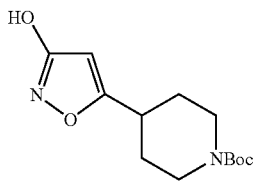

A solution of crude 5-piperidin-4-ylisoxazol-3-ol hydrochloride (1.77 g, 8.65 mmol) and NaOH (346 mg, 8.65 mmol) in a mixture of water (15 mL) and dioxane (10 mL) was treated dropwise with a solution of di-tert-butyl dicarbonate (3.78 g, 17.3 mmol) in 10 mL of dioxane. The resulting mixture was stirred at rt for 6 h, then was partially concentrated to remove the dioxane. To the resulting mixture was added 1N HCl solution and ether. The ethereal layer was then washed with brine, dried over MgSO4, filtered, and concentrated. A series of purifications were required as follows: MPLC (silica, 75 to 100% ethyl acetate/hexanes stepwise gradient), MPLC (silica, 50% ethyl acetate/hexanes), and finally flash chromatography (silica, 1/30/69 AcOH/ethyl acetate/hexanes). This afforded the desired tert-butyl 4-(3-hydroxyisoxazol-5-yl)piperidine-1-carboxylate. $^1$H NMR (500 MHz, CDCl$_3$) δ 5.68 (s, 1H), 4.15 (br m, 2H), 2.88 (br m, 2H), 2.83 (tt, J=11, 3.5 Hz, 1H), 1.99 (m, 2H), 1.62 (dq, J=4.0, 13.5 Hz, 2H), 1.49 (s, 9H).

Step E:

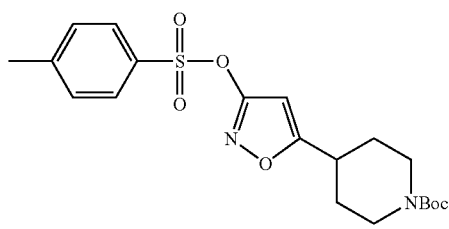

A cooled (0° C.) solution of tert-butyl 4-(3-hydroxyisoxazol-5-yl)piperidine-1-carboxylate (493 mg, 1.84 mmol) in 5 mL of THF was treated with toluenesulfonyl chloride (386 mg, 2.02 mmol) followed by triethylamine (295 µL, 2.12 mmol). The resulting mixture was warmed to rt and stirred for 2 h. The reaction mixture was filtered and the filtrate was concentrated. The residue was purified by MPLC (silica, 50% ethyl acetate/hexanes) to furnish tert-butyl 4-(3-{[(4-methylphenyl)sulfonyl]oxy}isoxazol-5-yl)piperidine-1-carboxylate. $^1$H NMR (500 MHz, CDCl$_3$) δ 7.87 (d, J=8.5 Hz, 2H), 7.39 (d, J=8.0 Hz, 2H), 6.06 (s, 1H), 4.15 (br m, 2H), 2.88 (m, 3H), 2.49 (s, 3H), 2.00 (dd, J=13, 2.5 Hz, 2H), 1.62 (dq, J=4.5, 12.5 Hz, 2H), 1.49 (s, 9H).

Step F:

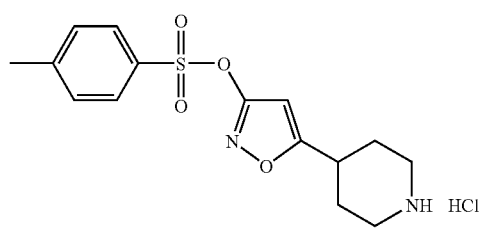

tert-Butyl 4-(3-{[(4-methylphenyl)sulfonyl]oxy}isoxazol-5-yl)piperidine-1-carboxylate (719 mg, 1.76 mmol) was dissolved in anhydrous 4N HCl in dioxane (15 mL) and the resulting solution was stirred at rt for 1 h. The reaction mixture was concentrated to afford 5-piperidin-4-ylisoxazol-3-yl 4-methylbenzenesulfonate hydrochloride, which did not require further purification.

ESI-MS calc. for C15H18N2O4S: 322; Found: 323 (M+H).

EXAMPLE 8

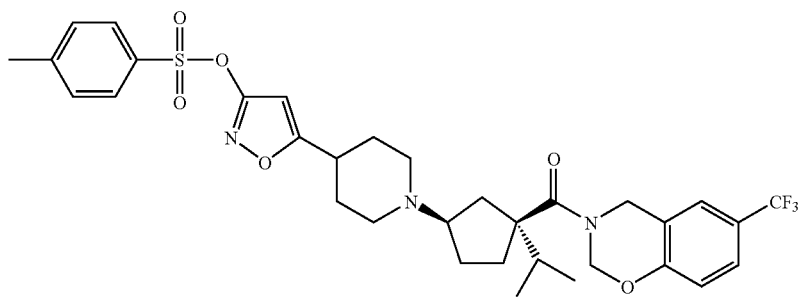

A mixture of 5-piperidin-4-ylisoxazol-3-yl 4-methylbenzenesulfonate hydrochloride (182 mg, 0.507 mmol), (3S)-3-isopropyl-3-{[6-(trifluoromethyl)-2H-1,3-benzoxazin-3(4H)-yl]carbonyl}cyclopentanone (93.3 mg, 0.263 mmol), triethylamine (71 μL, 0.507 mmol), 4 Å powdered molecular sieves (~100 mg), and sodium triacetoxyborohydride (334 mg, 1.58 mmol) was stirred at rt for 6 days (3 days is usually sufficient). The reaction mixture was diluted with DCM and washed with saturated NaHCO$_3$ solution followed by brine. The organic layer was dried over anhydrous MgSO$_4$, filtered, and concentrated. Purification and separation of the cis(5-[1-((1R,3S)-3-isopropyl-3-{[6-(trifluoromethyl)-2H-1,3-benzoxazin-3(4H)-yl]carbonyl}cyclopentyl)piperidin-4-yl]isoxazol-3-yl 4-methylbenzenesulfonate) and trans(5-[1-((1S,3S)-3-isopropyl-3-{[6-(trifluoromethyl)-2H-1,3-benzoxazin-3(4H)-yl]carbonyl}cyclopentyl)piperidin-4-yl]isoxazol-3-yl 4-methylbenzenesulfonate)isomers was accomplished by preparative TLC (silica, 40% THF/hexanes eluent) to give the higher eluting (cis) isomer and the lower eluting (trans) isomer. Analysis of the separated cis and trans product isomers by chiral analytical HPLC (chiralcel OD column) showed each to be clean single isomers.

Higher eluting (cis) isomer ESI-MS calc. for C33H38F3N3O6S: 661; Found: 662 (M+H).

Lower eluting (trans) isomer ESI-MS calc. for C33H38F3N3O6S: 661; Found: 662 (M+H).

EXAMPLE 9

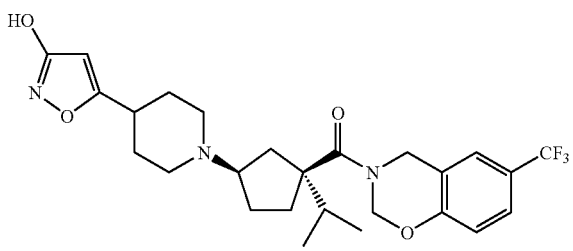

A solution of 5-[1-((1R,3S)-3-isopropyl-3-{[6-(trifluoromethyl)-2H-1,3-benzoxazin-3(4H)-yl]carbonyl}cyclopentyl)piperidin-4-yl]isoxazol-3-yl 4-methylbenzenesulfonate (97 mg, 0.15 mmol) in a mixture of THF (2 mL) and methanol (2 mL) was treated with a solution of LiOH H$_2$O (61.5 mg, 1.47 mmol) in deionized water (2 mL). The resulting mixture was stirred at rt for 1 h, then was concentrated brine was added to the residue and the pH was adjusted to 7 with 1N HCl solution. This mixture was extracted three times with chloroform and the combined organic layers were dried over anhydrous MgSO$_4$, filtered, and concentrated. Purification by reverse phase HPLC (YMC Pack Pro C18, 100×20 mm ID) gave the product as its TFA salt. This was converted to its HCl salt by dissolving in DCM and adding excess 1 N HCl/ether, then concentrating to give 5-[1-((1R,3S)-3-isopropyl-3-{[6-(trifluoromethyl)-2H-1,3-benzoxazin-3(4H)-yl]carbonyl}cyclopentyl)piperidin-4-yl]isoxazol-3-ol hydrochloride. ESI-MS calc. for C26H32F3N3O4: 507; Found: 508 (M+H).

Intermediate 12

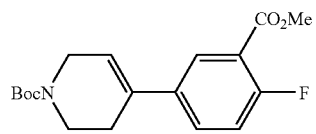

Procedure A

Step A:

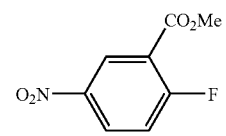

Thionyl chloride (16 mL, 0.22 mol) was added dropwise to cooled (0° C.) methanol (250 mL). After the addition the resulting anhydrous methanolic HCl solution was poured into a flask containing 2-fluoro-5-nitrobenzoic acid (13.77 g, 74.39 mmol). The mixture so obtained was stirred overnight at rt. The reaction mixture was concentrated and the residue collected was purified by flash chromatography using a gradient [silica, 5-30% (700 mL), then 30-50% (1 L)], giving methyl 2-fluoro-5-nitrobenzoate.

Step B:

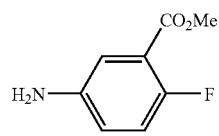

A mixture of methyl 2-fluoro-5-nitrobenzoate (14.52 g, 72.92 mmol) and Pd/C (10%, Degussa type, 726 mg) in methanol was agitated under 60 psi of $H_2$ using a Parr apparatus for 3 h. The reaction mixture was filtered and the filtrate was concentrated to give methyl 5-amino-2-fluorobenzoate.

Step C:

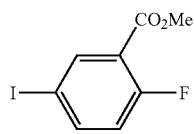

Methyl 5-amino-2-fluorobenzoate (5.21 g, 30.8 mmol) was added to a solution of concentrated sulfuric acid (45 mL) in water (110 mL). The resulting mixture was heated at 80° C. for 20 min then cooled to 0° C. and treated dropwise with a solution of $NaNO_2$ (2.34 g, 33.9 mmol) in 10 mL of water. After stirring for 30 min, a solution of KI (7.16 g, 43.1 mmol) in 20 mL of water was added. The reaction mixture was then warmed to rt and stirred overnight under a nitrogen atmosphere. Then the reaction mixture was stirred at 70° C. for 15 min, cooled to rt, and extracted twice with ether. The combined ethereal layers were washed four times with water, once with brine, dried over anhydrous $MgSO_4$, filtered, and concentrated. Purification by flash chromatography (silica, 10% ethyl acetate/hexanes) provided methyl 2-fluoro-5-iodobenzoate. $^1$H NMR (500 MHz, $CDCl_3$) δ 8.25 (dd, 1H), 7.82 (m, 1H), 6.94 (dd, 1H), 3.95 (s, 3H). ESI-MS calc. for C8H6FIO2: 280; Found: 281 (M+H).

Step D:

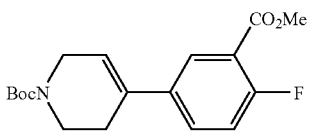

Methyl 2-fluoro-5-iodobenzoate (5.01 g, 17.9 mmol) was combined with LiCl (1.52 g, 35.7 mmol) and tert-butyl 4-(tri-methylstannyl)-3,6-dihydropyridine-1(2H)-carboxylate (4.28 g, 12.3 mmol) in 100 mL of DMF. After stirring for 20 min under a nitrogen atmosphere, $Pd_2dba_3$ (218 mg, 0.238 mmol) and P(2-furyl)$_3$ (276 mg, 1.19 mmol) were added and the reaction mixture was warmed to 90° C. under a nitrogen atmosphere and stirred for 1 h 45 min. The reaction mixture was then stirred at rt overnight. Then the reaction temperature was brought again to 90° C. for 1 h. To the mixture was added saturated $NaHCO_3$ solution and brine. The resulting aqueous mixture was then extracted three times with ether. The ethereal layers were combined and washed four times with water, dried over anhydrous $MgSO_4$, filtered, and concentrated. Purification by MPLC (silica, 5-25% gradient of ethyl acetate/hexanes, over 2L volume) gave tert-butyl 4-[4-fluoro-3-(methoxycarbonyl)phenyl]-3,6-dihydropyridine-1 (2H)-carboxylate. $^1$H NMR (500 MHz, $CDCl_3$) δ 7.94 (dd, J=7.0, 2.5 Hz, 1H), 7.53 (m, 1H), 7.13 (dd, J=10, 8.5 Hz, 1H), 6.07 (br s, 1H), 4.10 (br s, 2H), 3.96 (s, 3H), 3.66 (t, 6 Hz, 2H), 2.53 (br m, 2H), 1.52 (s, 9H). ESI-MS calc. for C18H22FNO4: 335; Found: 236 (M+Boc+H).

Step E:

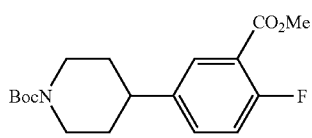

A mixture of tert-butyl 4-[4-fluoro-3-(methoxycarbonyl) phenyl]-3,6-dihydropyridine-1(2H)-carboxylate (2.11 g, 6.29 mmol) and 10% Pd/C (525 mg) in ethanol (60 mL) was stirred under an hydrogen atmosphere using a hydrogen filled balloon for 6 h. The reaction mixture was filtered and the filtrate was concentrated. $^1$H NMR analysis revealed that approximately 5% of the starting olefin remained, so the mixture was resubmitted to the above conditions for 4 h. Filtration, and concentration of the filtrate gave tert-butyl 4-[4-fluoro-3-(methoxycarbonyl)phenyl]piperidine-1-carboxylate which was used without further purification. $^1$H NMR (500 MHz, $CDCl_3$) δ 7.78 (dd, J=6.5, 2.0 Hz, 1H), 7.37 (m, 1H), 7.10 (dd, J=10.5, 8.0 Hz, 1H), 4.27 (br m, 2H), 3.95 (s, 3H), 2.82 (br m, 2H), 2.69 (tt, J=12.5, 3.5 Hz, 1H), 1.83 (br d, J=13 Hz, 2H), 1.62 (dq, J=4.5, 13 Hz, 2H), 1.50 (s, 9H).

Procedure B

Step A:

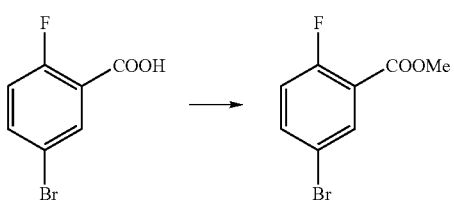

A mixture of 5-bromo-2-fluorobenzoic acid (25 g, 0.11 mol), methyl iodide (8.5 mL, 0.14 mol), and potassium carbonate (31 g, 0.23 mol) in DMF (200 mL) was heated to 50° C. for 18 hr. The cooled reaction mixture was diluted with EtOAc (200 mL) and the organic phase was washed with a saturated aqueous NaCl solution (4×). The organic phase was then dried over sodium sulfate and evaporated to dryness to give 24g of methyl 5-bromo-2-fluorobenzoate as a yellow oil.

Step B:

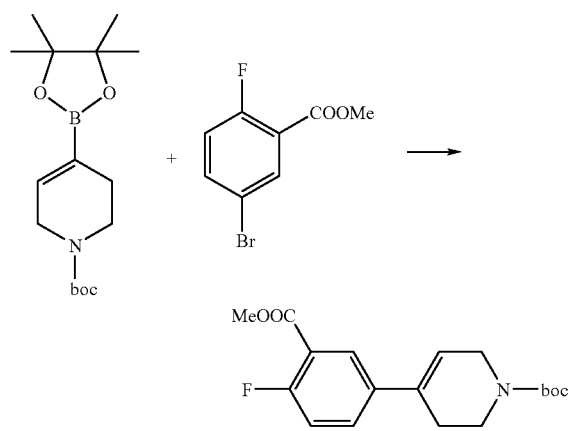

tert-Butyl 4-[4-fluoro-3-(methoxycarbonyl)phenyl]-3,6-dihydropyridine-1(2H)-carboxylate was synthesized as described for INTERMEDIATE 6 (step A) using tert-butyl 4-(4,4,5,5-tetramethyl-1,3,2-dioxaborolan-2-yl)-3,6-dihydropyridine-1(2H)-carboxylate (prepared according to Eastwood, P. R. Tetrahedron Lett., 41, 19, 2000, 3705-3708) and methyl 5-bromo-2-fluorobenzoate as starting material and PdCl$_2$dppf.CH$_2$Cl$_2$ as a catalyst.

Step C:

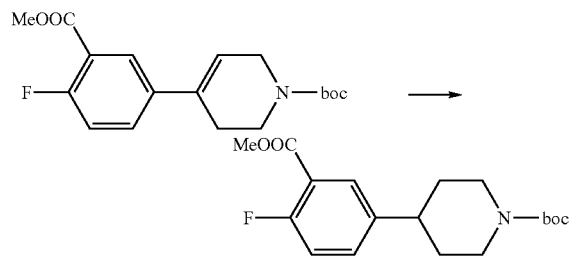

tert-Butyl 4-[4-fluoro-3-(methoxycarbonyl)phenyl]piperidine-1-carboxylate was synthesized as described for INTERMEDIATE 7 (procedure B, step C) using tert-butyl 4-[4-fluoro-3-(methoxycarbonyl)phenyl]-3,6-dihydropyridine-1(2H)-carboxylate as starting material.

Intermediate 13

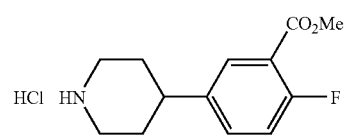

tert-Butyl 4-[4-fluoro-3-(methoxycarbonyl)phenyl]piperidine-1-carboxylate (471 mg, 1.40 mmol) was dissolved in anhydrous 4N HCl in dioxane (5 mL) and stirred at rt for 40 min. The reaction mixture was concentrated to afford methyl 2-fluoro-5-piperidin-4-ylbenzoate hydrochloride which was used without further purification. ESI-MS calc. for C13H16FNO2: 237; Found: 238 (M+H).

Intermediate 14

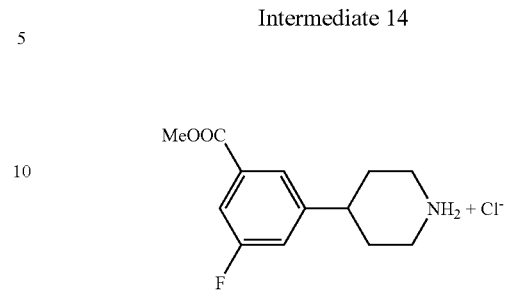

tert-Butyl 4-[3-fluoro-5-(methoxycarbonyl)phenyl]piperidine-1-carboxylate was synthesized as described for INTERMEDIATE 12 (procedure B). Methyl 3-Fluoro-5-piperidin-4-ylbenzoate was synthesized as described for INTERMEDIATE 13.

Intermediate 15

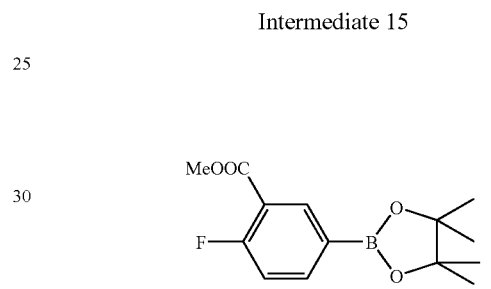

A mixture of methyl 5-bromo-2-fluorobenzoate (6.5 g, 27.9 mmol), 4,4,4',4',5,5,5',5'-octamethyl-2,2'-bi-1,3,2-dioxaborolane (8.5 g, 33.5 mmol), PdCl$_2$dppf.CH$_2$Cl$_2$ (1.1 g, 1.4 mmol), dppf (0.77 g, 1.4 mol), and KOAc (5.4 g, 55.8 mmol) in DMF (100 mL) was heated to 90° C. for 18 hr. The cooled reaction mixture was diluted with EtOAc (200 mL) and the organic phase was washed with a saturated aqueous NaCl solution (4×). The organic phase was then dried over sodium sulfate and evaporated to dryness. The dark residue was dissolved in CH$_2$Cl$_2$, filtered through a silica gel plug, and washed with CH$_2$Cl$_2$ (500 mL). The filtrate was evaporated to dryness and the residue was purified by column chromatography on silica gel eluting with a gradient of EtOAc and hexane to afford methyl 2-fluoro-5-(4,4,5,5-tetramethyl-1,3,2-dioxaborolan-2-yl)benzoate (5 g) as a green solid.

Intermediate 16

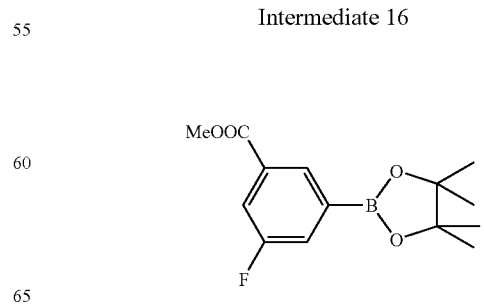

Methyl 3-fluoro-5-(4,4,5,5-tetramethyl-1,3,2-dioxaborolan-2-yl)benzoate was synthesized as described for INTERMEDIATE 15 using 3-bromo-5-fluorobenzoic acid as starting material.

Intermediate 17

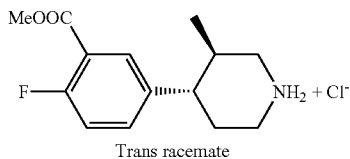

Trans racemate

The HCl salt of methyl 2-fluoro-5-[(3R,4S)-3-methylpiperidin-4-yl]benzoate was synthesized as described for INTERMEDIATE 6 (procedure B) using methyl 2-fluoro-5-(4,4,5,5-tetramethyl-1,3,2-dioxaborolan-2-yl)benzoate as starting material.

Intermediate 18

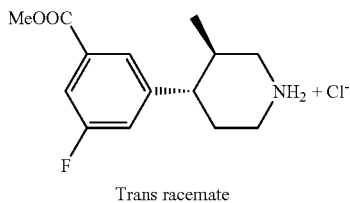

Trans racemate

The HCl salt of methyl 3-fluoro-5-[(3R,4S)-3-methylpiperidin-4-yl]benzoate was synthesized as described for INTERMEDIATE 7 (procedure B) using methyl 3-fluoro-5-(4,4,5,5-tetramethyl-1,3,2-dioxaborolan-2-yl)benzoate as starting material.

Intermediate 19

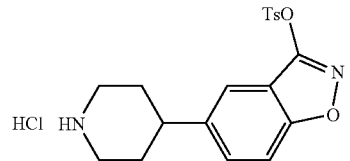

Step A:

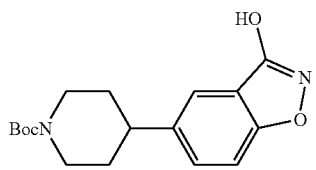

Acetoxyhydroxamic acid (334 mg, 4.45 mmol) was combined with potassium tert-butoxide (499 mg, 4.45 mmol) in 10 mL of DMF. The resulting slurry was stirred at rt for 43 min. Then a solution of tert-Butyl 4-[4-fluoro-3-(methoxycarbonyl)phenyl]piperidine-1-carboxylate (1.00 g, 2.96 mmol) in 5 mL of DMF was added. The reaction mixture was stirred at rt overnight. HPLC-MS analysis indicated that little product was present and that starting material accounted for the majority of material. Acetoxyhydroxamic acid (670 mg, 8.9 mmol) was combined with potassium tert-butoxide (980 mg, 8.9 mmol) in 10 mL of DMF. The resulting slurry was stirred at rt for 30 min. This mixture was then added to the reaction mixture and the resulting slurry was stirred at 50° C. for 1 h 20 min. The temperature was raised to 75° C. and the mixture was stirred for an additional 3 h. Then the temperature was raised to 90° C. and the mixture was stirred for 6 h. Then the temperature was raised to 100° C. and the mixture was stirred for 6 h. Since the reaction still had not progressed to completion, acetoxyhydroxamic acid (670 mg, 8.9 mmol) was again combined with potassium tert-butoxide (980 mg, 8.9 mmol) in 10 mL of DMF. The resulting slurry was stirred at rt for 30 min. This mixture was then again added to the reaction mixture and the resulting slurry was stirred at 100° C. for 16 h. Although approximately 20% of starting material remained, the reaction mixture was diluted with ether and washed with 1N HCl solution. The aqueous layer was back-extracted with ether and the ethereal layers were combined and washed twice with water and once with brine. The ethereal layer was dried over anhydrous MgSO$_4$, filtered, and concentrated. Purification by MPLC (silica, 70% ethyl acetate/hexanes) gave tert-butyl 4-(3-hydroxy-1,2-benzisoxazol-5-yl)piperidine-1-carboxylate. $^1$H NMR (500 MHz, CDCl$_3$) δ 7.62 (d, J=1.5 Hz, 1H), 7.49 (dd, J=8.5, 1.5 Hz, 1H), 7.37 (d, J=9.0 Hz, 1H), 4.30 (br m, 2H), 2.85 (br m, 2H), 2.80 (tt, J=12.5, 3.5 Hz, 1H), 1.89 (br d, J=12.5 Hz, 2H), 1.68 (dq, J=4.0, 12.5 Hz, 2H), 1.52 (s, 9H).

Step B:

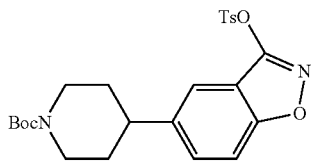

A cooled (0° C.) solution of tert-butyl 4-(3-hydroxy-1,2-benzisoxazol-5-yl)piperidine-1-carboxylate (286 mg, 0.898 mmol) in THF (5 mL) was treated with toluenesulfonyl chloride (188 mg, 0.988 mmol) followed by triethylamine (144 μL, 1.03 mmol). The reaction mixture was permitted to warm to rt and stir for 1.5 h. The reaction mixture was filtered, and the filtrate was concentrated. Purification by MPLC (silica, 50% ethyl acetate/hexanes) provided tert-butyl 4-(3-{[(4-methylphenyl)sulfonyl]oxy}-1,2-benzisoxazol-5-yl)piperidine-1-carboxylate. $^1$H NMR (500 MHz, CDCl$_3$) δ 7.94 (d, J=8.5 Hz, 2H), 7.47 (s, 3H), 7.41 (d, J=8.0 Hz, 2H), 4.31 (br m, 2H), 2.85 (br m, 2H), 2.80 (tt, J=12, 3.5 Hz), 2.50 (s, 3H), 1.87 (br d, J=13 Hz, 2H), 1.64 (dq, J=4.5, 13 Hz, 2H), 1.52 (s, 9H). ESI-MS calc. for C24H28N2O6S: 472; Found: 473 (M+H).

Step C:

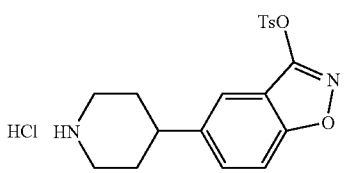

tert-Butyl 4-(3-{[(4-methylphenyl)sulfonyl]oxy}-1,2-benzisoxazol-5-yl)piperidine-1-carboxylate (285 mg, 0.603 mmol) was dissolved in anhydrous 4N HCl in dioxane (6 mL) and the resulting mixture was stirred at rt for 1 h. The reaction mixture was concentrated to afford 5-piperidin-4-yl-1,2-benzisoxazol-3-yl 4-methylbenzenesulfonate hydrochloride which did not require further purification.

ESI-MS calc. for C19H20N2O4S: 372; Found: 373 (M+H).

Intermediate 20

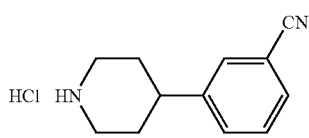

Step A:

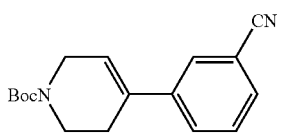

To a mixture of tert-butyl 4-{[(trifluoromethyl)sulfonyl]oxy}-3,6-dihydropyridine-1(2H)-carboxylate (prepared according to Wustrow, D. J., Wise, L. D., *Synthesis*, (1991), 993-995; 3.24 g, 9.77 mmol), 3-cyanophenylboronic acid (2.01 g, 13.7 mmol), lithium chloride (1.23 g, 29.3 mmol), and 2 M Na2CO3 solution (14 mL) in DME (35 mL) was added Pd(PPh3)4 (564 mg, 0.489 mmol), and the resulting mixture was stirred at reflux under a nitrogen atmosphere for 3.5 h. The reaction mixture was cooled to rt, stirred overnight, then partially concentrated to remove most of the DME. To the remaining aqueous mixture was added DCM, 2M Na2CO3 solution, and ~6 mL of 28% NH4OH solution. The layers were separated and the aqueous layer was extracted again with DCM. The combined organic layers were dried over anhydrous MgSO4, filtered, and concentrated. Purification by MPLC (silica, 45% ethyl acetate/hexanes eluent) afforded tert-butyl 4-(3-cyanophenyl)-3,6-dihydropyridine-1(2H)-carboxylate. $^1$HNMR (CDCl3, 500 MHz): δ 7.66 (s, 1H), 7.61 (dd, J=8.0, 1.5 Hz, 1H), 7.56 (d, J=8.0 Hz, 1H), 7.46 (t, J=7.5 Hz, 1H), 6.13 (br s, 1H), 4.12 (m, 2H), 3.68 (t, J=5.5 Hz, 2H), 2.53 (br s, 2H), 1.52 (s, 9H).

Step B:

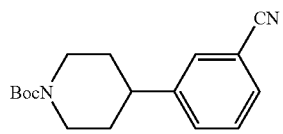

tert-Butyl 4-(3-cyanophenyl)-3,6-dihydropyridine-1(2H)-carboxylate (1.00 g, 3.52 mmol) was combined with 20% Pd(OH)2/C (1 g) in 25 mL of methanol. This mixture was stirred under a hydrogen atmosphere using a hydrogen filled balloon for 5 h. The reaction mixture was filtered through a celite plug and the filtrate was concentrated. Purification by MPLC (silica, 38% ethyl acetate/hexanes) gave tert-butyl 4-(3-cyanophenyl)piperidine-1-carboxylate. ESI-MS calc. for C17H22N2O2: 286; Found: 309 (M+Na+).

Step C:

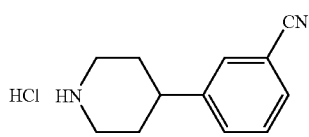

A solution of tert-butyl 4-(3-cyanophenyl)piperidine-1-carboxylate (376 mg, 1.31 mmol) in 10 mL of 1:1 TFA/DCM was stirred at rt for 1.25 h. The reaction mixture was concentrated. Purification by preparative TLC (silica, 1% of 28% NH4OH solution/9% methanl/UDCM) gave 3-piperidin-4-ylbenzonitrile as a white solid. ESI-MS calc. for C12H14N2: 186; Found: 187 (M+H).

Intermediate 21

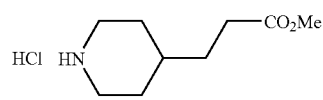

Thionyl chloride (2.23 mL, 30.6 mmol) was added dropwise to 25 mL of anhydrous methanol. The resulting anhydrous methanolic HCl solution was added to commercially available 3-[1-(tert-butoxycarbonyl)piperidin-4-yl]propanoic acid (1.97 g, 7.66 mmol) and the resulting mixture was stirred overnight at rt. The solvent was removed under reduced pressure to afford methyl 3-piperidin-4-ylpropanoate hydrochloride. ESI-MS calc. for C9H17NO2: 171; Found: 172 (M+H).

Intermediate 22

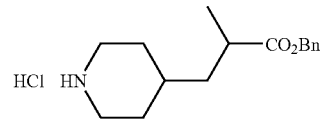

Step A:

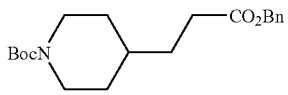

Benzyl bromide (2.29 mL, 19.3 mmol) was added dropwise to a cooled (0° C.) mixture of commercially available 3-[1-(tert-butoxycarbonyl)piperidin-4-yl]propanoic acid (4.96 g, 19.3 mmol) and $K_2CO_3$ (6.67 g, 48.3 mmol) in 40 mL of DMF. The reaction mixture was permitted to warm to rt and stir for 3 days (the reaction was likely complete after only a few h). The reaction mixture was diluted with ether and washed four times with water, then once with brine. The ethereal layer was dried over anhydrous $MgSO_4$, filtered, and concentrated. Purification by MPLC (silica, 30% ethyl acetate/hexanes) provided tert-butyl 4-[3-(benzyloxy)-3-oxopropyl]piperidine-1-carboxylate. $^1$HNMR (CDCl$_3$, 500 MHz): δ 7.38 (m, 5H), 5.14 (s, 2H), 4.09 (br m, 2H), 2.65 (m, 2H), 2.41 (t, J=7.5 Hz, 2H), 1.63 (m, 4H), 1.47 (s, 9H), 1.40 (m, 1H), 1.10 (dq, J=4.0, 12 Hz, 2H).

Step B:

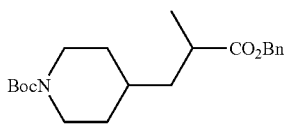

To a cooled (−78° C.) solution of 1.5M LDA/cyclohexane (6.48 mL, 9.73 mmol) in 50 mL of THF was added dropwise under a nitrogen atmosphere a solution of tert-butyl 4-[3-(benzyloxy)-3-oxopropyl]piperidine-1-carboxylate (2.60 g, 7.48 mmol) in 20 mL of THF. The resulting mixture was stirred at −78° C. for 45 min then was treated dropwise with neat iodomethane (1.40 mL, 22.4 mmol). After stirring at −78° C. for an additional 30 min, the reaction mixture was permitted to warm to rt and stir overnight. The reaction mixture was diluted with ether and washed in sequence with 1N HCl solution, saturated NaHCO$_3$ solution, and brine. The ethereal layer was dried over anhydrous $MgSO_4$, filtered, and concentrated. Purification by MPLC (silica, 25% ethyl acetate/hexanes) afforded tert-butyl 4-[3-(benzyloxy)-2-methyl-3-oxopropyl]piperidine-1-carboxylate.

$^1$HNMR (CDCl$_3$, 500 MHz): δ 7.38 (m, 5H), 5.17 (d, J=12 Hz, 1H), 5.12 (d, J=12 Hz, 1H), 4.06 (br m, 2H), 2.62 (m, 3H), 1.69 (m, 2H), 1.56 (m, 1H), 1.47 (s, 9H), 1.32 (m, 2H), 1.19 (d, J=7.5 Hz, 3H), 1.06 (m, 2H).

Step C:

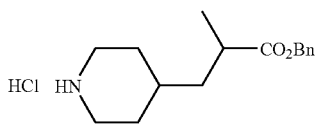

tert-Butyl 4-[3-(benzyloxy)-2-methyl-3-oxopropyl]piperidine-1-carboxylate was dissolved in 5 mL of anhydrous 4N HCl in dioxane and stirred at rt for 1 h. The reaction mixture was concentrated to afford benzyl 2-methyl-3-piperidin-4-ylpropanoate. ESI-MS calc. for C16H23NO2: 261; Found: 262 (M+H).

Intermediate 23

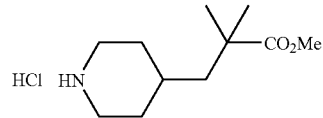

Step A:

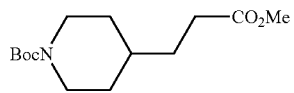

Iodomethane (556 μL, 8.93 mmol) was added dropwise to a cooled (0° C.) mixture of commercially available 3-[1-(tert-butoxycarbonyl)piperidin-4-yl]propanoic acid (2.09 g, 8.12 mmol) and $K_2CO_3$ (2.81 g, 20.3 mmol) in 20 mL of DMF. The reaction mixture was permitted to warm to rt and stir overnight. The reaction mixture was diluted with ether and washed four times with water, then once with brine. The ethereal layer was dried over anhydrous $MgSO_4$, filtered, and concentrated. Purification by MPLC (silica, 40% ethyl acetate/hexanes) provided tert-butyl 4-(3-methoxy-3-oxopropyl)piperidine-1-carboxylate.

Step B:

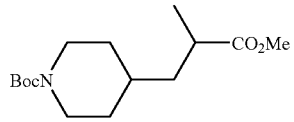

To a precooled (−78° C.) solution of 1.0M sodium bis(trimethylsilyl)amide in THF (13.1 mL, 13.1 mmol) was added dropwise under a nitrogen atmosphere a solution of tert-butyl 4-(3-methoxy-3-oxopropyl)piperidine-1-carboxylate (1.78 g, 6.56 mmol) in 11 mL of THF. After stirring for an additional 25 min, neat iodomethane (1.23 mL, 19.7 mmol) was added dropwise and the reaction mixture was stirred at −78° C. for two more h. The reaction mixture was then poured into 1N HCl solution and the resulting mixture was extracted twice with ether. The combined ethereal layers were washed with brine, dried over anhydrous $MgSO_4$, filtered, and concentrated. Purification by MPLC (silica, 40% ethyl acetate/hexanes) gave tert-butyl 4-(3-methoxy-2-methyl-3-oxopropyl)piperidine-1-carboxylate.

ESI-MS calc. for C15H27NO4: 285; Found: 186 (M+Boc+H).

Step C:

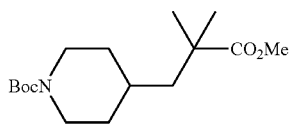

A cooled solution (−78° C.) of 2.0M LDA in THF/hexanes (Aldrich, 4.72 mL, 9.43 mmol) in 9 mL of THF was treated dropwise by a solution of tert-butyl 4-(3-methoxy-2-methyl-3-oxopropyl)piperidine-1-carboxylate (1.35 g, 4.72 mmol) in 12 mL of THF. After stirring for an additional 25 min, neat iodomethane (1.18 mL, 18.9 mmol) was added and the reaction mixture was maintained at −78° C. for 2 h. The reaction mixture was poured onto 1N HCl solution and the resulting mixture was extracted twice with ether. The combined ethereal layers were washed with brine, dried over anhydrous MgSO$_4$, filtered, and concentrated. Purification by MPLC (silica, 30% ethyl acetate/hexanes) aforded tert-butyl 4-(3-methoxy-2,2-dimethyl-3-oxopropyl)piperidine-1-carboxylate as an oil which crystallized to a pale yellow solid on standing. $^1$HNMR (CDCl$_3$, 500 MHz): δ 4.03 (br m, 2H), 3.68 (s, 3H), 2.67 (m, 2H), 1.54 (br m, 5H), 1.47 (s, 9H), 1.20 (s, 6H), 1.11 (m, 2H).

Step D:

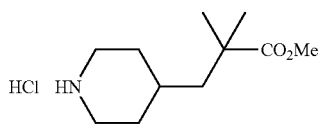

tert-Butyl 4-(3-methoxy-2,2-dimethyl-3-oxopropyl)piperidine-1-carboxylate (1.40 g, 4.67 mmol) was dissolved in anhydrous 4N HCl in dioxane (10 mL) and the resulting solution was stirred at rt for 1 h. The reaction mixture was concentrated to afford methyl 2,2-dimethyl-3-piperidin-4-yl-propanoate hydrochloride.

ESI-MS calc. for C11H21NO2: 199; Found: 200 (M+H).

Intermediate 24

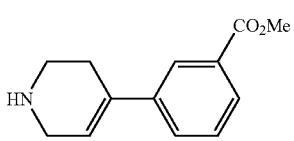

Step A:

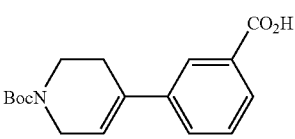

3-(dihydroxyborane)benzoic acid (4.65 g, 28.0 mmol) was coupled to tert-butyl 4-{[(trifluoromethyl)sulfonyl]oxy}-3,6-dihydropyridine-1(2H)-carboxylate (6.65 g, 20.0 mmol) in an analogous fashion to that described previously for the synthesis of tert-butyl 4-[3-(ethoxycarbonyl)phenyl]-3,6-dihydropyridine-1(2H)-carboxylate (INTERMEDIATE 6, Step A) to give 3-[1-(tert-butoxycarbonyl)-1,2,3,6-tetrahydropyridin-4-yl]benzoic acid.

Step B:

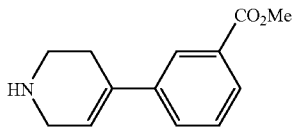

Thionyl chloride (2.39 mL, 32.7 mmol) was added dropwise to 15 mL of anhydrous methanol. The resulting anhydrous methanolic HCl solution was added to 3-[1-(tert-butoxycarbonyl)-1,2,3,6-tetrahydropyridin-4-yl]benzoic acid (3.31 g, 10.9 mmol) and the reaction mixture was stirred at rt for 6 h. The solvent was removed under reduced pressure and the residue was purified by flash chromatography (silica, 5-10% stepwise gradient in 1% increments of 10% NH$_4$OH (28% solution)/methanol in DCM) to give methyl 3-(1,2,3,6-tetrahydropyridin-4-yl)benzoate. ESI-MS calc. for C13H15NO2: 217; Found: 218 (M+H).

Intermediate 25

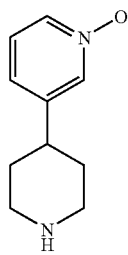

Step A:

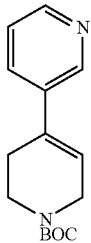

tert-Butyl 4-{[(trifluoromethyl)sulfonyl]oxy}-3,6-dihydropyridine-1(2H)-carboxylate (prepared according to Wustrow, D. J., Wise, L. D., *Synthesis*, (1991), 993-995; 2.73 g, 8.22 mmol) was dissolved in 80 mL of NMP. Triphenylarsine (220 mg, 0.66 mmol), LiCl (1.09 g, 24.7 mmol), and tris(dibenzylideneacetone)-dipalladium(0) (156 mg, 0.160 mmol) were then added to the reaction vessel. After 10 min of constant stirring, tributylstannyl pyridine (4.0 g, 9.7 mmol) in 10 mL of NMP was added using a syringe. The reaction vessel was repeatedly evacuated and flushed with N$_2$ $_{(g)}$ (4×). The reaction mixture was then stirred at rt for 30 min, then at 80°

C. for 2.5 h, and then at 65° C. for 16 h. Afterwards, 20 mL of 1M KF solution was added. The mixture was stirred for 1.5 h and then diluted with ethyl acetate (100 mL) and filtered. The filtrate was further diluted with 200 mL of 1M KF solution and 200 mL of ethyl acetate. The organic and aqueous layers were separated, and the aqueous layer was extracted once again with ethyl acetate (200 mL). The organic layers were combined, washed with water (6×200 mL) and then with brine (1×300 mL), dried over sodium sulfate, filtered, and concentrated under reduced pressure. Tert-Butyl 3',6'-dihydro-3,4'-bipyridine-1'(2'H)-carboxylate was obtained through silica gel flash column chromatography (1% MeOH in EtOAc). ESI-MS calculated for $C_{15}H_{20}N_2O_2$: 260.35, found 261 (M+H).

Step B:

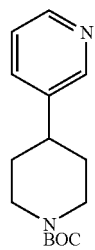

The tert-Butyl 3',6'-dihydro-3,4'-bipyridine-1'(2'H)-carboxylate prepared in Step A (1.14 g, 4.38 mmol) was dissolved in 20 mL of ethanol and added to a flask containing palladium hydroxide on carbon powder (20% Pd). The reaction mixture was subjected to 50 psi of $H_{2\ (g)}$ for 6.5 h with vigorous shaking. The reaction was then filtered and concentrated under reduced pressure. Purification by flash column chromatography (silica gel, 0-1% MeOH/EtOAc gradient eluent) afforded tert-butyl 4-pyridin-3-ylpiperidine-1-carboxylate. ESI-MS calc. for $C_{15}H_{22}N_2O_2$: 262.37, found 263 (M+H).

Step C:

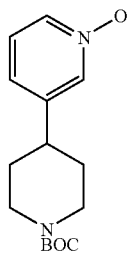

m-CPBA (1.12 g, 6.48 mmol) was added to a solution of tert-butyl 4-pyridin-3-ylpiperidine-1-carboxylate (850 mg, 3.24 mmol) in 50 mL of $CH_2Cl_2$. The reaction mixture was stirred at rt, under a nitrogen atmosphere for 20 h. The reaction was then diluted with dichloromethane (75 mL) and washed with a solution of sodium sulfite (1×100 mL), a saturated solution sodium bicarbonate (1×100 mL), and brine (1×100 mL). The product was then dried over magnesium sulfate, filtered, and concentrated under reduced pressure. The desired product was obtained and used in the subsequent reaction without further purification. ESI-MS calculated for $C_{15}H_{22}N_2O_3$: 278.35, found 223 (M+tBu+H).

Step D:

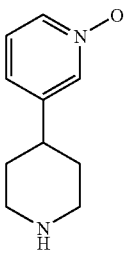

The N-oxide prepared in Step C (868 mg, 3.12 mmol) was dissolved in a 4N HCl/dioxane solution and stirred at rt for 1 h before concentrating to afford the desired amine as an HCl salt. ESI-MS calc. for $C_{10}H_{14}N_2O$: 178.23, found 179 (M+H).

Intermediate 26

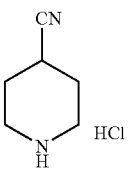

Step A:

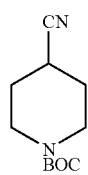

Isonipecotamide (10.2 g, 79.6 mmol) was dissolved in 37.0 mL of phosphorus oxychloride. The reaction mixture was heated at reflux for 4 h. Thereafter, the reaction was partially concentrated under reduced pressure, poured into a flask containing ice, and treated with a 5M NaOH solution until a pH of 12 was reached. A solution of di-tert-butyl dicarbonate (20.8 g, 95.5 mmol) and dioxane (40 mL) was added, and the reaction mixture was stirred at rt, under a nitrogen atmosphere, for 16 h. The reaction was then extracted with ethyl acetate (3×200 mL). The organic layer was washed once with brine solution, dried over magnesium sulfate, filtered, and concentrated under reduced pressure. Purification by MPLC (silica gel, 0-15% ethyl acetate/hexanes) afforded the desired tert-butyl 4-cyanopiperidine-1-carboxylate as a white crystalline solid.

Step B:

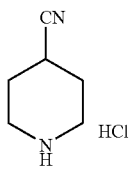

tert-Butyl 4-cyanopiperidine-1-carboxylate (4.87 g, 23.2 mmol) was dissolved in a solution of 4N HCl/dioxane (30 mL) and stirred at rt. After 45 min, starting material was no longer present by TLC, and the reaction mixture was concentrated. The product was obtained as an HCl salt.

Intermediate 27

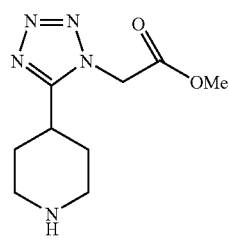

Step A:

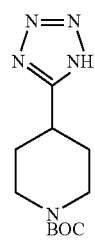

Tert-Butyl 4-cyanopiperidine-1-carboxylate (6.98 g, 33.2 mmol) was dissolved in 150 mL of toluene and treated with trimethyltinazide (10.0 g, 48.6 mmol). The reaction mixture was heated to reflux and stirred under a nitrogen atmosphere for 4 days. The reaction was judged complete by TLC and then concentrated under reduced pressure. The mixture was dissolved in 200 mL of ethyl acetate, and cooled to 0° C. HCl gas was then bubbled through the solution for 10 min. After another 2 h stirring at rt, the reaction mixture was concentrated under reduced pressure and resuspended in ethyl acetate before filtering. The filtered solids were collected and dried under vacuum to yield the desired tert-butyl 4-(1H-tetraazol-5-yl)piperidine-1-carboxylate. ESI-MS calculated for $C_{11}H_{19}N_5O_2$: 253.30, found 254 (M+H).

Step B:

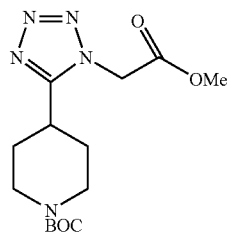

Triphenylphosphine (1.28 g, 4.89 mmol), DEAD (804 µL, 4.89 mmol), and methyl glycolate (378 µL, 4.89 mmol) were added to a solution of tert-butyl 4-(1H-tetraazol-5-yl)piperidine-1-carboxylate (619.7 mg, 2.447 mmol) in dichloromethane (20 mL). The reaction mixture was stirred for 16 h at rt and then concentrated under reduced pressure. Purification by MPLC (silica gel, 10-50% EtOAc/hexanes) afforded tert-butyl 4-[1-(2-methoxy-2-oxoethyl)-1H-tetraazol-5-yl]piperidine-1-carboxylate. ESI-MS calculated for $C_{14}H_{23}N_5O_4$: 325.36, found 348 (M+Na).

Step C:

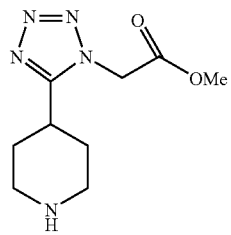

tert-Butyl 4-[1-(2-methoxy-2-oxoethyl)-1H-tetraazol-5-yl]piperidine-1-carboxylate (432.7 mg, 1.330 mmol) was dissolved in a solution of 4N HCl/dioxane (30 mL) and stirred at rt for 4 h before concentrating. The product was obtained as an HCl salt. ESI-MS calculated for $C_9H_{15}N_5O_2$: 225.25, found 226 (M+H).

Intermediate 28

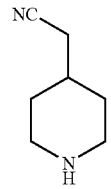

Step A:

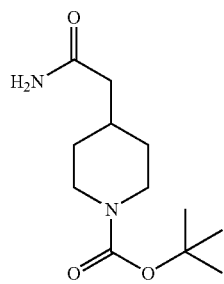

Triethylamine (3.15 mL, 22.6 mmol) and isobutylchloroformate (2.93 mL, 22.6 mmol) were added to a cooled (0° C.) solution of BOC-piperidineacetic acid (5.0 g, 21 mmol) in 125 mL of dichloromethane. The reaction mixture was allowed to warm to rt and stirred for 15 min under a nitrogen atmosphere. TLC showed complete consumption of starting material. Ammonia gas was bubbled directly into the reaction mixture for 5 min. The reaction mixture was then diluted with dichloromethane (100 mL) and washed with sodium bicarbonate solution (1×100 mL), 1N HCl solution (1×100 mL), and brine (1×100 mL). The organic layers were combined, dried over magnesium sulfate, filtered, and concentrated under reduced pressure. Purification by MPLC (silica gel, 20-100% EtOAc/hexanes) afforded the desired amide product. ESI-MS calculated for $C_{12}H_{22}N_2O_3$: 242.31, found 265 (M+Na).

Step B:

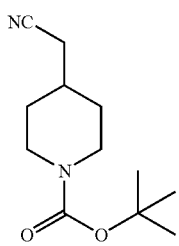

The compound prepared in Step A was dissolved in tetrahydrofuran (50 mL), placed under a nitrogen atmosphere, and cooled to 0° C. Pyridine (3.9 mL, 48 mmol) and trifluoroaceticanhydride (13.5 mL, 95.6 mmol) were added dropwise to the cooled solution. The reaction mixture was warmed to rt and stirred for 5 h. The reaction mixture was then diluted with diethyl ether (100 mL); washed with 1N HCl solution (1×100 mL), sodium bicarbonate solution (1×1000 mL), and brine (1×100 mL); dried over magnesium sulfate; filtered; and concentrated in vacuo. Purification by MPLC (silica gel, 10-100% EtOAc/hexanes) afforded the desired nitrile. ESI-MS calculated for $C_{12}H_{20}N_2O_2$: 224.30, found 169 (M+tBu+H). H NMR (CDCl$_3$, 500 MHz): δ 4.17 (s, 2H), 2.73 (s, 2H), 2.33 (d, J=6.0 Hz, 2H), 1.81 (d, J=13.0 Hz, 2H), 1.47 (s, 9H), 1.28 (d, J=12.5 Hz, 2H).

Step C:

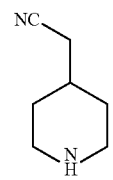

The nitrile prepared in Step B (3.12 g, 13.9 mmol) was dissolved in a solution of 4N HCl/dioxane (100 mL) and stirred at rt for 2 h before concentrating. The product was obtained as an HCl salt. ESI-MS calculated for $C_7H_{12}N_2$: 124.18, found 125 (M+H).

Intermediate 29

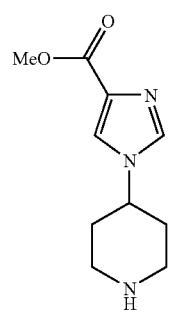

Step A:

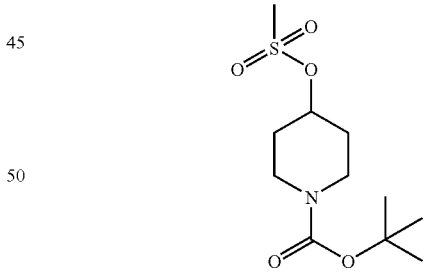

Methanesulfonyl chloride (4.2 mL, 55 mmol), triethylamine (10 mL, 75 mmol), and 4-dimethylaminopyridine (~10 mg) were added to a cooled (0° C.) solution of BOC-protected 4-hydroxypiperidine in 200 mL of methylene chloride. The reaction mixture was stirred at 0° C. for 1 h. The mixture was then washed with sodium bicarbonate solution (2×100 mL) and brine (1×100 mL), dried over magnesium sulfate, filtered, and concentrated under reduced pressure to afford tert-butyl 4-[(methylsulfonyl)oxy]piperidine-1-carboxylate, which was used without further purification. ESI-MS calculated for $C_{11}H_{21}NO_5S$: 279.35, found 302 (M+Na).

Step B:

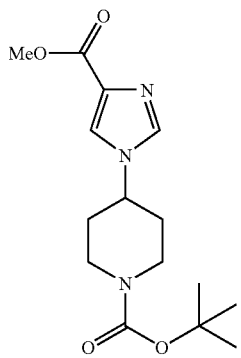

Sodium hydride (519 mg, 21.6 mmol) was added to a cooled (0° C.) solution of the compound prepared in Step A (4.03 g, 14.4 mmol) and methyl 4-imidazolecarboxylate (2.0 g, 16 mmol) in 100 mL of DMF. The reaction mixture was allowed to warm to rt. After 16 h at rt no desired product was observed, and the reaction mixture was heated to 50° C. for 163 h. Although a significant amount of the starting material (the mesyl intermediate) remained, the reaction mixture was diluted with 150 mL of diethyl ether, washed with water (5×150 mL) and brine (1×150 mL), dried over magnesium sulfate, filtered, and concentrated under reduced pressure. Purification by MPLC (silica gel, 0-60% EtOAc/hexanes) afforded the desired product and recovered starting material. ESI-MS calculated for $C_{15}H_{23}N_3O_4$: 309.36, found 310 (M+H).

Step C:

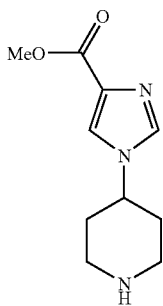

The compound prepared in Step B (174.5 mg, 0.5641 mmol) was dissolved in a solution of 4N HCl/dioxane (30 mL) and stirred at rt for 2 h before concentrating. The product was obtained as an HCl salt. ESI-MS calculated for $C_{10}H_{15}N_3O_2$: 209.25, found 210 (M+H).

Intermediate 30

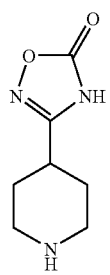

Step A:

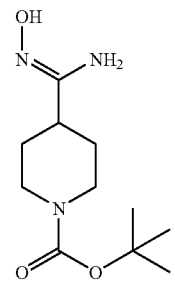

Hydroxylamine hydrochloride (6.0 g, 86 mmol) and triethylamine (12 mL, 86 mmol) were dissolved in DMSO (100 mL), filtered, and washed with THF (20 mL). The filtrate was partially concentrated under reduced pressure to remove the THF. The nitrile prepared in Step A of INTERMEDIATE 1 (3.62 g, 17.2 mmol) was dissolved in DMSO (15 mL) and added to the filtrate. The reaction mixture was heated at 75° C. for 27 h. The reaction mixture was then diluted with ethyl acetate (100 mL) and washed with water (1×100 mL). The aqueous portioned was back-washed with ethyl acetate (1×100 mL). The organic portions were combined, washed with water (1×100 mL) and then with brine (1×100 mL), dried over magnesium sulfate, filtered, and concentrated under reduced pressure. The desired product was obtained and used in subsequent steps without further purification.

ESI-MS calculated for $C_{11}H_{21}N_3O_3$: 243.30, found 188 (M+tBu+H).

Step B:

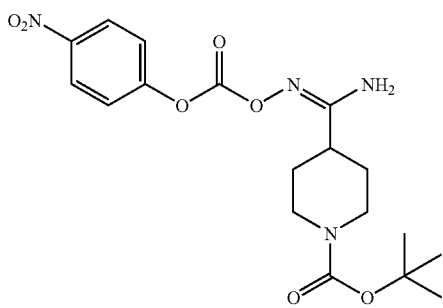

Triethylamine (2.05 mL, 14.7 mmol) and p-nitrophenylchloroformate (3.23 g, 16.0 mmol) were added to a solution of the compound prepared in Step A (3.25 g, 13.4 mmol) in DCM (100 mL). The reaction mixture was stirred at rt for 1 h. The reaction mixture was then washed with 1N HCl (1×75 mL), sodium bicarbonate solution (1×75 mL), and brine (1×75 mL); dried over magnesium sulfate; filtered; and concentrated in vacuo. The desired product was obtained and used in subsequent steps without further purification.

Step C:

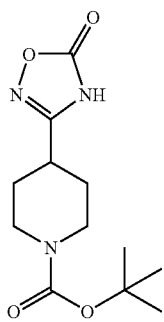

The compound prepared in Step B (4.86 g, 11.9 mmol) was dissolved in benzene (100 mL) and heated at reflux for 1 h. The reaction mixture was concentrated under reduced pressure and purified by MPLC (silica gel, 0-65% EtOAc/hexanes) to afford the desired heterocycle. ESI-MS calculated for $C_{12}H_{19}N_3O_4$: 269.30, found 170 (M−BOC+H).

Step D:

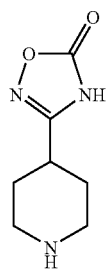

The compound prepared in Step C (2.19 g, 8.13 mmol) was dissolved in a solution of 4N HCl/dioxane (50 mL) and stirred at rt for 2 h before concentrating. The product was obtained as an HCl salt. ESI-MS calculated for $C_7H_{11}N_3O_2$: 169.18, found 170 (M+H).

Intermediate 31

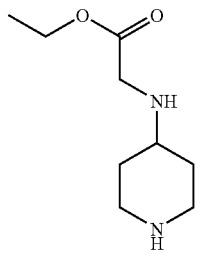

Step A:

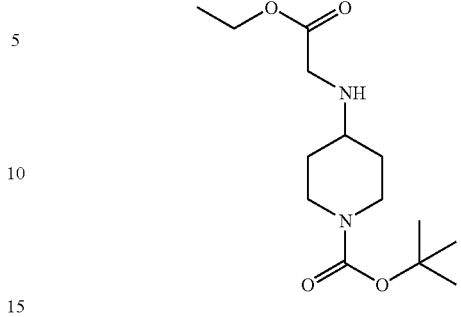

Ethyl aminoacetate hydrochloride (4.2 g, 30 mmol), triethylamine (4.2 mL, 30 mmol), and sodium triacetoxyborohydride (16 g, 75 mmol) were added to a solution of BOC-4-piperidone (3.04 g, 155.1 mmol) in DCM (100 mL). The reaction mixture was stirred at rt for 24 h and determined complete by HPLC/MS. The reaction mixture was diluted with DCM (50 mL), washed with sodium bicarbonate solution (1×100 mL) and brine (1×100 mL), dried over magnesium sulfate, filtered, and concentrated under reduced pressure. Purification by MPLC (silica gel, 10-100% EtOAc/hexanes) afforded the desired product.

ESI-MS calculated for $C_{14}H_{26}N_2O_4$: 286.37, found 231 (M+tBu+H).

Step B:

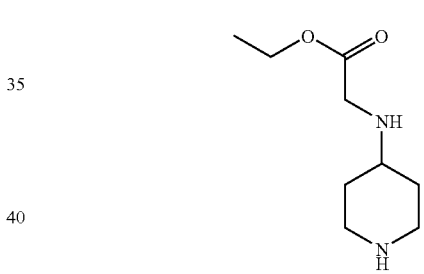

The compound prepared in Step A (2.59 g, 9.04 mmol) was dissolved in a solution of 4N HCl/dioxane (50 mL) and stirred at rt for 20 min before concentrating. The product was obtained as an HCl salt. ESI-MS calculated for $C_9H_{18}N_2O_2$: 186.25, found 187 (M+H).

Intermediate 32

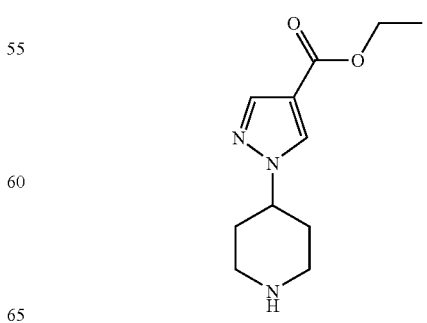

Step A:

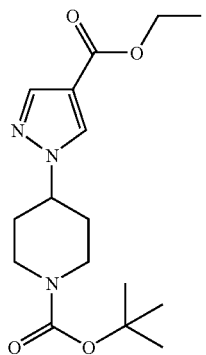

tert-Butyl 4-[(methylsulfonyl)oxy]piperidine-1-carboxylate (3.62 g, 13.0 mmol) was combined with ethyl 4-pyrazolecarboxylate (2.0 g, 14 mmol) in 50 mL of DMF. The mixture was cooled to 0° C., and sodium hydride (467 mg, 19.5 mmol) was added. The reaction mixture was then heated at 50° C. for 10 h. Afterwards, it was diluted with diethyl ether (100 mL), washed with water (5×100 mL) and brine (1×100 mL), dried over magnesium sulfate, filtered, and concentrated in vacuo. Purification by MPLC (silica gel, 5-100% EtOAc/hexanes) afforded the desired product. ESI-MS calculated for $C_{16}H_{25}N_3O_4$: 323.39, found 346 (M+Na).

Step B:

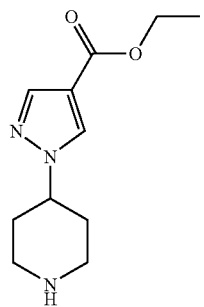

The compound prepared in Step A (1.81 g, 5.60 mmol) was dissolved in a solution of 4N HCl/dioxane (50 mL) and stirred at rt for 2 h before concentrating. The product was obtained as an HCl salt. ESI-MS calculated for $C_{11}H_{17}N_3O_2$: 223.27, found 224 (M+H).

Intermediate 33

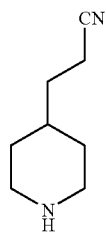

Step A:

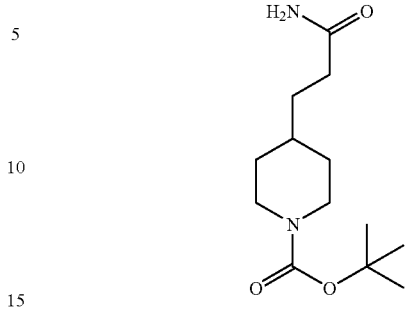

Commercially available BOC-piperidinyl propionic acid (2.79 g, 10.8 mmol) was dissolved in 100 mL of DCM and cooled to 0° C. Triethylamine (1.66 mL, 11.9 mmol) and isobutylchloroformate (1.55 mL, 11.9 mmol) were added to the cooled solution, and the reaction mixture was warmed to rt and stirred for 15 min. TLC showed complete consumption of the BOC-piperidinyl propionic acid. Ammonia gas was then bubbled into the reaction mixture for 5 min. The reaction mixture was washed with sodium bicarbonate solution (1×75 mL), 1N HCl (1×75 mL), and brine (1×75 mL); dried over magnesium sulfate; filtered; and concentrated. Purification by MPLC (silica gel, 0-100% EtOAc/hexanes) afforded the desired product. ESI-MS calculated for $C_{13}H_{24}N_2O_3$: 256.34, found 157 (M+BOC+H).

Step B:

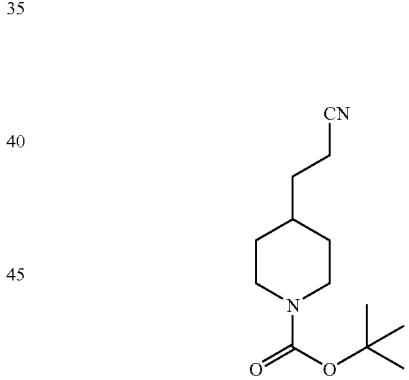

Pyridine (935 μL, 11.6 mmol) and trifluoroacetic anhydride (3.3 mL, 23 mmol) were added drop-wise to a stirring solution of the compound prepared in Step A (987.5 mg, 3.852 mmol) in tetrahydrofuran (20 mL) under a nitrogen atmosphere. The reaction temperature was stirred at rt, under a nitrogen atmosphere for 24 h. The reaction mixture was then diluted with diethyl ether (100 mL); washed with 1N HCl (3×100 mL), sodium bicarbonate solution (2×100 mL), and brine (1×100 mL); dried over magnesium sulfate; filtered; and concentrated in vacuo. Purification by MPLC (silica gel, 10-100% EtOAc/hexanes) afforded the desired product. ESI-MS calculated for $C_{13}H_{22}N_2O_2$: 238.33, found 183 (M+tBu+H).

Step C:

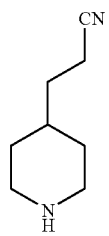

The compound prepared in Step B (709.1 mg, 2.977 mmol) was dissolved in a solution of 4N HCl/dioxane (50 mL) and stirred at rt. After 2 h, starting material was no longer present by TLC, and the reaction mixture was concentrated. The product was obtained as an HCl salt.

Intermediate 34

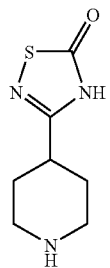

Step A:

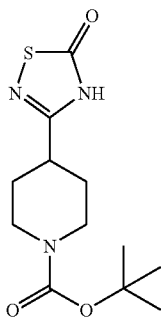

A mixture of previously described tert-butyl 4-[(Z)-amino(hydroxyimino)methyl]piperidine-1-carboxylate (1.26 g, 5.18 mol) and 1,1'-thiocarbonyldiimidazole (1.38 g, 7.77 mmol) in tetrahydrofuran (20 mL) was stirred at rt for 45 min. The reaction mixture was diluted with water (75 mL) and extracted with ethyl acetate (2×75 mL). The organic portions were combined, washed again with water (1×100 mL), dried over magnesium sulfate, filtered, and concentrated under reduced pressure. The resulting oil was dissolved in THF (20 mL). Borotrifluoride diethyl etherate (2.21 g, 15.5 mmol) was added to the solution, and the reaction mixture was stirred at rt for 1 h before concentrating under reduced pressure. The resulting mixture was dissolved in DCM (20 mL) and cooled to 0° C. Triethylamine (2.2 mL, 16 mmol) and di-tert-butyl dicarbonate (2.3 g, 10 mmol) were added to the dichloromethane solution, and the reaction mixture was stirred at rt for 2.5 h before concentrating. Purification by MPLC (silica gel, 0-100% ethyl acetate/hexanes) afforded the desired product. ESI-MS calculated for $C_{12}H_{19}N_3O_3S$: 285.36, found 212 (M+OtBu).

Step B:

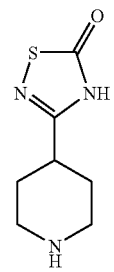

The compound prepared in Step A (411.5 mg, 1.442 mmol) was dissolved in a solution of 4N HCl/dioxane (20 mL) and stirred at rt. After 1.5 h, the reaction mixture was concentrated, and the desired product was obtained as an HCl salt. ESI-MS calculated for $C_7H_{11}N_3OS$: 185.25, found 186 (M+H).

A number of CCR-2 modulators were prepared in a similar fashion as described for Example 1 from (3S)-3-isopropyl-3-{[6-(trifluoromethyl)-2H-1,3-benzoxazin-3(4H)-yl]carbonyl}cyclopentanone (Intermediate 5) and amines available from commercial sources, known from the scientific literature, or described within this document. The cis and trans isomers that were obtained as a result of the reductive amination were separated either by chiral HPLC (using either a Chiralcel OD, 2 cm×25 cm, or a Chiralpak AD, 2 cm×25 cm column, both available from Chiral Technologies, Inc.) or by preparative TLC. In some cases where the amines used in the reductive amination reactions were themselves mixtures of more than one stereoisomer (i.e., if they had one or more stereocenters), it was generally possible to separate all possible isomers using chiral HPLC and or preparative TLC (sometimes a series of separations was required). Table 1 lists some representative examples of these analogs (only the more biologically active cis-isomers are shown).

TABLE 1
Analogs Prepared in an Analogous Fashion to EXAMPLE 1
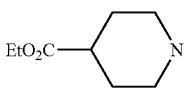
| EX. | Amine | Formula/calc. MW | ESI-MS observed M + H+ (M + 1) |
|---|---|---|---|
| 10 | 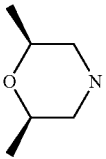 | C26H35F3N2O4 496 | 497 |
| 11 | 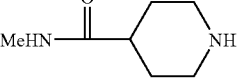 | C24H33F3N2O3 454 | 455 |
| 12 | 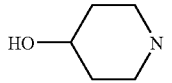 | C25H34F3N3O3 481 | 482 |
| 13 | 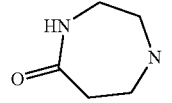 | C23H31F3N2O3 440 | 441 |
| 14 | 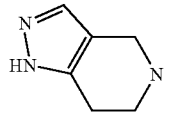 | C23H30F3N3O3 453 | 454 |
| 15 | 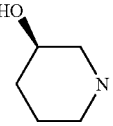 | C24H29F3N4O2 462 | 463 |
| 16 | 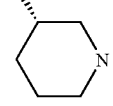 | C23H31F3N2O3 440 | 441 |
| 17 | 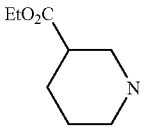 | C23H31F3N2O3 440 | 441 |
| 18 | EtO2C (mix 2 isomers) | C26H35F3N2O4 496 | 497 |

TABLE 1-continued
Analogs Prepared in an Analogous Fashion to EXAMPLE 1
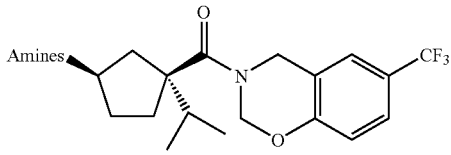
| EX. | Amine | Formula/calc. MW | ESI-MS observed M + H+ (M + 1) |
|---|---|---|---|
| 19 | 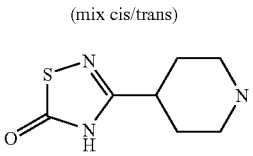<br>(mix cis/trans) | C24H31F3N6O2<br>492 | 493 |
| 20 | 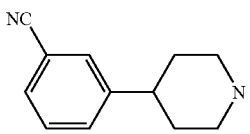 | C25H31F3N4O3S<br>524 | 525 |
| 21 | 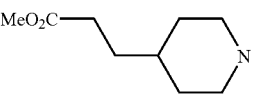 | C30H34F3N3O2<br>525 | 526 |
| 22 | 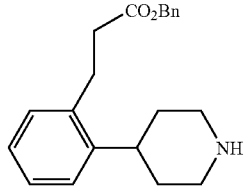 | C27H37F3N2O4<br>510 | 511 |
| 23 | 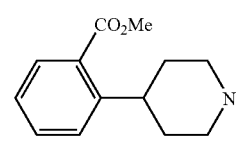 | C39H45F3N2O4<br>662 | 663 |
| 24 | 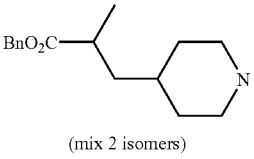 | C31H37F3N2O4<br>558 | 559 |
| 25 | 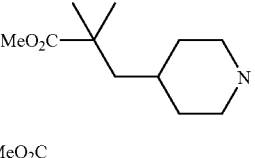<br>(mix 2 isomers) | C34H43F3N2O4<br>600 | 601 |
| 26 | 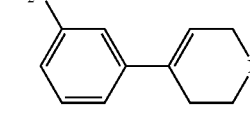 | C29H41F3N2O4<br>538 | 539 |
| 27 |  | C31H35F3N2O4<br>556 | 557 |

TABLE 1-continued
Analogs Prepared in an Analogous Fashion to EXAMPLE 1
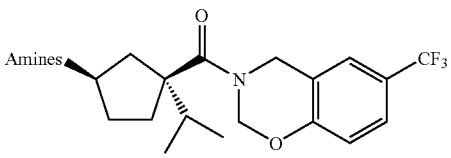
| EX. | Amine | Formula/calc. MW | ESI-MS observed M + H+ (M + 1) |
|---|---|---|---|
| 28 | 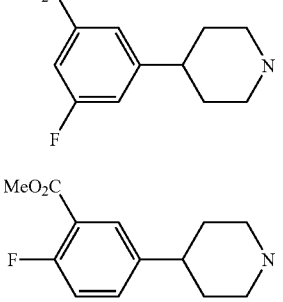 | C31H36F4N2O4 576 | 577 |
| 29 | 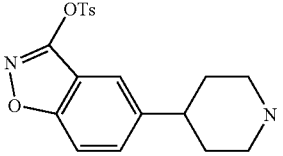 | C31H36F4N2O4 576 | 577 |
| 30 | 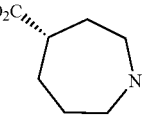 | C37H40F3N3O6S 711 | 712 |
| 31 | 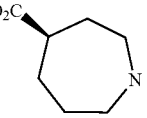 | C26H35F3N2O4 496 | 497 |
| 32 | 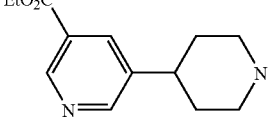 | C261435F3N2O4 496 | 497 |
| 33 | 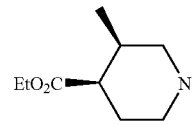 | C31H38F3N3O4 573 | 574 |
| 34 | 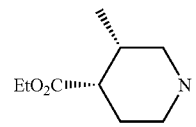 | C27H37F3N2O4 510 | 511 |
| 35 |  | C27H37F3N2O4 510 | 511 |

TABLE 1-continued
Analogs Prepared in an Analogous Fashion to EXAMPLE 1
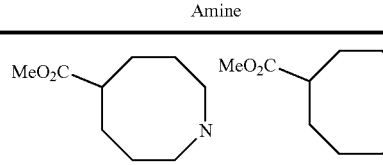
| EX. | Amine | Formula/calc. MW | ESI-MS observed M + H+ (M + 1) |
|---|---|---|---|
| 36 | 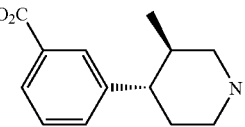<br>Mixture of regio and stereoisomers | C27H37F3N2O4<br>510 | 511 |
| 3A (see above) | 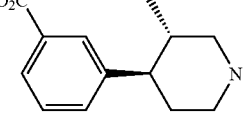 | C33H41F3N2O4<br>586 | 587 |
| 3B (see above) | 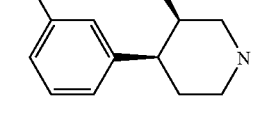 | C33H41F3N2O4<br>586 | 587 |
| 37 | 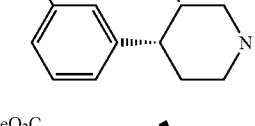 | C33H41F3N2O4<br>586 | 587 |
| 38 | 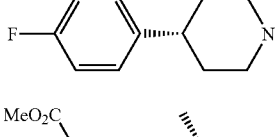 | C33H41F3N2O4<br>586 | 587 |
| 39 | 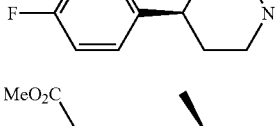 | C32H38F4N2O4<br>590 | 591 |
| 40 | 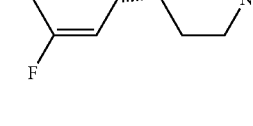 | C32H38F4N2O4<br>590 | 591 |
| 41 |  | C32H38F4N2O4<br>590 | 591 |

TABLE 1-continued

Analogs Prepared in an Analogous Fashion to EXAMPLE 1

| EX. | Amine | Formula/calc. MW | ESI-MS observed M + H+ (M + 1) |
|---|---|---|---|
| 42 | MeO₂C-[3-fluoro-5-(3-methylpiperidin-4-yl)phenyl] | C32H38F4N2O4 590 | 591 |
| 43 | methyl 3'-methylspiro[indene-1,4'-piperidine]-carboxylate (NH) | C34H39F3N2O4 596 | 597 |
| 44 | MeO₂C-spiro[indene-piperidine] N-substituted | C34H39F3N2O4 596 | 597 |
| 45 | EtO₂C-[3-(azepan-4-yl)phenyl] | C33H41F3N2O4 586 | 587 |
| 46 | EtO₂C-[3-(azepan-4-yl)phenyl] | C33H41F3N2O4 586 | 587 |
| 47 | NC-piperidin-4-yl | C24H30F3N3O2 449 | 450 |
| 48 | NC-CH2-piperidin-4-yl | C25H32F3N3O2 463 | 464 |

TABLE 1-continued

Analogs Prepared in an Analogous Fashion to EXAMPLE 1

| EX. | Amine | Formula/calc. MW | ESI-MS observed M + H$^+$ (M + 1) |
|---|---|---|---|
| 49 | NC-[CH2-piperidine] | C26H34F3N3O2<br>477 | 478 |
| 50 | EtO2C-CH2-NH-[4-piperidine] | C27H38F3N3O4<br>525 | 526 |
| 51 | MeO2C-CH2-[tetrazole]-[4-piperidine]<br>Either 1- or 2-isomer or both | C27H35F3N6O4<br>564 | 565 |
| 52 | EtO2C-[pyrazole]-N-[4-piperidine] | C29H37F3N4O4<br>562 | 563 |
| 53 | MeO2C-[imidazole]-N-[4-piperidine] | C28H35F3N4O4<br>548 | 549 |

In many cases the analogs listed in TABLE 1 could be further modified to generate new target chemokine receptor modulators. For example, the ester groups of the analogs in this table were hydrolyzed to give the corresponding carboxylic acids which were themselves potent modulators. These hydrolyses were usually accomplished under the conditions shown in EXAMPLE 2 and EXAMPLE 4, or with minor modifications to those conditions. Alternatively, in the case of benzyl esters, the carboxylic acid could be generated by hydrogenolysis by the protocol described for Step F of Intermediate 3, or a close modification thereof. A representative list of the resulting carboxylic acid containing chemokine receptor modulators is presented in TABLE 2.

TABLE 2

Carboxylic Acid Containing Analogs From Esters in Table 1

[Structure: Amines-substituted cyclopentane with isopropyl group, carbonyl linker to N of 6-(trifluoromethyl)-2H-benzo[e][1,3]oxazine]

| EX. | Amine | Formula/calc. MW | ESI-MS observed M + H$^+$ (M + 1) |
|---|---|---|---|
| 54 | HO$_2$C—[piperidin-4-yl] | C24H31F3N2O4<br>468 | 469 |
| 55 | HO$_2$C—[piperidin-3-yl]<br>(mix 2 isomers) | C24H31F3N2O4<br>468 | 469 |
| 56 | HO$_2$C—CH$_2$—[piperidin-4-yl] | C26H35F3N2O4<br>496 | 497 |
| 57 | [2-(piperidin-4-yl)phenyl]-CH$_2$CH$_2$-CO$_2$H | C32H39F3N2O4<br>572 | 573 |
| 58 | [2-(piperidin-4-yl)phenyl]-CO$_2$H | C30H35F3N2O4<br>544 | 545 |
| 59 | HO$_2$C—CH(CH$_3$)—CH$_2$—[piperidin-4-yl]<br>(mix 2 isomers) | C27H37F3N2O4<br>510 | 511 |
| 60 | HO$_2$C—C(CH$_3$)$_2$—CH$_2$—[piperidin-4-yl] | C28H39F3N2O4<br>524 | 525 |
| 61 | HO$_2$C—[3-(1,2,3,6-tetrahydropyridin-4-yl)phenyl] | C30H33F3N2O4<br>542 | 543 |

TABLE 2-continued

Carboxylic Acid Containing Analogs From Esters in Table 1

[Structure: Amines—cyclopentane with isopropyl group, connected via C(=O)—N to benzoxazine bearing CF₃]

| EX. | Amine | Formula/calc. MW | ESI-MS observed M + H⁺ (M + 1) |
|---|---|---|---|
| 62 | [4-(piperidin-4-yl)-2-fluorobenzoic acid] | C30H34F4N2O4<br>562 | 563 |
| 63 | [3-fluoro-5-(piperidin-4-yl)benzoic acid] | C30H34F4N2O4<br>562 | 563 |
| 64 | [azepane-4-carboxylic acid, one stereoisomer] | C25H33F3N2O4<br>482 | 483 |
| 65 | [azepane-4-carboxylic acid, other stereoisomer] | C25H33F3N2O4<br>482 | 483 |
| 66 | [5-(piperidin-4-yl)nicotinic acid] | C29H34F3N3O4<br>545 | 546 |
| 67 | [3-methylpiperidine-4-carboxylic acid, cis] | C25H33F3N2O4<br>482 | 483 |
| 68 | [3-methylpiperidine-4-carboxylic acid, trans] | C25H33F3N2O4<br>482 | 483 |
| 69 | [azocane-4/5-carboxylic acid, mixture] | C26H35F3N2O4<br>496 | 497 |

Mixture of regio and stereoisomers

TABLE 2-continued

Carboxylic Acid Containing Analogs From Esters in Table 1

| EX. | Amine | Formula/calc. MW | ESI-MS observed M + H⁺ (M + 1) |
|---|---|---|---|
| 4A (see above) | HO₂C-phenyl-piperidine (3-methyl) | C31H37F3N2O4 558 | 559 |
| 4B (see above) | HO₂C-phenyl-piperidine (3-methyl) | C31H37F3N2O4 558 | 559 |
| 70 | HO₂C-phenyl-piperidine (3-methyl) | C31H37F3N2O4 558 | 559 |
| 71 | HO₂C-phenyl-piperidine (3-methyl) | C31H37F3N2O4 558 | 559 |
| 72 | MeO₂C, F-phenyl-piperidine | C31H36F4N2O4 576 | 577 |
| 73 | MeO₂C, F-phenyl-piperidine | C31H36F4N2O4 576 | 577 |
| 74 | MeO₂C, F-phenyl-piperidine | C31H36F4N2O4 576 | 577 |
| 75 | MeO₂C, F-phenyl-piperidine | C31H36F4N2O4 576 | 577 |

TABLE 2-continued

Carboxylic Acid Containing Analogs From Esters in Table 1

| EX. | Amine | Formula/calc. MW | ESI-MS observed M + H+ (M + 1) |
|---|---|---|---|
| 76 | (4-methyl spiro-indene-piperidine with 6-CO2H) | C33H37F3N2O4 582 | 583 |
| 77 | (4-methyl spiro-indene-piperidine with 4-CO2H) | C33H37F3N2O4 582 | 583 |
| 78 | (3-(azepan-4-yl)benzoic acid) | C31H37F3N2O4 558 | 559 |
| 79 | (3-(azepan-4-yl)benzoic acid, other stereo) | C31H37F3N2O4 558 | 559 |
| 80 | (HO2C-CH2-NH-piperidin-4-yl-N) | C25H34F3N3O4 497 | 498 |
| 81 | (tetrazole-piperidine with two HO2CCH2 groups) Either 1- or 2-isomer or both | C26H33F3N6O4 550 | 551 |
| 82 | (pyrazole-4-CO2H, 1-piperidin-4-yl) | C27H33F3N4O4 534 | 535 |

TABLE 2-continued
Carboxylic Acid Containing Analogs From Esters in Table 1
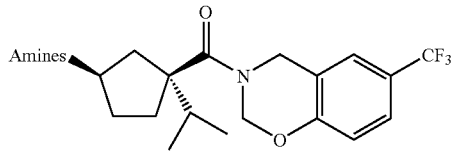
| EX. | Amine | Formula/calc. MW | ESI-MS observed M + H+ (M + 1) |
|---|---|---|---|
| 83 | | C27H33F3N4O4 534 | 535 |
TABLE 3
Analogs are Prepared in an Analogous Fashion to EXAMPLES 1 or 3 (followed by ester hydrolysis as described in EXAMPLES 2 or 4)

TABLE 3-continued

Analogs are Prepared in an Analogous Fashion to EXAMPLES 1 or 3 (followed by ester hydrolysis as described in EXAMPLES 2 or 4)

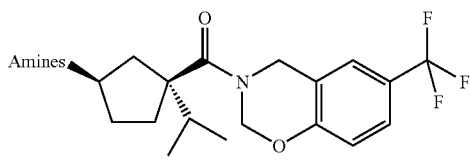

Amine:

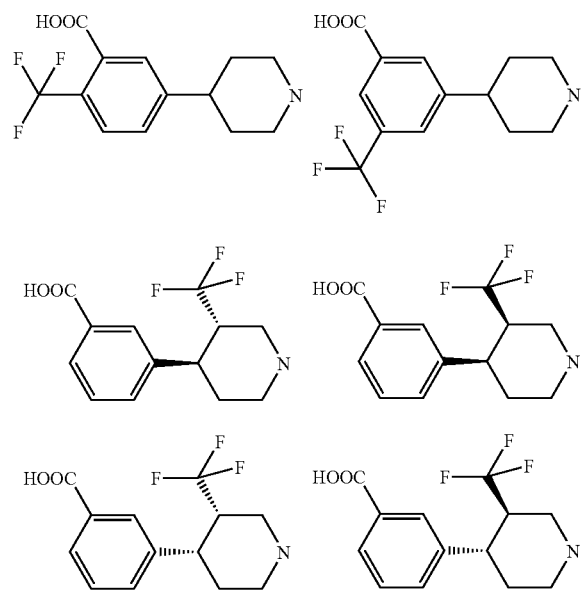

The benzoxazimes can be further replaced by substituted benzoxazines as seen in TABLE 4.

Intermediate 35

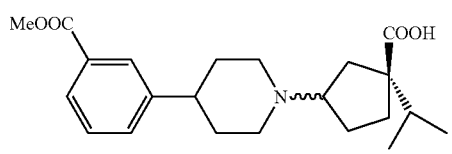

Step A:

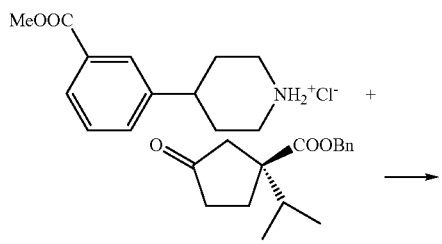

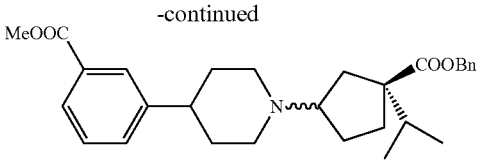

Methyl 3-(1-{(3S)-3-[(benzyloxy)carbonyl]-3-isopropylcyclopentyl}piperidin-4-yl)benzoate was synthesized as described in EXAMPLE 1 using benzyl (1S)-1-isopropyl-3-oxocyclopentanecarboxylate (from INTERMEDIATE 3, procedure A, step E) and methyl 3-piperidin-4-ylbenzoate (methyl analog of INTERMEDIATE 6). The desired was obtained as a 10:1 mixture of cis: trans around the cyclopentane ring.

Step B:

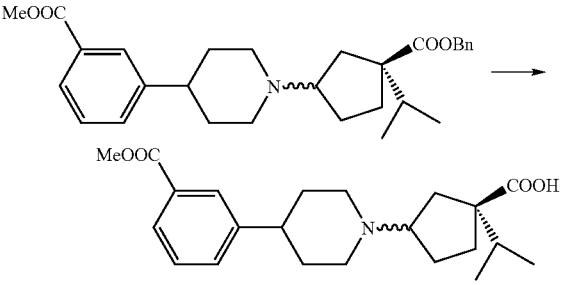

(1S)-1-Isopropyl-3-{4-[3-(methoxycarbonyl)phenyl]piperidin-1-yl}cyclopentane carboxylic acid was synthesized as described for INTERMEDIATE 3 (procedure A, step F) using methyl 3-(1-{(3S)-3-[(benzyloxy)carbonyl]-3-isopropylcyclopentyl}piperidin-4-yl)benzoate as starting material. The desired was obtained as a 10:1 mixture of cis: trans around the cyclopentane ring.

Intermediate 36

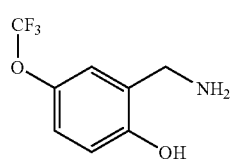

A solution of 5-(trifluoromethoxy)salicylaldehyde (4.85 mmol, 1.0 g), tert-butyl carbamate (14.55 mmol, 1.70 g), triethylsilane (14.55 mmol, 2.3 mL), trifluoroacetic acid (9.7 mmol, 0.72 mL) in acetonitrile was stirred at room temperature overnight. The reaction was quenched with saturated NaHCO3 and extracted with EtOAc. The combined organic layers were dried over Na2SO4 and purified by silica gel chromatography (15%-100% EtOAc/hexane). The resulting yellow solid was then dissolved in a mixture of TFA (10 mL) and dichloromethane (20 mL) and stirred for 2 hours at room temperature. The volatile solvents were then removed by rotovap to afford 2-(aminomethyl)-4-(trifluoromethoxy)phenol as a yellow oil. $^1$H NMR (CD$_3$OD) 7.28 (s, 1H), 7.22 (m, 1H), 6.97 (m, 1H), 4.13 (s, 2H), 1.59 (s, 1H).

EXAMPLE 84

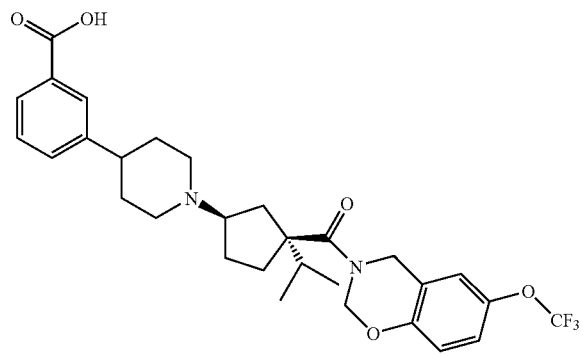

To a mixture of INTERMEDIATE 35 (1.23 mmol, 460 mg), INTERMEDIATE 36 (1.85 mmol, 383 mg), and DIEA (3.08 mmol, 0.54 mL) in 2.4 mL DMF was added HATU (2.46 mmol, 935 mg) at room temperature. The heterogeneous mixture immediately became homogeneous. The resulting solution was stirred at room temperature overnight. The reaction was quenched with saturated NaHCO$_3$ and extracted with dichloromethane. The combined organic layer was dried over MgSO$_4$ then purified by prep-plate TLC (10% MeOH/dichloromethane). The resulting amide and paraformaldehyde (10 eq) was then refluxed in 1:1 TFA/dichloromethane overnight. LC-MS indicated partial conversion. Additional paraformaldehyde (10 eq) and TFA were added and the mixture was reflux for another overnight. The final reaction mixture was cooled to room temperature and rotovapped to move volatile solvents. The residue was purified by prep-plate TLC (10% MeOH/DCM) to recover the benzoxazine product. The methyl ester benzoxazine was then hydrolyzed by vigorously stirring in a solution of LiOH (1M in H$_2$O, 10 eq), MeOH (2 vol eq to LiOH solution) and THF (2 vol eq to LiOH solution) at room temperature. The reaction mixture was rotovapped to remove volatile solvents. The residue was acidified with 1N HCl solution then extracted with dichloromethane. The combined organic layer was dried over MgSO$_4$ and then purified by HPLC (30%-100% ACN/water+0.1% TFA, Phenomenex column) to afford 3-[1-((1R,3S)-3-isopropyl-3-{[6-(trifluoromethoxy)-2H-1,3-benzoxazin-3(4H)-yl]carbonyl}cyclopentyl)piperidin-4-yl]benzoic acid (only the cis stereoisomer). $^1$H NMR (CD$_3$OD): 7.84 (s, 1H), 7.78 (m, 1H), 7.29 (m, 2H), 7.16 (m, 1H), 7.10 (m, 1H); 6.93 (d, 1H), 5.51 (m, 2H), 4.88 (m, 2H), 3.19 (m, 2H), 2.57 (m, 3H), 2.45 (m, 1H), 2.17 (m, 3H), 1.78 (m, 6H), 1.60 (m, 1H), 1.33 (m, 1H), 1.03 (d, 3H), 0.80 (d, 3H).

Several other examples are made according to the procedure described in EXAMPLE 84. These examples are compiled in Table 4.

TABLE 4

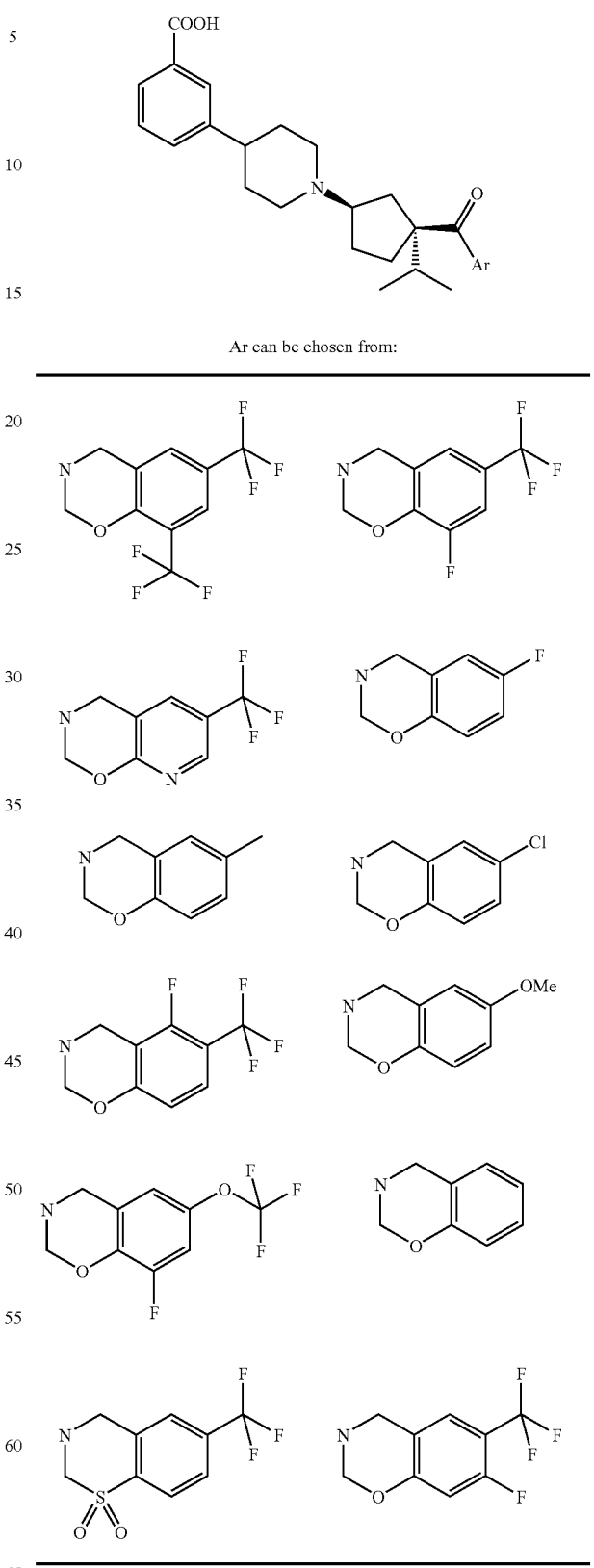

Ar can be chosen from:

EXAMPLE 85

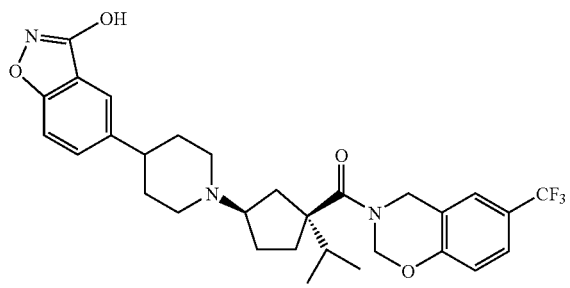

This was accomplished starting from EXAMPLE 30 in the same way as shown in EXAMPLE 9. ESI-MS calc. for C30H34F3N3O4: 557; Found: 558 (M+H).

Another way of modifying some of the analogs presented in TABLE 1 to give new, potent chemokine receptor modulators involves conversion of the nitrile groups found in some of the analogs in TABLE 1 into tetrazole groups. A method for accomplishing this is described for EXAMPLE 86 below:

EXAMPLE 86

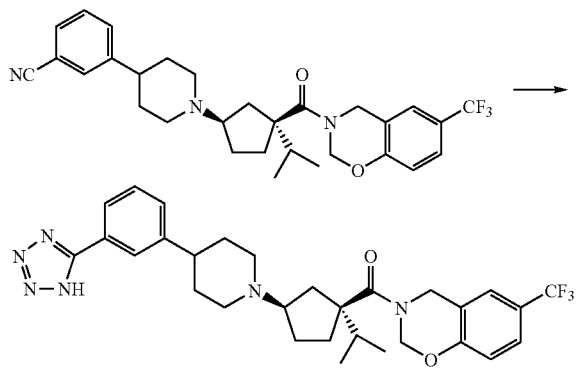

A solution of 3-[1-((1R,3S)-3-isopropyl-3-{[6-(trifluoromethyl)-2H-1,3-benzoxazin-3(4H)-yl]carbonyl}cyclopentyl)piperidin-4-yl]benzonitrile (prepared as described previously, 31.7 mg, 0.0603 mmol) and tributyltin azide (50 µL, 0.18 mmol) in 10 mL of toluene was stirred under a nitrogen atmosphere at reflux overnight. Since the reaction had not progressed far, more tributyltin azide (200 µL, 0.603 mmol) was added and the reaction was stirred under a nitrogen atmosphere at reflux for 4.5 h. At this point more tributyltin azide (200 µL, 0.603 mmol) was added and the reaction was stirred under a nitrogen atmosphere at reflux overnight. The reaction mixture was concentrated, then anhydrous 1N HCl in ether was added and the mixture was stirred for 15 min, then concentrated. The solids in the flask were separated from oil (presumably $Bu_3SnCl$) by pipetting out the oil. To the remaining solids was added brine and DCM. The aqueous layer was adjusted to pH 7 and the layers were separated. The aqueous layer was washed twice more with DCM, and then the organic layers were combined, dried over anhydrous $MgSO_4$, filtered, and concentrated. Purification by preparative TLC (silica, 50% ethyl actetate/hexanes to move the remaining $Bu_3SnCl$, and the baseline was collected) was followed by reverse phase HPLC (YMC Pack Pro C18, 100× 20 mm ID) to give the product as its TFA salt. This was converted to its HCl salt by dissolving in DCM and adding excess 1 N HCl/ether, then concentrating to give 3-[((1S,3R)-1-isopropyl-3-{4-[3-(1H-tetraazol-5-yl)phenyl]piperidin-1-yl}cyclopentyl)carbonyl]-6-(trifluoromethyl)-3,4-dihydro-2H-1,3-benzoxazine hydrochloride. ESI-MS calc. for C30H35F3N6O2: 568; Found: 569 (M+H).

In a similar fashion to that described immediately above, the EXAMPLES in TABLE 5 were prepared by conversion of nitrile containing analogs into the corresponding tetrazole containing analogs.

TABLE 5

Tetrazoles from nitriles in Table 1

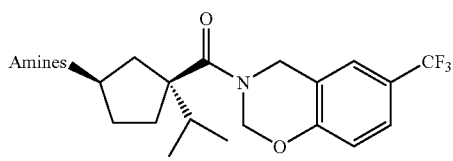

| EX. | Amine | Formula/calc. MW | ESI-MS observed M + H⁺ (M + 1) |
|---|---|---|---|
| 87 | (tetrazolyl-piperidine structure) | C24H31F3N6O2 492 | 493 |

TABLE 5-continued

Tetrazoles from nitriles in Table 1

| EX. | Amine | Formula/calc. MW | ESI-MS observed M + H⁺ (M + 1) |
|---|---|---|---|
| 88 | | C25H33F3N6O2 506 | 507 |
| 89 | | C26H35F3N6O2 520 | 521 |

Another example of modifying modulators to generate new modulators is described in the below two EXAMPLES:

EXAMPLE 90

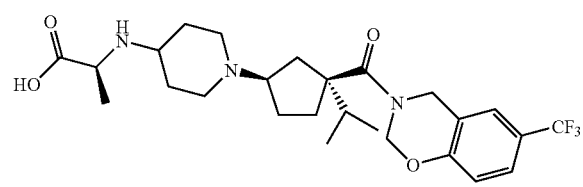

Step A:

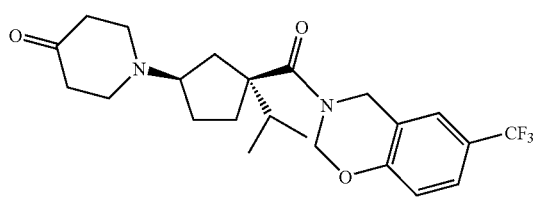

A solution of oxalyl chloride (35.0 µL, 0.402 mmol) in 15 mL of DCM was cooled to −78° C. DMSO (57.0 L, 0.805 mmol) was added drop-wise to the stirring solution. After 5 min 1-((1R,3S)-3-isopropyl-3-{[6-(trifluoromethyl)-2H-1,3-benzoxazin-3(4H)-yl]carbonyl}cyclopentyl)piperidin-4-ol (EXAMPLE 13, TABLE 1, 88 mg) in 5 mL of DCM was added drop-wise over 3 min to the reaction. After stirring for an additional 25 min at −78° C., triethylamine (224.0 µL, 1.609 mmol) in 5 mL of DCM was added drop-wise over 1 min. The reaction mixture was stirred at −78° C. for 10 min before the dry ice/acetone bath was removed. The reaction was allowed to warm to rt and stirred for 1.5 h. The reaction mixture was then diluted with DCM (50 mL) and washed with 1N HCl solution (1×75 mL), sodium bicarbonate solution (1×75 mL), and brine (1×75 mL). The aqueous layers were combined and extracted with dichloromethane (5×100 mL). The organic layers were combined, dried over magnesium sulfate, filtered, and concentrated under reduced pressure. Purification by preparatory TLC (silica gel, 0.4% ammonium hydroxide, 3.6% MeOH, 96% DCM) afforded 1-((1R,3S)-3-isopropyl-3-{[6-(trifluoromethyl)-2H-1,3-benzoxazin-3(4H)-yl]carbonyl}cyclopentyl)piperidin-4-one. ESI-MS calculated for $C_{23}H_{29}F_3N_2O_3$: 438.48, found 457 (hydrate+H).

Step B:

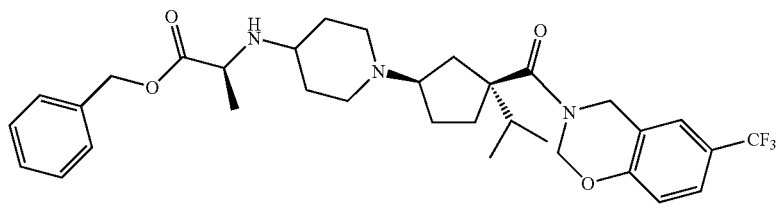

L-alanine benzylester hydrochloride (11 mg, 0.062 mmol), triethylamine (9.0 μL, 0.062 mmol), and sodium triacetoxyborohydride (22 mg, 0.10 mmol) were added to a stirring solution of 1-((1R,3S)-3-isopropyl-3-{[6-(trifluoromethyl)-2H-1,3-benzoxazin-3(4H)-yl]carbonyl}cyclopentyl)piperidin-4-one (19 mg, 0.021 mmol) in DCM (10 mL). The reaction mixture was stirred at rt for 96 h, however, the reaction had not gone to completion. Another 19 mg (0.11 mmol) of L-alanine benzylester hydrochloride and 15 μL (0.11 mmol) of triethylamine was added to the reaction mixture. After stirring for an additional 72 h at rt, the reaction mixture was diluted with dichloromethane (50 mL), washed with sodium bicarbonate solution (1×50 mL) and brine (1×50 mL), dried over magnesium sulfate, filtered, and concentrated under reduced pressure. Purification by preparatory TLC (silica gel, 0.25% ammonium hydroxide, 2.25% MeOH, 97.5% DCM) afforded the desired product. ESI-MS calculated for $C_{33}R_{42}F_3N_3O_4$: 601.70, found 602 (M+H).

Step C:

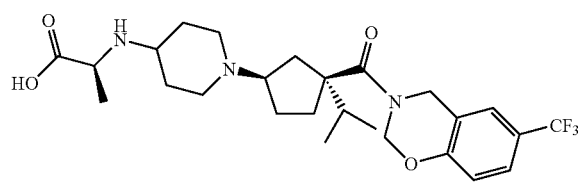

The compound prepared in Step B (5.6 mg, 0.0093 mmol) was dissolved in 5 mL of methanol and added to a flask containing palladium catalyst (~3 mg, 10 weight % on activated carbon). The reaction flask was repeatedly evacuated and flushed with hydrogen gas (3×). The reaction mixture was then stirred for 5 h at rt under a hydrogen balloon. The reaction was determined complete by HPLC/MS, filtered, and concentrated in vacuo. Purification by reverse-phase HPLC followed by treatment with 1.0 M HCl in diethyl ether afforded the HCl salt of the desired acid. ESI-MS calculated for $C_{26}H_{36}F_3N_3O_4$: 511.58, found 512 (M+H).

EXAMPLE 91

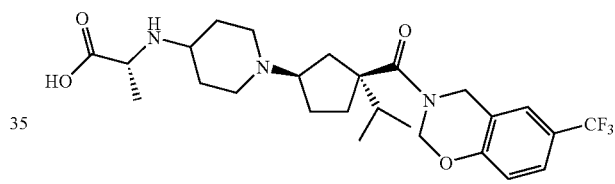

Step A:

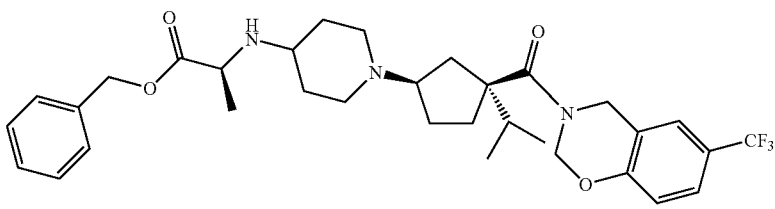

D-alanine benzylester p-toluenesulfonic acid salt (22 mg, 0.062 mmol), triethylamine (9.0 L, 0.062 mmol), and sodium triacetoxyborohydride (22 mg, 0.10 mmol) were added to a stirring solution of 1-((1R,3S)-3-isopropyl-3-{[6-(trifluoromethyl)-2H-1,3-benzoxazin-3(4H)-yl]carbonyl}cyclopentyl)piperidin-4-one (19 mg, 0.021 mmol) in DCM (10 mL). The reaction mixture was stirred at rt for 96 h, however, the reaction had not gone to completion. Another 39 mg (0.11 mmol) of L-alanine benzylester p-toluenesulfonic acid salt and 15 μL (0.11 mmol) of triethylamine was added to the reaction mixture. After stirring for an additional 72 h at rt, the reaction mixture was diluted with dichloromethane (50 mL), washed with sodium bicarbonate solution (1×50 mL) and brine (1×50 mL), dried over magnesium sulfate, filtered, and concentrated under reduced pressure. Purification by preparatory TLC (silica gel, 0.25% ammonium hydroxide, 2.25% MeOH, 97.5% DCM) afforded the desired product. ESI-MS calculated for $C_{33}H_{42}F_3N_3O_4$: 601.70, found 602 (M+H).

Step B:

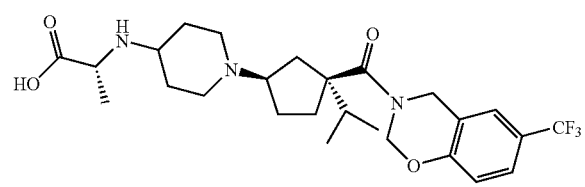

The compound prepared in Step A (5.3 mg, 0.0088 mmol) was dissolved in 5 mL of methanol and added to a flask containing palladium catalyst (~3 mg, 10 weight % on activated carbon). The reaction flask was repeatedly evacuated and flushed with hydrogen gas (3×). The reaction mixture was then stirred for 5 h at rt under a hydrogen balloon. The reaction was determined complete by HPLC/MS, filtered, and concentrated in vacuo. Purification by reverse-phase HPLC followed by treatment with 1.0M HCl in diethyl ether afforded the HCl salt of the desired acid. ESI-MS calculated for $C_{26}H_{36}F_3N_3O_4$: 511.58, found 512 (M+H).

In some cases the conditions for reductive amination described in EXAMPLE 1 and EXAMPLE 3 are not optimal for the preparation of certain analogs. This is particularly the case when the amine component in the reductive aminations has poor solubility. In those cases alternative conditions were used as described in EXAMPLE 92 below:

EXAMPLE 92

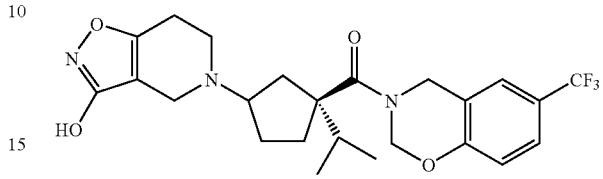

A mixture of commercially available Gaboxadol hydrochloride (134 mg, 0.760 mmol), (3S)-3-isopropyl-3-{[6-(trifluoromethyl)-2H-1,3-benzoxazin-3(4H)-yl] carbonyl}cyclopentanone (54 mg, 0.15 mmol), triethylamine (106 μL, 0.760 mmol), and sodium cyanoborohydride (57 mg, 0.91 mmol) in 5 mL of methanol was stirred at rt for 4 h. The reaction mixture was concentrated. Purification by reverse phase HPLC (YMC Pack Pro C18, 100×20 mm ID) gave the product as its TFA salt. This was converted to its HCl salt by dissolving in DCM and adding excess 1N HCl/ether, then concentrating to give target analog as its hydrochloride salt and as a mixture of cis and trans isomers. ESI-MS calc. for C24H28F3N3O4: 479; Found: 480 (M+H).

Other EXAMPLES prepared using the sodium cyanoborohydride reductive amination conditions described in EXAMPLE 92 are shown in TABLE 6.

TABLE 6

Analogs Prepared Using NaBH$_3$CN Conditions

| EX. | Amine | Formula/calc. MW | ESI-MS observed M + H$^+$ (M + 1) |
|---|---|---|---|
| 93 | (mix cis/tans) | C24H28F3N3O4 479 | 480 |
| 94 | (mix cis/tans) | C23H31F3N2O5S 504 | 505 |

TABLE 6-continued

Analogs Prepared Using NaBH₃CN Conditions

| EX. | Amine | Formula/calc. MW | ESI-MS observed M + H⁺ (M + 1) |
|---|---|---|---|
| 95 | | C25H31F3N4O4 508 | 509 |
| 96 | | C28H34F3N3O3 517 | 518 |

Intermediate 37

Step A:

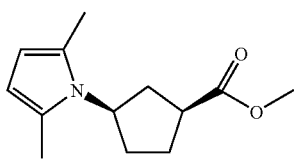

Methyl(1R,4S)-4-(2,5-dimethyl-1H-pyrrol-1-yl)cyclopent-2-ene-1-carboxylate (INTERMEDIATE 4, procedure B, step B) (40.6 g, 185 mmol), Pd/C (5.0 g, 10 wt %, 4.7 mmol Pd), and methanol (250 mL) were stirred vigorously under an atmosphere of H₂ for 18 h. The reaction mixture was filtered through Celite with methanol (250 mL), concentrated, and purified by silica gel chromatography (hexanes:ethyl acetate 19:1→4:1) to give an off-white solid. MS (ESI): 222.1 (M+H).

Step B:

n-Butyllithium (20 mL, 2.5M in hexanes, 50 mmol) was added in a slow stream (internal temperature kept ≦−40° C.) to a solution of diisopropylamine (7.7 mL, 55 mmol) and tetrahydrofuran (130 mL) at −78° C. under N₂. After 10 min, a solution of the above solid (10. g, 45 mmol) and tetrahydrofuran (20 mL) was added in a slow stream (internal temperature kept ≦55° C.). After an additional 2 h at −78° C., 2,2,2-trifluoroethyl iodide (6.2 mL, 64 mmol) was added dropwise (internal temperature kept ≦−70° C.). The reaction was maintained at −78° C. for 5 h, allowed to warm to rt overnight, and then poured into sat'd aq. NaHCO₃ (150 mL). The mixture was extracted with ethyl acetate (150 mL×2), dried (MgSO₄), filtered, and concentrated to give a yellow oil. MS (ESI): 304.5 (M+H).

Step C:

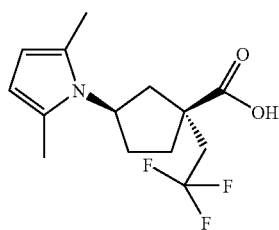

A mixture of the above oil, tetrahydrofuran (60 mL), methanol (60 mL), water (60 mL), and lithium hydroxide monohydrate (9.0 g, 0.24 mol) was heated at 60° C. for 15 h and then cooled to 0° C. Concentrated HCl (20 mL) was added carefully and the resulting mixture was extracted ethyl acetate (250 mL×2), dried (MgSO$_4$), filtered, and concentrated to give a red-orange solid. MS (ESI): 290.5 (M+H).

Step D:

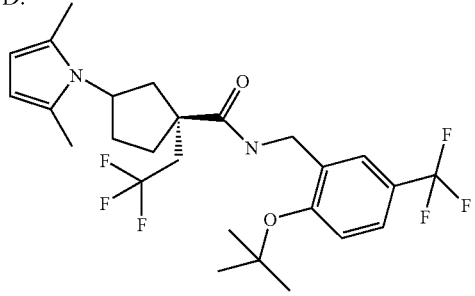

HATU (3.0 g, 7.9 mmol) was added to a solution of the above acid (1.74 g, 6.01 mmol), 1-hydroxy-7-azabenzotriazole (500. mg, 3.67 mmol), N,N-diisopropylethylamine (2.1 mL, 12 mmol) and dichloromethane (25 mL). After 1 h, INTERMEDIATE 1 (1.5 g, 6.1 mmol) was added and the reaction was maintained for 16 h. Silica gel (20 mL) was added, and the reaction was concentrated and purified by silica gel chromatography (hexanes:ethyl acetate 19:1→3:2) to give (1S)-N-[2-tert-butoxy-5-(trifluoromethyl)benzyl]-3-(2,5-dimethyl-1H-pyrrol-1-yl)-1-(2,2,2-trifluoroethyl)cyclopentanecarboxamide as an off-white solid. MS (ESI): 463.8 (M+tBu+H$_2$).

Intermediate 38

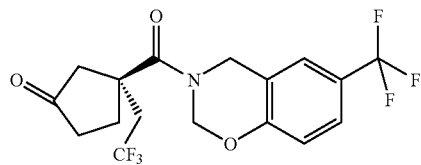

INTERMEDIATE 38 can be synthesized following the synthesis described for INTERMEDIATE 4 (procedure B, steps F and G) using (1S)-N-[2-tert-butoxy-5-(trifluoromethyl)benzyl]-3-(2,5-dimethyl-1H-pyrrol-1-yl)-1-(2,2,2-trifluoroethyl)cyclopentanecarboxamide as starting material.

EXAMPLE 97

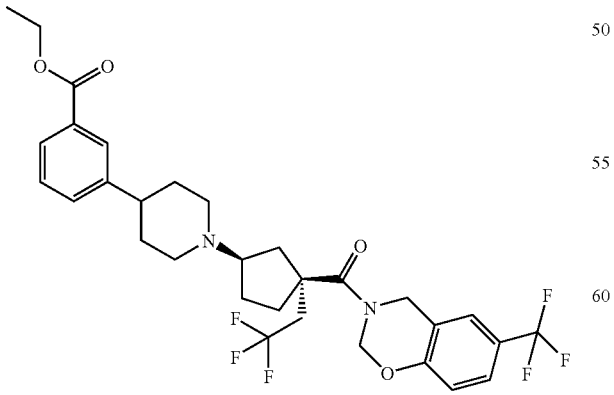

Ethyl 3-[1-((1R,3S)-3-(2,2,2-trifluoroethyl)-3-{[6-(trifluoromethyl)-2H-1,3-benzoxazin-3(4H)-yl]carbonyl}cyclopentyl)piperidin-4-yl]benzoate can be synthesized as described for EXAMPLE 1 using INTERMEDIATE 38 and INTERMEDIATE 6 as starting materials.

EXAMPLE 98

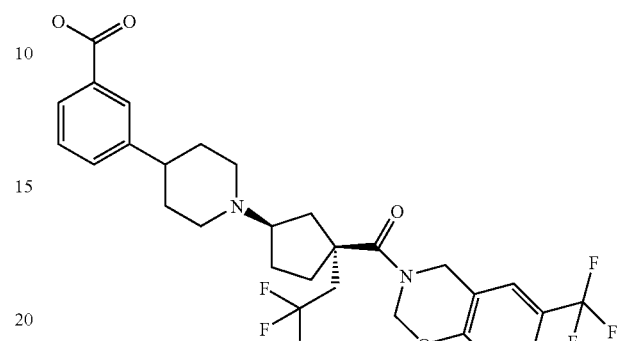

3-[1-((1R,3S)-3-(2,2,2-Trifluoroethyl)-3-{[6-(trifluoromethyl)-2H-1,3-benzoxazin-3(4H)-yl]carbonyl}cyclopentyl)piperidin-4-yl]benzoic acid can be synthesized as described for EXAMPLE 2 using ethyl 3-[1-((1R,3S)-3-(2,2,2-trifluoroethyl)-3-{[6-(trifluoromethyl)-2H-1,3-benzoxazin-3(4H)-yl]carbonyl}cyclopentyl)piperidin-4-yl]benzoate as starting material.

TABLE 7: Analogs are Prepared in an Analogous Fashion to EXAMPLES 97 (followed by ester hydrolysis as described in EXAMPLES 98)

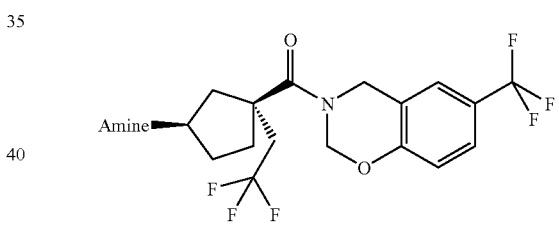

Amine:

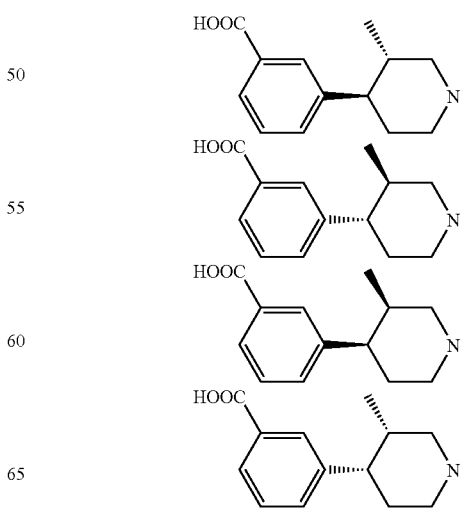

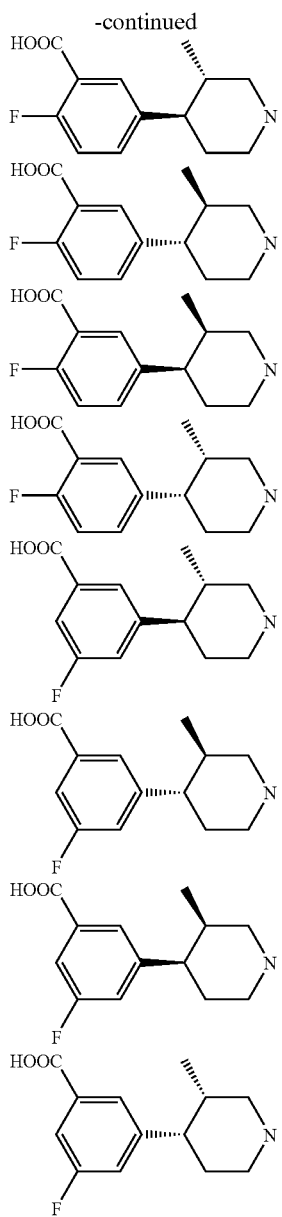

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. Therefore, the invention is defined by the claims which follow and not limited by the examples.

What is claimed is:

1. A compound represented by formula I:

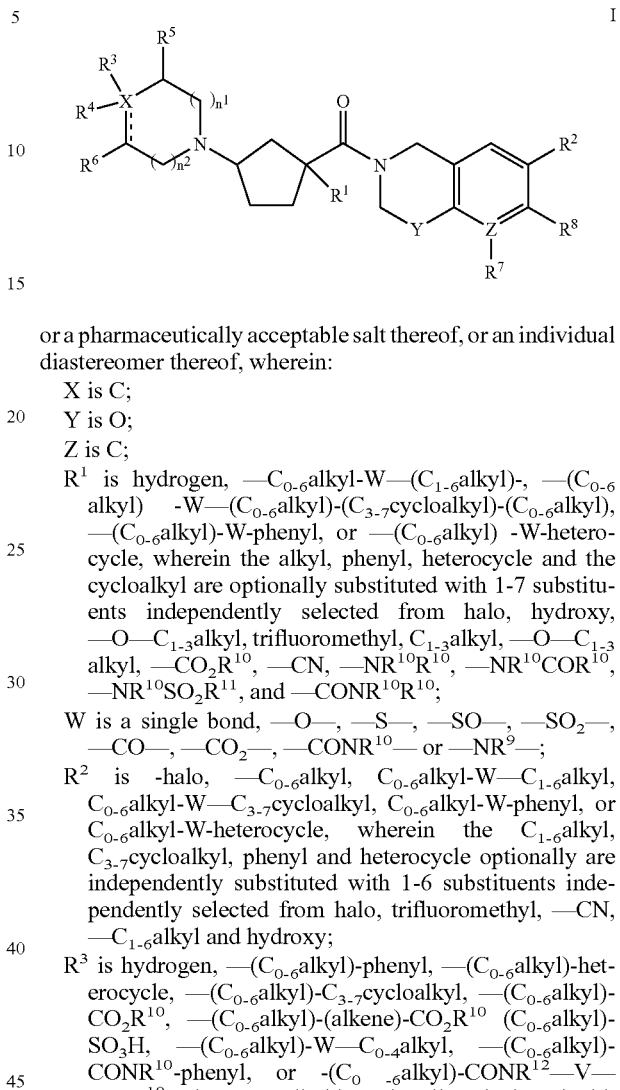

or a pharmaceutically acceptable salt thereof, or an individual diastereomer thereof, wherein:

X is C;

Y is O;

Z is C;

$R^1$ is hydrogen, —$C_{0-6}$alkyl-W—($C_{1-6}$alkyl)-, —($C_{0-6}$ alkyl) -W—($C_{0-6}$alkyl)-($C_{3-7}$cycloalkyl)-($C_{0-6}$alkyl), —($C_{0-6}$alkyl)-W-phenyl, or —($C_{0-6}$alkyl) -W-heterocycle, wherein the alkyl, phenyl, heterocycle and the cycloalkyl are optionally substituted with 1-7 substituents independently selected from halo, hydroxy, —O—$C_{1-3}$alkyl, trifluoromethyl, $C_{1-3}$alkyl, —O—$C_{1-3}$ alkyl, —$CO_2R^{10}$, —CN, —$NR^{10}R^{10}$, —$NR^{10}COR^{10}$, —$NR^{10}SO_2R^{11}$, and —$CONR^{10}R^{10}$;

W is a single bond, —O—, —S—, —SO—, —$SO_2$—, —CO—, —$CO_2$—, —$CONR^{10}$— or —$NR^9$—;

$R^2$ is -halo, —$C_{0-6}$alkyl, $C_{0-6}$alkyl-W—$C_{1-6}$alkyl, $C_{0-6}$alkyl-W—$C_{3-7}$cycloalkyl, $C_{0-6}$alkyl-W-phenyl, or $C_{0-6}$alkyl-W-heterocycle, wherein the $C_{1-6}$alkyl, $C_{3-7}$cycloalkyl, phenyl and heterocycle optionally are independently substituted with 1-6 substituents independently selected from halo, trifluoromethyl, —CN, —$C_{1-6}$alkyl and hydroxy;

$R^3$ is hydrogen, —($C_{0-6}$alkyl)-phenyl, —($C_{0-6}$alkyl)-heterocycle, —($C_{0-6}$alkyl)-$C_{3-7}$cycloalkyl, —($C_{0-6}$alkyl)-$CO_2R^{10}$, —($C_{0-6}$alkyl)-(alkene)-$CO_2R^{10}$ ($C_{0-6}$alkyl)-$SO_3H$, —($C_{0-6}$alkyl)-W—$C_{0-4}$alkyl, —($C_{0-6}$alkyl)-$CONR^{10}$-phenyl, or -($C_{0-6}$alkyl)-$CONR^{12}$—V—$CO_2R^{10}$, where $C_{0-6}$alkyl is optionally substituted with 1-5 substituents independently selected from halo, hydroxy, —$C_{0-6}$ alkyl, —O—$C_{1-3}$alkyl, trifluoromethyl, and —$C_{0-2}$alkyl-phenyl, where phenyl, heterocycle, cycloalkyl, and $C_{0-4}$alkyl are optionally substituted with 1-5 substituents independently selected from halo, trifluoromethyl, hydroxy, $C_{1-3}$alkyl, —O—$C_{1-3}$alkyl, —$C_{0-3}$—$CO_2R^{10}$, —CN, —$NR^{10}R^{10}$, —$CONR^{10}R^{10}$, and —$C_{0-3}$-heterocycle, or where phenyl and heterocycle may be fused to another heterocycle, which itself optionally may be substituted with 1-2 substituents independently selected from hydroxy, halo, —CO2R10, and —C1-3alkyl, and where alkene is optionally substituted with 1-3 substituents independently selected from halo, trifluoromethyl, $C_{1-3}$alkyl, phenyl, and heterocycle;

V is $C_{1-6}$alkyl or phenyl;

$R^{12}$ is hydrogen or $C_{1-4}$alkyl, or $R^{12}$ is joined via a 1-5 carbon tether to one of the carbons of V to form a ring;

$R^4$ is nothing when X is O or N or when a double bond joins the carbons to which $R^3$ and $R^6$ are attached, or $R^4$ is hydrogen, hydroxy, $C_{1-6}$alkyl, $C_{1-6}$alkyl-hydroxy, —O—$C_{1-3}$alkyl, —$CO_2R^{10}$, —$CONR^{10}R^{10}$, or —CN;

or $R^3$ and $R^4$ join to form a 1H-indenyl, 2,3-dihydro-1H-indenyl, 2,3-dihydro-benzofuranyl, 1,3-dihydro-isobenzofuranyl, 2,3-dihydro-benzothiofuranyl, 1,3-dihydro-isobenzothiofuranyl, 6H-cyclopenta[d]isoxazol-3-olyl, cyclopentanyl, or cyclohexanyl ring, wherein the ring optionally is substituted with 1-5 substituents independently selected from halo, trifluoromethyl, hydroxy, $C_{1-3}$alkyl, —O—$C_{1-3}$alkyl, —$C_{0-3}$—$CO_2R^{10}$, —CN, —$NR^{10}R^{10}$, —$CONR^{10}R^{10}$, and —$C_{0-3}$-heterocyclyl;

$R^5$ and $R^6$ are independently hydrogen, hydroxy, $C_{1-6}$alkyl, $C_{1-6}$alkyl-$CO_2R^{10}$, $C_{1-6}$alkyl-hydroxy, —O—$C_{1-3}$alkyl, or halo, or $R^5$ or $R^6$ is =O connected to the ring via a double bond;

or $R^3$ and $R^5$ or $R^4$ and $R^6$ join to form a phenyl or heterocyclyl ring, wherein the ring is optionally substituted with 1-7 substituents independently selected from halo, trifluoromethyl, hydroxy, $C_{1-3}$alkyl, —O—$C_{1-3}$alkyl, —$CO_2R^{10}$, —CN, —$NR^{10}R^{10}$ and —$CONR^{10}R^{10}$;

when Z=C, $R^7$ is hydrogen, hydroxy, halo or $C_{1-6}$alkyl optionally substituted with 1-6 substituents independently selected from fluro, —O—$C_{1-6}$alkyl optionally substituted with 1-6 fluro, —$NR^{10}R^{10}$, —$NR^{10}CO_2R^{11}$, —$NR^{10}CONR^{10}R^{10}$, —$NR^{10}$—$SO_2$—$NR^{10}R^{10}$, —$NR^{10}$—$SO_2R^{11}$, heterocycle, —CN, —$CONR^{10}R^{10}$, —$CO_2R^{10}$, —$NO_2$, —S—$R^{10}$, —SO—$R^{11}$, —$SO_2$—$R^{11}$ and —$SO_2$—$NR^{11}R^{11}$;

$R^8$ is hydrogen, $C_{1-6}$alkyl, trifluoromethyl, trifluoromethoxy, chloro, fluoro, bromo, phenyl, alkoxy, or cyano;

$R^9$ is $SO_2R^{11}$, $COR^{10}$, $CONHR^{10}$, $CO_2R^{11}$, or $SO_2NHR^{10}$;

$R^{10}$ is hydrogen, —$C_{1-6}$ alkyl, benzyl, phenyl, or —$C_{0-6}$alkyl-$C_{3-6}$ cycloalkyl, optionally substituted with 1-3 substituents independently selected from halo, $C_{1-3}$alkyl, $C_{1-3}$ alkoxy and trifluoromethyl;

$R^{11}$ is $C_{1-6}$alkyl, —$C_{0-6}$alkyl-$C_{3-6}$cycloalkyl, benzyl or phenyl, optionally substituted with 1-3 substituents independently selected from halo, $C_{1-3}$alkyl, $C_{1-3}$alkoxy and trifluoromethyl;

$n^1$ and $n^2$ are each 1; and the dashed line represents a single or a double bond.

2. The compound of claim 1, or a pharmaceutically acceptable salt or diastereomer thereof, wherein $R^8$ is selected from the group consisting of hydrogen, $C_{1-6}$alkyl, trifluoromethyl, trifluoromethoxy, chloro, fluoro, bromo, and phenyl.

3. The compound of claim 2, or a pharmaceutically acceptable salt or individual diastereomer thereof, wherein:

$R^3$ and $R^4$ join to form a 1H-indenyl, 2,3-dihydro-1H-indenyl, 2,3-dihydro-benzofuranyl, 1,3-dihydro-isobenzofuranyl, 2,3-dihydro-benzothiofuranyl, 1,3-dihydro-isobenzothiofuranyl, 6H-cyclopenta[d]isoxazol-3-olyl, cyclopentanyl, or cyclohexanyl ring, wherein the ring optionally is substituted with 1-5 substituents independently selected from halo, trifluoromethyl, hydroxy, $C_{1-3}$alkyl, —O—$C_{1-3}$alkyl, —$C_{0-3}$—$CO_2R^{10}$, —CN, —$NR^{10}R^{10}$, —$CONR^{10}R^{10}$ and —$C_{0-3}$-heterocyclyl;

or $R^3$ and $R^5$ or $R^4$ and $R^6$ join to form a phenyl or heterocyclyl ring, wherein the ring is optionally substituted with 1-7 substituents independently selected from halo, trifluoromethyl, hydroxy, $C_{1-3}$alkyl, —O—$C_{1-3}$alkyl, —$CO_2R^{10}$, —CN, —$NR^{10}R^{10}$ and —$CONR^{10}R^{10}$.

4. The compound of claim 2, represented by formula Ia:

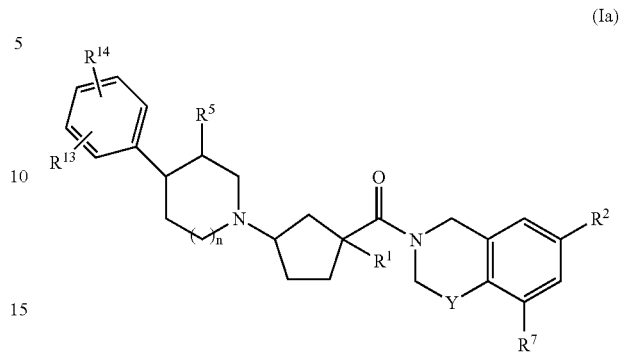

(Ia)

or a pharmaceutically acceptable salt or individual diastereomer thereof, wherein $R^{13}$ and $R^{14}$ are independently selected from hydrogen, halo, trifluoromethyl, hydroxy, —$C_{1-3}$alkyl, —O—$C_{1-3}$alkyl, —$C_{0-3}$—$CO_2H$, —$C_{0-3}$—$CO_2C_{1-3}$alkyl, —CN, and —$C_{0-3}$-heterocycle;

or $R^{13}$ and $R^{14}$ join to form a heterocycle which is fused to the phenyl ring, which heterocycle is unsubstituted or substituted with 1-2 substituents independently selected from hydroxy, halo, —$CO_2R^{10}$ and —$C_{1-3}$alkyl; and n is 1.

5. The compound of claim 2, represented by formula Ib:

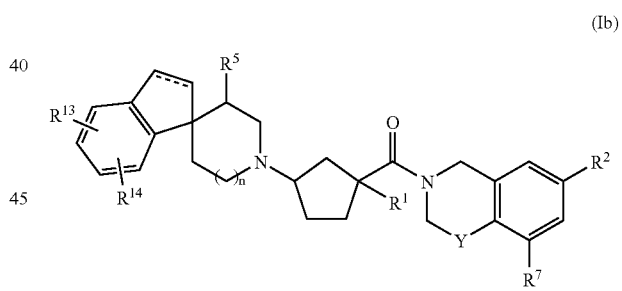

(Ib)

or a pharmaceutically acceptable salt or individual diastereomer thereof, wherein:

$R^{13}$ and $R^{14}$ are independently selected from hydrogen, halo, trifluoromethyl, hydroxy, —$C_{1-3}$alkyl, —O—$C_{1-3}$alkyl, —$C_{0-3}$—$CO_2H$, —$C_{0-3}$—$CO_2C_{1-3}$alkyl, —CN, and —$C_{0-3}$- heterocycle;

or $R^{13}$ and $R^{14}$ join to form a heterocycle which is fused to the phenyl ring, which heteocycle is unsubstituted or substituted with 1-2 substituents independently selected from hydroxy, halo, —$CO_2R^{10}$ and —$C_{1-3}$alkyl; and n is 1.

6. The compound of claim 2, represented by formula Ic:

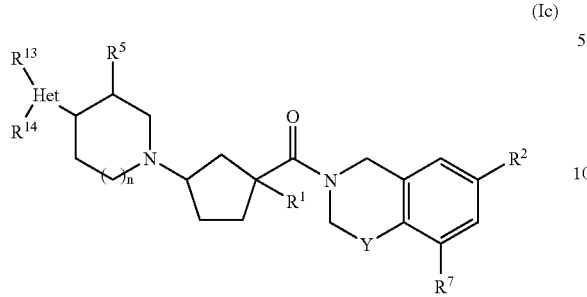

(Ic)

or a pharmaceutically acceptable salt or individual diastereomer thereof,
wherein $R^{13}$ and $R^{14}$ are independently selected from hydrogen, halo, trifluoromethyl, hydroxy, —$C_{1-3}$alkyl, —O—$C_{1-3}$alkyl, —$C_{0-3}$—$CO_2H$, —$C_{0-3}$—$CO_2C_{1-3}$alkyl, —CN, and —$C_{0-3}$-heterocycle;
or $R^{13}$ and $R^{14}$ join to form a heterocycle which is fused to the phenyl ring, which heterocycle is unsubstituted or substituted with 1-2 substituents independently selected from hydroxy, halo, —$CO_2R^{10}$ and —$C_{1-3}$alkyl;
n is 1; and
Het is a heterocycle.

7. The compound of claim 2, represented by formula Id:

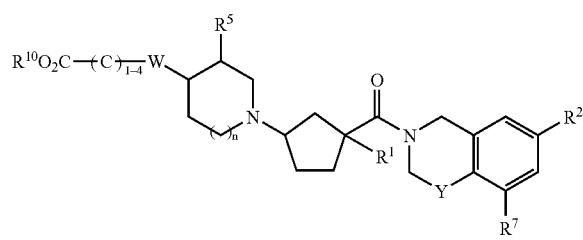

(Id)

or a pharmaceutically acceptable salt or individual diastereomer thereof, wherein
n is 1; and
the $C_{1-4}$ carbon chain is optionally substituted with 1-4 substituents independently selected from halo, hydroxy, —$C_{0-6}$alkyl, —O—$C_{1-3}$alkyl, trifluoromethyl, and —$C_{0-2}$alkyl-phenyl; or the $C_{1-4}$ carbon chain is part of a $C_{3-7}$cycloalkyl ring.

8. The compound of claim 2, represented by formula Ie:

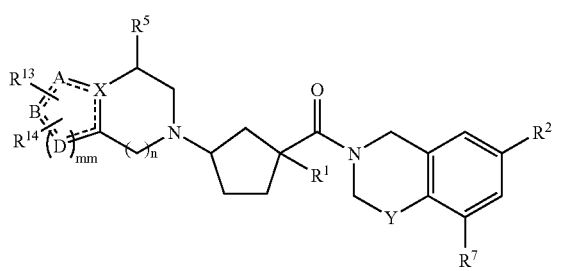

(Ie)

or a pharmaceutically acceptable salt or individual diastereomer thereof, wherein:
n is 1;
dotted lines represent an optional bond;
mm is 1 or 2, and
A, B, and D are each independently C, N, O, or S; or mm=2 and A, B, and D form a phenyl ring.

9. The compound of claim 2, represented by formula If:

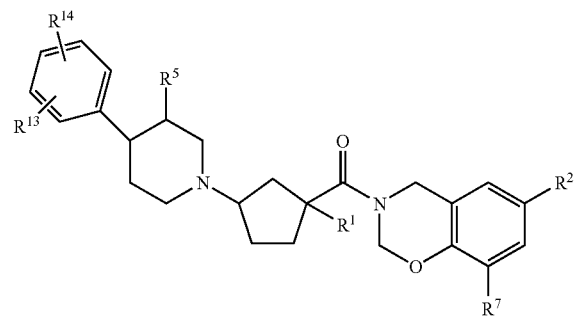

(If)

or a pharmaceutically acceptable salt or individual diastereomer thereof, wherein $R^{13}$ and $R^{14}$ join to form a heterocycle fused to the phenyl ring, and wherein the heterocycle is optionally substituted with 1-2 substituents independently selected from hydroxy, halo, —$CO_2R^{10}$ and —$C_{1-3}$alkyl.

10. The compound of claim 2, represented by formula Ig:

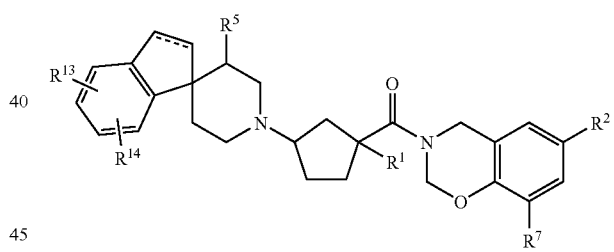

(Ig)

or a pharmaceutically acceptable salt or individual diastereomer thereof.

11. The compound of claim 2, represented by formula Ih:

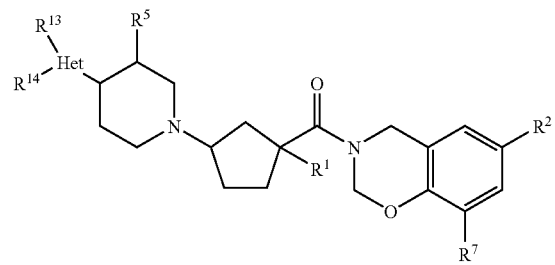

(Ih)

or a pharmaceutically acceptable salt or individual diastereomer thereof, wherein Het is a heterocycle.

12. The compound of claim 2, represented by formula Ii:
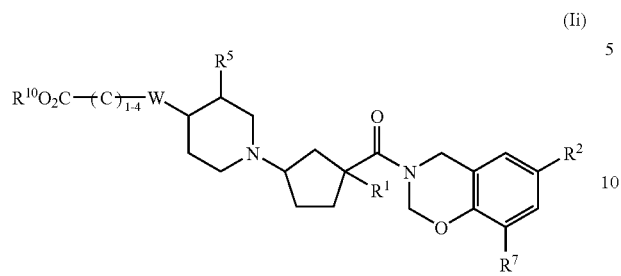
(Ii)
or a pharmaceutically acceptable salt or individual diastereomer thereof, wherein the $C_{1-4}$ carbon chain is optionally substituted with 1-4 substituents independently selected from halo, hydroxy, —$C_{0-6}$alkyl, —O—$C_{1-3}$alkyl, trifluoromethyl and —$C_{0-2}$alkyl-phenyl.
13. A compound of claim 2 selected from:
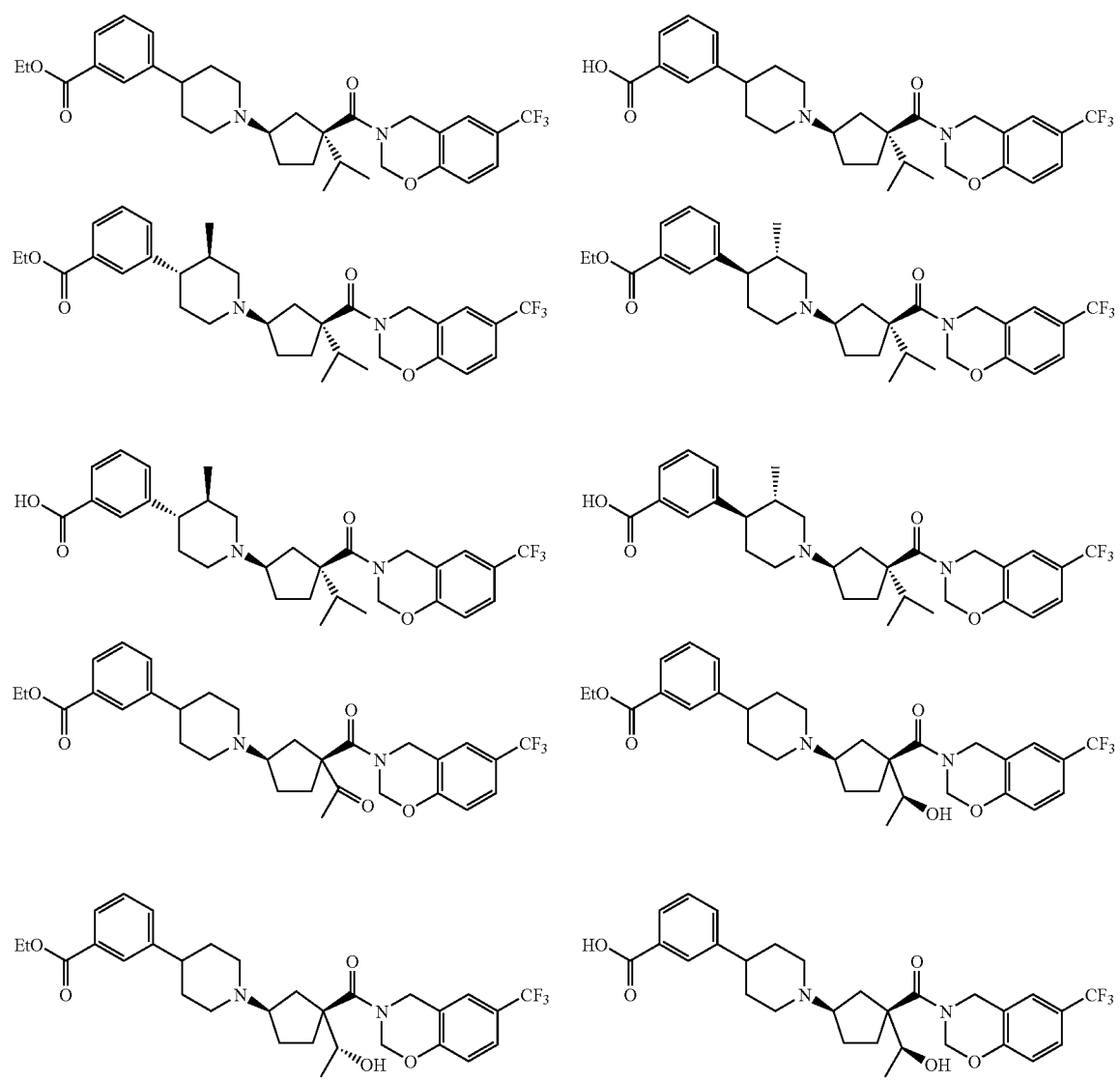

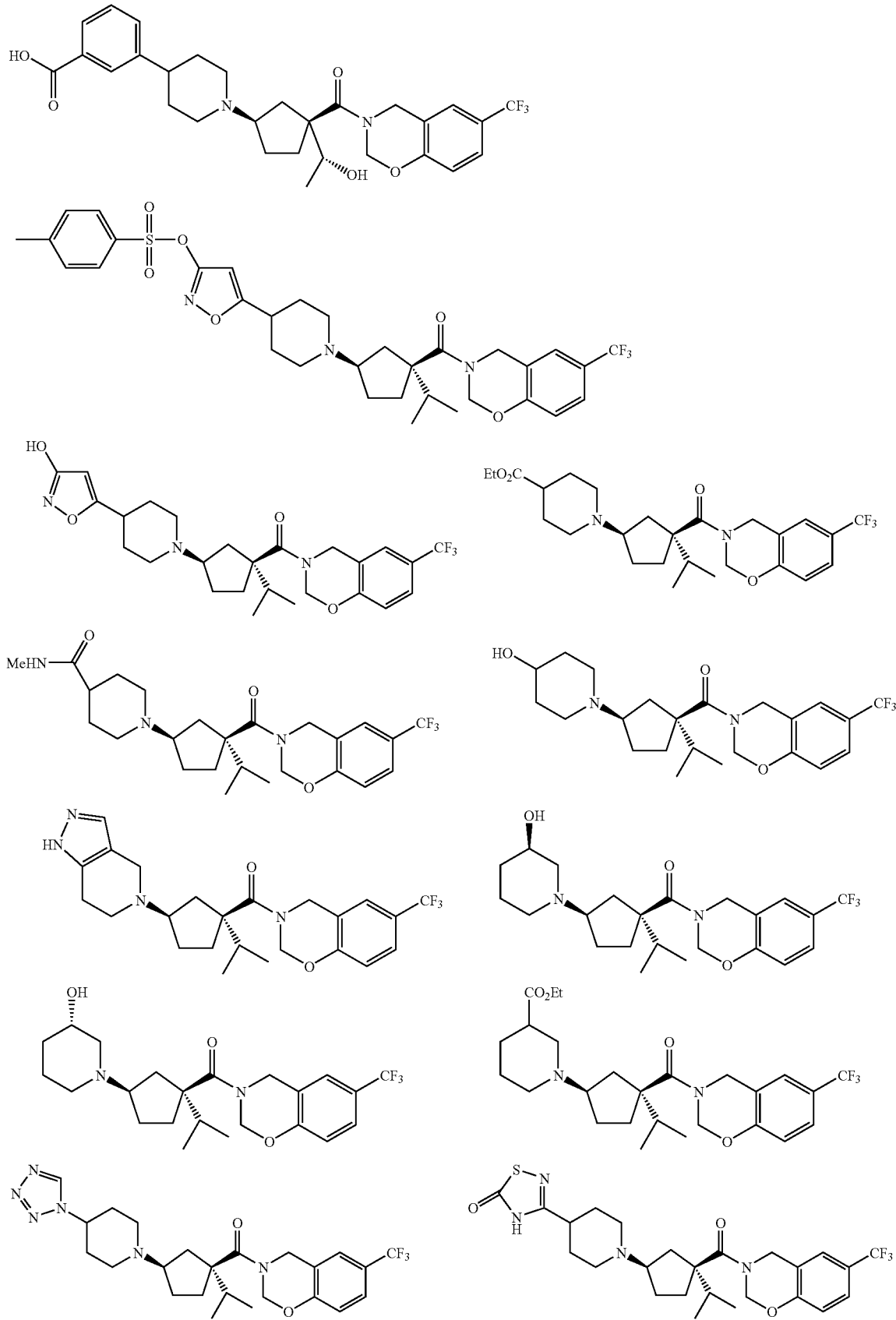

159
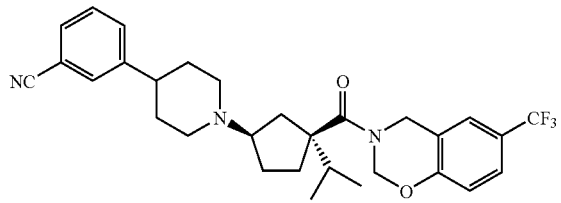
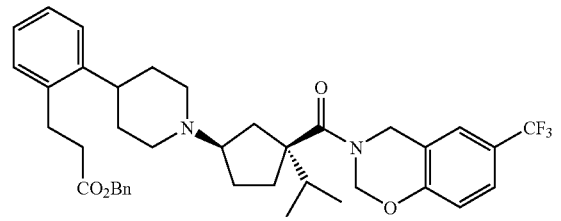
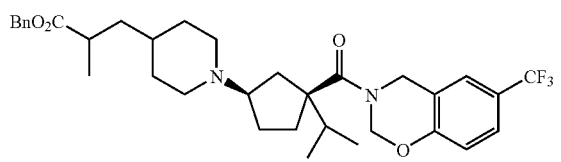
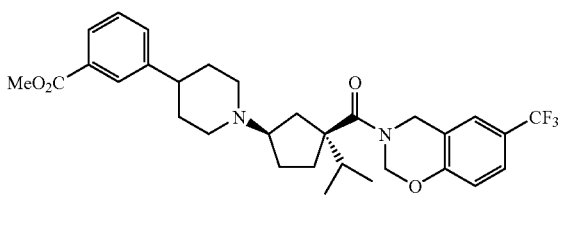
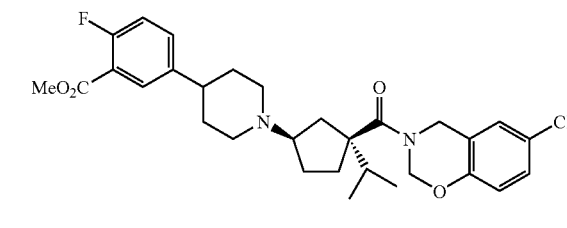
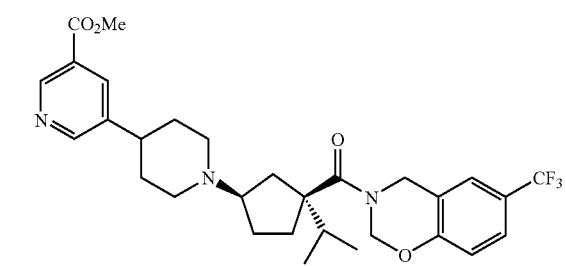
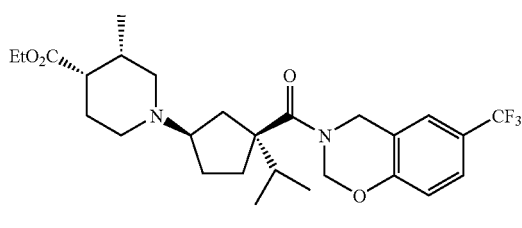
160
-continued
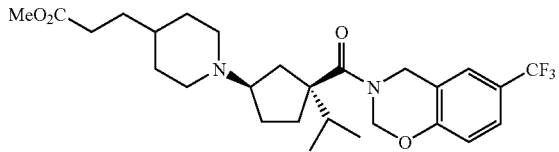
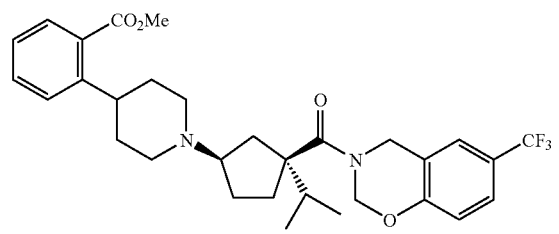
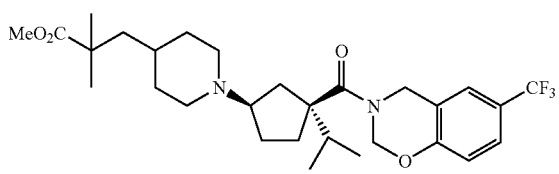
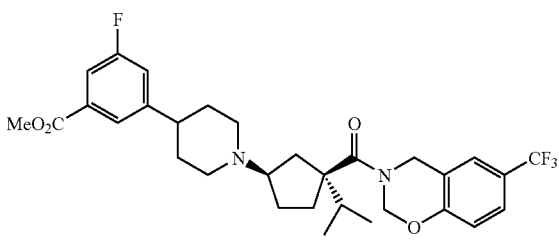
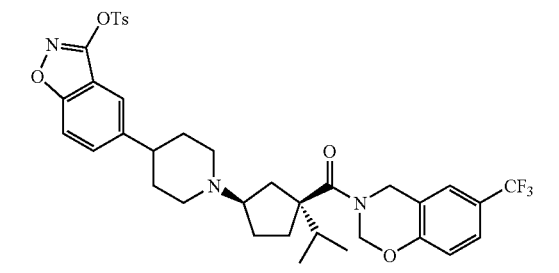
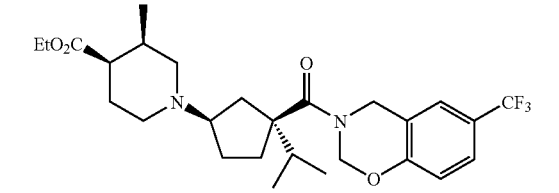
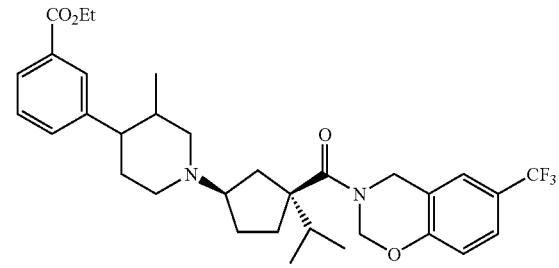

-continued
161
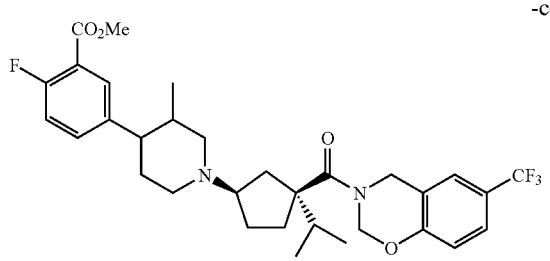
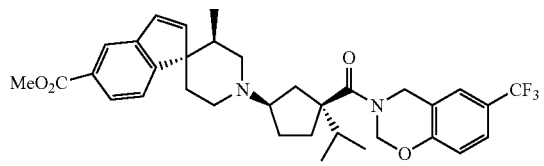
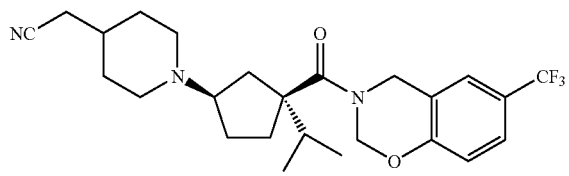
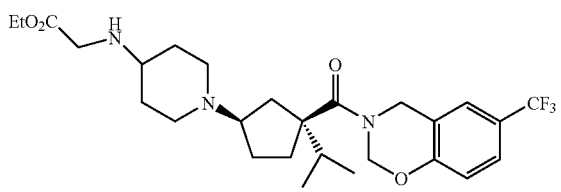
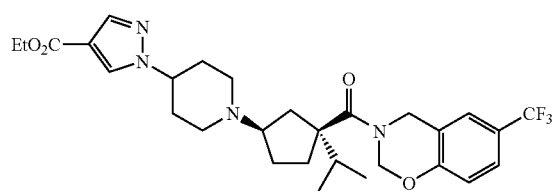
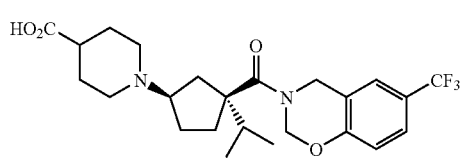
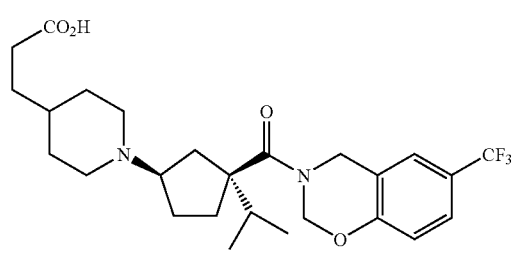
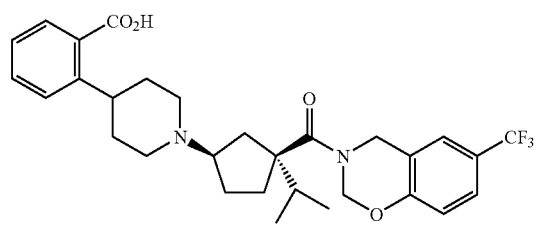
162
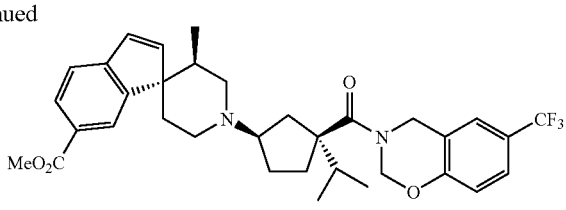
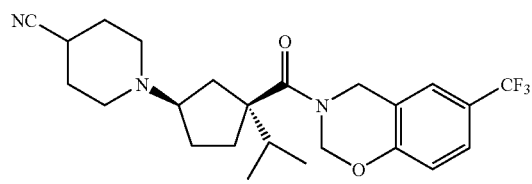
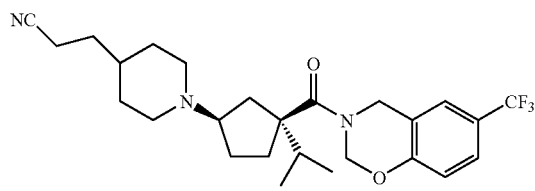
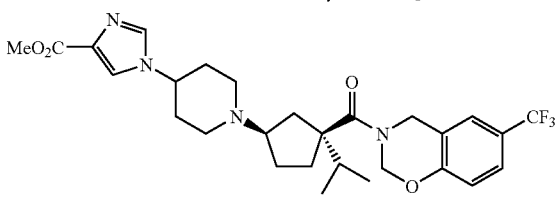
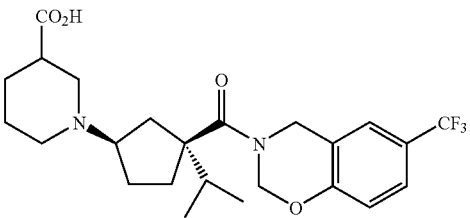
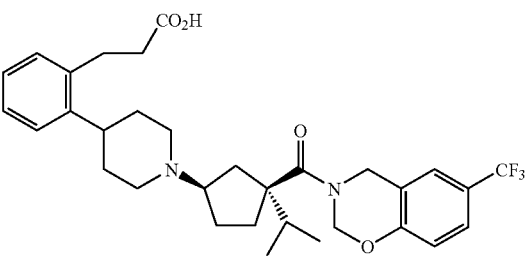
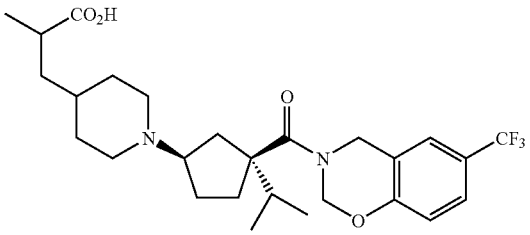

-continued
| 163 | 164 |
|---|---|
| 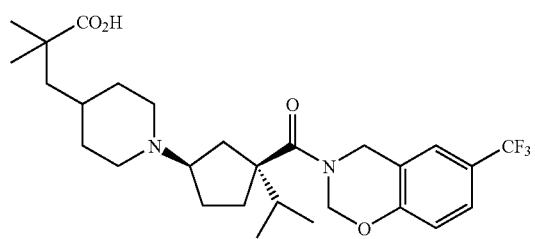 | 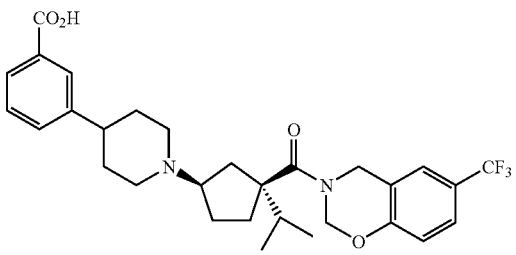 |
| 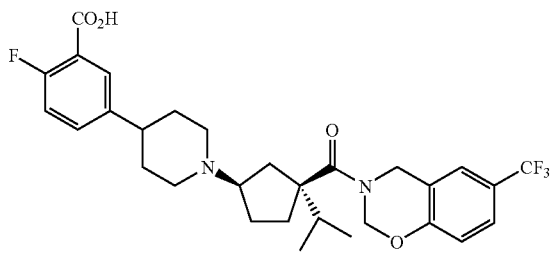 | 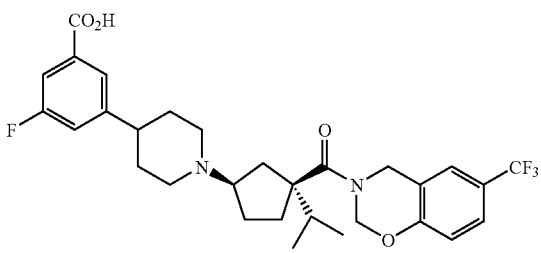 |
| 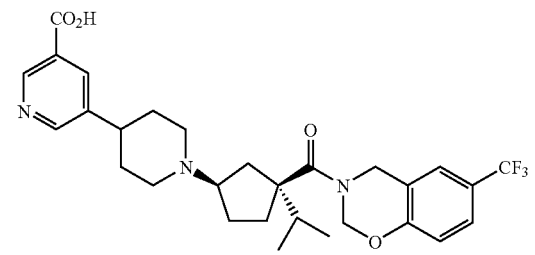 | 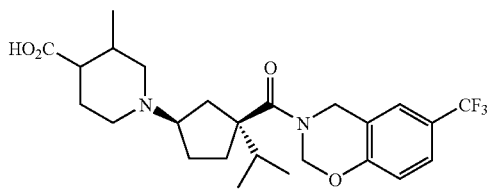 |
| 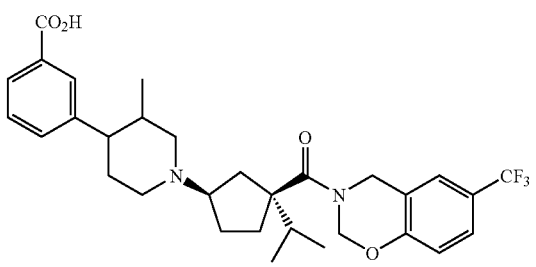 | 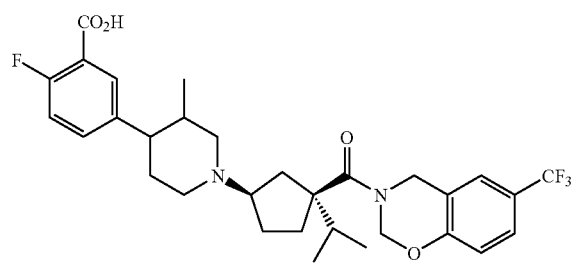 |
| 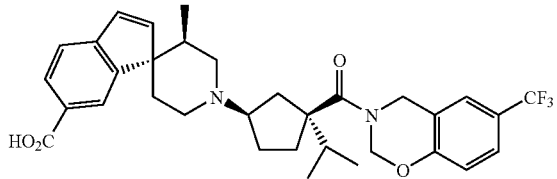 | 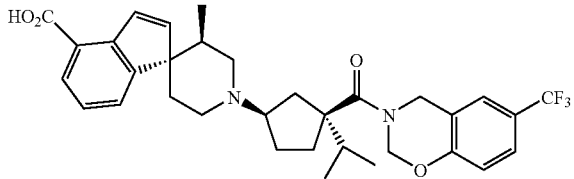 |
| 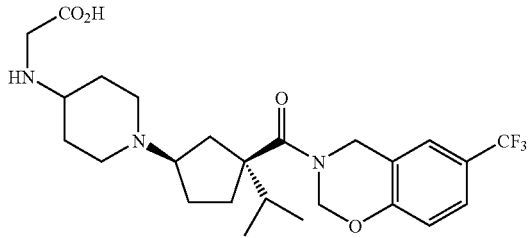 | 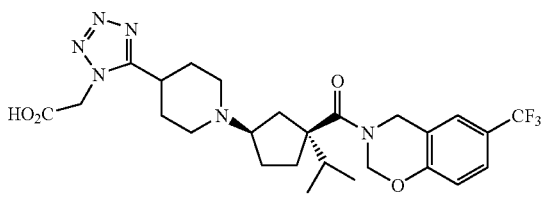 |
| 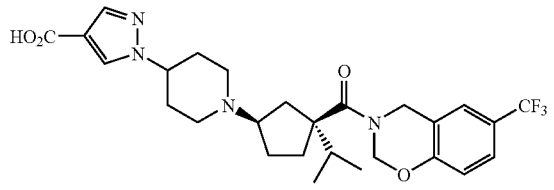 | 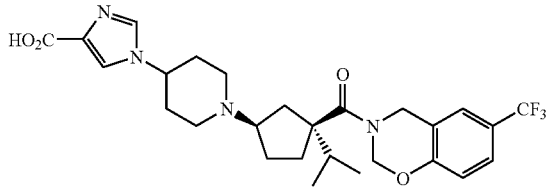 |

-continued
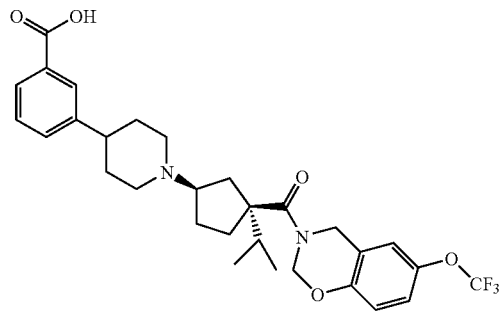
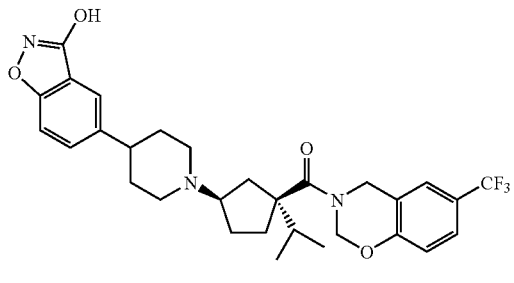
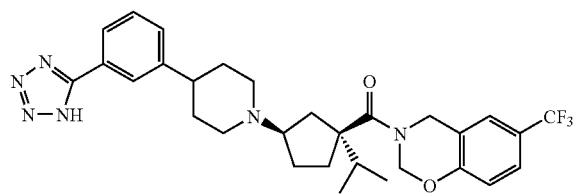
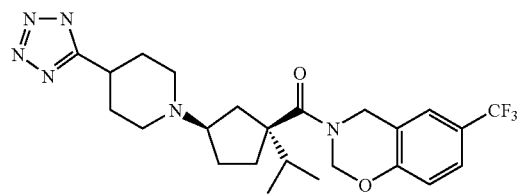
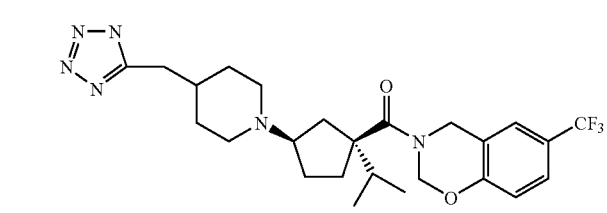
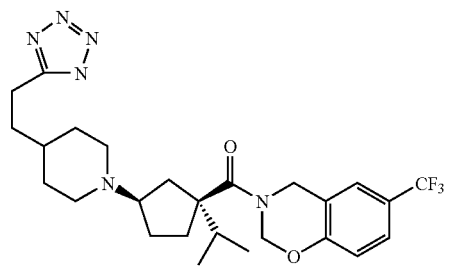
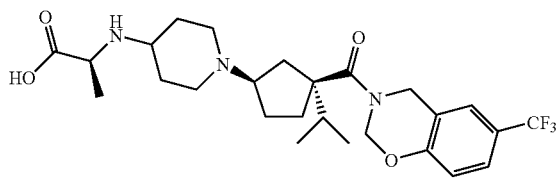
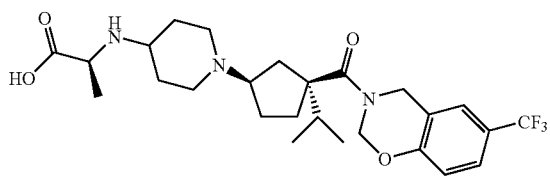
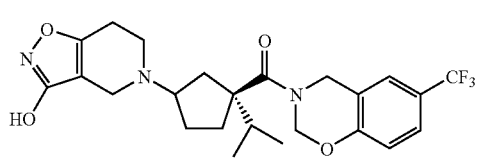
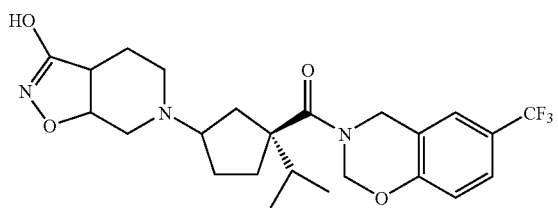
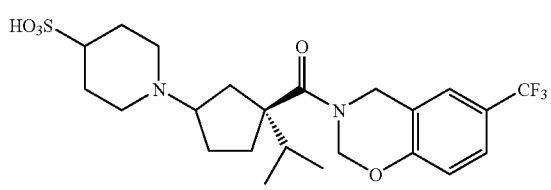
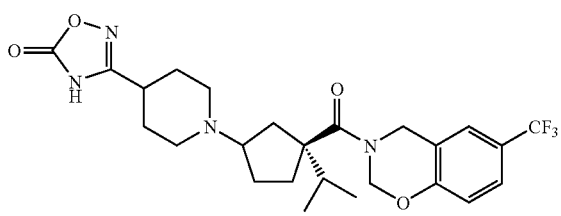

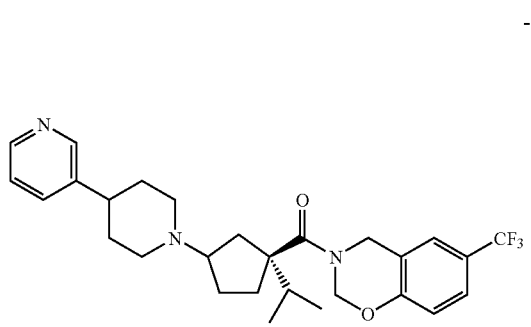
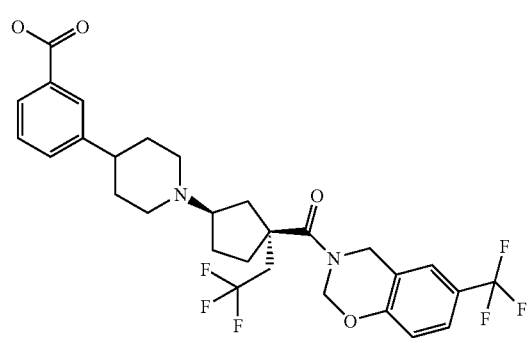
or a pharmaceutically acceptable salt or individual diastereomer thereof.
14. A compound of claim 2 selected from:
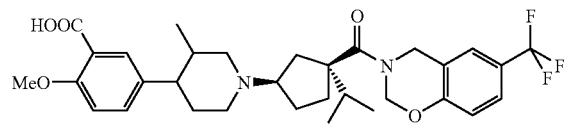
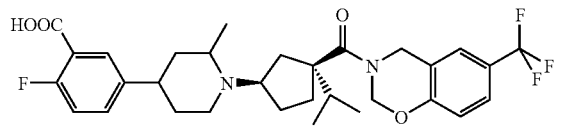
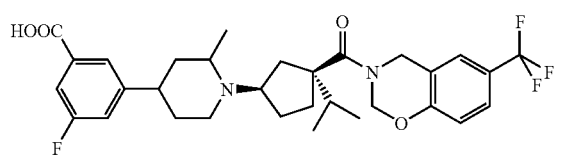
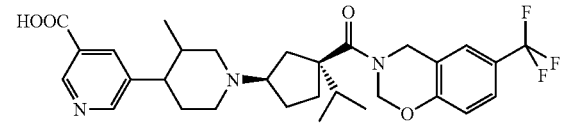
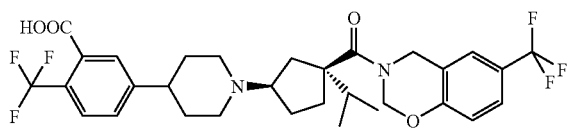
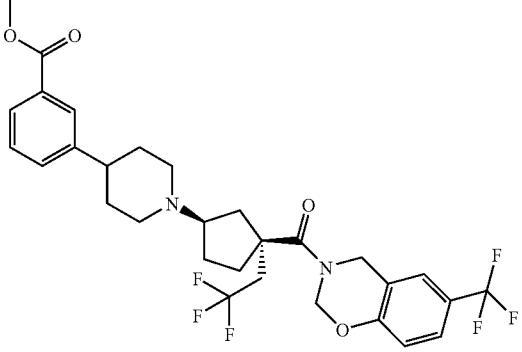
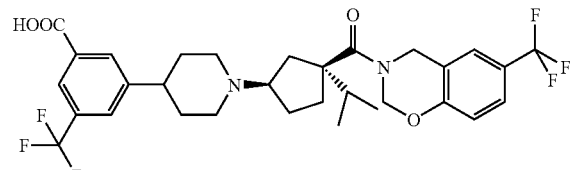
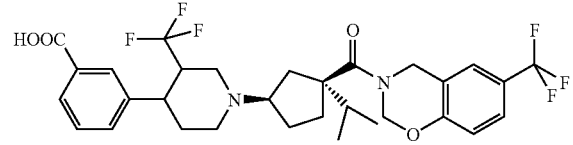
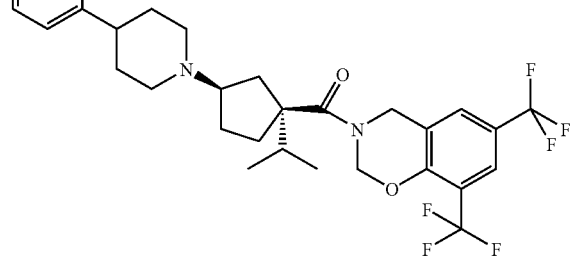

-continued
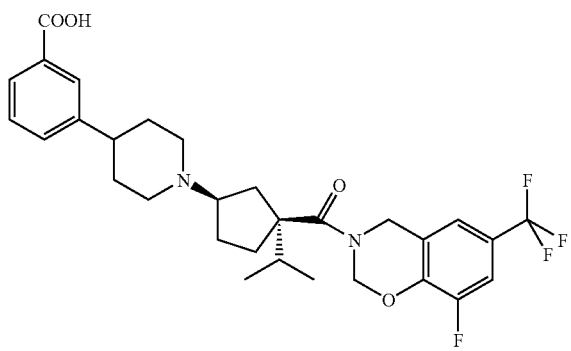
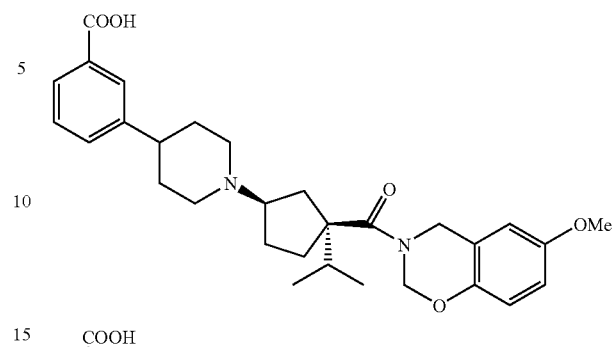
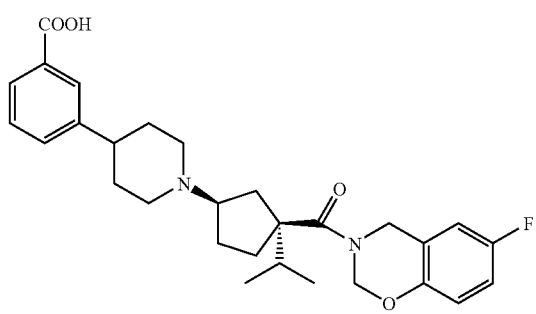
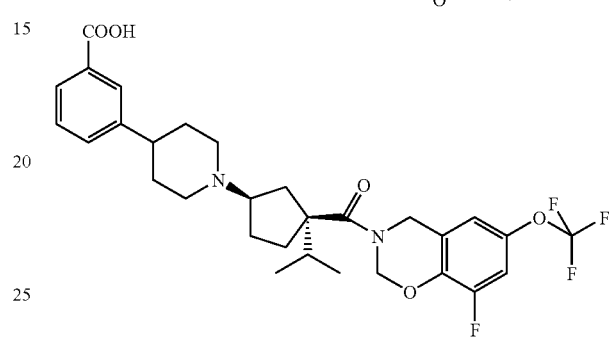
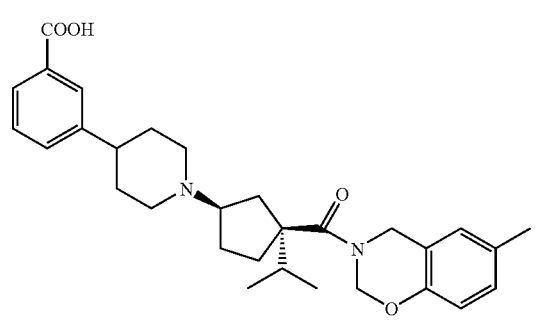
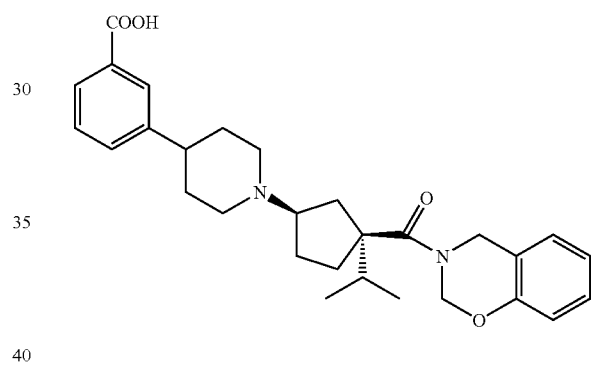
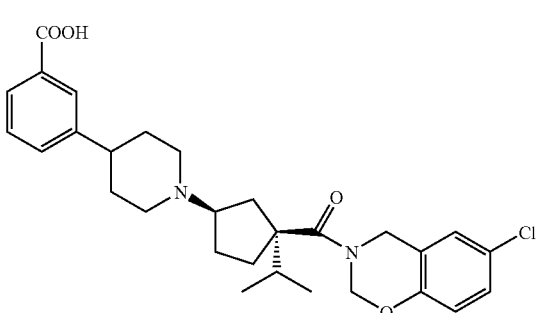
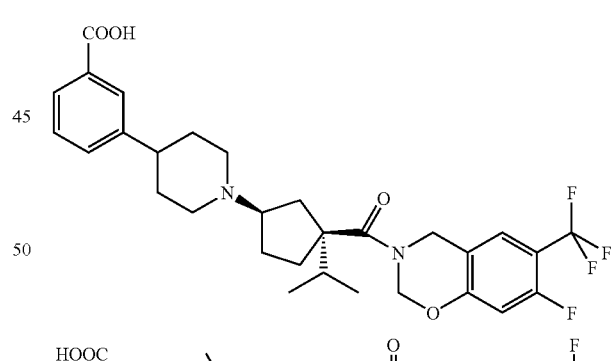
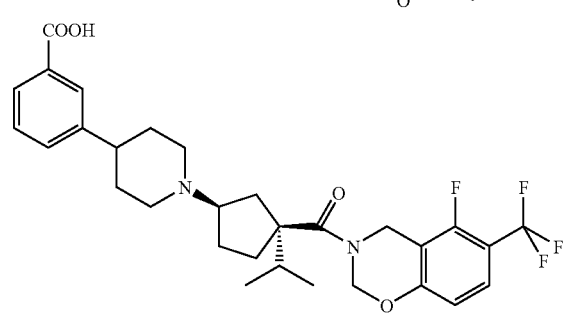
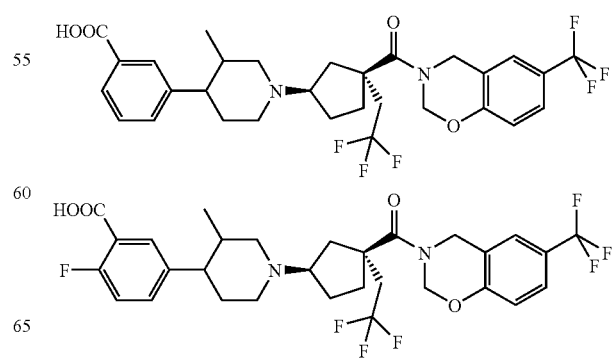

-continued
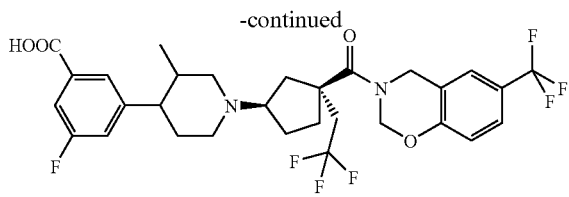
or a pharmaceutically acceptable salt or individual diastereomer thereof.
15. A pharmaceutical composition which comprises an inert carrier and the compound of claim 2.
16. The compound of claim 2 selected from the group consisting of the following compounds, or a pharmaceutically acceptable salt or individual diastereomer thereof:
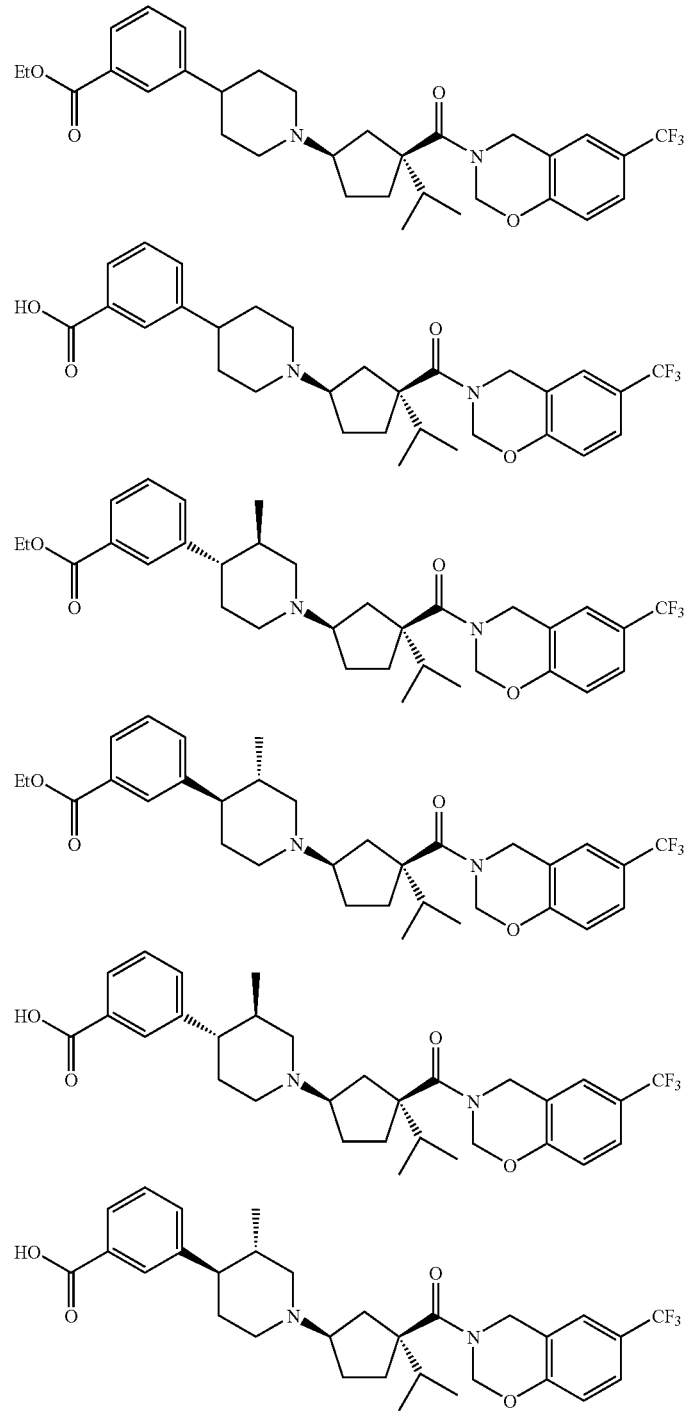

-continued
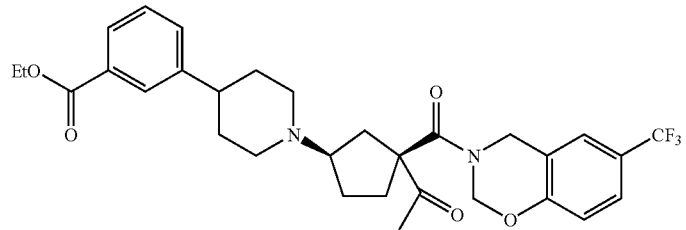
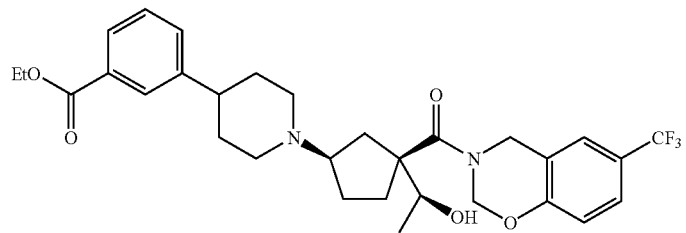
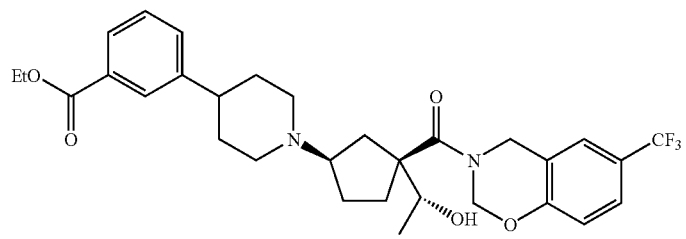
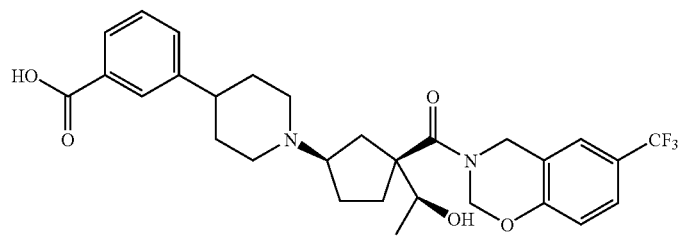
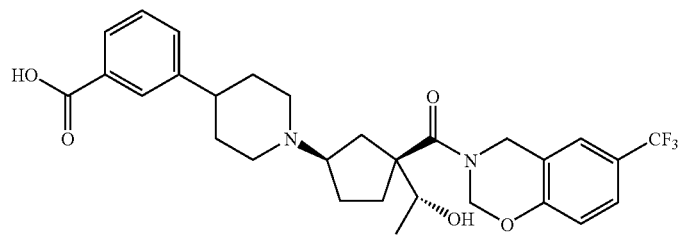
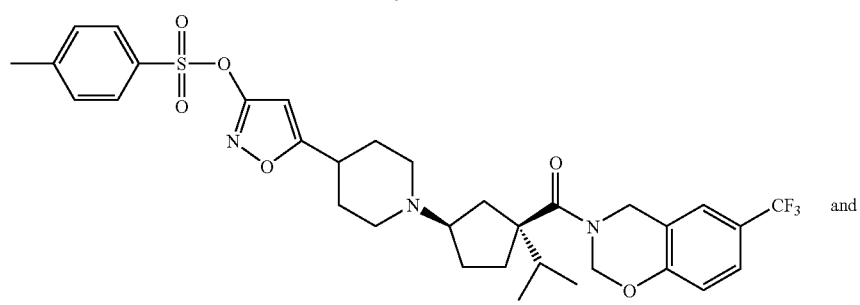
and -continued

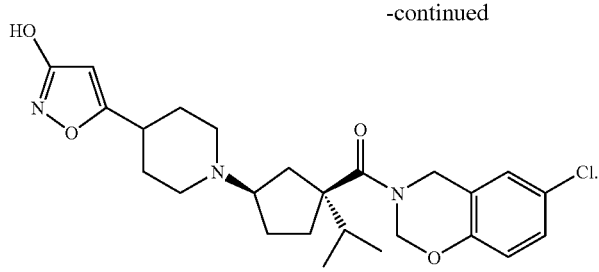

17. The compound of 2, or a pharmaceutically acceptable salt thereof:

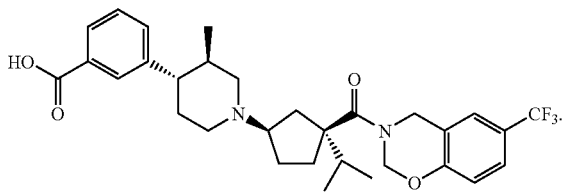

18. A compound of formula II:

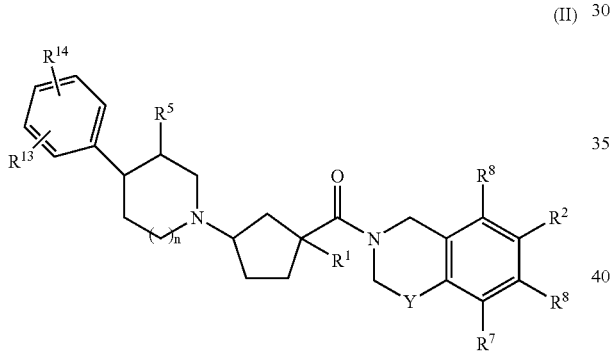

(II)

or a pharmaceutically acceptable salt or individual diastereomer thereof, wherein:

Y is O;

$R^1$ is hydrogen, —$C_{0-6}$alkyl-W—($C_{1-6}$alkyl)-, —($C_{0-6}$alkyl)-W—($C_{0-6}$alkyl)-($C_{3-7}$cycloalkyl)-($C_{0-6}$alkyl), —($C_{0-6}$alkyl)-W-phenyl, or —($C_{0-6}$alkyl)-W-heterocycle, wherein the alkyl, phenyl, heterocycle and the cycloalkyl are optionally substituted with 1-7 substituents independently selected from halo, hydroxy, —O—$C_{1-3}$alkyl, trifluoromethyl, $C_{1-3}$alkyl, —O—$C_{1-3}$alkyl, —$CO_2R^{10}$, —CN, —$NR^{10}R^{10}$, —$NR^{10}COR^{10}$, —$NR^{10}SO_2R^{11}$, and —$CONR^{10}R^{10}$;

W is a single bond, —O—, —S—, —SO—, —$SO_2$—, —CO—, —$CO_2$—, —$CONR^{10}$— or —$NR^9$—;

$R^2$ is -halo, —$C_{0-6}$alkyl, $C_{0-6}$alkyl-W—$C_{1-6}$alkyl, $C_{0-6}$alkyl-W—$C_{3-7}$cycloalkyl, $C_{0-6}$alkyl-W-phenyl, or $C_{0-6}$alkyl-W-heterocycle, wherein $C_{1-6}$alkyl, $C_{3-7}$cycloalkyl, phenyl and heterocycle optionally are independently substituted with 1-6 substituents independently selected from halo, trifluoromethyl, —CN, —$C_{1-6}$alkyl and hydroxy;

$R^5$ is hydrogen, hydroxy, $C_{1-6}$alkyl, $C_{1-6}$alkyl-$CO_2R^{10}$, $C_{1-6}$alkyl-hydroxy, —O—$C_{1-3}$ alkyl, or halo, or $R^5$ or $R^6$ is =O connected to the ring via a double bond;

$R^7$ is hydrogen, hydroxy, halo or $C_{1-6}$alkyl optionally substituted with 1-6 substituents independently selected from fluro, —O—$C_{1-6}$alkyl optionally substituted with 1-6 fluro, —$NR^{10}R^{10}$, —$NR^{10}CO_2R^{11}$, —$NR^{10}CONR^{10}R^{10}$, —$NR^{10}$—$SO_2$—$NR^{10}R^{10}$, —$NR^{10}$—$SO_2$—$R^{11}$, heterocycle, —CN, —$CONR^{10}R^{10}$, —$CO_2R^{10}$, —$NO_2$, —S—$R^{10}$, —SO—$R^{11}$, —$SO_2$—$R^{11}$ and —$SO_2$—$NR^{11}R^{11}$;

$R^8$ is hydrogen, $C_{1-6}$alkyl, trifluoromethyl, trifluoromethoxy, chloro, fluoro, bromo, or phenyl;

$R^9$ is $SO_2R^{11}$, $COR^{10}$, $CONHR^{10}$, $CO_2R^{11}$, or $SO_2NHR^{10}$;

$R^{10}$ is hydrogen, —$C_{1-6}$alkyl, benzyl, phenyl, or —$C_{0-6}$alkyl-$C_{3-6}$ cycloalkyl, optionally substituted with 1-3 substituents independently selected from halo, $C_{1-3}$alkyl, $C_{1-3}$ alkoxy and trifluoromethyl;

$R^{11}$ is $C_{1-6}$alkyl, —$C_{0-6}$alkyl-$C_{3-6}$cycloalkyl, benzyl or phenyl, optionally substituted with 1-3 substituents independently selected from halo, $C_{1-3}$alkyl, $C_{1-3}$alkoxy and trifluoromethyl;

$R^{13}$ and $R^{14}$ are independently hydrogen, halo, trifluoromethyl, hydroxy, —$C_{1-3}$alkyl, —O—$C_{1-3}$alkyl, —$C_{0-3}$—$CO_2H$, —$C_{0-3}$—$CO_2C_{1-3}$alkyl, —CN, or —$C_{0-3}$-heterocycle, or $R^{13}$ and $R^{14}$ join to form a heterocycle fused to the phenyl ring, which heterocycle is optionally substituted with 1-2 substituents independently selected from hydroxy, halo, —$CO_2R^{10}$, or —$C_{1-3}$alkyl; and n is 1.

* * * * *